(12) United States Patent
Sigurdsson

(10) Patent No.: US 12,162,929 B2
(45) Date of Patent: Dec. 10, 2024

(54) ALPHA-SYNUCLEIN SINGLE DOMAIN ANTIBODIES

(71) Applicant: NEW YORK UNIVERSITY, New York, NY (US)

(72) Inventor: Einar M. Sigurdsson, Scarsdale, NY (US)

(73) Assignee: NEW YORK UNIVERSITY, New York, NY (US)

( * ) Notice: Subject to any disclaimer, the term of this patent is extended or adjusted under 35 U.S.C. 154(b) by 793 days.

(21) Appl. No.: 16/971,157

(22) PCT Filed: Feb. 19, 2019

(86) PCT No.: PCT/US2019/018579
§ 371 (c)(1),
(2) Date: Aug. 19, 2020

(87) PCT Pub. No.: WO2019/161386
PCT Pub. Date: Aug. 22, 2019

(65) Prior Publication Data
US 2022/0033482 A1     Feb. 3, 2022

Related U.S. Application Data

(60) Provisional application No. 62/632,267, filed on Feb. 19, 2018.

(51) Int. Cl.
*C07K 16/18* (2006.01)
*G01N 33/68* (2006.01)

(52) U.S. Cl.
CPC ......... *C07K 16/18* (2013.01); *G01N 33/6896* (2013.01); *C07K 2317/21* (2013.01); *C07K 2317/22* (2013.01); *C07K 2317/24* (2013.01); *C07K 2317/569* (2013.01); *G01N 2800/28* (2013.01); *G01N 2800/56* (2013.01)

(58) Field of Classification Search
CPC ................ C07K 16/18; C07K 2317/21; C07K 2317/22; C07K 2317/24; C07K 2317/569; G01N 33/6896; G01N 2800/28; G01N 2800/56; A61K 39/3955; A61K 2039/505
See application file for complete search history.

(56) References Cited

U.S. PATENT DOCUMENTS

| 7,674,599 B2 | 3/2010 | Chilcote et al. |
| 2008/0300204 A1 | 12/2008 | Federoff et al. |
| 2016/0280787 A1 | 9/2016 | Igawa et al. |
| 2017/0145088 A1 | 5/2017 | Dreier et al. |

FOREIGN PATENT DOCUMENTS

| WO | 2016071438 A2 | 5/2016 | |
| WO | 2017153402 A1 | 9/2017 | |
| WO | 2017189964 A2 | 11/2017 | |
| WO | WO-2018111670 A2 * | 6/2018 | ......... A61K 47/6803 |

OTHER PUBLICATIONS

Bond CJ et al. Contributions of CDR3 to VHH domain stability and the design of monobody scaffolds for naïve antibody libraries. J. Mol. Biol. (2003) 332, 643-655. (Year: 2003).*
Paul, Fundamental Immunology, Third Edition, 1993, pp. 292-295, under the heading "Fv Structure and Diversity in Three Dimensions". (Year: 1993).*
Rudikoff et al. Proc Natl Acad Sci USA (1982) 79(6):1979-1983. (Year: 1982).*
International Search Report and Written Opinion for PCT International Application No. PCT/US2019/018579, dated Jul. 8, 2019.

* cited by examiner

*Primary Examiner* — Kimberly Ballard
(74) *Attorney, Agent, or Firm* — Troutman Pepper Hamilton Sanders LLP (Rochester)

(57) ABSTRACT

The present disclosure is directed to single domain antibodies that bind to α-synuclein and the use of these antibodies for the treatment and diagnosis of α-synucleinopathies The present disclosure is also directed to polynucleotides encoding the α-synuclein single domain antibodies, therapeutic vectors comprising these polynucleotides and methods of administering these therapeutic vectors for the treatment of α-synucleinopathies.

19 Claims, 7 Drawing Sheets
Specification includes a Sequence Listing.

ALPHA-SYNUCLEIN SINGLE DOMAIN ANTIBODIES

This application is a national stage application under 35 U.S.C. § 371 of PCT Application No. PCT/US19/18579, filed Feb. 19, 2019, which claims the priority benefit of U.S. Provisional Patent Application Ser. No. 62/632,267, filed Feb. 19, 2018, which is hereby incorporated by reference in its entirety.

This invention was made with government support under R21 AG059391 awarded by the National Institutes of Health. The government has certain rights in the invention.

FIELD OF THE INVENTION

The present invention is directed to antibodies for the treatment and diagnosis of α-synucleinopathies.

BACKGROUND OF THE INVENTION

Immunotherapies targeting various protein aggregates such as amyloid-β (Aβ), tau and α-synuclein (α-syn) are in different stages of clinical development, and collectively are the most common approach by the pharmaceutical industry to tackle diseases characterized by such depositions (Golde T E, "Open Questions for Alzheimer's Disease Immunotherapy," *Alzheimers Res Ther* 6:3 (2014); Valera and Masliah, "Immunotherapy for Neurodegenerative Diseases: Focus on Alphasynucleinopathies," *Pharmacol Ther* 138: 311-322 (2013); and Pedersen and Sigurdsson, "Tau Immunotherapy for Alzheimer's Disease," *Trends Mol Med* 2:394-402 (2015)). On the diagnostic side, a few dye-based Aβ positron emission tomography (PET) tracers are already in clinical use and at least three such small molecule tau-targeting PET tracers are in clinical development (Congdon et al., "Harnessing the Immune System for Treatment and Detection of Tau Pathology," *J Alzheimers Dis* 40(Suppl 1):S113-S121 (2014)). Similar approaches targeting α-syn are not as advanced (Eberling et al., "Alpha-synuclein Imaging: a Critical Need for Parkinson's Disease Research," *J Parkinsons Dis* 3:565-567 (2013)) There are no reports of selective or specific α-syn imaging probes. Interestingly, α-syn deposits are not only found in Parkinson's disease but also often found in Alzheimer's disease and are the main lesion in Lewy Body Dementia (Lippa et al., "DLB and PDD Boundary Issues: Diagnosis, Treatment, Molecular Pathology, and Biomarkers," *Neurology* 68:812-819 (2007)) and in Multiple System Atrophy (see e.g., Goedert et al., "The Synucleinopathies: Twenty Years On," *J. Parkinsons Dis.* 7(s1):S53-S71 (2017)). Hence, it is difficult to predict who is a candidate for α-syn targeting therapy, which would be greatly facilitated if an α-syn imaging probe would exist. Furthermore, based on Braak staging of Parkinson's disease brains, α-syn deposition is widely thought to precede dopaminergic loss (Hawkes et al., "A Timeline for Parkinson's Disease." *Parkinsonism Relat Disord* 16:79-84 (2010) and Dickson et al., "Neuropathological Assessment of Parkinson's Disease: Refining the Diagnostic Criteria," *Lancet Neurol* 8:1150-1157 (2009)). Hence, its in vivo detection by imaging would allow identification of presymptomatic individuals, who could then receive prophylactic therapies under development to target α-synuclein.

The present invention is directed to overcoming these and other deficiencies in the art.

SUMMARY OF THE INVENTION

A first aspect of the present disclosure is directed to an antibody or fragment thereof comprising a heavy chain variable region. The heavy chain variable region comprises a complementarity-determining region 1 (H-CDR1) comprising an amino acid sequence of any one of SEQ ID NOs: 1-36, 218, 222, 226, 230, 234, 238, 340 or a modified amino acid sequence of any one of SEQ ID NOs: 1-36, 218, 222, 226, 230, 234, 238, and 340 said modified sequence containing 1, 2, or 3 amino acid residue modifications as compared to any one of SEQ ID NOs: 1-36, 218, 222, 226, 230,234, 238, and 340; a complementarity-determining region 2 (H-CDR2) comprising an amino acid sequence of any one of SEQ ID NOs: 37-72, 219, 223, 227, 231, 235, 239, 341 or a modified amino acid sequence of any one of SEQ ID NOs: 37-72, 219, 223, 227, 231, 235, 239, and 341 said modified sequence containing 1, 2, or 3 amino acid residue modifications as compared to any one of SEQ ID NOs: 37-72, 219, 223, 227, 231, 235, 239, and 341; and a complementarity-determining region 3 (H-CDR3) comprising an amino acid sequence of any one of SEQ ID NOs: 73-108, 220, 224, 228, 232, 236, 240, 342 or a modified amino acid sequence of any one of SEQ ID NOs: 73-108, 220, 224, 228, 232, 236, 240, and 342 said modified sequence containing 1, 2, or 3 amino acid residue modifications as compared to any one of SEQ ID NOs: 73-108, 220, 224, 228, 232, 236, 240, and 342.

Another aspect of the present disclosure is directed to an antibody or fragment thereof comprising a heavy chain variable region. The heavy chain variable region comprises a complementarity-determining region 1 (H-CDR1) comprising an amino acid sequence of any one of SEQ ID NOs: 146-160, or a modified amino acid sequence of any one of SEQ ID NOs: 146-160, said modified sequence containing 1, 2, or 3 amino acid residue modifications as compared to any one of SEQ ID NOs: 146-160; a complementarity-determining region 2 (H-CDR2) comprising an amino acid sequence of any one of SEQ ID NOs: 161-175, or a modified amino acid sequence of any one of SEQ ID NOs: 161-175, said modified sequence containing 1, 2, or 3 amino acid residue modifications as compared to any one of SEQ ID NOs: 161-175; and a complementarity-determining region 3 (H-CDR3) comprising an amino acid sequence of any one of SEQ ID NOs: 176-190, or a modified amino acid sequence of any one of SEQ ID NOs: 176-190, said modified sequence containing 1, 2, or 3 amino acid residue modifications as compared to any one of SEQ ID NOs: 176-190.

Another aspect of the present disclosure is directed to a method of inhibiting onset of one or more symptoms of an α-synucleinopathy in a subject. This method involves administering to the subject a pharmaceutical composition comprising one or more antibodies or binding fragments thereof as described herein or polynucleotides encoding the one or more antibodies or binding fragments thereof as described herein in an amount effective to inhibit onset of one or more symptoms of the α-synucleinopathy in the subject.

Another aspect of the present disclosure is directed to a method of treating an α-synucleinopathy in a subject. This method involves administering to the subject a pharmaceutical composition comprising one or more antibodies or binding fragments thereof as described herein or polynucleotides encoding the one or more antibodies or binding fragments thereof as described herein in an amount effective to treat the α-synucleinopathy in the subject.

Another aspect of the present disclosure is directed to a method of diagnosing an α-synucleinopathy in a subject. This method involves detecting, in the subject, the presence of accumulated α-synuclein protein or peptide using the antibody or binding fragment as described herein, and diagnosing the α-synucleinopathy based on the detection of the accumulated α-synuclein protein or peptide in the subject.

Another aspect of the present disclosure is directed to a method of monitoring the progression of an α-synucleinopathy in a subject. This method involves detecting, in the subject, the presence of α-synuclein protein or peptide using the antibody or binding fragment thereof as described herein, repeating the detecting step periodically; and monitoring the progression of the α-synucleinopathy in the subject as a result of the repeated detecting.

Another aspect of the present disclosure is directed to a diagnostic kit. The diagnostic kit contains any one or more antibodies or binding fragments thereof as described herein, and a detectable label.

BRIEF DESCRIPTION OF THE DRAWINGS

FIG. 4A shows binding by a mixture of two commercial α-synuclein antibodies known to stain Lewy bodies and Lewy neurites. Immunoreactivity of polyclonal sdAbs panned against solid or solution phase α-synuclein is shown in FIGS. 4B and 4C, respectively. The binding profiles of particular clones, including sdAb 1G10 (FIG. 44), 2D10 (FIG. 4E), 2D8 (FIG. 4F), 2H7 (FIG. 4G), 2H1 (FIG. 4H), and 1D12 (FIG. 4I) are also shown.

Figure 7:
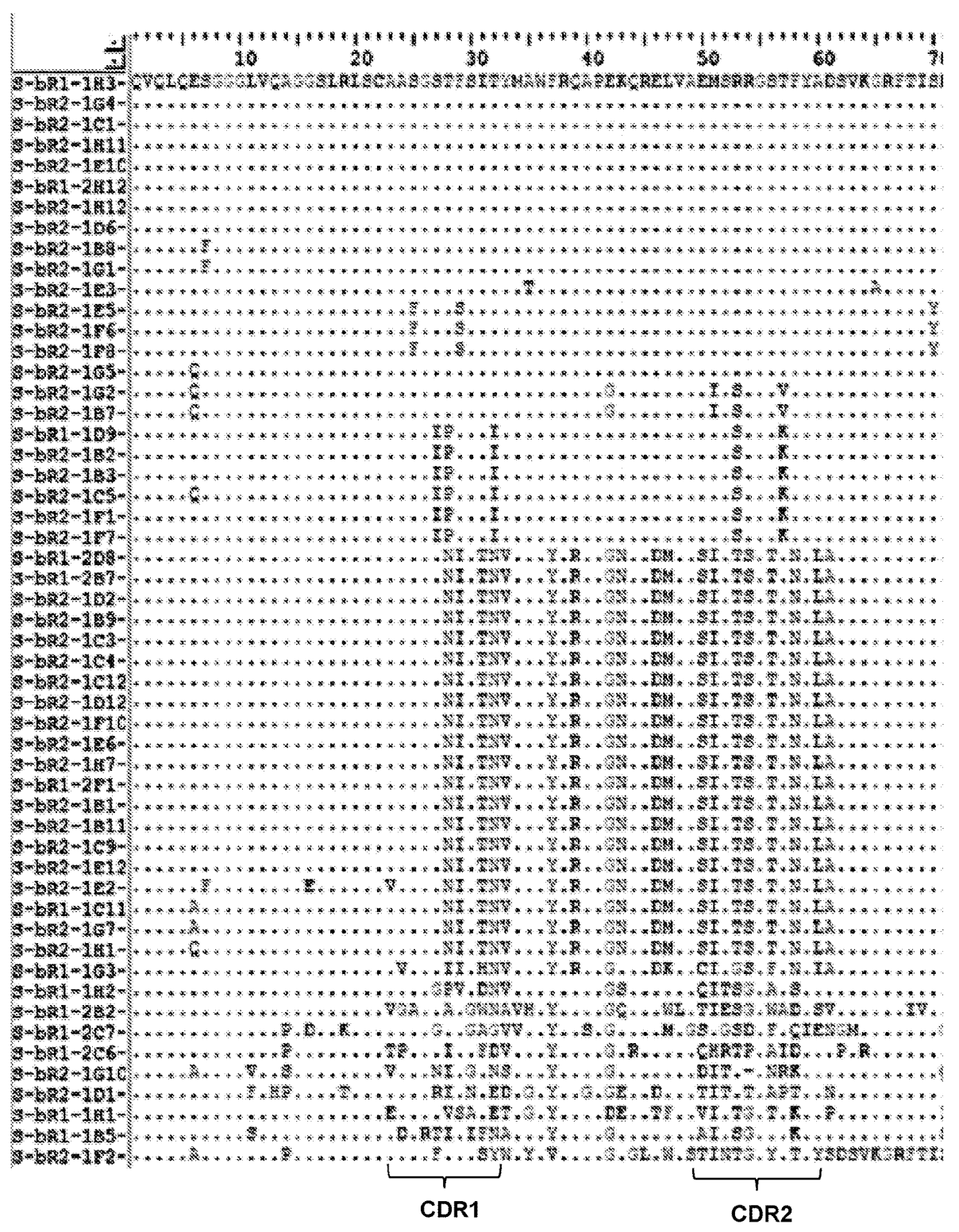
Figure 7:
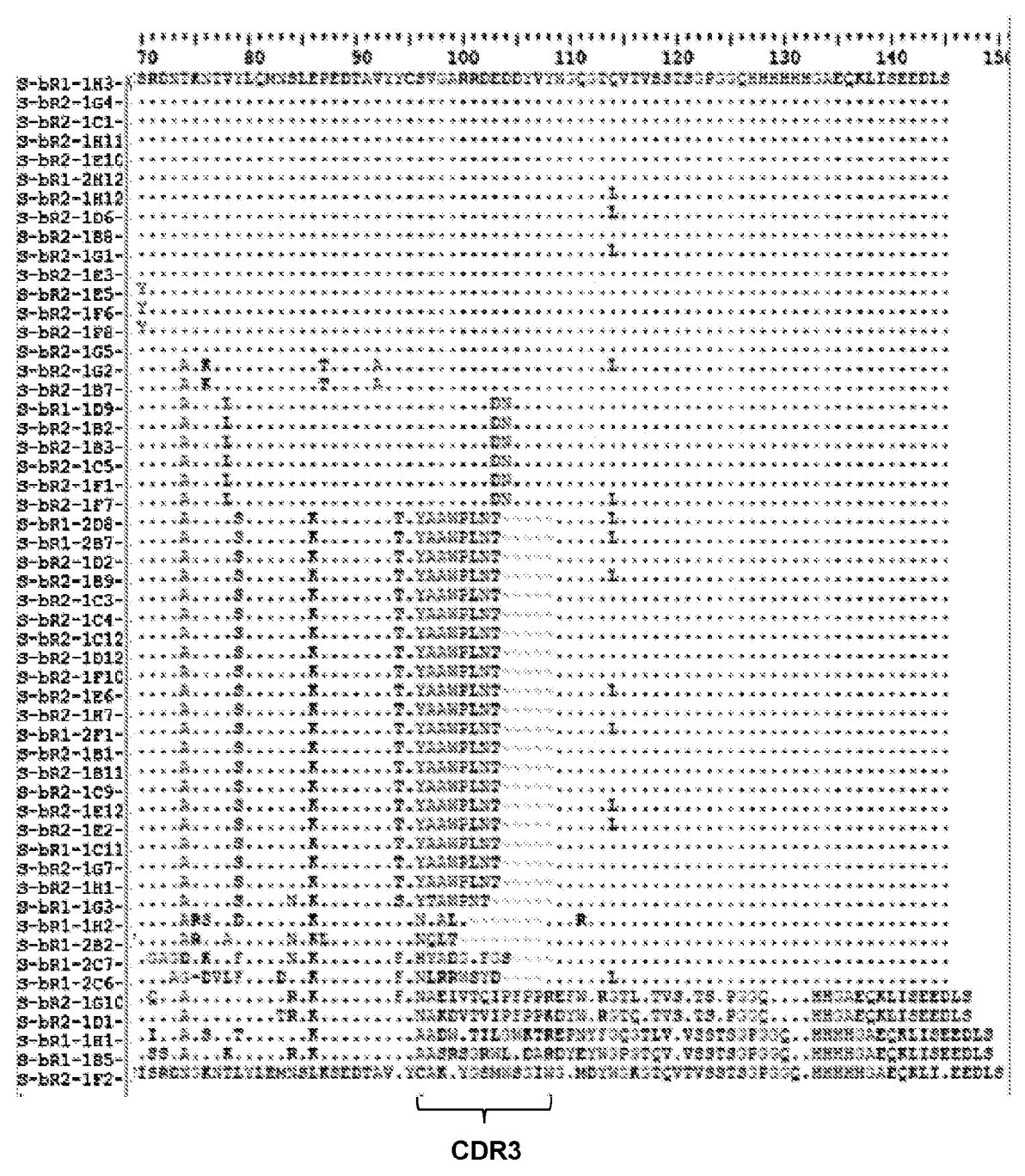

FIG. 7 is a sequence alignment of the anti-synuclein sdAb selected via solution-phase panning. The complementarity determining regions are shown.

DETAILED DESCRIPTION OF THE INVENTION

Figure 1A:
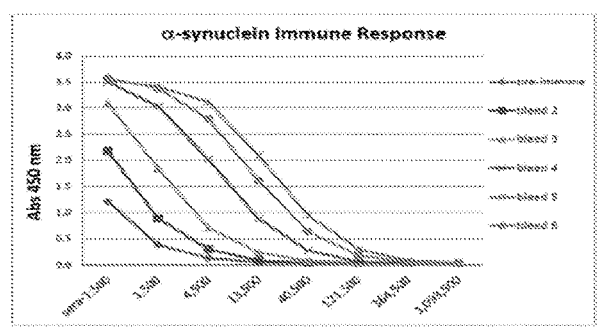
FIG. 1A shows the α-synuclein single domain antibody (sdAb) titer generated in llama following 1-5 immunizations with recombinant α-synuclein.

A first aspect of the present invention is directed to an antibody or binding fragment thereof that binds α-synuclein protein. In particular, the antibody or binding fragment as disclosed herein binds to human α-synuclein protein. In one embodiment, the antibody or binding fragment thereof of the present disclosure binds to aggregated forms of α-synuclein protein that are associated with the development and progression of α-synucleinopathies. In another embodiment, the antibody or binding fragment thereof of the present disclosure binds to the monomeric form of α-synuclein protein that accumulates with the development and progression of α-synucleinopathies.

In one embodiment, the antibodies described herein are single domain antibodies. The unique binding property or antigen binding specificity of a given antibody is determined by its complementarity determining regions (CDR) typically found in the light and heavy chain variable regions of an immunoglobulin. Single domain antibodies are antibodies whose CDRs are part of a single domain polypeptide. Examples include, but are not limited to, heavy chain variable domain antibodies (including three CDRs) and light chain variable domain antibodies (containing three CDRs). Single domain antibodies can be derived from heavy chains and light chains of conventional 4-chain antibodies, antibodies naturally devoid of light chains, engineered antibodies and single domain scaffolds other than those derived from antibodies. In one embodiment, the single domain antibody of the present invention is a heavy chain single domain antibody, i.e., a $V_HH$ or NANOBODY®. In on embodiment, the heavy chain single domain antibodies described herein are derived from naturally occurring heavy chain antibodies devoid of light chains.

Single domain antibodies are about 10-times smaller than conventional heavy chain and light chain containing IgG molecules. They are single polypeptides that are very stable, as they are resistant to extreme pH and temperature conditions. Moreover, unlike conventional antibodies, single domain antibodies are resistant to the action of proteases. In vitro expression of $V_HHs$ produces high yield, properly folded functional $V_HHs$. Given their small size, $V_HHs$ are capable of recognizing unique epitopes of an antigen that cannot be bound by traditional full sized antibodies. As such, the anti-α-synuclein single domain antibodies described herein bind unique epitopes of α-synuclein and/or bind epitopes more efficiently than conventional α-synuclein antibodies.

The single domain antibodies as described herein can be derived from antibodies raised in Camelidae species, for example in camel, dromedary, llama, vicuña, alpaca and guanaco. Single domain antibodies produced by other species are also within the scope of the invention. For example, single domain antibodies as disclosed herein may be derived from antibodies produced in any species including, but not limited to mouse, human, camel, llama, goat, rabbit, bovine, and cartilaginous fish.

In another embodiment, the antibody as described herein is an antibody fragment. In one embodiment, an antibody fragment is a single-chain polypeptide comprising one CDR as described herein. In another embodiment, the antibody fragment is a single-chain polypeptide comprising two CDRs as described herein. In another embodiment, the antibody fragment is a single-chain polypeptide containing all three CDRs of the heavy chain variable regions as described herein. An antibody fragment as referred to herein may be devoid of one or more framework regions (FR1, FR2, FR3, or FR4) or any portion thereof of the heavy chain variable region.

In one embodiment, the antibody as described herein comprises a $V_H$ domain coupled to one or more heavy chain constant regions ($C_H$). Mammalian heavy chain immunoglobulins typically have three or four constant region domains. Accordingly, the heavy chain variable regions described herein may be coupled to one heavy chain constant region, two heavy chain constant regions, three heavy chain constant regions, or four heavy chain constant regions.

In one embodiment, the antibody as described herein comprises a $V_H$ domain coupled to an Fc region, i.e., the antibody is an Fc-fusion antibody. The Fc region can be composed of the second and third constant domain regions (as it is for IgG, IgA, and IgD antibody isotypes), or composed of the second, third, and fourth constant domain regions (as it is for IgM and IgE antibody isotypes). In one embodiment, the Fc domain is derived from a human immunoglobulin. In one embodiment, the Fc domain is derived from human IgG1 including the $C_H2$ and $C_H3$ regions.

The Fc-region or domain of the fusion polypeptides described herein may impart non-antigen binding functions to the polypeptide, termed "effector functions", such as complement binding, antibody-dependent cell cytotoxicity (ADCC), and other functions mediated through the binding of subregions of this dimeric structure with immune cell surface receptors, Fc-receptors. Certain natural and synthetic variants of the Fc-region polypeptide sequences with altered effector functions that are suitable for use in the fusion polypeptides described herein include the subclass variants; e.g. IgGi, IgG2i, IgG3i, IgG24; and mutant polypeptides as described in e.g. U.S. Pat. No. 5,624,821 to Winter, U.S. Pat. No. 6,528,624 to Idusogie, U.S. Pat. No. 7,183,387 to Presta, and U.S. Pat. No. 7,317,091 to Lazar et al., which are hereby incorporated by reference in their entirety.

In another embodiment, the antibody or fragment thereof comprises two or more variable domain regions couple together. For example, in one embodiment, the antibody as described herein comprises two, or three, or more heavy chain variable regions linked together in tandem. In another embodiment, the heavy chain variable region is fused together with a light chain variable region to form a single-chain variable domain antibody (scFv) or a single-chain variable domain with an Fc portion (i.e., a scFv-Fc, e.g., a minibody). In another embodiment, two or more single-chain antibodies are linked together either in tandem (i.e., tandem scFvs), or such that they dimerize to form diabodies or triabodies. In another embodiment, the antibody is a tetrabody single chain variable fragment. In another embodiment, the antibody is a "linear antibody" which is an antibody comprising a pair of tandem Fd segments ($V_H$-$C_H1$-$V_H$-$C_H1$) that form a pair of antigen binding regions (see Zapata et al. *Protein Eng.* 8(10): 1057-1062 (1995), which is hereby incorporated by reference in its entirety).

In another embodiment, the antibody of the disclosure is a conventional immunoglobulin (Ig) molecule comprising four polypeptide chains, i.e., two heavy chains and two light chains linked by disulfide bonds. In accordance with this embodiment, the single-domain antibodies as described herein are coupled to constant domain regions and further coupled to Ig light chains to create a four chain conventional antibody.

Antibody and antibody fragments disclosed herein can be mono-valent, bi-valent, or tri-valent with regard to binding domains, and the binding domains may be mono-specific, bi-specific, or tri-specific in binding specificity by design.

In one embodiment, the antibody or fragment thereof is isolated. As used herein, the term "isolated" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., gel filtration, ion exchange or reverse phase HPLC). Method for assessing antibody purity are known in the art (see e.g., Flatman et al., *J. Chromatogr. B* 848:79-87 (2007), which is hereby incorporated by reference in its entirety).

In one embodiment, the antibody or binding fragment thereof described herein is a chimeric antibody. A chimeric antibody is an antibody where one portion of the amino acid sequence of each of the heavy chains is homologous to corresponding sequences in an antibody derived from a particular species or belonging to a particular class, while the remaining segment of each chain is homologous to corresponding sequences in another species or class. Typically, the variable region mimics the variable region of an antibody derived from one species of mammals, while the constant portions are homologous to sequences of antibodies derived from another. For example, the variable region can be any one of the heavy chain variable regions disclosed herein derived from a camelid antibody coupled to one or more constant regions derived from a human immunoglobulin. Methods of making chimeric antibodies are well known in the art, see e.g., U.S. Pat. No. 4,816,567; and Morrison et al., "Chimeric human antibody molecules: mouse antigen-binding domains with human constant region domains" *Proc. Natl. Acad. Sci. USA* 81:6851-6855 (1984), which are hereby incorporated by reference in their entirety).

In another embodiment, the antibody or binding fragment thereof is a CDR-grafted antibody A "CDR-grafted antibody" is an antibody which comprises variable region sequences of one species, where one or more of the CDR regions are replaced with CDR regions of another species. For example, in one embodiment the CDR grafted antibody comprises human or humanized heavy chain variable regions, where one or more of the CDRs within these regions is replaced with one or more CDRs disclosed herein that are derived from camelid heavy chain antibodies.

In another embodiment, the antibody or binding fragment thereof is a humanized antibody. A humanized antibody is an antibody or a variant derivative, analog or portion thereof which comprises a framework region having substantially the amino acid sequence of a human antibody and a complementary determining region having substantially the amino acid sequence of a non-human antibody. As used herein, the term "substantially" in the context of a CDR refers to a CDR having an amino acid sequence that is at least 65%, at least 70%, at least 75%, at least 80%, at least 85%, at least 90%, at least 95%, at least 98% or at least 99% identical to the amino acid sequence of a non-human antibody CDR. Likewise, the term "substantially" in the context of a FR refers to a FR having an amino acid sequence that is at least 65%, at least 70%, at least 75%, at least 80%, at least 85%, at least 90%, at least 95%, at least 98% or at least 99% identical to the amino acid sequence of a human FR. A humanized antibody in accordance with the present disclosure comprises, for example, substantially all of at least one variable domains (Fv) in which all or substantially all of the CDR regions correspond to those of a non-human immunoglobulin (i.e., the donor camelid antibody) and all or substantially all of the framework regions are those of a human or humanized immunoglobulin framework sequence (i.e., the acceptor antibody).

Methods of humanizing antibodies are well known in the art, see e.g., Almagro and Fransson, "Humanization of Antibodies," *Frontiers in Bioscience* 13:1619-1633 (2008), U.S. Pat. No. 6,054,297 to Carter et al., U.S. Pat. No. 8,343,489, and U.S. Patent Application Publication No. US20100261620 to Almagro et al., which are hereby incorporated by reference in their entirety. The human or humanized framework sequences can be chosen based on known structure, i.e., a fixed framework sequence, sequence homology to the framework sequences of the donor antibody (e.g., the antibody from which the CDRs are derived), i.e., a best-fit framework sequence, or a combination of both approaches. Regardless of the method chosen to select the human framework sequence, the sequences can be selected from mature framework sequences, germline gene sequences, or consensus framework sequences. Compatible human framework sequences are those that are similar in both length and sequence to the framework sequence of the donor antibody sequence (i.e., the antibody from which the CDRs are derived) to ensure proper folding of the antibody and binding domain formation.

In one embodiment, the humanized framework sequence of a humanized antibody of the disclosure comprises a consensus framework sequence. A consensus framework sequence is derived from a consensus immunoglobulin sequence, which is the sequence formed from the most frequently occurring amino acids (or nucleotides) in a family of related immunoglobulin sequences (see e.g., WINNAKER, "From Genes to Clones. Introduction to Gene Technology" (1987); Carter et al., *Proc. Natl. Acad. Sci. USA,* 89:4285 (1992); and Presta et al., *J. Immunol.,* 151:2623 (1993), which are hereby incorporated by reference in their entirety). In a family of immunoglobulins, each position in the consensus sequence is occupied by the amino acid residue occurring most frequently at that position in the family. If two amino acids occur equally frequently, either can be included in the consensus sequence.

In another embodiment, a humanized antibody or binding fragment thereof as disclosed herein comprises a fixed framework region. Human heavy chain FR sequences known in the art can be used as heavy chain "acceptor" framework sequences (or simply, "acceptor" sequences) to humanize a non-human antibody using techniques known in the art (see e.g., Sims et al., *J. Immunol.,* 151:2296 (1993); Chothia et al., *J. Mol. Biol.,* 196:901 (1987), which are hereby incorporated by reference in their entirety). In one embodiment, human heavy chain acceptor sequences are selected from the framework sequences listed in publically available databases such as V-base or in the international ImMunoGeneTics® (IMGT®) information system.

Humanized antibodies or binding fragments thereof as described herein may also comprise at least a portion of an immunoglobulin constant region (Fc), typically that of a human immunoglobulin. In one embodiment, the humanized antibody disclosed herein comprises the heavy chain variable domain. The humanized antibody may further comprise the CH1, hinge, CH2, CH3, and CH4 regions of a human heavy chain. In another embodiment, the humanized antibody comprises only a humanized heavy chain. Humanized antibodies and binding fragments thereof as described herein may be selected from any class of immunoglobulins, including IgM, IgG, IgD, IgA and IgE, and any isotype, including without limitation IgG1, IgG2, IgG3 and IgG4. The humanized antibody or binding fragment thereof may comprise sequences from more than one class or isotype, and particular constant domains may be selected to optimize desired effector functions using techniques well-known in the art.

The antibodies and binding fragments thereof described herein can be humanized antibodies (fully or partially humanized) as described supra. Alternatively, the antibodies and binding fragments thereof can be animal antibodies such as, but not limited to, a bird (for example, a duck or a goose), a shark, a whale, or a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.). In one embodiment, the antibodies and binding fragments thereof as described herein are derived from camelid antibodies.

Methods of antibody production, in particular, monoclonal antibody production, may be carried out using the methods described herein and those well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of an animal which has been previously immunized with the antigen of interest (e.g., full length α-synuclein as set forth in the Examples herein) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment, monoclonal antibodies can be isolated from antibody phage libraries generated using the techniques described herein or known in the art, see e.g., McCafferty et al., "Phage Antibodies: Filamentous Phage Displaying Antibody Variable Domains," *Nature* 348:552-554 (1990), which is hereby incorporated by reference in its entirety. Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., *BioTechnology* 10:779-783 (1992), which is hereby incorporated by reference in its entirety), as well as combinatorial infection and in vivo recombination as a strategy for constructing very large phage libraries (Waterhouse et al., *Nuc. Acids. Res.* 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the heavy chain constant domains of a camelid monoclonal antibody can be substituted for those regions of a human antibody to generate a chimeric antibody. Alternatively, the heavy chain constant domains of a camelid monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In one embodiment of the present disclosure, the antibody or binding fragment thereof as disclosed herein comprises a heavy chain variable region (HCVR) having a H-CDR1 with an amino acid sequence selected from SEQ ID NOs: 1-36, 218, 222, 226, 230, 234, 238, 340 or a modified amino acid sequence thereof containing 1, 2, 3, 4, 5, or 6 amino acid residue modifications as compared to SEQ ID NOs: 1-36, 218, 222, 226, 230, 234, 238, and 340 that maintain or enhance binding specificity of the H-CDR1. In one embodiment, the amino acid sequence of the H-CDR1 contains no more than 1, 2, or 3 amino acid modifications as compared to SEQ ID NOs: 1-36, 218, 222, 226, 230, 234, 238, and 340 respectively. The HCVR further comprises a H-CDR2 with an amino acid sequence selected from any one of SEQ ID NOs: 37-72, 219, 223, 227, 231, 235, 239, 341, or a modified amino acid sequence thereof containing 1, 2, 3, 4, 5, or 6, amino acid residue modifications as compared to SEQ ID NOs: 37-72, 219, 223, 227, 231, 235, 239, and 341 that maintain or enhance binding specificity of the H-CDR2. In one embodiment, the amino acid sequence of the H-CDR2 contains no more than 1, 2, or 3, amino acid modifications as compared to SEQ ID NOs: 37-72, 219, 223, 227, 231, 235, 239, and 341 respectively. The HCVR of the antibody or binding fragment thereof comprises a H-CDR3 with an amino acid sequence selected from any one of SEQ ID NOs: 73-108, 220, 224, 228, 232, 236, 240, 342, or a modified amino acid sequence thereof containing 1, 2, 3, 4, 5, 6 or 7 amino acid residue modifications as compared to SEQ ID NOs: 73-108, 220, 224, 228, 232, 236, 240, and 342 that maintain or enhance binding specificity of the H-CDR3. In one embodiment, the amino acid sequence of the H-CDR3 contains no more than 1, 2, or 3 amino acid modifications as compared to SEQ ID NOs: 73-108, 220, 224, 228, 232, 236, 240, and 342 respectively. The amino acid sequences of SEQ ID NOs: 1-108, 218-220, 222-224, 226-228, 230-232, 234-236, 238-240, and 340-342 are provided in Table 1 below.

TABLE 1

α-Synuclein Single Domain Antibody Complementarity Determining Regions

| Antibody ID | Descr | Sequence | SEQ ID NO: | Descr | Sequence | SEQ ID NO: | Descr | Sequence | SEQ ID NO: |
|---|---|---|---|---|---|---|---|---|---|
| 03-S-sR1-2D3 | CDR1 | ATVSGFSIG | 1 | CDR2 | ANVSPSGAKY | 37 | CDR3 | NIRRFSYLSGD | 73 |
| 07-S-sR2-1D12 47-S-sR2-1F11 | CDR1 | ASGFTFSSS | 2 | CDR2 | ASIMRYGTTT | 38 | CDR3 | NVRSFVRTY | 74 |
| 08-S-sR2-2E10 | CDR1 | ASGRTFSSF | 3 | CDR2 | TAINWSGSSTY | 39 | CDR3 | NAQRRWPLRDY | 75 |
| 11-S-sR1-2D12 | CDR1 | ASGLIFSIN | 4 | CDR2 | ARITTGGSTN | 40 | CDR3 | AADVRFGERTPY | 76 |
| 15-S-sR2-1E7 | CDR1 | ASGNIFRIN | 5 | CDR2 | AHIISGGSTN | 41 | CDR3 | NARTFVRTY | 77 |
| 16-S-sR2-2F6 | CDR1 | ASTSVFGNT | 6 | CDR2 | ARITTLGFTY | 42 | CDR3 | NRRGFRSY | 78 |
| 19-S-sR1-2G4 | CDR1 | ASGSIYHVN | 7 | CDR2 | ATLTHNNRVT | 43 | CDR3 | YYFVPRNPLFGRRIDFDA | 79 |
| 23-S-sR2-1E9 82-S-sR1-2C11 | CDR1 | ASGNIFRIN | 8 | CDR2 | AVVKSGGSTN | 44 | CDR3 | NAQTRLWSY | 80 |
| 24-S-sR2-2F7 | CDR1 | ASGNIFRIN | 9 | CDR2 | AHIISGGSTN | 45 | CDR3 | NAQTRLWSY | 81 |
| 31-S-sR2-1F7 | CDR1 | ASRSFFSIN | 10 | CDR2 | ATITSRDSTN | 46 | CDR3 | YADQPWRGRA | 82 |
| 32-S-sR2-2F11 | CDR1 | HSTITFRIN | 11 | CDR2 | ARINPAGRTY | 47 | CDR3 | STWRLGRNY | 83 |
| 34-5-sR1-1A12 | CDR1 | ASMTTLGFK | 12 | CDR2 | ATISSIGIST | 48 | CDR3 | FIVIRPSWMPQY | 84 |
| 39-S-sR2-1F8 | CDR1 | ASTSVFGNT | 13 | CDR2 | ARITTLGFTY | 49 | CDR3 | NRLWRPLA | 85 |
| 40-S-sR2-2G4 | CDR1 | ASGMRSSLA | 14 | CDR2 | ATITIGGNTN | 50 | CDR3 | NVRSFVRTY | 86 |
| 48-S-sR2-2G9 | CDR1 | ASGSTFISIK | 15 | CDR2 | AGITIKNNYIN | 51 | CDR3 | TVQRRLGRVY | 87 |
| 50-S-sR1-2B2 | CDR1 | ASGSTFRFN | 16 | CDR2 | ANINSSGRTM | 52 | CDR3 | NVRSFVRTY | 88 |
| 55-S-sR2-1G3 | CDR1 | ASGSRFSIN | 17 | CDR2 | AGITSLGFTN | 53 | CDR3 | NRRGFRSY | 89 |
| 56-S-sR2-2H1 | CDR1 | ASGSIFSIN | 18 | CDR2 | AGISRGGRTK | 54 | CDR3 | NVRSFVRTY | 90 |

TABLE 1-continued

α-Synuclein Single Domain Antibody Complementarity Determining Regions

| Antibody ID | Descr | Sequence | SEQ ID NO: | Descr | Sequence | SEQ ID NO: | Descr | Sequence | SEQ ID NO: |
|---|---|---|---|---|---|---|---|---|---|
| 58-S-sR1-2B4 | CDR1 | ASGSIFRIN | 19 | CDR2 | ATITNEGNTY | 55 | CDR3 | AGKVIRWY | 91 |
| 62-S-sR2-1A9 | CDR1 | ASTSVFGNT | 20 | CDR2 | ARITTLGFTY | 56 | CDR3 | RARRALRESH | 92 |
| 63-S-sR2-1G9 | CDR1 | ASGSIFSIN | 21 | CDR2 | AGISRGGRTK | 57 | CDR3 | NARSFVRTY | 93 |
| 64-S-sR2-2H2 | CDR1 | ASRNFFTFR | 22 | CDR2 | ASITTGGRTV | 58 | CDR3 | NARRRFPVPGPTDY | 94 |
| 66-S-sR1-2B0 | CDR1 | ASGITFRFN | 23 | CDR2 | ARVSSGGSTT | 59 | CDR3 | NVGNF | 95 |
| 70-S-sR2-1B3 | CDR1 | ASGRSILIK | 24 | CDR2 | ATISMAGVTN | 60 | CDR3 | NAQTRLWSY | 96 |
| 71-S-sR2-2A8 | CDR1 | ASGRIFGRN | 25 | CDR2 | ARITRDGRTM | 61 | CDR3 | NAQTRLWSY | 97 |
| 72-S-sR2-2H3 | CDR1 | ASRSTFRFN | 26 | CDR2 | AAISSRGGSTN | 62 | CDR3 | NVRSFVRTY | 98 |
| 74-S-sR1-2B12 | CDR1 | TSGSIFSIN | 27 | CDR2 | AAISGRGSTH | 63 | CDR3 | ALDQHMEVIVSPGRIGS | 99 |
| 78-S-sR2-1C9 | CDR1 | LSTTMFGFW | 28 | CDR2 | ATIDSRGRTN | 64 | CDR3 | NAQRRWPLRDY | 100 |
| 79-S-sR2-2B3 | CDR1 | ASGNIFRIN | 29 | CDR2 | ARISSGGSTN | 65 | CDR3 | NARRPLRWYFY | 101 |
| 80-S-sR2-2H5 | CDR1 | ASGSIFSTN | 30 | CDR2 | ASITKFGNTD | 66 | CDR3 | YQNSRGRWYDIFRDY | 102 |
| 80-S-sR2-2H9 | CDR1 | ASRSSFRIT | 31 | CDR2 | ASITTGGRTV | 67 | CDR3 | NACIFIRWPLRDY | 103 |
| 86-S-sR2-1D5 | CDR1 | ASGNIFRIN | 32 | CDR2 | AHIISGGSTN | 68 | CDR3 | NAERRFGMRQV | 104 |
| 87-S-sR2-2D8 | CDR1 | ASVVPFRYF | 33 | CDR2 | ASITSGGGVN | 69 | CDR3 | ARLLSLGSRWGYGMFT | 105 |
| 88-S-sR2-2H8 | CDR1 | ASGSIFSIK | 34 | CDR2 | AAIASGGFTN | 70 | CDR3 | NAQRRWPLRDY | 106 |
| 94-S-sR2-1D10 | CDR1 | ASGSAFRMN | 35 | CDR2 | AAISFRGSAN | 71 | CDR3 | AAGRPWQRTFY | 107 |
| 95-S-sR2-2D10 | CDR1 | ASGSIFSIN | 36 | CDR2 | AGISRGGRTK | 72 | CDR3 | AATRWSWGTKSY | 108 |
| S-sR2-2H7 | CDR1 | ASGNIFRINA | 218 | CDR2 | ASIDSAGRTNYG | 219 | CDR3 | CSTWRLGRNY | 220 |
| S-sR2-1F6 | CDR1 | ASGSTFSNNA | 222 | CDR2 | AYISSGGFTN | 223 | CDR3 | SAGGTYRSGNVYFFPRS | 224 |
| S-sR2-1G4 | CDR1 | ASGSIFSINS | 226 | CDR2 | ATISSRSTTY | 227 | CDR3 | KAGSVGRV | 228 |
| S-sR2-2C10 | CDR1 | ASMTTLGFKT | 230 | CDR2 | AAITSGGTAN | 231 | CDR3 | ASTrGWTEVGGRND | 232 |
| S-sR2-2E9 | CDR1 | ASGRTFRVNA | 234 | CDR2 | AAVTNGGSTT | 235 | CDR3 | NAERRFGMRQV | 236 |
| S-sR2-2G11 | CDR1 | ASGRVFSINT | 238 | CDR2 | ASMTRGGSAN | 239 | CDR3 | NAARGWRI | 240 |
| 90-S-sR1-2D1 | CDR1 | SGSIFRING | 340 | CDR1 | VAAVNWSGERT | 341 | CDR3 | AADTDYRLDGSTWITNL | 342 |

Suitable amino acid modifications to the heavy chain CDR sequences of the anti-α-synuclein antibody disclosed herein include, for example, conservative substitutions or functionally equivalent amino acid residue substitutions that result in variant CDR sequences having similar or enhanced binding characteristics to those of the CDR sequences disclosed herein. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed), Biochemistry, 2nd ed, WH Freeman and Co., 1981, winch is hereby incorporated by reference in its entirety). Non-conservative substitutions can also be made to the heavy chain CDR sequences and the light chain CDR sequences as disclosed herein. Non-conservative substitutions involve substituting one or more amino acid residues of the CDR with one or more amino acid residues from a different class of amino acids to improve or enhance the binding properties of CDR.

The amino acid sequences of the heavy chain variable region CDRs of the anti-α-synuclein antibody described herein may further comprise one or more internal neutral amino acid insertions or deletions that do not alter synuclein protein binding. In one embodiment, the H-CDR3 having an amino acid sequence of any one of SEQ ID NOs: 73-108, 220, 224, 228, 232, 236, 240, and 342 further contains one or more internal neutral amino acid insertions or deletions that do not alter α-synuclein binding.

In one embodiment, the antibody or binding fragment thereof has a heavy chain variable region with a H-CDR1 having the amino acid sequence of SEQ ID NO: 1, or a modified amino acid sequence thereof containing 1, 2, 3, or more amino acid residue modifications as compared to SEQ ID NO: 1; a H-CDR2 having the amino acid sequence of SEQ ID NO: 37, or a modified amino acid sequence thereof containing 1, 2, 3, or more amino acid residue modifications as compared to SEQ ID NO: 37; and a H-CDR3 comprising the amino acid sequence of SEQ ID NO: 73, or a modified amino acid sequence thereof, said modified amino acid sequence containing 1, 2, 3, or more amino acid modifications as compared to SEQ ID NO: 73.

An exemplary single domain antibody having this heavy chain variable region is referred to herein as the 03-S-sR1-2D3 antibody. The 03-S-sR1-2D3 antibody comprises a $V_H$ chain amino acid sequence of SEQ ID NO: 109 as shown below.

SEQ ID NO: 109
QVQLQQSGGGLVQAGGSLILRCRATVSGFSIGTMGWYRQAPGKEREFVAN

VSPSGAKYFADSVKGRFTISRDNANNTVYLQMNSLKPFDTGVYYCNIRRF

SYLSGDWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 109

In one embodiment, the antibody or binding fragment thereof of the present disclosure comprises a humanized variant of the heavy chain variable region of SEQ ID NO: 109, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 109), or a combination of these approaches. The humanized framework regions are designed to be similar in length and sequence to the parental framework sequences of SEQ ID NO: 109. In one embodiment, the humanized framework regions share 50%, 55%, 60%, 65%, 70%, 75%, 80%, 85%, 90%, 95% or more sequence identity to the framework regions of SEQ ID NO: 109. In another embodiment, the humanized framework regions are 60%, 65%, 70%, 75%, 80%, 85%, 90%, 95% or more similar in length to the framework regions of SEQ ID NO: 109. Humanized variants of the heavy chain variable region of SEQ ID NO: 109 share at least 50%, at least 55%, at least 60%, at least 65%, at least 70%, at least 75%, at least 80%, at least 85%, at least 90%, at least 95% sequence identity along the entire length of SEQ ID 109.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 109. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 2, or a modified amino acid sequence thereof containing 1, 2, 3, or more amino acid residue modifications as compared to SEQ ID NO: 2; a H-CDR2 having the amino acid sequence of SEQ ID NO: 38, or a modified amino acid sequence thereof containing 1, 2, 3, or more amino acid residue modifications as compared to SEQ ID NO: 38; and a H-CDR3 comprising the amino acid sequence of SEQ ID NO: 74, or a modified amino acid sequence thereof, said modified amino acid sequence containing 1, 2, 3, or more amino acid modifications as compared to SEQ ID NO: 74.

Exemplary single domain antibodies having this heavy chain variable region are referred to herein as the 07-S-sR2-1D12 antibody and the 47-S-sR2-1F11 antibody. These antibodies comprise a $V_H$ chain amino acid sequence of SEQ ID NO: 110 as shown below.

SEQ ID NO: 110
QVQLQESGGGLVQAGGSLRLSCAASGFTESSSSMGWYRQAPGKQRELVAS

IMRYGITTYTDSVKGRFTISRDNGQRTVYLQMNSLKPEDTFAVYYCNVRS

FVRTYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 110.

In one embodiment, the antibody or binding fragment thereof of the present disclosure comprises a humanized variant of the heavy chain variable region of SEQ ID NO: 110, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 110), or a combination of these approaches. The humanized framework regions are designed to be similar in length and sequence to the parental framework sequences of SEQ ID NO: 110. In one embodiment, the humanized framework regions share 50%, 55%, 60%, 65%, 70%, 75%, 80%, 85%, 90%, 95% or more sequence identity to the framework regions of SEQ ID NO: 110. In another embodiment, the humanized framework regions are 60%, 65%, 70%, 75%, 80%, 85%, 90%, 95% or more similar in length to the framework regions of SEQ ID NO: 110. Humanized variants of the heavy chain variable region of SEQ ID NO: 110 share at least 50%, at least 55%, at least 60%, at least 65%, at least 70%, at least 75%, at least 80%, at least 85%, at least 90%, at least 95% sequence identity along the entire length of SEQ ID 110.

Another aspect of the present disclosure relates to an antibody or binding portion thereof (e.g., a human antibody)

that competes for binding to human α-synuclein protein with the anti-α-synuclein antibody comprising a heavy chain variable region with the amino acid sequence of SEQ ID NO: 110. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 3, or a modified amino acid sequence thereof containing 1, 2, 3, or more amino acid residue modifications as compared to SEQ ID NO: 3; a H-CDR2 having the amino acid sequence of SEQ ID NO: 39, or a modified amino acid sequence thereof containing 1, 2, 3, or more amino acid residue modifications as compared to SEQ ID NO: 39; and a H-CDR3 comprising the amino acid sequence of SEQ ID NO: 75, or a modified amino acid sequence thereof, said modified amino acid sequence containing 1, 2, 3, or more amino acid modifications as compared to SEQ ID NO: 75.

An exemplary single domain antibody having this heavy chain variable region is referred to herein as the 08-S-sR2-2E10 antibody. The 08-S-sR2-2E10 antibody comprises a $V_H$ chain amino acid sequence of SEQ ID NO: 111 as shown below.

SEQ ID NO: 111
QVQLQESGGGLVQAGGSLRLSCAASGRTFSSFAMGWFRQAPGKEREINTA

INWSGSSTYYADSVKGRFTISRDNAKNYVYLQMNSLKPEDTAVYYCNAQR

RWPLRDYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 111.

In one embodiment, the antibody or binding fragment thereof of the present disclosure comprises a humanized variant of the heavy chain variable region of SEQ ID NO: 111, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 111), or a combination of these approaches. The humanized framework regions are designed to be similar in length and sequence to the parental framework sequences of SEQ ID NO: 111. In one embodiment, the humanized framework regions share 50%, 55%, 60%, 65%, 70%, 75%, 80%, 85%, 90%, 95% or more sequence identity to the framework regions of SEQ ID NO: 111. In another embodiment, the humanized framework regions are 60%, 65%, 70%, 75%, 80%, 85%, 90%, 95% or more similar in length to the framework regions of SEQ ID NO: 111. Humanized variants of the heavy chain variable region of SEQ ID NO: 111 share at least 50%, at least 55%, at least 60%, at least 65%, at least 70%, at least 75%, at least 80%, at least 85%, at least 90%, at least 95% sequence identity along the entire length of SEQ ID 111.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 111. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 4, or a modified amino acid sequence thereof containing 1, 2, 3, or more amino acid residue modifications as compared to SEQ ID NO: 4; a H-CDR2 having the amino acid sequence of SEQ ID NO: 40, or a modified amino acid sequence thereof containing 1, 2, 3, or more amino acid residue modifications as compared to SEQ ID NO: 40; and a H-CDR3 comprising the amino acid sequence of SEQ ID NO: 76, or a modified amino acid sequence thereof, said modified amino acid sequence containing 1, 2, 3, or more amino acid modifications as compared to SEQ ID NO: 76.

An exemplary single domain antibody having this heavy chain variable region is referred to herein as the 11-S-sR1-2D12 antibody. The 11-S-sR1-2D12 antibody comprises a $V_H$ chain amino acid sequence of SEQ ID NO: 112 as shown below.

SEQ ID NO: 112
QVQLQFSGGGLVQAGGSTRESCAASGLIFSINAMAWYRQAPGNQRELVAR

ITTGGSTNYADSVKGRFTISRDNAKNTVYLQMNSIKPEDTAVYFCAADVR

IGERTPYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 112.

In one embodiment, the antibody or binding fragment thereof of the present disclosure comprises a humanized variant of the heavy chain variable region of SEQ ID NO: 112, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 112), or a combination of these approaches. The humanized framework regions are designed to be similar in length and sequence to the parental framework sequences of SEQ ID NO: 112. In one embodiment, the humanized framework regions share 50%, 55%, 60%, 65%, 70%, 75%, 80%, 85%, 90%, 95% or more sequence identity to the framework regions of SEQ ID NO: 112. In another embodiment, the humanized framework regions are 60%, 65%, 70%, 75%, 80%, 85%, 90%, 95% or more similar in length to the framework regions of SEQ ID NO: 112. Humanized variants of the heavy chain variable region of SEQ ID NO: 112 share at least 50%, at least 55%, at least 60%, at least 65%, at least 70%, at least 75%, at least 80%, at least 85%, at least 90%, at least 95% sequence identity along the entire length of SEQ ID 112.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 112. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 5, or a modified amino acid sequence thereof containing 1, 2, 3, or more amino acid residue modifications as compared to SEQ ID NO: 5; a H-CDR2 having the amino acid sequence of SEQ ID NO: 41, or a modified amino acid sequence thereof containing 1, 2, 3, or more amino acid residue modifications as compared to SEQ ID NO: 41; and a H-CDR3 comprising the amino acid sequence of SEQ ID NO: 77, or a modified amino acid sequence thereof, said modified amino acid sequence containing 1, 2, 3, or more amino acid modifications as compared to SEQ ID NO: 77.

An exemplary single domain antibody having this heavy chain variable region is referred to herein as the 15-S-sR2-1E7 antibody. The 15-S-sR2-1E7 antibody comprises a $V_H$ chain amino acid sequence of SEQ ID NO: 113 as shown below.

SEQ ID NO: 113
QVQLQASGGGVVQSGGSLRLSCVASGNIFRINAMGWYRQAPGKQRELVAH

IISGGSINYADSVKGRFTISREYAKNMVYLQMNSLKPEDTAVYYCNARIF

VRTYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 113.

In one embodiment, the antibody or binding fragment thereof of the present disclosure comprises a humanized variant of the heavy chain variable region of SEQ ID NO: 113, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 113), or a combination of these approaches. The humanized framework regions are designed to be similar in length and sequence to the parental framework sequences of SEQ ID NO: 113. In one embodiment the humanized framework regions share 50%, 55%, 60%, 65%, 70%, 75%, 80%, 85%, 90%, 95% or more sequence identity to the framework regions of SEQ ID NO: 113. In another embodiment, the humanized framework regions are 60%, 65%, 70%, 75%, 80%, 85%, 90%, 95% or more similar in length to the framework regions of SEQ ID NO: 113. Humanized variants of the heavy chain variable region of SEQ ID NO: 113 share at least 50%, at least 55%, at least 60%, at least 65%, at least 70%, at least 75%, at least 80%, at least 85%, at least 90%, at least 95% sequence identity along the entire length of SEQ ID 113.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 113. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 6, or a modified amino acid sequence thereof containing 1, 2, 3, or more amino acid residue modifications as compared to SEQ ID NO: 6; a H-CDR2 having the amino acid sequence of SEQ ID NO: 42, or a modified amino acid sequence thereof containing 1, 2, 3, or more amino acid residue modifications as compared to SEQ ID NO: 42; and a H-CDR3 comprising the amino acid sequence of SEQ ID NO: 78, or a modified amino acid sequence thereof, said modified amino acid sequence containing 1, 2, 3, or more amino acid modifications as compared to SEQ ID NO: 78.

An exemplary single domain antibody having this heavy chain variable region is referred to herein as the 16-S-sR2-2F6 antibody. The 16-S-sR2-2F6 antibody comprises a $V_H$ chain amino acid sequence of SEQ ID NO: 114 as shown below.

SEQ ID NO: 114
QVQLQQFGGGLVQPGGSLRLSCQASTSVFGNTAMAWYRQAPGKQRELVAR

ITTLGFTYYADSAKGRFTISRDSAMNTVYLQMNSLKPEDTAVYYCNRRGF

RSYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 114.

In one embodiment, the antibody or binding fragment thereof of the present disclosure comprises a humanized variant of the heavy chain variable region of SEQ ID NO: 114, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 114), or a combination of these approaches. The humanized framework regions are designed to be similar in length and sequence to the parental framework sequences of SEQ ID NO: 114. In one embodiment, the humanized framework regions share 50%, 55%, 60%, 65%, 70%, 75%, 80%, 85%, 90%, 95% or more sequence identity to the framework regions of SEQ ID NO: 114. In another embodiment, the humanized framework regions are 60%, 65%, 70%, 75%, 80%, 85%, 90%, 95% or more similar in length to the framework regions of SEQ ID NO: 114. Humanized variants of the heavy chain variable region of SEQ ID NO: 114 share at least 50%, at least 55%, at least 60%, at least 65%, at least 70%, at least 75%, at least 80%, at least 85%, at least 90%, at least 95% sequence identity along the entire length of SEQ ID 114.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 114. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 7, or a modified amino acid sequence thereof containing 1, 2, 3, or more amino acid residue modifications as compared to SEQ ID NO: 7; a H-CDR2 having the amino acid sequence of SEQ ID NO: 43, or a modified amino acid sequence thereof containing 1, 2, 3, or more amino acid residue modifications as compared to SEQ ID NO: 43; and a H-CDR3 comprising the amino acid sequence of SEQ ID NO: 79, or a modified amino acid sequence thereof, said modified amino acid sequence containing 1, 2, 3, or more amino acid modifications as compared to SEQ ID NO: 79.

An exemplary single domain antibody having this heavy chain variable region is referred to herein as the 19-S-sR1-2G4 antibody. The 19-S-sR1-2G4 antibody comprises a $V_H$ chain amino acid sequence of SEQ ID NO: 115 as shown below.

SEQ ID NO: 115
QVQLQESGGGLVQSGDSLRLSCAASGSIYHVNTMGWYRQSPGKQRELVAT

LTHNNRVTYADSVKGRETISRDNAKMTVYLQMDSLKPDDTAVYYCYYFVP

RNPLFGRRIDFDAWGQGTQVTSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity to SEQ ID NO: 115.

In one embodiment, the antibody or binding fragment thereof of the present disclosure comprises a humanized variant of the heavy chain variable region of SEQ ID NO: 115, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 115), or a combination of these approaches. The humanized framework regions are designed to be similar in length and sequence to the parental framework sequences of SEQ ID NO: 115. In one embodiment, the humanized framework regions share 50%, 55%, 60%, 65%, 70%, 75%, 80%, 85%, 90%, 95% or more sequence identity to the framework regions of SEQ ID NO: 115. In another embodiment, the humanized framework regions are 60%, 65%, 70%, 75%, 80%, 85%, 90%, 95% or more similar in length to the framework regions of SEQ ID NO: 115. Humanized variants of the heavy chain variable region of SEQ ID NO: 115 share at least 50%, at least 55%, at least 60%, at least 65%, at least 70%, at least 75%, at least 80%, at least 85%, at least 90%, at least 95% sequence identity along the entire length of SEQ ID 115.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 115. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 8, or a modified amino acid sequence thereof containing 1, 2, 3, or more amino acid residue modifications as compared to SEQ ID NO: 8, a H-CDR2 having the amino acid sequence of SEQ ID NO: 44, or a modified amino acid sequence thereof containing 1, 2, 3, or more amino acid residue modifications as compared to SEQ ID NO: 44; and a H-CDR3 comprising the amino acid sequence of SEQ ID NO: 80, or a modified amino acid sequence thereof, said modified amino acid sequence containing 1, 2, 3, or more amino acid modifications as compared to SEQ ID NO: 80.

An exemplary single domain antibody having this heavy chain variable region is referred to herein as the 23-S-sR2-1E9 antibody. This antibody comprises a $V_H$ chain amino acid sequence of SEQ ID NO: 116 as shown below.

SEQ ID NO: 116
QVQLQESGGGVVQSGGSLRLSCVASGNIFRINVMGWYRQAPGKQRELVAV

VKSGGSTNYVDSAKGRFTISRDNAKNTAYLHMDSLKPEDTAVYYCNAQTR

LWSYWGQGTQVTSS

Another exemplary single domain antibody having this heavy chain variable region is referred to herein as the 82-S-sR1-2C11 antibody. This antibody comprises a $V_H$ chain amino acid sequence of SEQ ID NO: 140 as shown below.

SEQ ID NO: 140
QVQLQESGGGVVQSGGSLRLSCVASGNIFRINVMGWYRQAPGKQRELVAV

VKSGGSTNYVDSAKGRFTISRDNAKNTAYLHMDSLKPEDTAVYYCNAQTR

LWSYWGQGTLVTSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 116 or SEQ ID NO: 140.

In one embodiment, the antibody or binding fragment thereof of the present disclosure comprises a humanized variant of the heavy chain variable region of SEQ ID NO: 116 or SEQ ID NO: 140, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 116 or SEQ ID NO: 140), or a combination of these approaches. The humanized framework regions are designed to be similar in length and sequence to the parental framework sequences of SEQ ID NO: 116 or SEQ ID NO: 140. In one embodiment, the humanized framework regions share 50%, 55%, 60%, 65%, 70%, 75%, 80%, 85%, 90%, 95% or more sequence identity to the framework regions of SEQ ID NO: 116 or SEQ ID NO: 140. In another embodiment, the humanized framework regions are 60%, 65%, 70%, 75%, 80%, 85%, 90%, 95% or more similar in length to the framework regions of SEQ ID NO: 116 or SEQ ID NO: 140. Humanized variants of the heavy chain variable region of SEQ ID NO: 116 or SEQ ID NO: 140 share at least 50%, at least 55%, at least 60%, at least 65%, at least 70%, at least 75%, at least 80%, at least 85%, at least 90%, at least 95% sequence identity along the entire length of SEQ ID 116 or SEQ ID NO: 140, respectively.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 116. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 9, or a modified amino acid sequence thereof containing 1, 2, 3, or more amino acid residue modifications as compared to SEQ ID NO: 9; a H-CDR2 having the amino acid sequence of SEQ ID NO: 45, or a modified amino acid sequence thereof containing 1, 2, 3, or more amino acid residue modifications as compared to SEQ ID NO: 45; and a H-CDR3 comprising the amino acid sequence of SEQ ID NO: 81, or a modified amino acid sequence thereof, said modified amino acid sequence containing 1, 2, 3, or more amino acid modifications as compared to SEQ ID NO: 81.

An exemplary single domain antibody having this heavy chain variable region is referred to herein as the 24-S-sR2-2F7 antibody. The 24-S-sR2-2F7 antibody comprises a V$_H$ chain amino acid sequence of SEQ ID NO: 117 as shown below.

```
                                    SEQ ID NO: 117
QVQLQEFGGGVVQSGGSLRLSCVASGNIFRINAMGWYRQAPGKQRELVAH

IISGGSTNYADSVKGRFTISREYAKNMVYLQMNSLKPEDTAVYYCNAQTR

LWSYWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 117.

In one embodiment, the antibody or binding fragment thereof of the present disclosure comprises a humanized variant of the heavy chain variable region of SEQ ID NO: 117, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 117), or a combination of these approaches. The humanized framework regions are designed to be similar in length and sequence to the parental framework sequences of SEQ ID NO: 117. In one embodiment, the humanized framework regions share 50%, 55%, 60%, 65%, 70%, 75%, 80%, 85%, 90%, 95% or more sequence identity to the framework regions of SEQ ID NO: 117. In another embodiment, the humanized framework regions are 60%, 65%, 70%, 75%, 80%, 85%, 90%, 95% or more similar in length to the framework regions of SEQ ID NO: 117. Humanized variants of the heavy chain variable region of SEQ ID NO: 117 share at least 50%, at least 55%, at least 60%, at least 65%, at least 70%, at least 75%, at least 80%, at least 85%, at least 90%, at least 95% sequence identity along the entire length of SEQ ID 117.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 117. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 10, or a modified amino acid sequence thereof containing 1, 2, 3, or more amino acid residue modifications as compared to SEQ ID NO: 10, a H-CDR2 having the amino acid sequence of SEQ ID NO: 46, or a modified amino acid sequence thereof containing 1, 2, 3, or more amino acid residue modifications as compared to SEQ ID NO: 46; and a H-CDR3 comprising the amino acid sequence of SEQ ID NO: 82, or a modified amino acid sequence thereof, said modified amino acid sequence containing 1, 2, 3, or more amino acid modifications as compared to SEQ ID NO: 82.

An exemplary single domain antibody having this heavy chain variable region is referred to herein as the 31-S-sR2-

1F7 antibody. The 31-S-sR2-1F7 antibody comprises a $V_H$ chain amino acid sequence of SEQ ID NO: 118 as shown below.

SEQ ID NO: 118
QVQLQESGGGLVQPGGSLRLSCAASRSFFSINAMGWYRQAPGKQRELVAT

ITSRDSTNVADSVKGRFTISRDYAKNIVYLQMDSLRPEDTATYYCYADQP

WRGRAWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 118.

In one embodiment, the antibody or binding fragment thereof of the present disclosure comprises a humanized variant of the heavy chain variable region of SEQ ID NO: 118, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 118), or a combination of these approaches. The humanized framework regions are designed to be similar in length and sequence to the parental framework sequences of SEQ ID NO: 118. In one embodiment, the humanized framework regions share 50%, 55%, 60%, 65%, 70%, 75%, 80%, 85%, 90%, 95% or more sequence identity to the framework regions of SEQ ID NO: 118. In another embodiment, the humanized framework regions are 60%, 65%, 70%, 75%, 80%, 85%, 90%, 95% or more similar in length to the framework regions of SEQ ID NO: 118. Humanized variants of the heavy chain variable region of SEQ ID NO: 118 share at least 50%, at least 55%, at least 60%, at least 65%, at least 70%, at least 75%, at least 80%, at least 85%, at least 90%, at least 95% sequence identity along the entire length of SEQ ID 118.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 118. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 11, or a modified amino acid sequence thereof containing 1, 2, 3, or more amino acid residue modifications as compared to SEQ ID NO: 11; a H-CDR2 having the amino acid sequence of SEQ ID NO: 47, or a modified amino acid sequence thereof containing 1, 2, 3, or more amino acid residue modifications as compared to SEQ ID NO: 47; and a H-CDR3 comprising the amino acid sequence of SEQ ID NO: 83, or a modified amino acid sequence thereof, said modified amino acid sequence containing 1, 2, 3, or more amino acid modifications as compared to SEQ ID NO: 83.

An exemplary single domain antibody having this heavy chain variable region is referred to herein as the 32-S-sR2-2F11 antibody. The 32-S-sR2-2F11 antibody comprises a $V_H$ chain amino acid sequence of SEQ ID NO: 119 as shown below.

SEQ ID NO: 119
QVQLQFSGGGVNTQAGGSLNLSCTHSTITFRINTMAYYRQAPGSQRALVA

RINPAGRTYYPDSVKGRFTISRDNAKNQVYLQMNDLKPEDTAVYYCSTWR

LGRNYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 119.

In one embodiment, the antibody or binding fragment thereof of the present disclosure comprises a humanized variant of the heavy chain variable region of SEQ ID NO: 119, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 119), or a combination of these approaches. The humanized framework regions are designed to be similar in length and sequence to the parental framework sequences of SEQ ID NO: 119. In one embodiment, the humanized framework regions share 50%, 55%, 60%, 65%, 70%, 75%, 80%, 85%, 90%, 95% or more sequence identity to the framework regions of SEQ ID NO: 119. In another embodiment, the humanized framework regions are 60%, 65%, 70%, 75%, 80%, 85%, 90%, 95% or more similar in length to the framework regions of SEQ ID NO: 119. Humanized variants of the heavy chain variable region of SEQ ID NO: 119 share at least 50%, at least 55%, at least 60%, at least 65%, at least 70%, at least 75%, at least 80%, at least 85%, at least 90%, at least 95% sequence identity along the entire length of SEQ ID 119.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 119. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 12, or a modified amino acid sequence thereof containing 1, 2, 3, or more amino acid residue modifications as compared to SEQ ID NO: 12; a H-CDR2 having the amino acid sequence of SEQ ID NO: 48, or a modified amino acid sequence thereof containing 1, 2, 3, or more amino acid residue modifications as compared to SEQ ID NO: 48; and a H-CDR3 comprising the amino acid sequence of SEQ ID NO: 84, or a modified amino acid sequence thereof, said modified amino acid sequence containing 1, 2, 3, or more amino acid modifications as compared to SEQ ID NO: 84.

An exemplary single domain antibody having this heavy chain variable region is referred to herein as the 34-S-sR1-1A12 antibody. The 34-S-sR1-1A12 antibody comprises a $V_H$ chain amino acid sequence of SEQ ID NO: 120 as shown below.

SEQ ID NO: 120
QVQLQEFGGGLVQAGGVLRLSCVASMTTLGFKTMGWYRQAPCKQRELVAT

ISSIGISTYANSVKGRFTISRPNAKNTVYLQMNSLKPEPTAVYFCHVIRP

SWMPQYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 120.

In one embodiment, the antibody or binding fragment thereof of the present disclosure comprises a humanized variant of the heavy chain variable region of SEQ ID NO: 120, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 120), or a combination of these approaches. The humanized framework regions are designed to be similar in length and sequence to the parental framework sequences of SEQ ID NO: 120. In one embodiment, the humanized framework regions share 50%, 55%, 60%, 65%, 70%, 75%, 80%, 85%, 90%, 95% or more sequence identity to the framework regions of SEQ ID NO: 120. In another embodiment, the humanized framework regions are 60%, 65%, 70%, 75%, 80%, 85%, 90%, 95% or more similar in length to the framework regions of SEQ ID NO: 120. Humanized variants of the heavy chain variable region of SEQ ID NO: 120 share at least 50%, at least 55%, at least 60%, at least 65%, at least 70%, at least 75%, at least 80%, at least 85%, at least 90%, at least 95% sequence identity along the entire length of SEQ ID 120.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 120. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 13, or a modified amino acid sequence thereof containing 1, 2, 3, or more amino acid residue modifications as compared to SEQ ID NO: 13; a H-CDR2 having the amino acid sequence of SEQ ID NO: 49, or a modified amino acid sequence thereof containing 1, 2, 3, or more amino acid residue modifications as compared to SEQ ID NO: 49; and a H-CDR3 comprising the amino acid sequence of SEQ ID NO: 85, or a modified amino acid sequence thereof, said modified amino acid sequence containing 1, 2, 3, or more amino acid modifications as compared to SEQ ID NO: 85.

An exemplary single domain antibody having this heavy chain variable region is referred to herein as the 39-S-sR2-1F8 antibody. The 39-S-sR2-1F8 antibody comprises a $V_H$ chain amino acid sequence of SEQ ID NO: 121 as shown below.

SEQ ID NO: 121
QVQLQEFGGGLVQPGGSLRLSCQASTSVFGNTAMAWYRQAPGKQRELVAR

ITTLGFTYYADSAKGRFTISRDSAMNTVYLQMNSLKPEDTAVYYCNRLWR

PLAWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 121.

In one embodiment, the antibody or binding fragment thereof of the present disclosure comprises a humanized variant of the heavy chain variable region of SEQ ID NO: 121, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 121), or a combination of these approaches. The humanized framework regions are designed to be similar in length and sequence to the parental framework sequences of SEQ ID NO: 121. In one embodiment, the humanized framework regions share 50%, 55%, 60%, 65%, 70%, 75%, 80%, 85%, 90%, 95% or more sequence identity to the framework regions of SEQ ID NO: 121. In another embodiment, the humanized framework regions are 60%, 65%, 70%, 75%, 80%, 85%, 90%, 95% or more similar in length to the framework regions of SEQ ID NO: 121. Humanized variants of the heavy chain variable region of SEQ ID NO: 121 share at least 50%, at least 55%, at least 60%, at least 65%, at least 70%, at least 75%, at least 80%, at least 85%, at least 90%, at least 95% sequence identity along the entire length of SEQ ID 121.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 121. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 14, or a modified amino acid sequence thereof containing 1, 2, 3, or more amino acid residue modifications as compared to SEQ ID NO: 14; a H-CDR2 having the amino acid sequence of SEQ ID NO: 50, or a modified amino acid sequence thereof containing 1, 2, 3, or more amino acid residue modifications as compared to SEQ ID NO: 50; and a H-CDR3 comprising the amino acid sequence of SEQ ID NO: 86 or a modified amino acid sequence thereof, said modified amino acid sequence containing 1, 2, 3, or more amino acid modifications as compared to SEQ ID NO: 86.

An exemplary single domain antibody having this heavy chain variable region is referred to herein as the 40-S-sR2-2G4 antibody. The 40-S-sR2-2G4 antibody comprises a $V_H$ chain amino acid sequence of SEQ ID NO: 122 as shown below.

SEQ ID NO: 122
QVQLQESGGGLVQPGGSLRLSCAASGMRSSLAIMGWYRQAPGKQRELVAT

ITIGGNTNYADSVKGRFAISRDNTKRTVYLQMNSLTPEDTAVYYCNVRSF

VRTYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 122.

In one embodiment, the antibody or binding fragment thereof of the present disclosure comprises a humanized variant of the heavy chain variable region of SEQ ID NO: 122, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 122), or a combination of these approaches. The humanized framework regions are designed to be similar in length and sequence to the parental framework sequences of SEQ ID NO: 122. In one embodiment, the humanized framework regions share 50%, 55%, 60%, 65%, 70%, 75%, 80%, 85%, 90%, 95% or more sequence identity to the framework regions of SEQ ID NO: 122. In another embodiment, the humanized framework regions are 60%, 65%, 70%, 75%, 80%, 85%, 90%, 95% or more similar in length to the framework regions of SEQ ID NO: 122. Humanized variants of the heavy chain variable region of SEQ ID NO: 122 share at least 50%, at least 55%, at least 60%, at least 65%, at least 70%, at least 75%, at least 80%, at least 85%, at least 90%, at least 95% sequence identity along the entire length of SEQ ID 122.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 122. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 15, or a modified amino acid sequence thereof containing 1, 2, 3, or more amino acid residue modifications as compared to SEQ ID NO: 15; a H-CDR2 having the amino acid sequence of SEQ ID NO: 51, or a modified amino acid sequence thereof containing 1, 2, 3, or more amino acid residue modifications as compared to SEQ ID NO: 51; and a H-CDR3 comprising the amino acid sequence of SEQ ID NO: 87, or a modified amino acid sequence thereof, said modified amino acid sequence containing 1, 2, 3, or more amino acid modifications as compared to SEQ ID NO: 87.

An exemplary single domain antibody having this heavy chain variable region is referred to herein as the 48-S-sR2-2G9 antibody. The 48-S-sR2-2G9 antibody comprises a $V_H$ chain amino acid sequence of SEQ ID NO: 123 as shown below.

SEQ ID NO: 123
QVQLQQSGGGLVQAGGSLRLSCAASGSTFISIKTMGWYRQAPGKQRELVA

GITKNNYINYADSVKGRFTISRDNGKNTVYLQMNGLKPEDTAVYYCTVQR

RLGRVYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 123.

In one embodiment, the antibody or binding fragment thereof of the present disclosure comprises a humanized variant of the heavy chain variable region of SEQ ID NO: 123, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 123), or a combination of these approaches. The humanized framework regions are designed to be similar in length and sequence to the parental framework sequences of SEQ ID NO: 123. In one embodiment, the humanized framework regions share 50%, 55%, 60%, 65%, 70%, 75%, 80%, 85%, 90%, 95% or more sequence identity to the framework regions of SEQ ID NO: 123. In another embodiment, the humanized framework regions are 60%, 65%, 70%, 75%, 80%, 85%, 90%, 95% or more similar in length to the framework regions of SEQ ID NO: 123. Humanized variants of the heavy chain variable region of SEQ ID NO: 123 share at least 50%, at least 55%, at least 60%, at least 65%, at least 70%, at least 75%, at least 80%, at least 85%, at least 90%, at least 95% sequence identity along the entire length of SEQ ID 123.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 123. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 16, or a modified amino acid sequence thereof containing 1, 2, 3, or more amino acid residue modifications as compared to SEQ ID NO: 16; a H-CDR2 having the amino acid sequence of SEQ ID NO: 52, or a modified amino acid sequence thereof containing 1, 2, 3, or more amino acid residue modifications as compared to SEQ ID NO: 52; and a H-CDR3 comprising the amino acid sequence of SEQ ID NO: 88, or a modified amino acid sequence thereof, said modified amino acid sequence containing 1, 2, 3, or more amino acid modifications as compared to SEQ ID NO: 88.

An exemplary single domain antibody having this heavy chain variable region is referred to herein as the 50-S-sR1-2B2 antibody. The 50-S-sR1-2B2 antibody comprises a $V_H$ chain amino acid sequence of SEQ ID NO: 124 as shown below.

SEQ ID NO: 124
QVQLQESGGGLVQAGGSLRLSCTASGSTFRFNDMGWYRQAPGKQRELVAN

INSSGRTMYPDSVKGRFTISKDNVKNTVYLQMNSLTPEDTAVYYCNVRSF

VRTYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 124.

In one embodiment, the antibody or binding fragment thereof of the present disclosure comprises a humanized variant of the heavy chain variable region of SEQ ID NO: 124, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 124), or a combination of these approaches. The humanized framework regions are designed to be similar in length and sequence to the parental framework sequences of SEQ ID NO: 124. In one embodiment, the humanized framework regions share 50%, 55%, 60%, 65%, 70%, 75%, 80%, 85%, 90%, 95% or more sequence identity to the framework regions of SEQ ID NO: 124. In another embodiment, the humanized framework regions are 60%, 65%, 70%, 75%, 80%, 85%, 90%, 95% or more similar in length to the framework regions of SEQ ID NO: 124. Humanized variants of the heavy chain variable region of SEQ ID NO: 124 share at least 50%, at least 55%, at least 60%, at least 65%, at least 70%, at least 75%, at least 80%, at least 85%, at least 90%, at least 95% sequence identity along the entire length of SEQ ID 124.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 124. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 17, or a modified amino acid sequence thereof containing 1, 2, 3, or more amino acid residue modifications as compared to SEQ ID NO: 17; a H-CDR2 having the amino acid sequence of SEQ ID NO: 53, or a modified amino acid sequence thereof containing 1, 2, 3, or more amino acid residue modifications as compared to SEQ ID NO: 53; and a H-CDR3 comprising the amino acid sequence of SEQ ID NO: 89, or a modified amino acid sequence thereof, said modified amino acid sequence containing 1, 2, 3, or more amino acid modifications as compared to SEQ ID NO: 89.

An exemplary single domain antibody having this heavy chain variable region is referred to herein as the 55-S-sR2-1G3 antibody. The 55-S-sR2-1G3 antibody comprises a $V_H$ chain amino acid sequence of SEQ ID NO: 125 as shown below.

SEQ ID NO: 125
QVQLQFSGGGLVQAGGSLTLSCVASGSRFSINTMGWYRQAPGKQRELVAG

ITSLGFTNYADSVKGRFTISRDNAKNTVYLQMNNLKVEDTAVYYCNRRGF

RSYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 125.

In one embodiment, the antibody or binding fragment thereof of the present disclosure comprises a humanized variant of the heavy chain variable region of SEQ ID NO: 125, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 125), or a combination of these approaches. The humanized framework regions are designed to be similar in length and sequence to the parental framework sequences of SEQ ID NO: 125. In one embodiment, the humanized framework regions share 50%, 55%, 60%, 65%, 70%, 75%, 80%, 85%, 90%, 95% or more sequence identity to the framework regions of SEQ ID NO: 125. In another embodiment, the humanized framework regions are 60%, 65%, 70%, 75%, 80%, 85%, 90%, 95% or more similar in length to the framework regions of SEQ ID NO: 125. Humanized variants of the heavy chain variable region of SEQ ID NO: 125 share at least 50%, at least 55%, at least 60%, at least 65%, at least 70%, at least 75%, at least 80%, at least 85%, at least 90%, at least 95% sequence identity along the entire length of SEQ ID 125.

Another aspect of the present disclosure relates to an antibody or binding portion thereof (e.g., a human antibody)

that competes for binding to human α-synuclein protein with the anti-α-synuclein antibody comprising a heavy chain variable region with the amino acid sequence of SEQ ID NO: 125. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 18, or a modified amino acid sequence thereof containing 1, 2, 3, or more amino acid residue modifications as compared to SEQ ID NO: 18; a H-CDR2 having the amino acid sequence of SEQ ID NO: 54, or a modified amino acid sequence thereof containing 1, 2, 3, or more amino acid residue modifications as compared to SEQ ID NO: 54; and a H-CDR3 comprising the amino acid sequence of SEQ ID NO: 90, or a modified amino acid sequence thereof, said modified amino acid sequence containing 1, 2, 3, or more amino acid modifications as compared to SEQ ID NO: 90.

An exemplary single domain antibody having this heavy chain variable region is referred to herein as the 56-S-sR2-2H1 antibody. The 56-S-sR2-2H1 antibody comprises a V$_H$ chain amino acid sequence of SEQ ID NO: 126 as shown below.

SEQ ID NO: 126
QVQLVESGGGFVQAGGSLRLSCAASGSIFSINYGNWYRQAPGKQRELVAG

ISRGGRTKYADSVKGRFTISRDSAKTLTLQMTSLKPEDTAVYYCNVRSFV

RTYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 126.

In one embodiment, the antibody or binding fragment thereof of the present disclosure comprises a humanized variant of the heavy chain variable region of SEQ ID NO: 126, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 126), or a combination of these approaches. The humanized framework regions are designed to be similar in length and sequence to the parental framework sequences of SEQ ID NO: 126. In one embodiment the humanized framework regions share 50%, 55%, 60%, 65%, 70%, 75%, 80%, 85%, 90%, 95% or more sequence identity to the framework regions of SEQ ID NO: 126. In another embodiment, the humanized framework regions are 60%, 65%, 70%, 75%, 80%, 85%, 90%, 95% or more similar in length to the framework regions of SEQ ID NO: 126. Humanized variants of the heavy chain variable region of SEQ ID NO: 126 share at least 50%, at least 55%, at least 60%, at least 65%, at least 70%, at least 75%, at least 80%, at least 85%, at least 90%, at least 95% sequence identity along the entire length of SEQ ID 126.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 126. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 19, or a modified amino acid sequence thereof containing 1, 2, 3, or more amino acid residue modifications as compared to SEQ ID NO: 19; a H-CDR2 having the amino acid sequence of SEQ ID NO: 55, or a modified amino acid sequence thereof containing 1, 2, 3, or more amino acid residue modifications as compared to SEQ ID NO: 55; and a H-CDR3 comprising the amino acid sequence of SEQ ID NO: 91, or a modified amino acid sequence thereof, said modified amino acid sequence containing 1, 2, 3, or more amino acid modifications as compared to SEQ ID NO: 91.

An exemplary single domain antibody having this heavy chain variable region is referred to herein as the 58-S-sR1-2B4 antibody. The 58-S-sR1-2B4 antibody comprises a V$_H$ chain amino acid sequence of SEQ ID NO: 127 as shown below.

SEQ ID NO: 127
QVQLQESGGGLVQSGGSLRLSCSASGSIFRINLMGWYRQAPGKQRELVAT

ITNEGNTYYADSVKGRFTISRDNANNTWYLQMNSLKPEDTAVYECAGKVI

RWYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 127.

In one embodiment, the antibody or binding fragment thereof of the present disclosure comprises a humanized variant of the heavy chain variable region of SEQ ID NO: 127, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 127), or a combination of these approaches. The humanized framework regions are designed to be similar in length and sequence to the parental framework sequences of SEQ ID NO: 127. In one embodiment, the humanized framework regions share 50%, 55%, 60%, 65%, 70%, 75%, 80%, 85%, 90%, 95% or more sequence identity to the framework regions of SEQ ID NO: 127. In another embodiment, the humanized framework regions are 60%, 65%, 70%, 75%, 80%, 85%, 90%, 95% or more similar in length to the framework regions of SEQ ID NO: 127. Humanized variants of the heavy chain variable region of SEQ ID NO: 127 share at least 50%, at least 55%, at least 60%, at least 65%, at least 70%, at least 75%, at least 80%, at least 85%, at least 90%, at least 95% sequence identity along the entire length of SEQ ID 127.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 127. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 20, or a modified amino acid sequence thereof containing 1, 2, 3, or more amino acid residue modifications as compared to SEQ ID NO: 20; a H-CDR2 having the amino acid sequence of SEQ ID NO: 56, or a modified amino acid sequence thereof containing 1, 2, 3, or more amino acid residue modifications as compared to SEQ ID NO: 56; and a H-CDR3 comprising the amino acid sequence of SEQ ID NO: 92, or a modified amino acid sequence thereof, said modified amino acid sequence containing 1, 2, 3, or more amino acid modifications as compared to SEQ ID NO: 92.

An exemplary single domain antibody having this heavy chain variable region is referred to herein as the 62-S-sR2-1A9 antibody. The 62-S-sR2-1A9 antibody comprises a $V_H$ chain amino acid sequence of SEQ ID NO: 128 as shown below.

```
                                         SEQ ID NO: 128
QVQLQEFGGGLVQPGGSLRLSCQASTSVFGNTAMAWYRQAPCKQRELVAR

ITTLGFTYYADSAKGRFTISRDSAMNTVYLQMNSLKPEDTAVYYCRARRA

LRESHWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 128.

In one embodiment, the antibody or binding fragment thereof of the present disclosure comprises a humanized variant of the heavy chain variable region of SEQ ID NO: 128, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 128), or a combination of these approaches. The humanized framework regions are designed to be similar in length and sequence to the parental framework sequences of SEQ ID NO: 128. In one embodiment, the humanized framework regions share 50%, 55%, 60%, 65%, 70%, 75%, 80%, 85%, 90%, 95% or more sequence identity to the framework regions of SEQ ID NO: 128. In another embodiment, the humanized framework regions are 60%, 65%, 70%, 75%, 80%, 85%, 90%, 95% or more similar in length to the framework regions of SEQ ID NO: 128. Humanized variants of the heavy chain variable region of SEQ ID NO: 128 share at least 50%, at least 55%, at least 60%, at least 65%, at least 70%, at least 75%, at least 80%, at least 85%, at least 90%, at least 95% sequence identity along the entire length of SEQ ID NO: 128.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 128. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 21, or a modified amino acid sequence thereof containing 1, 2, 3, or more amino acid residue modifications as compared to SEQ ID NO: 21, a H-CDR2 having the amino acid sequence of SEQ ID NO: 57, or a modified amino acid sequence thereof containing 1, 2, 3, or more amino acid residue modifications as compared to SEQ ID NO: 57; and a H-CDR3 comprising the amino acid sequence of SEQ ID NO: 93, or a modified amino acid sequence thereof, said modified amino acid sequence containing 1, 2, 3, or more amino acid modifications as compared to SEQ ID NO: 93.

An exemplary single domain antibody having this heavy chain variable region is referred to herein as the 63-S-sR2-1G9 antibody. The 63-S-sR2-1G9 antibody comprises a $V_H$ chain amino acid sequence of SEQ ID NO: 129 as shown below.

```
                                         SEQ ID NO: 129
QVQLQESGGGFVQAGGSLRLSCAASGSIFSINYGNWYRQAPGKQRELVAG

ISRGGRTKYADSVKGRFTISRDSAKTLTLQMTSLKPEDTAIYSCNARSFV

RTYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 129.

In one embodiment, the antibody or binding fragment thereof of the present disclosure comprises a humanized variant of the heavy chain variable region of SEQ ID NO: 129, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 129), or a combination of these approaches. The humanized framework regions are designed to be similar in length and sequence to the parental framework sequences of SEQ ID NO: 129. In one embodiment, the humanized framework regions share 50%, 55%, 60%, 65%, 70%, 75%, 80%, 85%, 90%, 95% or more sequence identity to the framework regions of SEQ ID NO: 129. In another embodiment, the humanized framework regions are 60%, 65%, 70%, 75%, 80%, 85%, 90%, 95% or more similar in length to the framework regions of SEQ ID NO: 129. Humanized variants of the heavy chain variable region of SEQ ID NO: 129 share at least 50%, at least 55%, at least 60%, at least 65%, at least 70%, at least 75%, at least 80%, at least 85%, at least 90%, at least 95% sequence identity along the entire length of SEQ ID 129.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 129. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 22, or a modified amino acid sequence thereof containing 1, 2, 3, or more amino acid residue modifications as compared to SEQ ID NO: 22; a H-CDR2 having the amino acid sequence of SEQ ID NO: 58, or a modified amino acid sequence thereof containing 1, 2, 3, or more amino acid residue modifications as compared to SEQ ID NO: 58; and a H-CDR3 comprising the amino acid sequence of SEQ ID NO: 94, or a modified amino acid sequence thereof, said modified amino acid sequence containing 1, 2, 3, or more amino acid modifications as compared to SEQ ID NO: 94.

An exemplary single domain antibody having this heavy chain variable region is referred to herein as the 64-S-sR2-2H2 antibody. The 64-S-sR2-2H2 antibody comprises a $V_H$ chain amino acid sequence of SEQ ID NO: 130 as shown below.

SEQ ID NO: 130
QVQLQESGGGLVTAGGSLRLSCAASRNFFTFRAMGWYRQAPGKQREMVAS

ITTGGRTVYADSVKGRFTISKSNANNTVYLQMNSLEAEDTAVYYCNARRR

FPVPGPTDYWGRGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 130.

In one embodiment, the antibody or binding fragment thereof of the present disclosure comprises a humanized variant of the heavy chain variable region of SEQ ID NO: 130, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 130), or a combination of these approaches. The humanized framework regions are designed to be similar in length and sequence to the parental framework sequences of SEQ ID NO: 130. In one embodiment, the humanized framework regions share 50%, 55%, 60%, 65%, 70%, 75%, 80%, 85%, 90%, 95% or more sequence identity to the framework regions of SEQ ID NO: 130. In another embodiment, the humanized framework regions are 60%, 65%, 70%, 75%, 80%, 85%, 90%, 95% or more similar in length to the framework regions of SEQ ID NO: 130. Humanized variants of the heavy chain variable region of SEQ ID NO: 130 share at least 50%, at least 55%, at least 60%, at least 65%, at least 70%, at least 75%, at least 80%, at least 85%, at least 90%, at least 95% sequence identity along the entire length of SEQ ID 130.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 130. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 23, or a modified amino acid sequence thereof containing 1, 2, 3, or more amino acid residue modifications as compared to SEQ ID NO: 23; a H-CDR2 having the amino acid sequence of SEQ ID NO: 59, or a modified amino acid sequence thereof containing 1, 2, 3, or more amino acid residue modifications as compared to SEQ ID NO: 59; and a H-CDR3 comprising the amino acid sequence of SEQ ID NO: 95, or a modified amino acid sequence thereof, said modified amino acid sequence containing 1, 2, 3, or more amino acid modifications as compared to SEQ ID NO: 95.

An exemplary single domain antibody having this heavy chain variable region is referred to herein as the 66-S-sR1-2B10 antibody. The 66-S-sR1-2B10 antibody comprises a $V_H$ chain amino acid sequence of SEQ ID NO: 131 as shown below.

SEQ ID NO: 131
QVQLQESGGGLVQAGGSLRLSCAASGITRFNAMGWYRQAPGKERELVARV

SSGGSTTYADSVKARFTTFRDNVKNIGYLQMTSLKPEDTAVYYCNVGNFW

GQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 131.

In one embodiment, the antibody or binding fragment thereof of the present disclosure comprises a humanized variant of the heavy chain variable region of SEQ ID NO: 131, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 131), or a combination of these approaches. The humanized framework regions are designed to be similar in length and sequence to the parental framework sequences of SEQ ID NO: 131. In one embodiment, the humanized framework regions share 50%, 55%, 60%, 65%, 70%, 75%, 80%, 85%, 90%, 95% or more sequence identity to the framework regions of SEQ ID NO: 131. In another embodiment, the humanized framework regions are 60%, 65%, 70%, 75%, 80%, 85%, 90%, 95% or more similar in length to the framework regions of SEQ ID NO: 131. Humanized variants of the heavy chain variable region of SEQ ID NO: 131 share at least 50%, at least 55%, at least 60%, at least 65%, at least 70%, at least 75%, at least 80%, at least 85%, at least 90%, at least 95% sequence identity along the entire length of SEQ ID 131.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 131. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 24, or a modified amino acid sequence thereof containing 1, 2, 3, or more amino acid residue modifications as compared to SEQ ID NO: 24; a H-CDR2 having the amino acid sequence of SEQ ID NO: 60, or a modified amino acid sequence thereof containing 1, 2, 3, or more amino acid residue modifications as compared to SEQ ID NO: 60; and a H-CDR3 comprising the amino acid sequence of SEQ ID NO: 96, or a modified amino acid sequence thereof, said modified amino acid sequence containing 1, 2, 3, or more amino acid modifications as compared to SEQ ID NO: 96.

An exemplary single domain antibody having this heavy chain variable region is referred to herein as the 70-S-sR2-1B3 antibody. The 70-S-sR2-1B3 antibody comprises a $V_H$ chain amino acid sequence of SEQ ID NO: 132 as shown below.

SEQ ID NO: 132
QVQLQESGGGLVRTGESLGLSCAASGRSILIKGMGWYRQAPGKEREMVAT

ISMAGVTNYSDSVKGRFTISRDNYKKTVSLQMNNLRPEDTAVYVCNAQTR

LWSYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 132.

In one embodiment, the antibody or binding fragment thereof of the present disclosure comprises a humanized variant of the heavy chain variable region of SEQ ID NO: 132, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 132), or a combination of these approaches. The humanized framework regions are designed to be similar in length and sequence to the parental framework sequences of SEQ ID NO: 132. In one embodiment, the humanized framework regions share 50%, 55%, 60%, 65%, 70%, 75%, 80%, 85%, 90%, 95% or more sequence identity to the framework regions of SEQ ID NO: 132. In another embodiment, the humanized framework regions are 60%, 65%, 70%, 75%, 80%, 85%, 90%, 95% or more similar in length to the framework regions of SEQ ID NO: 132. Humanized variants of the heavy chain variable region of SEQ ID NO: 132 share at least 50%, at least 55%, at least 60%, at least 65%, at least 70%, at least 75%, at least 80%, at least 85%, at least 90%, at least 95% sequence identity along the entire length of SEQ ID 132.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 132. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 25, or a modified amino acid sequence thereof containing 1, 2, 3, or more amino acid residue modifications as compared to SEQ ID NO: 25; a H-CDR2 having the amino acid sequence of SEQ ID NO: 61, or a modified amino acid sequence thereof containing 1, 2, 3, or more amino acid residue modifications as compared to SEQ ID NO: 61; and a H-CDR3 comprising the amino acid sequence of SEQ ID NO: 97, or a modified amino acid sequence thereof, said modified amino acid sequence containing 1, 2, 3, or more amino acid modifications as compared to SEQ ID NO: 97.

An exemplary single domain antibody having this heavy chain variable region is referred to herein as the 71-S-sR2-2A8 antibody. The 71-S-sR2-2A8 antibody comprises a $V_H$ chain amino acid sequence of SEQ ID NO: 133 as shown below.

SEQ ID NO: 133
QVQLVESGGGLVQAGGSLRLSCAASGRIFGRNAMAWYRQVPGKERELVAR

ITRDGRTMYVDSAKGRFTISRDNAKNTAYLHMDSLKPEDTAVYYCNAQTR

LWSYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 133.

In one embodiment, the antibody or binding fragment thereof of the present disclosure comprises a humanized variant of the heavy chain variable region of SEQ ID NO: 133, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 133), or a combination of these approaches. The humanized framework regions are designed to be similar in length and sequence to the parental framework sequences of SEQ ID NO: 133. In one embodiment, the humanized framework regions share 50%, 55%, 60%, 65%, 70%, 75%, 80%, 85%, 90%, 95% or more sequence identity to the framework regions of SEQ ID NO: 133. In another embodiment, the humanized framework regions are 60%, 65%, 70%, 75%, 80%, 85%, 90%, 95% or more similar in length to the framework regions of SEQ ID NO: 133. Humanized variants of the heavy chain variable region of SEQ ID NO: 133 share at least 50%, at least 55%, at least 60%, at least 65%, at least 70%, at least 75%, at least 80%, at least 85%, at least 90%, at least 95% sequence identity along the entire length of SEQ ID 133.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 133. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 26, or a modified amino acid sequence thereof containing 1, 2, 3, or more amino acid residue modifications as compared to SEQ ID NO: 26; a H-CDR2 having the amino acid sequence of SEQ ID NO: 62, or a modified amino acid sequence thereof containing 1, 2, 3, or more amino acid residue modifications as compared to SEQ ID NO: 62; and a H-CDR3 comprising the amino acid sequence of SEQ ID NO: 98, or a modified amino acid sequence thereof, said modified amino acid sequence containing 1, 2, 3, or more amino acid modifications as compared to SEQ ID NO: 98.

An exemplary single domain antibody having this heavy chain variable region is referred to herein as the 72-S-sR2-2H3 antibody. The 72-S-sR2-2H3 antibody comprises a $V_H$ chain amino acid sequence of SEQ ID NO: 134 as shown below.

SEQ ID NO: 134
QVQLQESGGGLVQAGGSLRLSCAASRSTFRFNYMGWYRQAPGKQRELVAA

ISSRGGSTNYADSVQGRFTISRDNAKNYVSLQMNSLKPEDTAVYYCNVRS

FVRTYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 134.

In one embodiment, the antibody or binding fragment thereof of the present disclosure comprises a humanized variant of the heavy chain variable region of SEQ ID NO: 134, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 134), or a combination of these approaches. The humanized framework regions are designed to be similar in length and sequence to the parental framework sequences of SEQ ID NO: 134. In one embodiment, the humanized framework regions share 50%, 55%, 60%, 65%, 70%, 75%, 80%, 85%, 90%, 95% or more sequence identity to the framework regions of SEQ ID NO: 134. In another embodiment, the humanized framework regions are 60%, 65%, 70%, 75%, 80%, 85%, 90%, 95% or more similar in length to the framework regions of SEQ ID NO: 134. Humanized variants of the heavy chain variable region of SEQ ID NO: 134 share at least 50%, at least 55%, at least 60%, at least 65%, at least 70%, at least 75%, at least 80%, at least 85%, at least 90%, at least 95% sequence identity along the entire length of SEQ ID 134.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 134. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 27, or a modified amino acid sequence thereof containing 1, 2, 3, or more amino acid residue modifications as compared to SEQ ID NO: 27; a H-CDR2 having the amino acid sequence of SEQ ID NO: 63, or a modified amino acid sequence thereof containing 1, 2, 3, or more amino acid residue modifications as compared to SEQ ID NO: 63; and a H-CDR3 comprising the amino acid sequence of SEQ ID NO: 99, or a modified amino acid sequence thereof, said modified amino acid sequence containing 1, 2, 3, or more amino acid modifications as compared to SEQ ID NO: 99.

An exemplary single domain antibody having this heavy chain variable region is referred to herein as the 74-S-sR1-2B12 antibody. The 74-S-sR1-2B12 antibody comprises a $V_H$ chain amino acid sequence of SEQ ID NO: 135 as shown below.

SEQ ID NO: 135
QVQLQEFGGGLVQAGGSLRLSCATSGSIFSINAVGWYRQAPGNQRELVAA

ISGRGSTHYADSVKGRFTISRDTAKNTVYLQMNSLKPEDTAVYYCALDQH

MEVIVSPGRIGSWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 135.

In one embodiment, the antibody or binding fragment thereof of the present disclosure comprises a humanized variant of the heavy chain variable region of SEQ ID NO: 135, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 135), or a combination of these approaches. The humanized framework regions are designed to be similar in length and sequence to the parental framework sequences of SEQ ID NO: 135. In one embodiment, the humanized framework regions share 50%, 55%, 60%, 65%, 70%, 75%, 80%, 85%, 90%, 95% or more sequence identity to the framework regions of SEQ ID NO: 135. In another embodiment, the humanized framework regions are 60%, 65%, 70%, 75%, 80%, 85%, 90%, 95% or more similar in length to the framework regions of SEQ ID NO: 135. Humanized variants of the heavy chain variable region of SEQ ID NO: 135 share at least 50%, at least 55%, at least 60%, at least 65%, at least 70%, at least 75%, at least 80%, at least 85%, at least 90%, at least 95% sequence identity along the entire length of SEQ ID 135.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 135. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 28, or a modified amino acid sequence thereof containing 1, 2, 3, or more amino acid residue modifications as compared to SEQ ID NO: 28; a H-CDR2 having the amino acid sequence of SEQ ID NO: 64, or a modified amino acid sequence thereof containing 1, 2, 3, or more amino acid residue modifications as compared to SEQ ID NO: 64; and a H-CDR3 comprising the amino acid sequence of SEQ ID NO: 100, or a modified amino acid sequence thereof, said modified amino acid sequence containing 1, 2, 3, or more amino acid modifications as compared to SEQ ID NO: 100.

An exemplary single domain antibody having this heavy chain variable region is referred to herein as the 78-S-sR2-1C9 antibody. The 78-S-sR2-1C9 antibody comprises a V$_H$ chain amino acid sequence of SEQ ID NO: 136 as shown below.

```
                                           SEQ ID NO: 136
QVQLQESGGGLVQAGESLTLSCALSTTMFGFWPMA

WFRQTPGQRRELIATIDSRGRTNIADSVKGRFTIS

RDNTKNTLYLRMNSLKPEDTAVYYCNAQRRWPLRD

YWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 136.

In one embodiment, the antibody or binding fragment thereof of the present disclosure comprises a humanized variant of the heavy chain variable region of SEQ ID NO: 136, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 136), or a combination of these approaches. The humanized framework regions are designed to be similar in length and sequence to the parental framework sequences of SEQ ID NO: 136. In one embodiment, the humanized framework regions share 50%, 55%, 60%, 65%, 70%, 75%, 80%, 85%, 90%, 95% or more sequence identity to the framework regions of SEQ ID NO: 136. In another embodiment, the humanized framework regions are 60%, 65%, 70%, 75%, 80%, 85%, 90%, 95% or more similar in length to the framework regions of SEQ ID NO: 136. Humanized variants of the heavy chain variable region of SEQ ID NO: 136 share at least 50%, at least 55%, at least 60%, at least 65%, at least 70%, at least 75%, at least 80%, at least 85%, at least 90%, at least 95% sequence identity along the entire length of SEQ ID 136.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 136. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 29, or a modified amino acid sequence thereof containing 1, 2, 3, or more amino acid residue modifications as compared to SEQ ID NO: 29, a H-CDR2 having the amino acid sequence of SEQ ID NO: 65, or a modified amino acid sequence thereof containing 1, 2, 3, or more amino acid residue modifications as compared to SEQ ID NO: 65; and a H-CDR3 comprising the amino acid sequence of SEQ ID NO: 101, or a modified amino acid sequence thereof, said modified amino acid sequence containing 1, 2, 3, or more amino acid modifications as compared to SEQ ID NO: 101.

An exemplary single domain antibody having this heavy chain variable region is referred to herein as the 79-S-sR2-

2B3 antibody. The 79-S-sR2-2B3 antibody comprises a $V_H$ chain amino acid sequence of SEQ ID NO: 137 as shown below.

SEQ ID NO: 137
QVQLQEFGGGVVQSGGSLRLSCVASGNIFRINAMG

WYRQAPGKQRELVARISSGGSTNYADSVKGRFTIS

RDNVKNTVTLQMNSLKPEDTAVYYCNARRPLRWYE

YWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 137.

In one embodiment, the antibody or binding fragment thereof of the present disclosure comprises a humanized variant of the heavy chain variable region of SEQ ID NO: 137, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 137), or a combination of these approaches. The humanized framework regions are designed to be similar in length and sequence to the parental framework sequences of SEQ ID NO: 137. In one embodiment, the humanized framework regions share 50%, 55%, 60%, 65%, 70%, 75%, 80%, 85%, 90%, 95% or more sequence identity to the framework regions of SEQ ID NO: 137. In another embodiment, the humanized framework regions are 60%, 65%, 70%, 75%, 80%, 85%, 90%, 95% or more similar in length to the framework regions of SEQ ID NO: 137. Humanized variants of the heavy chain variable region of SEQ ID NO: 137 share at least 50%, at least 55%, at least 60%, at least 65%, at least 70%, at least 75%, at least 80%, at least 85%, at least 90%, at least 95% sequence identity along the entire length of SEQ ID 137.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 137. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 30, or a modified amino acid sequence thereof containing 1, 2, 3, or more amino acid residue modifications as compared to SEQ ID NO: 30; a H-CDR2 having the amino acid sequence of SEQ ID NO: 66, or a modified amino acid sequence thereof containing 1, 2, 3, or more amino acid residue modifications as compared to SEQ ID NO: 66; and a H-CDR3 comprising the amino acid sequence of SEQ ID NO: 102, or a modified amino acid sequence thereof, said modified amino acid sequence containing 1, 2, 3, or more amino acid modifications as compared to SEQ ID NO: 102.

An exemplary single domain antibody having this heavy chain variable region is referred to herein as the 80-S-sR2-2H5 antibody. The 80-S-sR2-2H5 antibody comprises a $V_H$ chain amino acid sequence of SEQ ID NO: 138 as shown below.

SEQ ID NO: 138
QVQLQASGGGLVQPGGSLRLSCAASGSIFSTNAMG

WYRQAPGKQREVIASITKFGNTDYADSVKGRFTIS

RDNAKNIVYLQMNSLKPEDTAVYYCYQNSRGRWYD

IFRDYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 138.

In one embodiment, the antibody or binding fragment thereof of the present disclosure comprises a humanized variant of the heavy chain variable region of SEQ ID NO: 138, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 138), or a combination of these approaches. The humanized framework regions are designed to be similar in length and sequence to the parental framework sequences of SEQ ID NO: 138. In one embodiment, the humanized framework regions share 50%, 55%, 60%, 65%, 70%, 75%, 80%, 85%, 90%, 95% or more sequence identity to the framework regions of SEQ ID NO: 138. In another embodiment, the humanized framework regions are 60%, 65%, 70%, 75%, 80%, 85%, 90%, 95% or more similar in length to the framework regions of SEQ ID NO: 138. Humanized variants of the heavy chain variable region of SEQ ID NO: 138 share at least 50%, at least 55%, at least 60%, at least 65%, at least 70%, at least 75%, at least 80%, at least 85%, at least 90%, at least 95% sequence identity along the entire length of SEQ ID 138.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 138. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 31, or a modified amino acid sequence thereof containing 1, 2, 3, or more amino acid residue modifications as compared to SEQ ID NO: 31; a H-CDR2 having the amino acid sequence of SEQ ID NO: 67, or a modified amino acid sequence thereof containing 1, 2, 3, or more amino acid residue modifications as compared to SEQ ID NO: 67; and a H-CDR3 comprising the amino acid sequence of SEQ ID NO: 103, or a modified amino acid sequence thereof, said modified amino acid sequence containing 1, 2, 3, or more amino acid modifications as compared to SEQ ID NO: 103.

An exemplary single domain antibody having this heavy chain variable region is referred to herein as the 80-S-sR2-2H9 antibody. The 80-S-sR2-2H9 antibody comprises a $V_H$ chain amino acid sequence of SEQ ID NO: 139 as shown below.

SEQ ID NO: 139
QVQLVESGGGFVQAGGSLRLSCVASRSSFRITTMN

WYRQAPGKQREMVASITTGGRTVYADSVKGRFTIS

KSNANNTVYLQMNSLEAEDTAVYYGNAGRRWPLRD

YWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 139.

In one embodiment, the antibody or binding fragment thereof of the present disclosure comprises a humanized variant of the heavy chain variable region of SEQ ID NO: 139, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 139), or a combination of these approaches. The humanized framework regions are designed to be similar in length and sequence to the parental framework sequences of SEQ ID NO: 139. In one embodiment, the humanized framework regions share 50%, 55%, 60%, 65%, 70%, 75%, 80%, 85%, 90%, 95% or more sequence identity to the framework regions of SEQ ID NO: 139. In another embodiment, the humanized framework regions are 60%, 65%, 70%, 75%, 80%, 85%, 90%, 95% or more similar in length to the framework regions of SEQ ID NO: 139. Humanized variants of the heavy chain variable region of SEQ ID NO: 139 share at least 50%, at least 55%, at least 60%, at least 65%, at least 70%, at least 75%, at least 80%, at least 85%, at least 90%, at least 95% sequence identity along the entire length of SEQ ID 139.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 139. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 32, or a modified amino acid sequence thereof containing 1, 2, 3, or more amino acid residue modifications as compared to SEQ ID NO: 32; a H-CDR2 having the amino acid sequence of SEQ ID NO: 68, or a modified amino acid sequence thereof containing 1, 2, 3, or more amino acid residue modifications as compared to SEQ ID NO: 68; and a H-CDR3 comprising the amino acid sequence of SEQ ID NO: 104, or a modified amino acid sequence thereof, said modified amino acid sequence containing 1, 2, 3, or more amino acid modifications as compared to SEQ ID NO: 104.

An exemplary single domain antibody having this heavy chain variable region is referred to herein as the 86-S-sR2-1D5 antibody. The 86-S-sR2-1D5 antibody comprises a $V_H$ chain amino acid sequence of SEQ ID NO: 141 as shown below.

SEQ ID NO: 141
QVQLQEFGGGVVQSGGSLRLSCVASGNIFRINAMG

WYRQAPGKQRELVAHIISGGSTNYADSVKGRFTIS

REYAKNMVYLQMNSLKPEDTAVYYCNAERRFGMRQ

VWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 141.

In one embodiment, the antibody or binding fragment thereof of the present disclosure comprises a humanized variant of the heavy chain variable region of SEQ ID NO: 141, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 141), or a combination of these approaches. The humanized framework regions are designed to be similar in length and sequence to the parental framework sequences of SEQ ID NO: 141. In one embodiment, the humanized framework regions share 50%, 55%, 60%, 65%, 70%, 75%, 80%, 85%, 90%, 95% or more sequence identity to the framework regions of SEQ ID NO: 141. In another embodiment, the humanized framework regions are 60%, 65%, 70%, 75%, 80%, 85%, 90%, 95% or more similar in length to the framework regions of SEQ ID NO: 141. Humanized variants of the heavy chain variable region of SEQ ID NO: 141 share at least 50%, at least 55%, at least 60%, at least 65%, at least 70%, at least 75%, at least 80%, at least 85%, at least 90%, at least 95% sequence identity along the entire length of SEQ ID 141.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 141. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 33, or a modified amino acid sequence thereof containing 1, 2, 3, or more amino acid residue modifications as compared to SEQ ID NO: 33; a H-CDR2 having the amino acid sequence of SEQ ID NO: 69, or a modified amino acid sequence thereof containing 1, 2, 3, or more amino acid residue modifications as compared to SEQ ID NO: 69; and a H-CDR3 comprising the amino acid sequence of SEQ ID NO: 105, or a modified amino acid sequence thereof, said modified amino acid sequence containing 1, 2, 3, or more amino acid modifications as compared to SEQ ID NO: 105.

An exemplary single domain antibody having this heavy chain variable region is referred to herein as the 87-S-sR2-2D8 antibody. The 87-S-sR2-2D8 antibody comprises a $V_H$ chain amino acid sequence of SEQ ID NO: 142 as shown below.

```
                                           SEQ ID NO: 142
QVQLQESGGGLVQAGGSLRLSCAASYYTFRYFPMG

WYRQAPGRQRELVASTTSGGGVNYADFVEGRFTIS

RDNAKNTFYLQMSSLKPEDTAVYYCARLLSLGSRW

GYGMFTWGKGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 142.

In one embodiment, the antibody or binding fragment thereof of the present disclosure comprises a humanized variant of the heavy chain variable region of SEQ ID NO: 142, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 142), or a combination of these approaches. The humanized framework regions are designed to be similar in length and sequence to the parental framework sequences of SEQ ID NO: 142. In one embodiment, the humanized framework regions share 50%, 55%, 60%, 65%, 70%, 75%, 80%, 85%, 90%, 95% or more sequence identity to the framework regions of SEQ ID NO: 142. In another embodiment, the humanized framework regions are 60%, 65%, 70%, 75%, 80%, 85%, 90%, 95% or more similar in length to the framework regions of SEQ ID NO: 142. Humanized variants of the heavy chain variable region of SEQ ID NO: 142 share at least 50%, at least 55%, at least 60%, at least 65%, at least 70%, at least 75%, at least 80%, at least 85%, at least 90%, at least 95% sequence identity along the entire length of SEQ ID 142.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 142. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 34, or a modified amino acid sequence thereof containing 1, 2, 3, or more amino acid residue modifications as compared to SEQ ID NO: 34; a H-CDR2 having the amino acid sequence of SEQ ID NO: 70, or a modified amino acid sequence thereof containing 1, 2, 3, or more amino acid residue modifications as compared to SEQ ID NO: 70; and a H-CDR3 comprising the amino acid sequence of SEQ ID NO: 106, or a modified amino acid sequence thereof, said modified amino acid sequence containing 1, 2, 3, or more amino acid modifications as compared to SEQ ID NO: 106.

An exemplary single domain antibody having this heavy chain variable region is referred to herein as the 88-S-sR2-2H8 antibody. The 88-S-sR2-2H8 antibody comprises a $V_H$ chain amino acid sequence of SEQ ID NO: 143 as shown below.

```
                                           SEQ ID NO: 143
QVQLQESGGGLVQPGGSLRLSCAASGSIFSIKTMG

WYRQAPGKQRELVAAIASGGFTNYADSVKGRFTIS

RDNARNTVYLQMNSLKPEDTAVYYCNAQRRWPLRD

YWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 143.

In one embodiment, the antibody or binding fragment thereof of the present disclosure comprises a humanized variant of the heavy chain variable region of SEQ ID NO: 143, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 143), or a combination of these approaches. The humanized framework regions are designed to be similar in length and sequence to the parental framework sequences of SEQ ID NO: 143. In one embodiment the humanized framework regions share 50%, 55%, 60%, 65%, 70%, 75%, 80%, 85%, 90%, 95% or more sequence identity to the framework regions of SEQ ID NO: 143. In another embodiment, the humanized framework regions are 60%, 65%, 70%, 75%, 80%, 85%, 90%, 95% or more similar in length to the framework regions of SEQ ID NO: 143. Humanized variants of the heavy chain variable region of SEQ ID NO: 143 share at least 50%, at least 55%, at least 60%, at least 65%, at least 70%, at least 75%, at least 80%, at least 85%, at least 90%, at least 95% sequence identity along the entire length of SEQ ID 143.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 143. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 35, or a modified amino acid sequence thereof containing 1, 2, 3, or more amino acid residue modifications as compared to SEQ ID NO: 35; a H-CDR2 having the amino acid sequence of SEQ ID NO: 71, or a modified amino acid sequence thereof containing 1, 2, 3, or more amino acid residue modifications as compared to SEQ ID NO: 71; and a H-CDR3 comprising the amino acid sequence of SEQ ID NO: 107, or a modified amino acid sequence thereof, said modified amino acid sequence containing 1, 2, 3, or more amino acid modifications as compared to SEQ ID NO: 107.

An exemplary single domain antibody having this heavy chain variable region is referred to herein as the 94-S-sR2-1D10 antibody. The 94-S-sR2-1D10 antibody comprises a $V_H$ chain amino acid sequence of SEQ ID NO: 144 as shown below.

```
                                          SEQ ID NO: 144
QVQLQESGGGLVRDGGSLTLSCAASGSAFRMNSMA

WYRQVPGKQRELVAAISFRGSANYANSVKGRFTIS

RDNGKNTVYLQMNSLKPEDTAYYYCAAGRPWQRTF

YWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 144.

In one embodiment, the antibody or binding fragment thereof of the present disclosure comprises a humanized variant of the heavy chain variable region of SEQ ID NO: 144, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 144), or a combination of these approaches. The humanized framework regions are designed to be similar in length and sequence to the parental framework sequences of SEQ ID NO: 144. In one embodiment, the humanized framework regions share 50%, 55%, 60%, 65%, 70%, 75%, 80%, 85%, 90%, 95% or more sequence identity to the framework regions of SEQ ID NO: 144. In another embodiment, the humanized framework regions are 60%, 65%, 70%, 75%, 80%, 85%, 90%, 95% or more similar in length to the framework regions of SEQ ID NO: 144. Humanized variants of the heavy chain variable region of SEQ ID NO: 144 share at least 50%, at least 55%, at least 60%, at least 65%, at least 70%, at least 75%, at least 80%, at least 85%, at least 90%, at least 95% sequence identity along the entire length of SEQ ID 144.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 144. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 36, or a modified amino acid sequence thereof containing 1, 2, 3, or more amino acid residue modifications as compared to SEQ ID NO: 36; a H-CDR2 having the amino acid sequence of SEQ ID NO: 72, or a modified amino acid sequence thereof containing 1, 2, 3, or more amino acid residue modifications as compared to SEQ ID NO: 72; and a H-CDR3 comprising the amino acid sequence of SEQ ID NO: 108, or a modified amino acid sequence thereof, said modified amino acid sequence containing 1, 2, 3, or more amino acid modifications as compared to SEQ ID NO: 108.

An exemplary single domain antibody having this heavy chain variable region is referred to herein as the 95-S-sR2-2D10 antibody. The 95-S-sR2-2D10 antibody comprises a $V_H$ chain amino acid sequence of SEQ ID NO: 145 as shown below.

```
                                          SEQ ID NO: 145
QVQLQESGGGFVQAGGSLRLSCAASGSIFSINYGN

WYRQAPGKQRELVAGISRGGRTKYADSVKGRFTIS

RDSAKTLTLQMTSLKPEDSGVYYCAATRWSWGTKS

YWGQGTQVWSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 145.

In one embodiment, the antibody or binding fragment thereof of the present disclosure comprises a humanized variant of the heavy chain variable region of SEQ ID NO: 145, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 145), or a combination of these approaches. The humanized framework regions are designed to be similar in length and sequence to the parental framework sequences of SEQ ID NO: 145. In one embodiment, the humanized framework regions share 50%, 55%, 60%, 65%, 70%, 75%, 80%, 85%, 90%, 95% or more sequence identity to the framework regions of SEQ ID NO: 145. In another embodiment, the humanized framework regions are 60%, 65%, 70%, 75%, 80%, 85%, 90%, 95% or more similar in length to the framework regions of SEQ ID NO: 145. Humanized variants of the heavy chain variable region of SEQ ID NO: 145 share at least 50%, at least 55%, at least 60%, at least 65%, at least 70%, at least 75%, at least 80%, at least 85%, at least 90%, at least 95% sequence identity along the entire length of SEQ ID 145.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 145. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 218, or a modified amino acid sequence thereof containing 1, 2, 3, or more amino acid residue modifications as compared to SEQ ID NO: 218; a H-CDR2 having the amino acid sequence of SEQ ID NO: 219, or a modified amino acid sequence thereof containing 1, 2, 3, or more amino acid residue modifications as compared to SEQ ID NO: 219, and a H-CDR3 comprising the amino acid sequence of SEQ ID NO: 220, or a modified amino acid sequence thereof, said modified amino acid sequence containing 1, 2, 3, or more amino acid modifications as compared to SEQ ID NO: 220.

An exemplary single domain antibody having this heavy chain variable region is referred to herein as the S-sR2-2H7 antibody. The S-sR2-2H7 antibody comprises a $V_H$ chain amino acid sequence of SEQ ID NO: 221 as shown below.

```
                                        SEQ ID NO: 221
QVQLQEFGGGVVQSGGSLRLSCVASGNLFRINAMG

WYRQAPGKSRVLVASIDSAGRTNYGDAVEDRFTIS

RDIANNTVNLQMNSLKPEDTAVYYCSTWRLGRNYW

GQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 221.

In one embodiment, the antibody or binding fragment thereof of the present disclosure comprises a humanized variant of the heavy chain variable region of SEQ ID NO: 221, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 221), or a combination of these approaches. The humanized framework regions are designed to be similar in length and sequence to the parental framework sequences of SEQ ID NO: 221. In one embodiment, the humanized framework regions share 50%, 55%, 60%, 65%, 70%, 75%, 80%, 85%, 90%, 95% or more sequence identity to the framework regions of SEQ ID NO: 221. In another embodiment, the humanized framework regions are 60%, 65%, 70%, 75%, 80%, 85%, 90%, 95% or more similar in length to the framework regions of SEQ ID NO: 221. Humanized variants of the heavy chain variable region of SEQ ID NO: 221 share at least 50%, at least 55%, at least 60%, at least 65%, at least 70%, at least 75%, at least 80%, at least 85%, at least 90%, at least 95% sequence identity along the entire length of SEQ ID 221.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 221. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 222, or a modified amino acid sequence thereof containing 1, 2, 3, or more amino acid residue modifications as compared to SEQ ID NO: 222; a H-CDR2 having the amino acid sequence of SEQ ID NO: 223, or a modified amino acid sequence thereof containing 1, 2, 3, or more amino acid residue modifications as compared to SEQ ID NO: 223; and a H-CDR3 comprising the amino acid sequence of SEQ ID NO: 224, or a modified amino acid sequence thereof, said modified amino acid sequence containing 1, 2, 3, or more amino acid modifications as compared to SEQ ID NO: 224.

An exemplary single domain antibody having this heavy chain variable region is referred to herein as the S-sR2-1F6 antibody. The S-sR2-1F6 antibody comprises a $V_H$ chain amino acid sequence of SEQ ID NO: 225 as shown below.

```
                                        SEQ ID NO: 225
QVQLQESGGGLVQAGGSLRLSCAASGSTFSNNAMA

WYRQAPGKQRELVAYTSSGGFTNYGDSVKGRFTIS

EDNAKSTVYLQMTSLKPEDTAVYYCSAGGTYRSGN

VYFFPRSWGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 225.

In one embodiment, the antibody or binding fragment thereof of the present disclosure comprises a humanized variant of the heavy chain variable region of SEQ ID NO: 225, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 225), or a combination of these approaches. The humanized framework regions are designed to be similar in length and sequence to the parental framework sequences of SEQ ID NO: 225. In one embodiment, the humanized framework regions share 50%, 55%, 60%, 65%, 70%, 75%, 80%, 85%, 90%, 95% or more sequence identity to the framework regions of SEQ ID NO: 225. In another embodiment, the humanized framework regions are 60%, 65%, 70%, 75%, 80%, 85%, 90%, 95% or more similar in length to the framework regions of SEQ ID NO: 225. Humanized variants of the heavy chain variable region of SEQ ID NO: 225 share at least 50%, at least 55%, at least 60%, at least 65%, at least 70%, at least 75%, at least 80%, at least 85%, at least 90%, at least 95% sequence identity along the entire length of SEQ ID 225.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 225. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 226, or a modified amino acid sequence thereof containing 1, 2, 3, or more amino acid residue modifications as compared to SEQ ID NO: 226; a H-CDR2 having the amino acid sequence of SEQ ID NO: 227, or a modified amino acid sequence thereof containing 1, 2, 3, or more amino acid residue modifications as compared to SEQ ID NO: 227; and a H-CDR3 comprising the amino acid sequence of SEQ ID NO: 228, or a modified amino acid sequence thereof, said modified amino acid sequence containing 1, 2, 3, or more amino acid modifications as compared to SEQ ID NO: 228.

An exemplary single domain antibody having this heavy chain variable region is referred to herein as the S-sR2-1G4 antibody. The S-sR2-1G4 antibody comprises a $V_H$ chain amino acid sequence of SEQ ID NO: 229 as shown below.

```
                                    SEQ ID NO: 229
QVQLQQSGGGLVQPGCISLRLSCAASGSIFSINSM

AWYRQAPGNQRELVATISSRSTTYYAPSYKGRYNS

RDNAKINIVYLQMNSLKPEDTAVYYCKAGSVGIWY

WGQGTLYIVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 229.

In one embodiment, the antibody or binding fragment thereof of the present disclosure comprises a humanized variant of the heavy chain variable region of SEQ ID NO: 229, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 229), or a combination of these approaches. The humanized framework regions are designed to be similar in length and sequence to the parental framework sequences of SEQ ID NO: 229. In one embodiment, the humanized framework regions share 50%, 55%, 60%, 65%, 70%, 75%, 80%, 85%, 90%, 95% or more sequence identity to the framework regions of SEQ ID NO: 229. In another embodiment, the humanized framework regions are 60%, 65%, 70%, 75%, 80%, 85%, 90%, 95% or more similar in length to the framework regions of SEQ ID NO: 229. Humanized variants of the heavy chain variable region of SEQ ID NO: 229 share at least 50%, at least 55%, at least 60%, at least 65%, at least 70%, at least 75%, at least 80%, at least 85%, at least 90%, at least 95% sequence identity along the entire length of SEQ ID 229.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 229. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 230, or a modified amino acid sequence thereof containing 1, 2, 3, or more amino acid residue modifications as compared to SEQ ID NO: 230; a H-CDR2 having the amino acid sequence of SEQ ID NO: 231, or a modified amino acid sequence thereof containing 1, 2, 3, or more amino acid residue modifications as compared to SEQ ID NO: 231; and a H-CDR3 comprising the amino acid sequence of SEQ ID NO: 232, or a modified amino acid sequence thereof, said modified amino acid sequence containing 1, 2, 3, or more amino acid modifications as compared to SEQ ID NO: 232.

An exemplary single domain antibody having this heavy chain variable region is referred to herein as the S-sR2-2C10 antibody. The S-sR2-2C10 antibody comprises a $V_H$ chain amino acid sequence of SEQ ID NO: 233 as shown below.

```
                                    SEQ ID NO: 233
QVQLQESGGGLVQAGGSLRLSCLASMTTLGFKTMG

WYRQAPGKQRELVAMTSGGTANYADSVKGRFAISR

ENAKNTLYLQMNSLKPEDTALYYCASTTGWTEVGG

RNDYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 233.

In one embodiment, the antibody or binding fragment thereof of the present disclosure comprises a humanized variant of the heavy chain variable region of SEQ ID NO: 233, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 233), or a combination of these approaches. The humanized framework regions are designed to be similar in length and sequence to the parental framework sequences of SEQ ID NO: 233. In one embodiment, the humanized framework regions share 50%, 55%, 60%, 65%, 70%, 75%, 80%, 85%, 90%, 95% or more sequence identity to the framework regions of SEQ ID NO: 233. In another embodiment, the humanized framework regions are 60%, 65%, 70%, 75%, 80%, 85%, 90%, 95% or more similar in length to the framework regions of SEQ ID NO: 233. Humanized variants of the heavy chain variable region of SEQ ID NO: 233 share at least 50%, at least 55%, at least 60%, at least 65%, at least 70%, at least 75%, at least 80%, at least 85%, at least 90%, at least 95% sequence identity along the entire length of SEQ ID 233.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 233. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 234, or a modified amino acid sequence thereof containing 1, 2, 3, or more amino acid residue modifications as compared to SEQ ID NO: 234; a H-CDR2 having the amino acid sequence of SEQ ID NO: 235, or a modified amino acid sequence thereof containing 1, 2, 3, or more amino acid residue modifications as compared to SEQ ID NO: 235; and a H-CDR3 comprising the amino acid sequence of SEQ ID NO: 236, or a modified amino acid sequence thereof, said modified amino acid sequence containing 1, 2, 3, or more amino acid modifications as compared to SEQ ID NO: 236.

An exemplary single domain antibody having this heavy chain variable region is referred to herein as the S-sR2-2E9 antibody. The S-sR2-2E9 antibody comprises a $V_H$ chain amino acid sequence of SEQ ID NO: 237 as shown below.

SEQ ID NO: 237
QVQLQESGGGLVQTGGSLRLSCAASGRTFRVNAMG

VVYRQAPGKQREFVAAVTNGGSTTYADSVKGRFTI

SRDNAKNTIYLQMNRLEPEDTALYYCNAERRFGMR

QVWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 237.

In one embodiment, the antibody or binding fragment thereof of the present disclosure comprises a humanized variant of the heavy chain variable region of SEQ ID NO: 237, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 237), or a combination of these approaches. The humanized framework regions are designed to be similar in length and sequence to the parental framework sequences of SEQ ID NO: 237. In one embodiment, the humanized framework regions share 50%, 55%, 60%, 65%, 70%, 75%, 80%, 85%, 90%, 95% or more sequence identity to the framework regions of SEQ ID NO: 237. In another embodiment, the humanized framework regions are 60%, 65%, 70%, 75%, 80%, 85%, 90%, 95% or more similar in length to the framework regions of SEQ ID NO: 237. Humanized variants of the heavy chain variable region of SEQ ID NO: 237 share at least 50%, at least 55%, at least 60%, at least 65%, at least 70%, at least 75%, at least 80%, at least 85%, at least 90%, at least 95% sequence identity along the entire length of SEQ ID 237.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 237. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 238, or a modified amino acid sequence thereof containing 1, 2, 3, or more amino acid residue modifications as compared to SEQ ID NO: 238; a H-CDR2 having the amino acid sequence of SEQ ID NO: 239, or a modified amino acid sequence thereof containing 1, 2, 3, or more amino acid residue modifications as compared to SEQ ID NO: 239; and a H-CDR3 comprising the amino acid sequence of SEQ ID NO: 240, or a modified amino acid sequence thereof, said modified amino acid sequence containing 1, 2, 3, or more amino acid modifications as compared to SEQ ID NO: 240.

An exemplary single domain antibody having this heavy chain variable region is referred to herein as the S-sR2-G11 antibody. The S-sR2-G11 antibody comprises a $V_H$ chain amino acid sequence of SEQ ID NO: 241 as shown below.

SEQ ID NO: 241
QVQLQESGGCLVQPGGSLRLSCAASGRVFSINTMG

WYRQAPGKQRELVASMTRGGSANYADSVKGRFTTS

RDNAKNMVYLQMNRLKAEDTAVYYCNAARGWRIYW

GKGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 241.

In one embodiment, the antibody or binding fragment thereof of the present disclosure comprises a humanized variant of the heavy chain variable region of SEQ ID NO: 241, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 241), or a combination of these approaches. The humanized framework regions are designed to be similar in length and sequence to the parental framework sequences of SEQ ID NO: 241. In one embodiment the humanized framework regions share 50%, 55%, 60%, 65%, 70%, 75%, 80%, 85%, 90%, 95% or more sequence identity to the framework regions of SEQ ID NO: 241. In another embodiment, the humanized framework regions are 60%, 65%, 70%, 75%, 80%, 85%, 90%, 95% or more similar in length to the framework regions of SEQ ID NO: 241. Humanized variants of the heavy chain variable region of SEQ ID NO: 241 share at least 50%, at least 55%, at least 60%, at least 65%, at least 70%, at least 75%, at least 80%, at least 85%, at least 90%, at least 95% sequence identity along the entire length of SEQ ID 241.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 241. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 340, or a modified amino acid sequence thereof containing 1, 2, 3, or more amino acid residue modifications as compared to SEQ ID NO: 340; a H-CDR2 having the amino acid sequence of SEQ ID NO: 341, or a modified amino acid sequence thereof containing 1, 2, 3, or more amino acid residue modifications as compared to SEQ ID NO: 341; and a H-CDR3 comprising the amino acid sequence of SEQ ID NO: 342, or a modified amino acid sequence thereof, said modified amino acid sequence containing 1, 2, 3, or more amino acid modifications as compared to SEQ ID NO: 342.

An exemplary single domain antibody having this heavy chain variable region is referred to herein as the 90-S-sR1-2D1 antibody. The 90-S-sR1-2D1 antibody comprises a $V_H$ chain amino acid sequence of SEQ ID NO: 343 as shown below.

SEQ ID NO: 343
QVQLQESGGGLVQAGGSLRLSCAASGSIFRINGMGWIRQAPGKEREVVAAV

NWSGERTYYVDSVKGRFTISREKGNRIYLQMNDLEPDDTAVYYCAADTDYR

LDGSTWITNLYSGSLGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 343.

In one embodiment, the antibody or binding fragment thereof of the present disclosure comprises a humanized variant of the heavy chain variable region of SEQ ID NO: 343, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 343), or a combination of these approaches. The humanized framework regions are designed to be similar in length and sequence to the parental framework sequences of SEQ ID NO: 343. In one embodiment, the humanized framework regions share 50%, 55%, 60%, 65%, 70%, 75%, 80%, 85%, 90%, 95% or more sequence identity to the framework regions of SEQ ID NO: 343. In another embodiment, the humanized framework regions are 60%, 65%, 70%, 75%, 80%, 85%, 90%, 95% or more similar in length to the framework regions of SEQ ID NO: 343. Humanized variants of the heavy chain variable region of SEQ ID NO: 343 share at least 50%, at least 55%, at least 60%, at least 65%, at least 70%, at least 75%, at least 80%, at least 85%, at least 90%, at least 95% sequence identity along the entire length of SEQ ID 343.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 343. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In another embodiment, the antibody or binding fragment thereof as disclosed herein comprises a heavy chain variable region having a H-CDR1 with an amino acid sequence selected from SEQ ID NOs: 146-160, or a modified amino acid sequence thereof containing 1, 2, 3, 4, 5, or 6 amino acid residue modifications as compared to SEQ ID NOs: 146-160 that maintain or enhance binding specificity of the H-CDR1. In one embodiment, the amino acid sequence of the H-CDR1 contains no more than 1, 2, or 3 amino acid modifications as compared to SEQ ID NOs: 146-160, respectively. The HCVR further comprises a H-CDR2 with an amino acid sequence selected from SEQ ID NOs: 161-175, or a modified amino acid sequence thereof containing 1, 2, 3, 4, 5, or 6, amino acid residue modifications as compared to SEQ ID NOs: 161-175 that maintain or enhance binding specificity of the H-CDR2. In one embodiment, the amino acid sequence of the H-CDR2 contains no more than 1, 2, or 3, amino acid modifications as compared to SEQ ID NOs: 161-175, respectively. The HCVR of the antibody or binding fragment thereof comprises a H-CDR3 with an amino acid sequence selected from SEQ ID NOs: 176-190, or a modified amino acid sequence thereof containing 1, 2, 3, 4, 5, 6 or 7 amino acid residue modifications as compared to SEQ ID NOs: 176-190 that maintain or enhance binding specificity of the H-CDR3. In one embodiment, the amino acid sequence of the H-CDR3 contains no more than 1, 2, or 3 amino acid modifications as compared to SEQ ID NOs: 176-190, respectively. The amino acid sequences of SEQ ID NOs: 146-190 are provided in Table 2 below.

as compared to SEQ ID NO: 161; and a H-CDR3 comprising the amino acid sequence of SEQ ID NO: 176, or a modified amino acid sequence thereof, said modified amino acid

TABLE 2

α-Synuclein Single Domain Antibody Complementarity Determining Regions

| Antibody ID | descr | sequence | SEQ ID NO: | descr | sequence | SEQ ID NO: | descr | sequence | SEQ ID NO: |
|---|---|---|---|---|---|---|---|---|---|
| 02-S-bR1-2C7 | CDR1 | ASGGTFGAGV | 146 | CDR2 | SMGSDGFTQIEN | 161 | CDR3 | HYADGRFGS | 176 |
| 04-S-bR2-1C4; 10-S-bR1-2D8; 13-S-bR2-1E12; 14-S-bR2-1G7; 17-S-bR1-1C11; 18-S-bR1-2F1-; 20-S-bR2-1C9; 27-S-bR2-1B1; 28-S-bR2-1C12; 30-S-bR2-1H1; 38-S-bR2-1H7; 44-S-bR2-1D2; 60-S-bR2-1D12; 67-S-bR2-1B9; 68-S-bR2-1E2; 69-S-bR2-1F10; 75-S-bR2-1B11; 81-S-bR1-2B7; 91-S-bR2-1C3; 92-S-bR2-1E6 | CDR1 | ASGSNISTNV | 147 | CDR2 | SISTSGTTNYLA | 162 | CDR3 | YAAWPLNT | 177 |
| 05-S-bR2-1E10; 06-S-bR2-1G5; 26-S-bR1-2H12; 46-S-bR2-1H11; 52-S-bR2-1D6; 54-S-bR2-1H12; 57-S-bR1-1H3; 59-S-bR2-1B8; 76-S-bR2-1E3; 77-S-bR2-1G1; 83-S-bR2-1C1; 93-S-bR2-1G4 | CDR1 | ASGSTFSITY | 148 | CDR2 | EMSRRGSTFYAD | 163 | CDR3 | SVGARRDEDDYVY | 178 |
| 09-S-bR1-1B5 | CDR1 | DSRTIFIFNA | 149 | CDR2 | AISSGGSTKYAD | 164 | CDR3 | AASRSGRWLDDAR | 179 |
| 12-S-bR2-1C5; 21-S-bR2-1F1; 25-S-bR1-1D9; 35-S-bR2-1B2; 43-S-bR2-1B3; 53-S-bR2-1F7 | CDR1 | ASGIPFSIIY | 150 | CDR2 | EMSSRGSKFYAD | 165 | CDR3 | SVGARRDDNDYVY | 180 |
| 22-S-bR2-1G10 | CDR1 | ASGNIFGINS | 151 | CDR2 | DITRGNRKYAD | 166 | CDR3 | NAEIVTQIPFPPR | 181 |
| 29-S-bR2-1F2 | CDR1 | ASGFTFSSYW | 152 | CDR2 | TINTGGYTTYYS | 167 | CDR3 | CAKAYGSMWSGIW | 182 |
| 33-S-bR1-1G3 | CDR1 | VSGSIISHNV | 153 | CDR2 | CISGSGFTNYIA | 168 | CDR3 | YTAWPNT | 183 |
| 36-S-bR1-1D1 | CDR1 | ASGRIFN1ED | 154 | CDR2 | TITRTGAPTYAN | 169 | CDR3 | NAKDVTVIPFPPK | 184 |
| 41-S-bR1-1H1 | CDR1 | ASGSVSAIET | 155 | CDR2 | VISTGGTTKYAP | 170 | CDR3 | AADWRTILGWKTR | 185 |
| 45-S-bR2-1F6; 61-S-bR2-1F8; 84-S-bR2-1E5 | CDR1 | AFGSTSSITY | 156 | CDR2 | EMSRRGSTFYAD | 171 | CDR3 | SVGARRDEDDYVY | 186 |
| 49-S-bR1-1H2 | CDR1 | ASGGPVSDNV | 157 | CDR2 | QITSGGATSYAD | 172 | CDR3 | NVALRY | 187 |
| 51-S-bR2-1B7; 85-S-bR2-1G2 | CDR1 | ASGSTFSITY | 158 | CDR2 | EISSRGSVFYAD | 173 | CDR3 | SVGARRDEDDYVY | 188 |
| 73-S-bR1-2B2 | CDR1 | GAGSAFGWNA | 159 | CDR2 | TIESGGWADYSV | 174 | CDR3 | NQLTY | 189 |
| 89-S-bR1-2C6 | CDR1 | PSGSIFSFDV | 160 | CDR2 | QHRTPGAIDYAD | 175 | CDR3 | NLRRWSYDY | 190 |

In one embodiment, the antibody or binding fragment thereof has a heavy chain variable region with a H-CDR1 having the amino acid sequence of SEQ ID NO: 146, or a modified amino acid sequence thereof containing 1, 2, 3, or more amino acid residue modifications as compared to SEQ ID NO: 146; a H-CDR2 having the amino acid sequence of SEQ ID NO: 161, or a modified amino acid sequence thereof containing 1, 2, 3, or more amino acid residue modifications as compared to SEQ ID NO: 161; and a H-CDR3 comprising the amino acid sequence of SEQ ID NO: 176, or a modified amino acid sequence containing 1, 2, 3, or more amino acid modifications as compared to SEQ ID NO: 176.

An exemplary single domain antibody having this heavy chain variable region is referred to herein as the 02-S-bR1-2C7 antibody. The 02-S-bR1-2C7 antibody comprises a V$_H$ chain amino acid sequence of SEQ ID NO: 191 as shown below.

SEQ ID NO: 191
QVQLQESGGGLVQPGDSLKLSCAASGGTFGAGVVAWYRQSPGKQREMVGSM

GSDGFTQIENGMKGRFTISGAGDKKTVFLQMNNLKPEDTAVYFCHYADGRF

GSWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 191.

In one embodiment, the antibody or binding fragment thereof of the present disclosure comprises a humanized variant of the heavy chain variable region of SEQ ID NO: 191, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 191), or a combination of these approaches. The humanized framework regions are designed to be similar in length and sequence to the parental framework sequences of SEQ ID NO: 191. In one embodiment, the humanized framework regions share 50%, 55%, 60%, 65%, 70%, 75%, 80%, 85%, 90%, 95% or more sequence identity to the framework regions of SEQ ID NO: 191. In another embodiment, the humanized framework regions are 60%, 65%, 70%, 75%, 80%, 85%, 90%, 95% or more similar in length to the framework regions of SEQ ID NO: 191. Humanized variants of the heavy chain variable region of SEQ ID NO: 191 share at least 50%, at least 55%, at least 60%, at least 65%, at least 70%, at least 75%, at least 80%, at least 85%, at least 90%, at least 95% sequence identity along the entire length of SEQ ID 191.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 191. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 147, or a modified amino acid sequence thereof containing 1, 2, 3, or more amino acid residue modifications as compared to SEQ ID NO: 147; a H-CDR2 having the amino acid sequence of SEQ ID NO: 162, or a modified amino acid sequence thereof containing 1, 2, 3, or more amino acid residue modifications as compared to SEQ ID NO: 162; and a H-CDR3 comprising the amino acid sequence of SEQ ID NO: 177, or a modified amino acid sequence thereof, said modified amino acid sequence containing 1, 2, 3, or more amino acid modifications as compared to SEQ ID NO: 177.

An exemplary single domain antibody having this combination of heavy chain variable region CDRs is referred to herein as the 04-S-bR2-1C4 antibody. The 04-S-bR2-1C4 antibody comprises a $V_H$ chain amino acid sequence of SEQ ID NO: 192 as shown below.

SEQ ID NO: 192
QVQLQESGGGLVQAGGSLRLSCAASGSNISTNVMAWYRRAPGNQRDMVASI

STSGTTNYLASVKGRFTISRDNAKNTVSLQMNSLKPEDTAVYTCYAAWPLN

TWGQGTQVTVSS

Other antibodies of the disclosure comprising the amino acid sequence of SEQ ID NO: 192 include 20-S-bR2-1C9; 27-S-bR2-1B1; 28-S-bR2-1C12; 38-S-bR2-1H7; 44-S-bR2-1D2; 60-S-bR2-1D12; 69-S-bR2-1F10; 75-S-bR2-1B11; and 91-S-bR2-1C3.

Another exemplary single domain antibody having this combination of heavy chain variable region CDRs is referred to herein as the 10-S-bR1-2D8 antibody. The 10-S-bR1-2D8 antibody comprises a $V_H$ chain amino acid sequence of SEQ ID NO: 1% as shown below.

SEQ ID NO: 196
QVQLQESGGGLVQAGGSLRLSCAASGSNISTNVMAWYRRAPGNQRDMVASI

STSGTTNYLASVKGRFTISRDNAKNTVSLQMNSLKPEDTAVYTCYAAWPLN

TWGQGTLVTVSS

Other antibodies of the disclosure comprising the amino acid sequence of SEQ ID NO: 196 include 13-S-bR2-1E12; 18-S-bR1-2F1; 67-S-bR2-1B9; 81-S-bR1-2B7; and 92-S-bR2-1E6.

Other exemplary single domain antibodies having this combination of heavy chain variable region CDRs are referred to herein as the 14-S-bR2-1G7 antibody and the 17-S-bR1-1C11 antibody. These antibodies comprises a $V_H$ chain amino acid sequence of SEQ ID NO: 198 as shown below.

SEQ ID NO: 198
QVQLQASGGGLVQAGGSLRLSCAASGSNISTNVMAWYRRAPGNQRDMVASI

STSGTTNYLASVKGRFTISRDNAKNTVSLQMNSLKPEDTAVYTCYAAWPLN

TWGQGTQVTVSS

Another exemplary single domain having this combination of heavy chain variable region CDRs is referred to herein as the 30-S-bR2-1H1 antibody. The 30-S-bR2-1H1 antibody comprises a $V_H$ chain amino acid sequence of SEQ ID NO: 202 as shown below.

SEQ ID NO: 202
QVQLQQSGGGLVQAGGSLRLSCAASGSNISTNVMAWYRRAPGNQRDMVASI

STSGTTNYLASVKGRFTISRDNAKNTVSLQMNSLKPEDTAVYTCYAAWPLN

TWGQGTQVTVSS

Another exemplary single domain antibody having this combination of heavy chain variable region CDRs is referred to herein as the 68-S-bR2-1E2 antibody. The 68-S-bR2-1E2 antibody comprises a $V_H$ chain amino acid sequence of SEQ ID NO: 212 as shown below.

SEQ ID NO: 212
QVQLQEFGGGLVQAGESLRLSCVASGSNISTNVMAWYRRAPGNQRDMVASI

STSGTTNYLASVKGRFTISRDNAKNTVSLQMNSLKPEDTAVYTCYAAWPLN

TWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 192, SEQ ID NO: 196, SEQ ID NO: 198, SEQ ID NO: 202, or SEQ ID NO: 212.

In one embodiment, the antibody or binding fragment thereof of the present disclosure comprises a humanized variant of the heavy chain variable region of SEQ ID NO: 192, SEQ ID NO: 196, SEQ ID NO: 198, SEQ ID NO: 202, or SEQ ID NO: 212, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 192, SEQ ID NO: 1%, SEQ ID NO: 198, SEQ ID NO: 202, or SEQ ID NO: 212), or a combination of these approaches. The humanized framework regions are designed to be similar in length and sequence to the parental framework sequences of SEQ ID NO: 192, SEQ ID NO: 196, SEQ ID NO: 198, SEQ ID NO: 202, or SEQ ID NO: 212. In one embodiment, the humanized framework regions share 50%, 55%, 60%, 65%, 70%, 75%, 80%, 85%, 90%, 95% or more sequence identity to the framework regions of SEQ ID NO: 192, SEQ ID NO: 196, SEQ ID NO: 198, SEQ ID NO: 202, or SEQ ID NO: 212. In another embodiment, the humanized framework regions are 60%, 65%, 70%, 75%, 80%, 85%, 90%, 95% or more similar in length to the framework regions of SEQ ID NO: 192, SEQ ID NO: 196, SEQ ID NO: 198, SEQ ID NO: 202, or SEQ ID NO: 212. Humanized variants of the heavy chain variable region of SEQ ID NO: 192, SEQ ID NO: 196, SEQ ID NO: 198, SEQ ID NO: 202, or SEQ ID NO: 212 share at least 50%, at least 55%, at least 60%, at least 65%, at least 70%, at least 75%, at least 80%, at least 85%, at least 90%, at least 95% sequence identity along the entire length of SEQ ID NO: 192, SEQ ID NO: 196, SEQ ID NO: 198, SEQ ID NO: 202, or SEQ ID NO: 212, respectively.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 192, SEQ ID NO: 196, SEQ ID NO: 198, SEQ ID NO: 202, or SEQ ID NO: 212. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 148, or a modified amino acid sequence thereof containing 1, 2, 3, or more amino acid residue modifications as compared to SEQ ID NO: 148; a H-CDR2 having the amino acid sequence of SEQ ID NO: 163, or a modified amino acid sequence thereof containing 1, 2, 3, or more amino acid residue modifications as compared to SEQ ID NO: 163; and a H-CDR3 comprising the amino acid sequence of SEQ ID NO: 178, or a modified amino acid sequence thereof, said modified amino acid sequence containing 1, 2, 3, or more amino acid modifications as compared to SEQ ID NO: 178.

An exemplary single domain antibody having this combination of heavy chain variable region CDRs is referred to herein as the 05-S-bR2-1E10 antibody. The 05-S-bR2-1E10 antibody comprises a $V_H$ chain amino acid sequence of SEQ ID NO: 193 as shown below.

SEQ ID NO: 193
QVQLQESGGGLVQAGGSLRLSCAASGSTFSITYMAWFRQAPEKQRELVAEM

SRRGSTFYADSVKGRFTISRDNTKNTVYLQMNSLEPEDTAVYYCSVGARRD

EDDYVYWGQGTQVTVSS

Other antibodies of the disclosure comprising the amino acid sequence of SEQ ID NO: 193 include 26-S-bR1-2H12; 46-S-bR2-1H11; 57-S-bR1-1H3; 83-S-bR2-1C1; 93-S-bR2-1G4.

Another exemplary single domain antibody having this combination of heavy chain variable region CDRs is referred to herein as the 06-S-bR2-1G5 antibody. The 06-S-bR2-1G5 antibody comprises a $V_H$ chain amino acid sequence of SEQ ID NO: 194 as shown below.

SEQ ID NO: 194
QVQLQQSGGGLVQAGGSLRLSCAASGSTFSITYMAWFRQAPEKQRELVAEM

SRRGSTFYADSVKGRFTISRDNTKNTVYLQMNSLEPEDTAVYYCSVGARRD

EDDYVYWGQGTQVTVSS

Other exemplary single domain antibodies having this combination of heavy chain variable region CDRs are referred to herein as the 52-S-bR2-1D6 antibody and the 54-S-bR2-1H12 antibody. These antibodies comprises a $V_H$ chain amino acid sequence of SEQ ID NO: 209 as shown below.

SEQ ID NO: 209
QVQLQESGGGLVQAGGSLRLSCAASGSTFSITYMAWFRQAPEKQRELVAEM

SRRGSTFYADSVKGRFTISRDNTKNTVYLQMNSLEPEDTAVYYCSVGARRD

EDDYVYWGQGTLVTVSS

Another exemplary single domain antibody having this combination of heavy chain variable region CDRs is referred to herein as the 59-S-bR2-1B8 antibody. The 59-S-bR2-1B8 antibody comprises a $V_H$ chain amino acid sequence of SEQ ID NO: 211 as shown below.

SEQ ID NO: 211
QVQLQEFGGGLVQAGGSLRLSCAASGSTFSITYMAWFRQAPEKQRELVAEM

SRRGSTFYADSVKGRFTISRDNTKNTVYLQMNSLEPEDTAVYYCSVGARRD

EDDYVYWGQGTQVTVSS

Another exemplary single domain antibody having this combination of heavy chain variable region CDRs is referred to herein as the 76-S-bR2-1E3 antibody. The 76-S- bR2-1E3 antibody comprises a $V_H$ chain amino acid sequence of SEQ ID NO: 214 as shown below.

SEQ ID NO: 214
QVQLQESGGGLVQAGGSLRLSCAASGSTFSITYMTWFRQAPEKQRELVAEM

SRRGSTFYADSVKARFTISRDNTKNTVYLQMNSLEPEDTAVYYCSVGARRD

EDDYVYWGQGTQVTVSS

Another exemplary single domain antibody having this combination of heavy chain variable region CDRs is referred to herein as the 77-S-bR2-1G1 antibody. The 77-S-bR2-1G1 antibody comprises a $V_H$ chain amino acid sequence of SEQ ID NO: 215 as shown below.

SEQ ID NO: 215
QVQLQEFGGGLVQAGGSLRLSCAASGSTFSITYMAWFRQAPEKQRELVAEM

SRRGSTFYADSVKGRFTISRDNTKNTVYLQMNSLEPEDTAVYYCSVGARRD

EDDYVYWGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 193, SEQ ID NO: 194, SEQ ID NO: 209, SEQ ID NO: 211, SEQ ID NO: 214, or SEQ ID NO: 215.

In one embodiment, the antibody or binding fragment thereof of the present disclosure comprises a humanized variant of the heavy chain variable region of SEQ ID NO: 193, SEQ ID NO: 194, SEQ ID NO: 209, SEQ ID NO: 211, SEQ ID NO: 214, or SEQ ID NO: 215, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 193, SEQ ID NO: 194, SEQ ID NO: 209, SEQ ID NO: 211, SEQ ID NO: 214, or SEQ ID NO: 215), or a combination of these approaches. The humanized framework regions are designed to be similar in length and sequence to the parental framework sequences of SEQ ID NO: 193, SEQ ID NO: 194, SEQ ID NO: 209, SEQ ID NO: 211, SEQ ID NO: 214, or SEQ ID NO: 215. In one embodiment, the humanized framework regions share 50%, 55%, 60%, 65%, 70%, 75%, 80%, 85%, 90%, 95% or more sequence identity to the framework regions of SEQ ID NO: 193, SEQ ID NO: 194, SEQ ID NO: 209, SEQ ID NO: 211, SEQ ID NO: 214, or SEQ ID NO: 215 In another embodiment, the humanized framework regions are 60%, 65%, 70%, 75%, 80%, 85%, 90%, 95% or more similar in length to the framework regions of SEQ ID NO: 193, SEQ ID NO: 194, SEQ ID NO: 209, SEQ ID NO: 211, SEQ ID NO: 214, or SEQ ID NO: 215. Humanized variants of the heavy chain variable region of SEQ ID NO: 193, SEQ ID NO: 194, SEQ ID NO: 209, SEQ ID NO: 211, SEQ ID NO: 214, or SEQ ID NO: 215 share at least 50%, at least 55%, at least 60%, at least 65%, at least 70%, at least 75%, at least 80%, at least 85%, at least 90%, at least 95% sequence identity along the entire length of SEQ ID NO: 193, SEQ ID NO: 194, SEQ ID NO: 209, SEQ ID NO: 211, SEQ ID NO: 214, or SEQ ID NO: 215, respectively.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 193, SEQ ID NO: 194, SEQ ID NO: 209, SEQ ID NO: 211, SEQ ID NO: 214, or SEQ ID NO: 215. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 149, or a modified amino acid sequence thereof containing 1, 2, 3, or more amino acid residue modifications as compared to SEQ ID NO: 149; a H-CDR2 having the amino acid sequence of SEQ ID NO: 164, or a modified amino acid sequence thereof containing 1, 2, 3, or more amino acid residue modifications as compared to SEQ ID NO: 164; and a H-CDR3 comprising the amino acid sequence of SEQ ID NO: 179, or a modified amino acid sequence thereof, said modified amino acid sequence containing 1, 2, 3, or more amino acid modifications as compared to SEQ ID NO: 179.

An exemplary single domain antibody having this heavy chain variable region is referred to herein as the 09-S-bR1-1B5 antibody. The 09-S-bR1-1B5 antibody comprises a $V_H$ chain amino acid sequence of SEQ ID NO: 195 as shown below.

SEQ ID NO: 195
QVQLQESGGGSVQAGGSLRLSCADSRTIFIFNAMAWYRQAPGKQRELVAAI

SSGGSTKYADSVKGRFTISSSNAKNTKYLQMNRLKPEDTAVYYCAASRSGR

WLDDARDYEYWGPGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 195.

In one embodiment, the antibody or binding fragment thereof of the present disclosure comprises a humanized variant of the heavy chain variable region of SEQ ID NO: 195, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 195), or a combination of these approaches. The humanized framework regions are designed to be similar in length and sequence to the parental framework sequences of SEQ ID NO: 195. In one embodiment, the humanized framework regions share 50%, 55%, 60%, 65%, 70%, 75%, 80%, 85%, 90%, 95% or more sequence identity to the framework regions of SEQ ID NO: 195. In another embodiment, the humanized framework regions are 60%, 65%, 70%, 75%, 80%, 85%, 90%, 95% or more similar in length to the framework regions of SEQ ID NO: 195. Humanized variants of the heavy chain variable region of SEQ ID NO: 195 share at least 50%, at least 55%, at least 60%, at least 65%, at least 70%, at least 75%, at least 80%, at least 85%, at least 90%, at least 95% sequence identity along the entire length of SEQ ID 195.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 195. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 150, or a modified amino acid sequence thereof containing 1, 2, 3, or more amino acid residue modifications as compared to SEQ ID NO: 150; a H-CDR2 having the amino acid sequence of SEQ ID NO: 165, or a modified amino acid sequence thereof containing 1, 2, 3, or more amino acid residue modifications as compared to SEQ ID NO: 165; and a H-CDR3 comprising the amino acid sequence of SEQ ID NO: 180, or a modified amino acid sequence thereof, said modified amino acid sequence containing 1, 2, 3, or more amino acid modifications as compared to SEQ ID NO: 180.

An exemplary single domain antibody having this heavy chain variable region is referred to herein as the 12-S-bR2-1C5 antibody. The 12-S-bR2-1C5 antibody comprises a $V_H$ chain amino acid sequence of SEQ ID NO: 197 as shown below.

SEQ ID NO: 197
QVQLQQSGGGLVQAGGSLRLSCAASGIPFSIIYMAWFRQAPEKQRELVAE

MSSRGSKFYADSVKGRFTISRDNAKNTLYLQMNSLEPEDTAVYYCSVGAR

RDDNDYVYWGQGTQVTVSS

Other exemplary single domain antibodies having this combination of heavy chain CDRs described herein include, the 21-S-bR2-1F1 antibody, the 25-S-bR1-1D9 antibody, the 35-S-bR2-1B2 antibody, and the 43-S-bR2-1B3 antibody. These antibodies comprise the $V_H$ chain amino acid sequence of SEQ ID NO: 199 as shown below.

SEQ ID NO: 199
QVQLQESGGGLVQAGGSLRLSCAASGIPFSIIYMAWFRQAPEKQRELVAE

MSSRGSKFYADSVKGRFTISRDNAKNTLYLQMNSLEPEDTAVYYCSVGAR

RDDNDYVYWGQGTQVTVSS

Another exemplary single domain antibody having this combination of heavy chain CDRs is referred to herein as the 53-S-bR2-1F7 antibody. The 53-S-bR2-1F7 antibody comprises a $V_H$ chain amino acid sequence of SEQ ID NO: 210 as shown below.

SEQ ID NO: 210
QVQLQESGGGLVQAGGSLRLSCAASGIPFSIIYMAWFRQAPEKQRELVAE

MSSRGSKFYADSVKGRFTISRDNAKNTLYLQMNSLEPEDTAVYYCSVGAR

RDDNDYVYWGQGTLNTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 197, SEQ ID NO: 199, or SEQ ID NO: 210.

In one embodiment, the antibody or binding fragment thereof of the present disclosure comprises a humanized variant of the heavy chain variable region of SEQ ID NO: 197, SEQ ID NO: 199, or SEQ ID NO: 210, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 197, SEQ ID NO: 199, or SEQ ID NO: 210), or a combination of these approaches. The humanized framework regions are designed to be similar in length and sequence to the parental framework sequences of SEQ ID NO: 197, SEQ ID NO: 199, or SEQ ID NO: 210. In one embodiment, the humanized framework regions share 50%, 55%, 60%, 65%, 70%, 75%, 80%, 85%, 90%, 95% or more sequence identity to the framework regions of SEQ ID NO: 197, SEQ ID NO: 199, or SEQ ID NO: 210. In another embodiment, the humanized framework regions are 60%, 65%, 70%, 75%, 80%, 85%, 90%, 95% or more similar in length to the framework regions of SEQ ID NO: 197, SEQ ID NO: 199, or SEQ ID NO: 210. Humanized variants of the heavy chain variable region of SEQ ID NO: 197, SEQ ID NO: 199, or SEQ ID NO: 210 share at least 50%, at least 55%, at least 60%, at least 65%, at least 70%, at least 75%, at least 80%, at least 85%, at least 90%, at least 95% sequence identity along the entire length of SEQ ID NO: 197, SEQ ID NO: 199, or SEQ ID NO: 210, respectively.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 197, SEQ ID NO: 199, or SEQ ID NO: 210. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 151, or a modified amino acid sequence thereof containing 1, 2, 3, or more amino acid residue modifications as compared to SEQ ID NO: 151; a H-CDR2 having the amino acid sequence of SEQ ID NO: 166, or a modified amino acid sequence thereof containing 1, 2, 3, or more amino acid residue modifications as compared to SEQ ID NO: 166; and a H-CDR3 comprising the amino acid sequence of SEQ ID NO: 181, or a modified amino acid sequence thereof, said modified amino acid sequence containing 1, 2, 3, or more amino acid modifications as compared to SEQ ID NO: 181.

An exemplary single domain antibody having this heavy chain variable region is referred to herein as the 22-S-bR2-1G10 antibody. The 22-S-bR2-1G10 antibody comprises a V$_H$ chain amino acid sequence of SEQ ID NO: 200 as shown below.

SEQ ID NO: 200
QVQLQASGGGVVQSGGSLRLSCVASGNIFGINSMAWYRQAPGKQRELVAD

ITRGNRKYADSVKGRFISQDNAKNTVYLQMNRLKPEDTAVYFCNAEIVTQ

IPFPPREFWGRGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 200.

In one embodiment, the antibody or binding fragment thereof of the present disclosure comprises a humanized variant of the heavy chain variable region of SEQ ID NO: 200, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 200), or a combination of these approaches. The humanized framework regions are designed to be similar in length and sequence to the parental framework sequences of SEQ ID NO: 200. In one embodiment, the humanized framework regions share 50%, 55%, 60%, 65%, 70%, 75%, 80%, 85%, 90%, 95% or more sequence identity to the framework regions of SEQ ID NO: 200. In another embodiment, the humanized framework regions are 60%, 65%, 70%, 75%, 80%, 85%, 90%, 95% or more similar in length to the framework regions of SEQ ID NO: 200. Humanized variants of the heavy chain variable region of SEQ ID NO: 200 share at least 50%, at least 55%, at least 60%, at least 65%, at least 70%, at least 75%, at least 80%, at least 85%, at least 90%, at least 95% sequence identity along the entire length of SEQ ID 200.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 200. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 152, or a modified amino acid sequence thereof containing 1, 2, 3, or more amino acid residue modifications as compared to SEQ ID NO: 152; a H-CDR2 having the amino acid sequence of SEQ ID NO: 167, or a modified amino acid sequence thereof containing 1, 2, 3, or more amino acid residue modifications as compared to SEQ ID NO: 167; and a H-CDR3 comprising the amino acid sequence of SEQ ID NO: 182, or a modified amino acid sequence thereof, said modified amino acid sequence containing 1, 2, 3, or more amino acid modifications as compared to SEQ ID NO: 182.

An exemplary single domain antibody having this heavy chain variable region is referred to herein as the 29-S-bR2-1F2 antibody. The 29-S-bR2-1F2 antibody comprises a V$_H$ chain amino acid sequence of SEQ ID NO: 201 as shown below.

SEQ ID NO: 201
QVQLQASGGGLVQPGGSLRLSCAASGFTFSSYWMYWVRQAPGKGLEWVST

INTGGYTTYYSDSVKGRFTISRDNGKNTLYLEMNSLKSEDTAVYYCAKAY

GSMWSGIWGGMDYWGKGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 201.

In one embodiment, the antibody or binding fragment thereof of the present disclosure comprises a humanized variant of the heavy chain variable region of SEQ ID NO: 201, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 201), or a combination of these approaches. The humanized framework regions are designed to be similar in length and sequence to the parental framework sequences of SEQ ID NO: 201. In one embodiment, the humanized framework regions share 50%, 55%, 60%, 65%, 70%, 75%, 80%, 85%, 90%, 95% or more sequence identity to the framework regions of SEQ ID NO: 201. In another embodiment, the humanized framework regions are 60%, 65%, 70%, 75%, 80%, 85%, 90%, 95% or more similar in length to the framework regions of SEQ ID NO: 201. Humanized variants of the heavy chain variable region of SEQ ID NO: 201 share at least 50%, at least 55%, at least 60%, at least 65%, at least 70%, at least 75%, at least 80%, at least 85%, at least 90%, at least 95% sequence identity along the entire length of SEQ ID 201.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 201. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 153, or a modified amino acid sequence thereof containing 1, 2, 3, or more amino acid residue modifications as compared to SEQ ID NO: 153; a H-CDR2 having the amino acid sequence of SEQ ID NO: 168, or a modified amino acid sequence thereof containing 1, 2, 3, or more amino acid residue modifications as compared to SEQ ID NO: 168; and a H-CDR3 comprising the amino acid sequence of SEQ ID NO: 183, or a modified amino acid sequence thereof, said modified amino acid sequence containing 1, 2, 3, or more amino acid modifications as compared to SEQ ID NO: 183.

An exemplary single domain antibody having this heavy chain variable region is referred to herein as the 33-S-bR1-1G3 antibody. The 33-S-bR1-1G3 antibody comprises a $V_H$ chain amino acid sequence of SEQ ID NO: 203 as shown below.

SEQ ID NO: 203
QVQLQESGGGLVQAGGSLRLSCAVSGSIISHNVMAWYRRAPGKQRDKVAC

ISGSGFTNYIASVKGRFTISRDNAKNTVSLQMNNLKPEDTAVYSCYTAWP

NTWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 203.

In one embodiment, the antibody or binding fragment thereof of the present disclosure comprises a humanized variant of the heavy chain variable region of SEQ ID NO: 203, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 203), or a combination of these approaches. The humanized framework regions are designed to be similar in length and sequence to the parental framework sequences of SEQ ID NO: 203. In one embodiment, the humanized framework regions share 50%, 55%, 60%, 65%, 70%, 75%, 80%, 85%, 90%, 95% or more sequence identity to the framework regions of SEQ ID NO: 203. In another embodiment, the humanized framework regions are 60%, 65%, 70%, 75%, 80%, 85%, 90%, 95% or more similar in length to the framework regions of SEQ ID NO: 203. Humanized variants of the heavy chain variable region of SEQ ID NO: 203 share at least 50%, at least 55%, at least 60%, at least 65%, at least 70%, at least 75%, at least 80%, at least 85%, at least 90%, at least 95% sequence identity along the entire length of SEQ ID 203.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 203. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 154, or a modified amino acid sequence thereof containing 1, 2, 3, or more amino acid residue modifications as compared to SEQ ID NO: 154; a H-CDR2 having the amino acid sequence of SEQ ID NO: 169, or a modified amino acid sequence thereof containing 1, 2, 3, or more amino acid residue modifications as compared to SEQ ID NO: 169; and a H-CDR3 comprising the amino acid sequence of SEQ ID NO: 184, or a modified amino acid sequence thereof, said modified amino acid sequence containing 1, 2, 3, or more amino acid modifications as compared to SEQ ID NO: 184.

An exemplary single domain antibody having this heavy chain variable region is referred to herein as the 36-S-bR2-1D1 antibody. The 36-S-bR2-1D1 antibody comprises a $V_H$ chain amino acid sequence of SEQ ID NO: 204 as shown below.

SEQ ID NO: 204
QVQLQESGGGFVHPGGSLTLSCAASGRIFNIEDMGWYRQGPGEQRDLVAT

ITRTGAPTYANSVKGRFTISRDNAKNTVYLQMTRLKPEDTAVYYCNAKDV

TVIPFPPKDYWGRGTFQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 204.

In one embodiment, the antibody or binding fragment thereof of the present disclosure comprises a humanized variant of the heavy chain variable region of SEQ ID NO: 204, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 204), or a combination of these approaches. The humanized framework regions are designed to be similar in length and sequence to the parental framework sequences of SEQ ID NO: 204. In one embodiment, the humanized framework regions share 50%, 55%, 60%, 65%, 70%, 75%, 80%, 85%, 90%, 95% or more sequence identity to the framework regions of SEQ ID NO: 204. In another embodiment, the humanized framework regions are 60%, 65%, 70%, 75%, 80%, 85%, 90%, 95% or more similar in length to the framework regions of SEQ ID NO: 204. Humanized variants of the heavy chain variable region of SEQ ID NO: 204 share at least 50%, at least 55%, at least 60%, at least 65%, at least 70%, at least 75%, at least 80%, at least 85%, at least 90%, at least 95% sequence identity along the entire length of SEQ ID 204.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 204. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 155, or a modified amino acid sequence thereof containing 1, 2, 3, or more amino acid residue modifications as compared to SEQ ID NO: 155; a H-CDR2 having the amino acid sequence of SEQ ID NO: 170, or a modified amino acid sequence thereof containing 1, 2, 3, or more amino acid residue modifications as compared to SEQ ID NO: 170; and a H-CDR3 comprising the amino acid sequence of SEQ ID NO: 185, or a modified amino acid sequence thereof, said modified amino acid sequence containing 1, 2, 3, or more amino acid modifications as compared to SEQ ID NO: 185.

An exemplary single domain antibody having this heavy chain variable region is referred to herein as the 41-S-bR1-1H1 antibody. The 41-S-bR1-1H1 antibody comprises a V$_H$ chain amino acid sequence of SEQ ID NO: 205 as shown below.

SEQ ID NO: 205
QVQLQESGGGLVQAGGSLRLSCEASGSVSAIETMGWYRQAPDEQRTFVAV

ISTGGTTKYAPSVKGRFTISIDNAKSTVTLQMNSLKPEDTAVYYCAADWR

TILGWKTREPNYFGQGTLVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 205.

In one embodiment, the antibody or binding fragment thereof of the present disclosure comprises a humanized variant of the heavy chain variable region of SEQ ID NO: 205, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 205), or a combination of these approaches. The humanized framework regions are designed to be similar in length and sequence to the parental framework sequences of SEQ ID NO: 205. In one embodiment, the humanized framework regions share 50%, 55%, 60%, 65%, 70%, 75%, 80%, 85%, 90%, 95% or more sequence identity to the framework regions of SEQ ID NO: 205. In another embodiment, the humanized framework regions are 60%, 65%, 70%, 75%, 80%, 85%, 90%, 95% or more similar in length to the framework regions of SEQ ID NO: 205. Humanized variants of the heavy chain variable region of SEQ ID NO: 205 share at least 50%, at least 55%, at least 60%, at least 65%, at least 70%, at least 75%, at least 80%, at least 85%, at least 90%, at least 95% sequence identity along the entire length of SEQ ID 205.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 205. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 156, or a modified amino acid sequence thereof containing 1, 2, 3, or more amino acid residue modifications as compared to SEQ ID NO: 156; a H-CDR2 having the amino acid sequence of SEQ ID NO: 171, or a modified amino acid sequence thereof containing 1, 2, 3, or more amino acid residue modifications as compared to SEQ ID NO: 171; and a H-CDR3 comprising the amino acid sequence of SEQ ID NO: 186, or a modified amino acid sequence thereof, said modified amino acid sequence containing 1, 2, 3, or more amino acid modifications as compared to SEQ ID NO: 186.

Exemplary single domain antibodies having this heavy chain variable region as described herein include the 45-S-bR2-1F6 antibody, the 61-S-bR2-1F8 antibody, and the 84-S-bR2-1E5 antibody. These antibodies comprise a V$_H$ chain amino acid sequence of SEQ ID NO: 206 as shown below.

SEQ ID NO: 206
QVQLQESGGGLVQAGGSLRLSCAAFGSTSSITYMAWFRQAPEKQRELVAE

MSRRGSTFYADSVKGRFTIYRDNTKNTVYLQMNSLEPEDTAVYYCSVGAR

RDEDDYVYWGQGTQVTVSS

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 206.

In one embodiment, the antibody or binding fragment thereof of the present disclosure comprises a humanized variant of the heavy chain variable region of SEQ ID NO: 206, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 206), or a combination of these approaches. The humanized framework regions are designed to be similar in length and sequence to the parental framework sequences of SEQ ID NO: 206. In one embodiment the humanized framework regions share 50%, 55%, 60%, 65%, 70%, 75%, 80%, 85%, 90%, 95% or more sequence identity to the framework regions of SEQ ID NO: 206. In another embodiment, the humanized framework regions are 60%, 65%, 70%, 75%, 80%, 85%, 90%, 95% or more similar in length to the framework regions of SEQ ID NO: 206. Humanized variants of the heavy chain variable region of SEQ ID NO: 206 share at least 50%, at least 55%, at least 60%, at least 65%, at least 70%, at least 75%, at least 80%, at least 85%, at least 90%, at least 95% sequence identity along the entire length of SEQ ID 206.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 206. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 157 or a modified amino acid sequence thereof containing 1, 2, 3, or more amino acid residue modifications as compared to SEQ ID NO: 157; a H-CDR2 having the amino acid sequence of SEQ ID NO: 172, or a modified amino acid sequence thereof containing 1, 2, 3, or more amino acid residue modifications as compared to SEQ ID NO: 172; and a H-CDR3 comprising the amino acid sequence of SEQ ID NO: 187, or a modified amino acid sequence thereof, said modified amino acid sequence containing 1, 2, 3, or more amino acid modifications as compared to SEQ ID NO: 187.

An exemplary single domain antibody having this heavy chain variable region is referred to herein as the 49-S-bR1-1H2 antibody. This antibody comprises a $V_H$ chain amino acid sequence of SEQ ID NO: 207 as shown below.

```
                                              SEQ ID NO: 207
QVQLQESGGGLVQAGGSLRLSCAASGGPVSDNVMAWFRQAPGSQRELVAQ

ITSGGATSYADSVKGRFTISRDNARSTVDLQMNSLKPEDTAVYYCNVALR

YWGRGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 207.

In one embodiment, the antibody or binding fragment thereof of the present disclosure comprises a humanized variant of the heavy chain variable region of SEQ ID NO: 207, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 207), or a combination of these approaches. The humanized framework regions are designed to be similar in length and sequence to the parental framework sequences of SEQ ID NO: 207. In one embodiment, the humanized framework regions share 50%, 55%, 60%, 65%, 70%, 75%, 80%, 85%, 90%, 95% or more sequence identity to the framework regions of SEQ ID NO: 207. In another embodiment, the humanized framework regions are 60%, 65%, 70%, 75%, 80%, 85%, 90%, 95% or more similar in length to the framework regions of SEQ ID NO: 207. Humanized variants of the heavy chain variable region of SEQ ID NO: 207 share at least 50%, at least 55%, at least 60%, at least 65%, at least 70%, at least 75%, at least 80%, at least 85%, at least 90%, at least 95% sequence identity along the entire length of SEQ ID 207.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 207. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 158 or a modified amino acid sequence thereof containing 1, 2, 3, or more amino acid residue modifications as compared to SEQ ID NO: 158; a H-CDR2 having the amino acid sequence of SEQ ID NO: 173, or a modified amino acid sequence thereof containing 1, 2, 3, or more amino acid residue modifications as compared to SEQ ID NO: 173; and a H-CDR3 comprising the amino acid sequence of SEQ ID NO: 188, or a modified amino acid sequence thereof, said modified amino acid sequence containing 1, 2, 3, or more amino acid modifications as compared to SEQ ID NO: 188.

An exemplary single domain antibody having this heavy chain variable region is referred to herein as the 51-S-bR2-1B7 antibody. This antibody comprises a $V_H$ chain amino acid sequence of SEQ ID NO: 208 as shown below.

```
                                              SEQ ID NO: 208
QVQLQQSGGGLVQAGGSLRLSCAASGSTFSITYMAWFRQAPGKQRELVAE

ISSRGSVFYADSVKGRFTISRDNAKKTVYLQMNSLETEDTAAYYCSVGAR

RDEDDYVYWGQGTQVTVSS
```

Another exemplary single domain antibody having this heavy chain variable region is referred to herein as the 85-S-bR2-1G2 antibody. This antibody comprises a $V_H$ chain amino acid sequence of SEQ ID NO: 216 as shown below.

```
                                              SEQ ID NO: 216
QVQLQQSGGGLVQAGGSLRLSCAASGSTFSITYMAWFRQAPGKQRELVAE

ISSRGSVFYADSVKGRFTISRDNAKKTVYLQMNSLETEDTAAYYCSVGAR

RDEDDYVYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 208 or SEQ ID NO: 216.

In one embodiment, the antibody or binding fragment thereof of the present disclosure comprises a humanized variant of the heavy chain variable region of SEQ ID NO: 208 or SEQ ID NO: 216, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 208 or SEQ ID NO: 216), or a combination of these approaches. The humanized framework regions are designed to be similar in length and sequence to the parental framework sequences of SEQ ID NO: 208 or SEQ ID NO: 216. In one embodiment, the humanized framework regions share 50%, 55%, 60%, 65%, 70%, 75%, 80%, 85%, 90%, 95% or more sequence identity to the framework regions of SEQ ID NO: 208 or SEQ ID NO: 216. In another embodiment, the humanized framework regions are 60%, 65%, 70%, 75%, 80%, 85%, 90%, 95% or more similar in length to the framework regions of SEQ ID NO: 208 or SEQ ID NO: 216. Humanized variants of the heavy chain variable region of SEQ ID NO: 208 or SEQ ID NO: 216 share at least 50%, at least 55%, at least 60%, at least 65%, at least 70%, at least 75%, at least 80%, at least 85%, at least 90%, at least 95% sequence identity along the entire length of SEQ ID 208 or SEQ ID NO: 216, respectively.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 208. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 159 or a modified amino acid sequence thereof containing 1, 2, 3, or more amino acid residue modifications as compared to SEQ ID NO: 159; a H-CDR2 having the amino acid sequence of SEQ ID NO: 174, or a modified amino acid sequence thereof containing 1, 2, 3, or more amino acid residue modifications as compared to SEQ ID NO: 174; and a H-CDR3 comprising the amino acid sequence of SEQ ID NO: 189, or a modified amino acid sequence thereof, said modified amino acid sequence containing 1, 2, 3, or more amino acid modifications as compared to SEQ ID NO: 189.

An exemplary single domain antibody having this heavy chain variable region is referred to herein as the 73-S-bR1-2B2 antibody. This antibody comprises a $V_H$ chain amino acid sequence of SEQ ID NO: 213 as shown below.

```
                                        SEQ ID NO: 213
QVQLQESGGGLVQAGGSLRLSCVGAGSAEGWNAVHWYRQAPGQQREWLAT

IESGGWADYSVSVKGRFIVSRDNARNTAYLQMNNLKLEDTAVYYCNQLTY

WGQGTQVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 213.

In one embodiment, the antibody or binding fragment thereof of the present disclosure comprises a humanized variant of the heavy chain variable region of SEQ ID NO: 213, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 213), or a combination of these approaches. The humanized framework regions are designed to be similar in length and sequence to the parental framework sequences of SEQ ID NO: 213. In one embodiment, the humanized framework regions share 50%, 55%, 60%, 65%, 70%, 75%, 80%, 85%, 90%, 95% or more sequence identity to the framework regions of SEQ ID NO: 213. In another embodiment, the humanized framework regions are 60%, 65%, 70%, 75%, 80%, 85%, 90%, 95% or more similar in length to the framework regions of SEQ ID NO: 213. Humanized variants of the heavy chain variable region of SEQ ID NO: 213 share at least 50%, at least 55%, at least 60%, at least 65%, at least 70%, at least 75%, at least 80%, at least 85%, at least 90%, at least 95% sequence identity along the entire length of SEQ ID 213.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 213. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 160 or a modified amino acid sequence thereof containing 1, 2, 3, or more amino acid residue modifications as compared to SEQ ID NO: 160; a H-CDR2 having the amino acid sequence of SEQ ID NO: 175, or a modified amino acid sequence thereof containing 1, 2, 3, or more amino acid residue modifications as compared to SEQ ID NO: 175; and a H-CDR3 comprising the amino acid sequence of SEQ ID NO: 190, or a modified amino acid sequence thereof, said modified amino acid sequence containing 1, 2, 3, or more amino acid modifications as compared to SEQ ID NO: 190.

An exemplary single domain antibody having this heavy chain variable region is referred to herein as the 89-S-bR1-2C6 antibody. This antibody comprises a $V_H$ chain amino acid sequence of SEQ ID NO: 217 as shown below.

```
                                        SEQ ID NO: 217
QVQLQESGGGLVQPGGSLRLSCTPSGSIFSFDVMAWYRQAPGKRRELVAQ

HRTPGAIDYADPVRGRFTISRDAGDVLFLQMDSLKPEDTAVYFCNLRRWS

YDYWGQGTLVTVSS
```

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 217.

In one embodiment, the antibody or binding fragment thereof of the present disclosure comprises a humanized variant of the heavy chain variable region of SEQ ID NO: 217, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NO: 217), or a combination of these approaches. The humanized framework regions are designed to be similar in length and sequence to the parental framework sequences of SEQ ID NO: 217. In one embodiment, the humanized framework regions share 50%, 55%, 60%, 65%, 70%, 75%, 80%, 85%, 90%, 95% or more sequence identity to the framework regions of SEQ ID NO: 217. In another embodiment, the humanized framework regions are 60%, 65%, 70%, 75%, 80%, 85%, 90%, 95% or more similar in length to the framework regions of SEQ ID NO: 217. Humanized variants of the heavy chain variable region of SEQ ID NO: 217 share at least 50%, at least 55%, at least 60%, at least 65%, at least 70%, at least 75%, at least 80%, at least 85%, at least 90%, at least 95% sequence identity along the entire length of SEQ ID 217.

Another aspect of the present disclosure relates to an antibody or binding portion thereof (e.g., a human antibody) that competes for binding to human α-synuclein protein with the anti-α-synuclein antibody comprising a heavy chain variable region with the amino acid sequence of SEQ ID NO: 217. In accordance with this aspect of the disclosure, a competitive binding assay, such as Bio-Layer Interferometry (BLI) can be utilized to identify an antibody or binding portion thereof that competes for binding to an α-synuclein protein with the enumerated monoclonal antibody. Other competitive binding assays known in the art can also be utilized to identify a competitive binding antibody in accordance with this aspect of the disclosure.

Antibody "specificity" refers to selective recognition of the antibody or binding portion thereof as described herein for a particular epitope of the α-synuclein protein. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. The epitope of the antibodies described herein may be "linear" or "conformational". In a linear epitope, all of the points of interaction between the protein and the antibody occur linearly along the primary amino acid sequence of the protein. In a conformational epitope, the points of interaction occur across amino acid residues on the protein that are separated from one another, i.e., non-contiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, 6, 7, 8, 9, 10, 11, 12, 13, 14, 15, 16, 17, 18, 19, 20 or more amino acids in a unique spatial conformation. Antibodies that recognize the same epitope can be verified in a simple immunoassay showing the ability of one antibody to block the binding of another antibody to a target antigen.

In one embodiment, the epitope recognized by the isolated antibody of the present invention is a non-linear or conformational epitope, i.e. a tertiary or quaternary structure that is shared by pathological proteins. For example, the non-linear or conformational epitope recognized by the antibodies described herein is a conformational epitope that is common or shared with one or more, or all, amyloidogenic proteins, e.g., synuclein, tau, Aβ, prion, etc. Accordingly, in one embodiment, the antibodies described herein have antigenic specificity for a shared conformational epitope common to all amyloidogenic proteins known in the art.

Another aspect of the present disclosure is directed to an antibody mimetic that binds α-synuclein protein. An "antibody mimetic" as referred to herein encompasses any organic compound, e.g., a peptide or polypeptide, that can specifically bind an antigen like an antibody, and is about 3-20 kDa. In one embodiment, the antibody mimetic comprises a scaffold which binds its antigen via amino acids in exposed loops similar to the CDR loops of an antibody. These antibody mimetics include, without limitation, adnectins, lipocalins, Kunitz domain-based binders, avimers, knottins, fynomers, atrimers, and cytotoxic T-lymphocyte associated protein-4 (CTLA4)-based binders (reviewed in Weidle et al., "The Emerging Role of New Protein Scaffold-based Agents for the Treatment of Cancer," *Cancer Genomics & Proteomics* 10:155-168 (2013), which is hereby incorporated by reference in its entirety). In accordance with this aspect of the present disclosure, the loop binding regions of the antibody mimetic are adapted to comprise one or more of the heavy chain CDRs of the antibodies disclosed herein. For example, an antibody mimetic of the present disclosure may comprise a first loop region having an amino acid sequence of any one of SEQ ID NOs: 1-36, 218, 222, 226, 230, 234, 238, 340 or a modified amino acid sequence of any one of SEQ ID NOs: 1-36, 218, 222, 226, 230, 234, 238, and 340 said modified sequence containing 1, 2, or 3 amino acid residue modifications as compared to any one of SEQ ID NOs: 1-36, 218, 222, 226, 230, 234, 238, and 340. The antibody mimetic may comprise another loop region having an amino acid sequence of any one of SEQ ID NOs: 37-72, 219, 223, 227, 231, 235, 239, 341 or a modified amino acid sequence of any one of SEQ ID NOs: 37-72, 219, 223, 227, 231, 235, 239, and 341 said modified sequences containing 1, 2, or 3, amino acid residue modifications as compared to any one of SEQ ID NOs: 37-72, 219, 223, 227, 231, 235, 239, and 341. The antibody mimetic may comprise another loop region having an amino acid sequence any one of SEQ ID NOs: 73-108, 220, 224, 228, 232, 236, 240, 342 or a modified amino acid sequence of any one of SEQ ID NOs: 73-108, 220, 224, 228, 232, 236, 240, and 342 said modified sequence containing 1, 2, or 3 amino acid residue modifications as compared to any one of SEQ ID NOs: 73-108, 220, 224, 228, 232, 236, 240, and 342.

In another embodiment, an antibody mimetic of the present disclosure may comprise a first loop region having an amino acid sequence of any one of SEQ ID NOs: 146-160 or a modified amino acid sequence of any one of SEQ ID NOs: 146-160, said modified sequence containing 1, 2, or 3 amino acid residue modifications as compared to any one of SEQ ID NOs: 146-160. The antibody mimetic may comprise another loop region having an amino acid sequence of any one of SEQ ID NOs: 161-175, or a modified amino acid sequence of any one of SEQ ID NOs: 161-175, said modified sequences containing 1, 2, or 3, amino acid residue modifications as compared to any one of SEQ ID NOs: 161-175. The antibody mimetic may comprise another loop region having an amino acid sequence any one of SEQ ID NOs: 176-190, or a modified amino acid sequence of any one of SEQ ID NOs: 176-190, said modified sequence containing 1, 2, or 3 amino acid residue modifications as compared to any one of SEQ ID NOs: 176-190.

In one embodiment, the antibody mimetic comprises one or more modified fibronectin type III (FN3) domains (e.g., an adnectin or centyrin molecule), where each modified FN3 domain has one or more loop regions that comprise one or more CDR sequences or modified CDR sequences as disclosed herein.

The FN3 domain is an evolutionary conserved protein domain that is about 100 amino acids in length and possesses a beta sandwich structure. The beta sandwich structure of human FN3 comprises seven beta-strands, referred to as strands A, B, C, D, E, F, G, with six connecting loops, referred to as loops AB, BC, CD, DE, EF, and FG that exhibit structural homology to immunoglobulin binding domains. Three of the six loops, i.e., loops DE, BC, and FG, correspond topologically to the complementarity determining regions of an antibody, i.e., CDR1, CDR2, and CDR3. The remaining three loops are surface exposed in a manner similar to antibody CDR3. In accordance with the present disclosure, one or more of the loop regions of each FN3 domain of the binding molecule are modified to comprise one or more CDR sequences disclosed herein.

The modified FN3 domain can be a FN3 domain derived from any of the wide variety of animal, yeast, plant, and bacterial extracellular proteins containing these domains. In one embodiment, the FN3 domain is derived from a mammalian FN3 domain. Exemplary FN3 domains include, for example and without limitation, any one of the 15 different FN3 domains present in human tenascin C, or the 15 different FN3 domains present in human fibronectin (FN) (e.g., the $10^{th}$ fibronectin type III domain). Exemplary FN3 domains also include non-natural synthetic FN3 domains, such as those described in U S. Pat. Publ. No. 2010/0216708 to Jacobs et al., which is hereby incorporated by reference in its entirety. Individual FN3 domains are referred to by domain number and protein name, e.g., the $3^{rd}$ FN3 domain of tenascin (TN3), or the $10^{th}$ FN3 domain of fibronectin (FN10).

Another aspect of the present disclosure is directed to isolated polynucleotides encoding the α-synuclein antibody or binding fragment thereof or antibody mimetic as described herein. The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

In one embodiment, an isolated polynucleotide encodes a H-CDR1 of any one or more of SEQ ID NOs: 1-36, 218, 222, 226, 230, 234, 238, and 340; a H-CDR2 of any one of SEQ ID NOs: 37-72, 219, 223, 227, 231, 235, 239, and 341; and a H-CDR3 of any one of SEQ ID NOs: 73-108, 220, 224, 228, 232, 236, 240, and 342. In another embodiment, an isolated polynucleotide as described herein encodes a H-CDR1 of any one or more of SEQ ID NOs: 146-160, a H-CDR2 of any one of SEQ ID NOs: 161-175, and a H-CDR3 of any one of SEQ ID NOs: 176-190.

In another embodiment, an isolated polynucleotide as described herein encodes a heavy chain variable region of an α-synuclein antibody having the amino acid sequence of any one of SEQ ID NOs: 109-145, 221, 225, 229, 233, 237, 241, and 343. The nucleotide sequences of these isolated polynucleotides are enumerated in Table 3 herein and include SEQ ID NOs: 242-286. In another embodiment, the isolated polynucleotide encodes a heavy chain variable region of an α-synuclein antibody having the amino acid sequence of any one of SEQ ID NOs: 191-217. The nucleotide sequences of these isolated polynucleotides are enumerated in Table 4 herein and include SEQ ID NOs: 287-339. Nucleic acid molecules having nucleotide sequences that differ from SEQ ID NOs: 242-339, which as a result of the degeneracy of the genetic code, also encode the α-synuclein antibody described herein are also encompassed by the present disclosure. Such nucleic acid molecules may share 80%, 85%, 90%, or 95% sequence identity to any one of the sequences of SEQ ID NOs: 249-339.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that provide, for example, a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the disclosure is directed to a vector comprising at least one polynucleotide encoding the antibody or binding fragment thereof or antibody mimetic as described herein. Such vectors include, without limitation, plasmid vectors, viral vectors, including without limitation, vaccina vector, lentiviral vector, adenoviral vector, adeno-associated viral vector, vectors for baculovirus expression, transposon based vectors or any other vector suitable for introduction of the polynucleotides described herein into a given organism or genetic background by any means to facilitate expression of the encoded antibody polypeptide. The polynucleotide sequences encoding the heavy chain variable domains as described herein are combined with sequences of a promoter, a translation initiation segment (e.g., a ribosomal binding sequence and start codon), a 3' untranslated region, polyadenylation signal, a termination codon, and transcription termination to form one or more expression vector constructs.

In one embodiment, the vector is an adenoviral-associated viral (AAV) vector. A number of therapeutic AAV vectors suitable for delivery of the polynucleotides encoding α-synuclein antibodies described herein to the central nervous system are known in the art. See e.g., Deverman et al., "Gene Therapy for Neurological Disorders: Progress and Prospects," *Nature Rev.* 17:641-659 (2018), which in hereby incorporated by reference in its entirety. Suitable AAV vectors include serotypes AAV1, AAV2, AAV3, AAV4, AAV5, AAV6, AAV7, AAV8, AAV9, AAV10, or AAV11 in their native form or engineered for enhanced tropism. AAV vectors known to have tropism for the CNS that are particularly suited for therapeutic expression of the α-synuclein antibodies described herein include, AAV1, AAV2, AAV4, AAV5, AAV8 and AAV9 in their native form or engineered for enhanced tropism. In one embodiment, the AAV vector is an AAV2 vector. In another embodiment, the AAV vector is an AAV5 vector as described by Vitale et al., "Anti-tau Conformational scFv MCI Antibody Efficiently Reduces Pathological Tau Species in Adult JNPL3 Mice," *Acta Neuropathol. Commun.* 6:82 (2018), optionally containing the GFAP or CAG promoter and the Eoodchuck hepatitis virus (WPRE) post-translational regulatory element. In another embodiment, the AAV vector is an AAV9 vector as described by Haiyan et al., "Targeting Root Cause by Systemic scAAV9-hIDS Gene Delivery: Functional Correction and Reversal of Severe MPSII in Mice," *Mol. Ther. Methods Clin. Dev.* 10:327-340 (2018), which is hereby incorporated by reference in its entirety. In another embodiment, the AAV vector is an AAVrh10 vector as described by Liu et al., "Vectored Intracerebral Immunizations with the Anti-Tau Monoclonal Antibody PHF1 Markedly Reduces Tau Pathology in Mutant Transgenic Mice," *J. Neurosci.* 36(49): 12425-35 (2016), which is hereby incorporated by reference in its entirety.

In another embodiment the AAV vector is a hybrid vector comprising the genome of one serotype, e.g., AAV2, and the capsid protein of another serotype, e.g., AAV1 or AAV3-9 to control tropism. See e.g., Broekman et al., "Adeno-associated Virus Vectors Serotyped with AAV8 Capsid are More Efficient than AAV-1 or -2 Serotypes for Widespread Gene Delivery to the Neonatal Mouse Brain," *Neuroscience* 138: 501-510 (2006), which is hereby incorporated by reference in its entirety. In one embodiment, the AAV vector is an AAV2/8 hybrid vector as described by Ising et al., "AAV-mediated Expression of Anti-Tau ScFv Decreases Tau Accumulation in a Mouse Model of Tauopathy," *J. Exp. Med.* 214(5): 1227 (2017), which is hereby incorporated by reference in its entirety. In another embodiment the AAV vector is an AAV2/9 hybrid vector as described by Simon et al., "A Rapid Gene Delivery-Based Mouse Model for Early-Stage Alzheimer Disease-Type Tauopathy," *J. Neuropath. Exp. Neurol.* 72(11): 1062-71 (2013), which is hereby incorporated by reference in its entirety.

In another embodiment, the AAV vector is one that has been engineered or selected for its enhanced CNS transduction after intraparenchymal administration, e.g., AAV-DJ (Grimm et al., *J. Viol.* 82:5887-5911 (2008), which is hereby incorporated by reference in its entirety); increased transduction of neural stem and progenitor cells, e.g., SCH9 and AAV4.18 (Murlidharan et al., *J. Virol.* 89: 3976-3987 (2015) and Ojala et al., *Mol. Ther.* 26:304-319 (2018), which are hereby incorporated by reference in their entirety); enhanced retrograde transduction, e.g., rAAV2-retro (Muller et al., *Nat. Biotechnol.* 21:1040-1046 (2003), which is hereby incorporated by reference in its entirety); selective transduction into brain endothelial cells, e.g., AAV-BRI (Korbelin et al., *EMBO Mol. Med.* 8: 609-625 (2016), which is hereby incorporated by reference in its entirety); or enhanced transduction of the adult CNS after IV administration, e.g., AAV-PHP.B and AAVPHP.eB (Deverman et al., *Nat. Biotechnol.* 34: 204-209 (2016) and Chan et al., *Nat. Neurosci.* 20: 1172-1179 (2017), which are hereby incorporated by reference in their entirety.

In accordance with this embodiment, the expression vector construct encoding the anti-α-synuclein antibody or binding portion thereof can include the nucleic acid encoding the heavy chain variable region polypeptide, a fragment thereof, a variant thereof, or combinations thereof. In one embodiment, the heavy chain variable region polynucleotide encodes only a variable heavy chain (VH) region. In another embodiment, the heavy chain variable region polynucleotide is engineered to further comprise a region encoding at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

The promoter sequence of the expression vector construct is suitable for driving expression of the antibody or binding fragment thereof. The promoter can be inducible or constitutive. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), artificial CMV-chicken β-actin promoter with β-globin splice acceptor (CAG), chicken β-actin (CBA) promoter, a chimeric liver-specific promoter (LSP) a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein. The expression construct can further encode enhance-promoter elements that control or restrict expression of the encoded antibody. Enhancer-promoter elements that restrict expression to several neuronal and glial cell types in the CNS are known in the art and suitable for inclusion in the vector expression constructs described herein. See e.g., Lee et al., "GFAP Promoter Elements Required for Region-Specific and Astrocyte-Specific Expression," *Glia* 56: 481-493 (2008); Dimidschstein et al., "A Viral Strategy for Targeting and Manipulating Interneurons Across Vertebrate Species," *Nat. Neuroscience"* 19:1743-49 (2016); and de Leeuq et al., "rAAV-compatible MiniPromoters for Restricted Expression in the Brain and Eye," *Mol. Brain* 9:52 (2016), which are hereby incorporated by reference in their entirety.

The expression construct can further encode a linker sequence. The linker sequence can encode an amino acid sequence that spatially separates and/or links the one or more components of the expression construct.

Another embodiment of the invention is a host cell comprising the vectors described herein. The antibodies and binding fragments thereof described herein can be optionally produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

The host cell chosen for expression may be of mammalian origin or may be selected from COS-1, COS-7, HEK293, BHK21, CHO, BSC-1, He G2, SP2/0, HeLa, myeloma, lymphoma, yeast, insect, or plant cells, or any derivative, immortalized or transformed cell thereof. Alternatively, the host cell may be selected from a species or organism incapable of glycosylating polypeptides, e.g., a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The antibodies described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA,* 77: 4216-4220 (1980), which is hereby incorporated by reference in its entirety). Other suitable mammalian host cells include, without limitation, NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibodies and fragments thereof. It is understood that variations on the above procedure are within the scope of the present disclosure. For example, it may be desirable to transfect a host cell with DNA encoding functional fragments the heavy chain of an antibody described herein. Recombinant DNA technology may also be used to remove some or all of the DNA encoding portions of the heavy chain that are not necessary for binding to the antigens of interest. The molecules expressed from such truncated DNA molecules are also encompassed by the antibodies described herein.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

In another embodiment, the antibody or binding fragment thereof, or the polynucleotide encoding the antibody or binding fragment thereof is a component of a pharmaceutical composition. In one embodiment, the pharmaceutical composition comprises a monoclonal antibody composition. In another embodiment, the pharmaceutical composition comprises two or more different single-domain antibodies, e.g., a polyclonal antibody composition. In another embodiment, the pharmaceutical composition comprises polynucleotides encoding the monoclonal antibody composition. In another embodiment, the pharmaceutical composition comprises polynucleotides encoding two or more different single-domain antibodies as described herein. In another embodiment, the pharmaceutical composition comprises one or more antibodies or polynucleotides encoding the same as described herein and one or more prophylactic or therapeutic agents other than the antibodies described herein that are useful for preventing or treating a condition mediated by a toxic α-synuclein protein.

The therapeutically effective amount of antibody present in the pharmaceutical composition or formulation is determined by taking into account the desired dose volumes and models) of administration. Exemplary antibody concentrations in the pharmaceutical compositions of the present disclosure include from about 0.1 mg/mL to about 50 mg/mL, from about 0.5 mg/mL to about 25 mg/mL, and from about 2 mg/mL to about 10 mg/mL.

An aqueous formulation is prepared comprising the antibody in a pH-buffered solution. The buffer has a pH in the range from about 4.5 to about 10, from about 5 to about 9, or from about 6 to 8. Examples of buffers include phosphate buffers (e.g., phosphate buffered saline), acetate (e.g. sodium acetate), succinate (such as sodium succinate), gluconate, histidine, citrate and other organic acid buffers.

A polyol, which acts as a tonicifier and may stabilize the antibody, may be included in the formulation. In one embodiment, the tonicifying polyol is a salt such as sodium chloride. In another embodiment, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, or in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant may also be added to the pharmaceutical composition containing the antibody. Exemplary surfactants include nonionic surfactants such as polysorbates (e.g. polysorbates 20, 80 etc), poloxamers (e.g. poloxamer 188), Pluronic F68, and PEG (polyethylene glycol). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, or from about 0.01% to about 0.1%.

In one embodiment, the pharmaceutical composition contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the pharmaceutical composition, particularly where the formulation is a multi-dose formulation. Suitable preservatives include, without limitation phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. The concentration of preservative may be in the range from about 0.01% to about 5%, from about 0.5% to about 2% and any range or value therein. Non-limiting examples include, no preservative, 0.1-2% m-cresol, 0.1-3% benzyl alcohol, 0.001-0.5% thimerosal, 0.001-2.0% phenol, 0.0005-1.0% alkylparaben(s), and the like. One or more other pharmaceutically acceptable carriers, excipients or stabilizers such as those described in *Remington's Pharmaceutical Sciences* 16th edition, Osol, A. Ed. (1980), which is hereby incorporated by reference in its entirety, may be included in the composition provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes), biodegradable polymers such as polyesters; and/or salt-forming counterions such as sodium.

The pharmaceutical compositions to be used for in vivo administration must be sterile. This is readily accomplished by filtration through sterile filtration membranes, prior to, or following, preparation of the composition.

The pharmaceutical compositions comprising antibodies or binding fragments thereof, or polynucleotides encoding the antibodies or binding fragments thereof, are for use in, but not limited to, preventing, treating, managing, or ameliorating an α-synucleinopathy, or one or more symptoms thereof.

In another aspect of the present disclosure the anti-α-synuclein antibodies described herein, binding fragments thereof, or a pharmaceutical composition containing the same, are employed in a method of inhibiting onset of one or more symptoms of an α-synucleinopathy in a subject. This method involves administering to the subject the anti-α-synuclein antibodies described, polynucleotides encoding the anti-α-synuclein antibodies described herein, or a pharmaceutical composition containing the same to the subject in an amount effective to inhibit the onset of one or more symptoms of an α-synucleinopathy in the subject.

In another aspect of the present disclosure the α-synuclein antibodies described herein, polynucleotides encoding the α-synuclein antibodies described herein, or a pharmaceutical composition containing the same, are employed in a method of treating a subject having an α-synucleinopathy. This method involves selecting a subject having an α-synucleinopathy and administering to the subject the α-synuclein antibody, a polynucleotide encoding an α-synuclein antibody, or a pharmaceutical composition containing the same in an amount effective to treat the α-synucleinopathy in the subject.

In accordance with these embodiments, an α-synucleinopathy is any condition associated with or mediated by a pathological form of α-synuclein protein, α-synucleinopathies include, without limitation, Parkinson's disease, Alzheimer's disease, Lewy Body Dementia, and Multiple System Atrophy.

In accordance with these embodiments, the "subject" is typically a human. However, other non-human mammals amenable to treatment in accordance with the methods described herein include, without limitation, primates, dogs, cats, rodents (e.g., mouse, rat, guinea pig), horses, deer, cervids, cattle and cows, sheep, and pigs.

In prophylactic applications, the pharmaceutical compositions of the present invention are administered to a subject that is susceptible to, or otherwise at risk of developing a particular condition mediated by a pathological form of α-synuclein protein, i.e., an α-synucleinopathy, in an amount sufficient to eliminate or reduce the risk of the condition or to delay, inhibit, or prevent the onset of the condition. Prophylactic application also includes the administration of an antibody composition to prevent or delay the recurrence or relapse of a condition mediated by the α-synuclein protein or peptide in its pathological form. The present methods and compositions are especially suitable for prophylactic treatment of individuals who have a known genetic risk of developing an α-synucleinopathy. Genetic markers associated with a risk of developing an α-synucleinopathy, such as Parkinson's disease include mutations in the SNCA gene, the gene encoding α-synuclein. Mutations in SCNA gene have been linked to both familial and sporadic cases of PD (see Stefanis L., "α-Synuclein in Parkinson's Disease," *Cold Spring Harb. Perspect. Med.* 2(2): 1009399 (2012), which is hereby incorporated by reference in its entirety). Genetic markers of other α-synucleinopathies, such as Alzheimer's disease are also known in the art. For example, mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis.

In therapeutic applications, pharmaceutical compositions are administered to a subject suspected of, or already suffering from a condition associated with or caused by a pathological form of α-synuclein protein in an amount sufficient to cure, or at least partially arrest or alleviate, one or more symptoms of the condition and its complications. An amount adequate to accomplish this is defined as a therapeutically- or pharmaceutically-effective dose. In both prophylactic and therapeutic regimes, agents are usually administered in several dosages until a sufficient response has been achieved. An effective dose of the composition of the present invention, for the treatment of the above described conditions will vary depending upon many different factors, including means of administration, target site, physiological state of the patient, whether the patient is human or an animal, other medications administered, and whether treatment is prophylactic or therapeutic.

In accordance with the prophylactic and therapeutic methods described herein, compositions comprising the antibody or binding fragments thereof are administered in a dosage ranging from about 0.0001 to 100 mg/kg, and more usually 0.01 to 10 mg/kg of the recipient's body weight. For example, the antibody or binding fragment thereof is administered in a dosage of 1, 2, 3, 4, 5, 6, 7, 8, 9 or 10 mg/kg, or higher, for example 15, 20, 25, 30, 35, 40, 45, 50, 55, 60, 65, 70, 75, 80, 85, 90, 95, or 100 mg/kg. An exemplary treatment regime entails administration once per every two weeks or once a month or once every 3 to 6 months. Intervals between single dosages can be weekly, monthly or yearly. Intervals can also be irregular as indicated by measuring blood levels of antibody in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The mode of administration of the antibody, binding fragment thereof, or pharmaceutical composition described herein may be any suitable route that delivers the compositions to the host, such as parenteral administration, e.g., intradermal, intramuscular, intraperitoneal, intravenous or subcutaneous, pulmonary; transmucosal (e.g., oral, intranasal); using a formulation in a tablet, capsule, solution, powder, gel, particle; and contained in a syringe, an implanted device, osmotic pump, cartridge, micropump, or other means appreciated by the skilled artisan, as well known in the art. Site specific administration may be achieved by, for example, intraarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapericardiac, intraperitoneal, intrapleural, intraprostatic, intrapulmonary, intrarenal, intraretinal, intraspinal, intrasynovial, intrathoracic, intravascular, intravesical, intralesional, sublingual, intranasal, or transdermal delivery.

Administration can be systemic or local. In one embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices.

In another embodiment, compositions containing the antibody or binding fragment thereof are delivered in a controlled release or sustained release system. In one embodiment, a pump is used to achieve controlled or sustained release. In another embodiment, polymeric materials can be used to achieve controlled or sustained release of the antibody compositions described herein. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, polyethylene glycol), polylactides (PLA), poly(lactide-co-glycolides) (PLGA), and polyorthoesters. The polymer used in a sustained release formulation is preferably inert, free of teachable impurities, stable on storage, sterile, and biodegradable. Also, the use of liposomes, microcapsules or microspheres, inclusion complexes, or other types of carriers known in the art are also contemplated.

In yet another embodiment, a controlled or sustained release system can be placed in proximity of the prophylactic or therapeutic target, thus requiring only a fraction of the systemic dose. Controlled and/or release systems for delivery of antibodies known in the art are suitable for use and delivery of compositions containing the antibodies and binding fragments thereof as described herein, see e.g., Song et al, "Antibody Mediated Lung Targeting of Long-Circulating Emulsions," *PDA Journal of Pharmaceutical Science & Technology* 50:372-397 (1995), Cleek et al, "Biodegradable Polymeric Carriers for a bFGF Antibody for Cardiovascular Application," *Pro. Int'l. Symp. Control. Rel. Bioact. Mater.* 24:853-854 (1997), and Lam et al., "Microencapsulation of Recombinant Humanized Monoclonal Antibody for Local Delivery," *Proc. Int'l. Symp. Control Rel. Bioact. Mater.* 24:759-760 (1997), each of which is incorporated herein by reference in their entireties.

In embodiments where the pharmaceutical composition comprises polynucleotides encoding the antibody or binding fragment thereof as described herein, the nucleic acid can be administered in vivo to promote expression of its encoded antibody, by constructing it as part of an appropriate nucleic acid expression vector and administering it so that it becomes intracellular, e.g., the by use of a retroviral vector (see e.g., U.S. Pat. No. 4,980,286 to Morgan et al., which is hereby incorporated by reference in its entirety). In one embodiment, polynucleotides encoding the α-synuclein antibody as described herein are incorporated into an AAV vector as described supra (e.g., AAV2, AAV4, AAV5, AAV7, AABV8, AAV9, AAVrh10, AAV2/8, AAV2/9, etc.) and delivered via intraparenchymal administration, including convection enhanced delivery (CED), intrathecal administration, intracerebroventricular administration, subpial administration, intramuscular administration, or intravenous administration. Other forms of nucleic acid delivery can also be employed, e.g., direct injection, use of microparticle bombardment (see e.g., a gene gun; Biolistic, Dupont), coating with lipids or cell-surface receptors or transfecting agents, or by administering it in linkage to a homeobox-like peptide which is known to enter the nucleus (see e.g., Joliot et al, *Proc. Natl. Acad. Sci. USA* 88: 1864-1868 (1991), which is hereby incorporated by reference in its entirety). Alternatively, a nucleic acid can be introduced intracellularly and incorporated within host cell DNA for expression by homologous recombination.

If the methods described herein involve intranasal administration of the antibody composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the methods described herein involve oral administration of the antibody compositions described herein, the compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica), disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate.

In another embodiment, a pharmaceutical composition comprising a recombinant nucleic acid sequence encoding an antibody or binding portion thereof as described herein, is administered to a subject to facilitate in vivo expression and formation of the antibody for the treatment or prevention of conditions mediated by toxic oligomeric proteins or peptides in a subject Expression vector constructs suitable for use in this embodiment of the disclosure are described supra.

The polynucleotide compositions can result in the generation of the antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody in the subject. The composition can result in the generation of the antibody in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

The antibodies, binding fragments thereof, or pharmaceutical compositions containing the same can be packaged in hermetically sealed containers such as an ampoule or sachette indicating the quantity of the antibody or binding fragment thereof. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention are supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies and binding fragments described herein can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form).

Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Additional surfactants include but are not limited to polysorbate 20 and BRIJ surfactants. The pharmaceutical composition comprising the antibodies described herein prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions (see WO 04/078140 to Bookbinder et al., and U.S. Patent Appl. Publication No. US2006104968 to Bookbinder et al., which are hereby incorporated herein by reference in their entirety).

The antibodies and binding fragments described herein can also be employed in a number of diagnostic, prognostic and research applications.

Another aspect of the present disclosure is directed to a method of diagnosing an α-synucleinopathy or related disease in a subject. This method involves detecting, in the subject, the presence of α-synuclein protein or peptide using a diagnostic reagent wherein the diagnostic reagent comprises an antibody or binding fragment described herein. The diagnosis of an α-synucleinopathy in the subject is based on the detection of α-synuclein protein or peptide in the subject.

In one embodiment the method of diagnosing an α-synucleinopathy or related disease in the subject involves the detection of an aggregated form of α-synuclein protein or peptide. In another embodiment, the method of diagnosing an α-synucleinopathy or related disease in the subject involves the detection of accumulated monomeric forms of the α-synuclein protein or peptide. In another embodiment, the method of diagnosing an α-synucleinopathy or related disease in the subject involves the detection of aggregated and non-aggregated (i.e. monomeric forms) of α-synuclein protein or peptide.

Detecting the presence of α-synuclein protein or peptide in a subject using the antibodies or antibody fragments thereof as described herein can be achieved by obtaining a biological sample from the subject (e.g., blood, urine, cerebral spinal fluid, ocular lacrimal secretion, saliva, feces, nasal brushings and tissue or organ biopsy), contacting the biological sample with the diagnostic antibody reagent, and detecting binding of the diagnostic antibody reagent to α-synuclein protein or peptide if present in the sample from the subject. Assays for carrying out the detection of α-synuclein protein or peptide in a biological sample using a diagnostic antibody are well known in the art and include, without limitation, ELISA, immunohistochemistry, SIMOA (single molecule array), and Western blot.

In accordance with this and other embodiments described herein, the α-synuclein antibody or binding fragments described herein are coupled to a detectable label. The label can be any detectable moiety known and used in the art. Suitable labels include, without limitation, radioisotopes or radionuclides (e.g., $^{3}$H, $^{14}$C, $^{18}$F, $^{35}$S, $^{90}$Y, $^{90}$Tc, $^{111}$In, $^{124}$I, $^{125}$I, $^{131}$I, $^{177}$LU, $^{166}$Ho, $^{89}$Zr, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

Detecting the presence of α-synuclein in a subject using the diagnostic antibody reagent of the present invention can also be achieved using in vivo imaging techniques. In vivo imaging involves administering to the subject the antibody or binding fragments thereof described herein, and detecting the binding of the antibody or binding fragment thereof to the α-synuclein in vivo.

Diagnostic antibodies or similar reagents can be administered by intravenous injection into the body of the patient, or directly into the brain by intracranial injection or by drilling a hole through the skull. The dosage of antibody should be within the same ranges as for treatment methods. In accordance with this embodiment, the antibody or binding fragment is coupled to an imaging agent to facilitate in vim imaging. The imaging agent can be any agent known to one of skill in the art to be useful for imaging, preferably being a medical imaging agent. Examples of medical imaging agents include, but are not limited to, single photon emission computed tomography (SPECT) agents, positron emission tomography (PET) agents, magnetic resonance imaging (MRI) agents, nuclear magnetic resonance imaging (NMR) agents, x-ray agents, optical agents (e.g., fluorophores, bioluminescent probes, near infrared dyes, quantum dots), ultrasound agents and neutron capture therapy agents, computer assisted tomography agents, two photon fluorescence microscopy imaging agents, and multi-photon microscopy imaging agents. Exemplary detectable markers include radioisotopes (e.g., $^{18}$F, $^{11}$C, $^{13}$N, $^{64}$Cu, $^{124}$I, $^{76}$Br, $^{82}$Rb, $^{68}$Ga $^{99m}$Tc, $^{111}$In, $^{201}$Tl, $^{89}$Zr, or $^{15}$O, which are suitable for PET and/or SPECT use) and ultra-small superparamagnetic particles of iron oxide (USPIO) which are suitable for MRI.

Diagnosis of an α-synucleinopathy is performed by comparing the amount, size, and/or intensity of detected α-synuclein in a sample from the subject or in the subject, to corresponding baseline values. An appropriate baseline value can be the average level of α-synuclein found in a population of undiseased individuals. Alternatively, an appropriate baseline value may be the level of α-synuclein in the same subject determined at an earlier time.

The diagnostic methods described herein can also be used to monitor a subject's response to therapy. In this embodiment, detection of α-synuclein in the subject is determined prior to or concurrent with the commencement of treatment. The level of α-synuclein in the subject at this timepoint is used as a baseline value. At various times during the course of treatment the detection of α-synuclein is repeated, and the measured values thereafter compared with the baseline values. A decrease in values relative to baseline signals a positive response to treatment. No change or an increase in values relative to baseline signals an inadequate response to treatment. The treatment plan of an individual can be modified based on the results of monitoring the levels of α-synuclein in the subject.

A related aspect of the disclosure is directed to a method of identifying a subject's risk for developing an α-synucleinopathy or other condition mediated by or associated with a pathological form of α-synuclein. This method involves detecting, in the subject, the presence of accumulated α-synuclein protein or peptide using a diagnostic reagent comprising the antibody or binding fragment thereof described herein, and identifying the subject's risk of developing an α-synucleinopathy or condition mediated by or associated with accumulated α-synuclein based on the results of the detecting step.

Methods of detecting the presence of α-synuclein in the subject or in a sample from the subject include the in vitro and in vivo methods described supra. In one embodiment, the subject is not exhibiting any definitive signs or symptoms of an α-synucleinopathy, and employment of this method serves as an early diagnostic. In another embodiment, the subject is not exhibiting any signs or symptoms of an α-synucleinopathy, but has a genetic predisposition to a condition and employment of this method serves to predict the likelihood that the individual will develop the α-synucleinopathy in the future. In either embodiment, appropriate therapeutic and/or prophylactic intervention can be employed, e.g., administration of a therapeutic composition containing an antibody or polynucleotides encoding an antibody in an amount effective to slow or prevent the onset or progression of the α-synucleinopathy.

Another aspect of the present disclosure is directed to a diagnostic kit that comprises the antibody or binding fragment thereof as described herein and a detectable label.

A suitable detectable label is any moiety attached to an antibody or an analyte to render the reaction between the antibody and the analyte detectable. A label can produce a signal that is detectable by visual or instrumental means. Various labels include signal-producing substances, such as chromogens, fluorescent compounds, chemiluminescent compounds, radioactive compounds, and the like. Representative examples of detectable labels include moieties that produce light, e.g., acridinium compounds, and moieties that produce fluorescence, e.g., fluorescein. In this regard, the moiety itself may not be detectable, but becomes detectable upon reaction with yet another moiety.

Other suitable detectable labels include radioactive labels (e.g., H, I, S, C, P, and P), enzymatic labels (e.g., horseradish peroxidase, alkaline peroxidase, glucose 6-phosphate dehydrogenase, and the like), chemiluminescent labels (e.g., acridinium esters, thioesters, or sulfonamides; luminol, isoluminol, phenanthridinium esters, and the like), fluorescent labels (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label.

TABLE 3

Polynucleotide Sequences of Synuclein Antibodies Enriched by Solid Phase Panning

| Antibody ID | Nucleotide Sequence | NA SEQ ID NO: | AA SEQ ID NO: |
|---|---|---|---|
| 03-S-sR1-2D3 | ATGAAATACCTATTGCCTACGGCGGCCGCTGGATTGTTATTACTCGCGG CCCAGCCGGCCATGGCGCAGGTGCAGTTGCAGCAGTCTGGGGGAGGC TTGGTGCAGGCTGGGGGATCTCTGATTCTCCGTTGTAGAGCAACTGTA AGTGGCTTCAGTATCGGGACCATGGGCTGGTACCGCCAGGCTCCCGG GAAGGAGCGCGAGTTCGTCGCGAACGTTAGTCCTAGCGGTGCAAAAT ACTTCGCTGACTCCGTGAAGGGCCGATTCACCATCTCCAGAGACAACG CCAATAATACAGTGTATCTGCAAATGAACAGTCTGAAACCTGAAGACA CGGGCGTCTATTATTGTAATATACGAAGGTTTTCGTACCTCAGTGGCGA CTGGGGCCAGGGGACCCAGGTCACCGTCTCCTCAACTAGTGGCCCGG GAGGCCAACACCATCACCACCATCATGGCGCAGAACAAAAACTCATCT CAGAAGAGGATCTGTCTTAG | 242 | 109 |
| 07-S-sR2-1D12 | ATGAAATACCTATTGCCTACGGCGGCCGCTGGATTGTTATTACTCGCGG CCCAGCCGGCCATGGCGCAGGTGCAGTTGCAGGAGTCTGGGGGAGGC TTGGTGCAGGCTGGGGGGTCTCTGAGACTCTCCTGTGCAGCCTCTGGA TTCACCTTCAGTAGCAGTTCCATGGGCTGGTACCGCCAGGCTCCAGGG AAGCAGCGCGAGTTGGTCGCTTCTATTATGCGTTATGGTACTACAACCT ATACAGACTCCGTGAAGGGCCGATTCACCATCTCCAGAGACAACGGCC AGAGAACAGTCTATCTGCAAATGAACAGCCTGAAGCCTGAGGACACG GCCGTCTATTATTGTAATGTTCGAAGTTTCGTTCGAACCTACTGGGGCC AGGGGACCCTGGTCACCGTCTCCTCAACTAGTGGCCCGGGAGGCCAAC ACCATCACCACCATCATGGCGCAGAACAAAAACTCATCTCAGAAGAGG ATCTGTCTTAG | 243 | 110 |
| 08-S-sR2-2E10 | ATGAAATACCTATTGCCTACGGCGGCCGCTGGATTGTTATTACTCGCGG CCCAGCCGGCCATGGCGCAGGTGCAGNTGCAGGAGTCTGGGGGAGG TTGGTGCAGGCTGGGGGCTCTCTGAGACTCTCCTGTGCAGCCTCTGG ACGCACCTTCAGTAGTTTTGCCATGGGCTGGTTCCGCCAGGCTCCAGG GAAGGAGCGTGAGTTTGTTACAGCTATTAACTGGAGTGGTAGTAGCAC ATACTATGCAGACTCCGTGAAGGGCCGATTCACCATCTCCAGAGACAA CGCCAAGAACACGGTGTATCTGCAAATGAACAGCCTGAAACCTGAGGA CACGGCCGTCTATTACTGTAATGCCCAGCGGAGGTGGCCTCTTCGTGA CTATTGGGGCCAGGGGACCCAGGTCACCGTCTCCTCAACTAGTGGCCC GGGAGGCCAACACCATCACCACCATCATGGCGCAGAACAAAAACTCAT CTCAGAAGAGGATCTGTCTTAG | 244 | 111 |
| 11-S-sR1-2D12 | ATGAAATACCTATTGCCTACGGCGGCCGCTGGATTGTTATTACTCGCGG CCCAGCCGGCCATGGCGCAGGTGCAAAAAAAGAGTCTGGGGGAGGC TTGGTGCAGGCTGGGGGGTCTCTGAGACTCTCCTGTGCAGCCTCTGGA CTCATCTTCAGTATCAATGCCATGGCCTGGTACCGCCAGGCTCCAGGG AACCAGCGCGAGTTGGTCGCACGTATTACTACTGGTGGTAGCACAAAC | 245 | 112 |

TABLE 3-continued

Polynucleotide Sequences of Synuclein Antibodies
Enriched by Solid Phase Panning

| Antibody ID | Nucleotide Sequence | NA SEQ ID NO: | AA SEQ ID NO: |
|---|---|---|---|
| | TATGCAGACTCCGTGAAGGGCCGATTCACCATCTCCAGAGACAACGCC<br>AAGAACACGGTGTATCTGCAAATGAACAGCCTGAAACCTGAGGACACA<br>GCCGTCTATTTCTGTGCAGCAGATGTAAGGTTTGGGGAACGGACTCCC<br>TACTGGGGCCAGGGGACCCAGGTCACCGTCTCCTCAACTAGTGGCCCG<br>GGAGGCCAACACCATCACCACCATCATGGCGCAGAACAAAAACTCATC<br>TCAGAAGAGGATCTGTCTTAG | | |
| 15-S-sR2-1E7 | ATGAAATACCTATTGCCTACGGCGGCCGCTGGATTGTTATTACTCGCGG<br>CCCAGCCGGCCATGGCGCAGGTGCAGTTGCAGGCGTCTGGGGGAGGC<br>GTGGTGCAGTCTGGGGGGTCTCTGAGACTCTCCTGTGTAGCCTCTGGA<br>AACATCTTCAGGATCAATGCCATGGGCTGGTACCGCCAGGCTCCAGGG<br>AAGCAGCGCGAGTTGGTCGCACATATTATTAGTGGTGGTAGCACAAAC<br>TATGCAGACTCCGTGAAGGGCCGATTCACCATCTCCAGAGAATACGCC<br>AAGAATATGGTGTATCTGCAAATGAACAGCCTGAAACCTGAGGACACG<br>GCCGTCTATTACTGTAATGCCCGAACTTTCGTGAGAACCTACTGGGGCC<br>AGGGGACCCAGGTCACCGTCTCCTCAACTAGTGGCCCGGGAGGCCAA<br>CACCATCACCACCATCATGGCGCAGAACAAAAACTCATCTCAGAAGAG<br>GATCTGTCTTAG | 246 | 113 |
| 16-S-sR2-2F6 | ATGAAATACCTATTGCCTACGGCGGCCGCTGGATTGTTATTACTCGCGG<br>CCCAGCCGGCCATGGCGCAGGTGCAGTTGCAGCAGTTTGGGGGAGGC<br>TTGGTGCAGCCTGGGGGGTCTCTGAGACTCTCCTGTCAAGCCTCTACA<br>AGTGTCTTCGGTAACACTGCCATGGCCTGGTACCGCCAGGCTCCTGGG<br>AAGCAGCGCGAGTTGGTCGCACGAATTACTACCCTTGGTTTCACATACT<br>ATGCAGACTCCGCGAAGGGCCGATTCACCATCTCTAGAGACAGCGCCA<br>TGAACACGGTGTATCTGCAAATGAACAGCCTGAAACCTGAGGACACGG<br>CCGTCTATTACTGTAACCGCAGAGGATTTCGGAGCTACTGGGGCCAGG<br>GGACCCTGGTCACCGTCTCCTCAACTAGTGGCCCGGGAGGCCAACACC<br>ATCACCACCATCATGGCGCAGAACAAAAACTCATCTCAGAAGAGGATC<br>TGTCTTAG | 247 | 114 |
| 19-S-sR1-2G4 | ATGAAATACCTATTGCCTACGGCGGCCGCTGGATTGTTATTACTCGCGG<br>CCCAGCCGGCCATGGCGCAGGTGCAGTTGCAGGAGTCCGGGGGAGGC<br>NTNGGTGCAGTCTGGCGATTCTCTGAGACTCTCCTGTGCAGCCTCTGG<br>AAGCATCTATCATGTCAATACCATGGGTTGGTACCGCCAGTCTCCAGG<br>AAAGCAGCGCGAGTTGGTCGCAACTCTTACACATAACAACCGCGTAAC<br>CTATGCAGACTCCGTGAAGGGTCGATTCACCATCTCCAGAGACAACGC<br>CAAGATGACGGTGTATCTGCAAATGGACAGCCTGAAACCCGATGACAC<br>GGCCGTATATTACTGTTACTACTTCGTCCCGCGTAATCCATTATTCGGG<br>AGAAGGATTGACTTTGATGCCTGGGGCCAGGGGACCCAGGTCACCGT<br>CTCCTCAACTAGTGGCCCGGGAGGCCAACACCATCACCACCATCATGG<br>CGCAGAACAAAAACTCATCTCAGAAGAGGATCTGTCTTAG | 248 | 115 |
| 23-S-sR2-1E9 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>GTGGTGCAGTCTGGGGGGTCTCTGAGACTCTCCTGTGTAGCCTCTGGA<br>AACATCTTCAGGATCAATGTCATGGGCTGGTACCGCCAGGCTCCAGGG<br>AAGCAGCGCGAGTTGGTCGCGGTTGTAAAGAGTGGTGGTAGCACAAA<br>CTATGTAGACTCCGCGAAGGGACGATTCACCATCTCCAGGGACAACGC<br>CAAGAACACAGCGTATCTGCACATGGACAGCCTGAAACCTGAGGACAC<br>GGCCGTCTATTACTGTAATGCACAAACCCGACTCTGGAGCTACTGGGG<br>CCAGGGGACCCAGGTCACCGTTTCCTCAACTAGTGGCCCGGGAGGCCA<br>ACACCATCACCACCATCATGGCGCAGAACAAAAACTCATCTCAGAAGA<br>GGATCTGTCTTAG | 249 | 116 |
| 24-S-sR2-2F7 | ATGAAATACCTATTGCCTACGGCGGCCGCTGGATTGTTATTACTCGCGG<br>CCCAGCCGGCCATGGCGCAGGTGCAGCTGCAGGAGTTTGGGGGAGGC<br>GTGGTGCAGTCTGGGGGGTCTCTGAGACTCTCCTGTGTAGCCTCTGGA<br>AACATCTTCAGGATCAATGCCATGGGCTGGTACCGCCAGGCTCCAGGG<br>AAGCAGCGCGAGTTGGTCGCACATATTATTAGTGGTGGTAGCACAAAC<br>TATGCAGACTCCGTGAAGGGCCGATTCACCATCTCCAGAGAATACGCC<br>AAGAATATGGTGTATCTGCAAATGAACAGCCTGAAACCTGAGGACACG<br>GCCGTCTATTACTGTAATGCACAAACCCGACTCTGGAGCTACTGGGGC<br>CAGGGGACCCAGGTCACCGTCTCCTCAACTAGTGGCCCGGGAGGCCA<br>ACACCATCACCACCATCATGGCGCAGAACAAAAACTCATCTCAGAAGA<br>GGATCTGTCTTAG | 250 | 117 |
| 31-S-sR2-1F7 | ATGAAATACCTATTGCCTACGGCGGCCGCTGGATTGTTATTACTCGCGG<br>CCCAGCCGGCCATGGCGCAGGTGCAGCTGCAGGAGTCTGGGGGAGGC<br>TTGGTGCAGCCTGGGGGGTCTCTGAGACTCTCCTGTGCAGCCTCTCGA<br>AGCTTCTTCAGTATCAATGCCATGGGCTGGTACCGCCAGGCTCCAGGG<br>AAGCAGCGCGAGTTGGTCGCAACTATTACTAGTCGTGATAGCACAAAC | 251 | 118 |

TABLE 3-continued

Polynucleotide Sequences of Synuclein Antibodies
Enriched by Solid Phase Panning

| Antibody ID | Nucleotide Sequence | NA SEQ ID NO: | AA SEQ ID NO: |
|---|---|---|---|
| | GTTGCAGACTCCGTGAAGGGCCGATTCACCATCTCCAGAGACTACGCC<br>AAGAACATAGTGTATCTGCAAATGGACAGCCTGAGACCTGAGGACAC<br>GGCCACATATTACTGCTACGCTGATCAACCGTGGAGGGGTCGTGCCTG<br>GGGCCAGGGGACCCAGGTCACCGTCTCCTCAACTAGTGGCCCGGGAG<br>GCCAACACCATCACCACCATCATGGCGCAGAACAAAAACTCATCTCAG<br>AAGAGGATCTGTCTTAG | | |
| 32-S-sR2-2F11 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>GTGGTGCAGGCCGGGGGGTCTCTGAACCTCTCCTGTACACACTCAACA<br>ATCACCTTCAGGATCAACACCATGGCGTACTATCGCCAGGCTCCAGGG<br>TCTCAGCGCGCCCTGGTCGCGCGGATTAATCCAGCAGGGAGGACGTAT<br>TATCCAGATTCCGTGAAGGGCCGATTCACCATCTCCAGAGACAACGCC<br>AAGAACCAAGTGTATCTACAAATGAACGACCTCAAACCTGAGGACACG<br>GCCGTCTATTACTGTTCTACATGGCGACTAGGACGCAACTACTGGGGC<br>CAGGGGACCCTGGTCACCGTCTCCTCAACTAGTGGCCCGGGAGGCCAA<br>CACCATCACCACCATCATGGCGCAGAACAAAAACTCATCTCAGAAGAG<br>GATCTGTCTTAG | 252 | 119 |
| 34-S-sR1-1A12 | ATGAAATACCTATTGCCTACGGCGGCCGCTGGATTGTTATTACTCGCGG<br>CCCAGCCGGCCATGGCGCAGGTGCAGTTGCAGGAGTTTGGGGGAGGC<br>TTGGTGCAGGCTGGGGGGGTTCTGAGACTCTCCTGTGTAGCCTCTATG<br>ACTACCCTCGGTTTCAAGACCATGGGCTGGTACCGCCAGGCTCCAGGG<br>AAGCAGCGCGAGTTGGTCGCAACTATTAGTAGTATTGGTATCTCAACC<br>TATGCAAACTCCGTGAAGGGCCGATTCACCATCTCCAGAGACAATGCC<br>AAGAACACAGTGTATCTACAAATGAACAGCCTGAAACCTGAGGACACG<br>GCCGTCTATTTCTGTCATGTAATTCGGCCTAGTTGGATGCCGCAGTACT<br>GGGGCCAGGGGACCCTGGTCACCGTCTCCTCAACTAGTGGCCCGGGA<br>GGCCAACACCATCACCACCATCATGGCGCAGAACAAAAACTCATCTCA<br>GAAGAGGATCTGTCTTAG | 253 | 120 |
| 39-S-sR2-1F8 | ATGAAATACCTATTGCCTACGGCGGCCGCTGGATTGTTATTACTCGCGG<br>CCCAGCCGGCCANNAAAANCAGGTGCAGCTGCAGGAGTTTGGGGGAG<br>GCTTGGTGCAGCCTGGGGGGTCTCTGAGACTCTCCTGTCAAGCCTCTA<br>CAAGTGTCTTCGGTAACACTGCCATGGCCTGGTACCGCCAGGCTCCTG<br>GGAAGCAGCGCGAGTTGGTCGCACGAATTACTACCCTTGGTTTCACAT<br>ACTATGCAGACTCCGCGAAGGGCCGATTCACCATCTCTAGAGACAGCG<br>CCATGAACACGGTGTATCTGCAAATGAACAGCCTGAAACCTGAGGACA<br>CGGCCGTGTATTACTGTAATAGATTATGGCGGCCTCTAGCGTGGGGTC<br>AGGGGGACCCAGGTCACCGTCTCCTCAACTAGTGGCCCGGGAGGCCAA<br>CACCATCACCACCATCATGGCGCAGAACAAAAACTCATCTCAGAAGAG<br>GATCTGTCTTAG | 254 | 121 |
| 40-S-sR2-2G4 | ATGAAATACCTATTGCCTACGGCGGCCGCTGGATTGTTATTACTCGCGG<br>CCCAGCCGGCCATGNAAACANAAAACAGCTGCAGGAGTCTGGGGGAG<br>GCTTGGTGCAGCCTGGGGGGTCTCTGAGACTCTCCTGTGCAGCCTCTG<br>GAATGCGCAGCAGTCTCGCTATCATGGGCTGGTACCGCCAGGCTCCAG<br>GGAAGCAGCGCGAGTTGGTCGCAACTATTACTATTGGTGGTAACACAA<br>ACTATGCAGACTCCGTGAAGGGCCGGTTCGCCATCTCCAGAGACAACA<br>CCAAGCGCACGGTGTATCTGCAGATGAACAGCCTGACACCTGAGGACA<br>CGGCCGTCTATTACTGTAATGTTCGAAGTTTCGTTAGAACCTACTGGGG<br>CCAGGGGACCCAGGTCACCGTCTCCTCAACTAGTGGCCCGGGAGGCCA<br>ACACCATCACCACCATCATGGCGCAGAACAAAAACTCATCTCAGAAGA<br>GGATCTGTCTTAG | 255 | 122 |
| 47-S-sR2-1F11 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>TTGGTGCAGGCTGGGGGGTCTCTGAGACTCTCCTGTGCAGCCTCTGGA<br>TTCACCTTCAGTAGCAGTTCCATGGGCTGGTACCGCCAGGCTCCAGGG<br>AAGCAGCGCGAGTTGGTCGCTTCTATTATGCGTTATGGTACTACAACCT<br>ATACAGACTCCGTGAAGGGCCGATTCACCATCTCCAGAGACAACGGCC<br>AGAGAACAGTCTATCTGCAAATGAACAGCCTGAAGCCTGAGGACACG<br>GCCGTCTATTATTGTAATGTTCGAAGTTTCGTTCGAACCTACTGGGGCC<br>AGGGGACCCTGGTCACCGTCTCCTCAACTAGTGGCCCGGGAGGCCAAC<br>ACCATCACCACCATCATGGCGCAGAACAAAAACTCATCTCAGAAGAGG<br>ATCTGTCTTAG | 256 | 110 |
| 48-S-sR2-2G9 | ATGAAATACCTATTGCCTACGGCGGCCGCTGGATTGTTATTACTCGCGG<br>CCCAGCCGGCCATGGCGCAGGTGCAGTTGCAGCAGTCTGGGGGAGGC<br>TTGGTGCAGGCTGGGGGGTCTCTGAGACTCTCCTGTGCAGCCTCTGGA<br>AGCACCTTCATCAGTATCAAAACCATGGGCTGGTACCGCCAGGCTCCA<br>GGGAAGCAGCGCGAGTTGGTCGCTGGTATTACTAAGAATAATTACATA | 257 | 123 |

TABLE 3-continued

Polynucleotide Sequences of Synuclein Antibodies
Enriched by Solid Phase Panning

| Antibody ID | Nucleotide Sequence | NA SEQ ID NO: | AA SEQ ID NO: |
|---|---|---|---|
| | AACTATGCAGACTCCGTGAAGGGCCGATTCACCATCTCCAGAGACAAC
GGCAAGAATACAGTGTATCTGCAAATGAACGGCCTGAAACCTGAGGA
CACGGCCGTCTATTACTGTACTGTACAACGTCGCTTAGGGCGTGTCTAC
TGGGGCCAGGGGACCCTGGTCACCGTCTCCTCAACTAGTGGCCCGGGA
GGCCAACACCATCACCACCATCATGGCGCAGAACAAAAACTCATCTCA
GAAGAGGATCTGTCTTAG | | |
| 50-S-sR1-2B2 | ATGAAATACCTATTGCCTACGGCGGCCGCTGGATTGTTATTACTCGCGG
CCCAGCCGGCCATGGCGCAGGTGCAGCTGCAGGAGTCTGGGGGAGGC
TTGGTGCAGGCTGGGGGGTCTCTGAGACTCTCCTGTACGGCCTCTGGA
AGCACCTTCAGGTTCAATGACATGGGCTGGTACCGCCAGGCTCCAGGG
AAGCAGCGCGAATTGGTCGCAAATATTAATAGTAGTGGTAGAACCATG
TATCCAGACTCCGTCAAGGGCCGATTCACAATCTCCAAAGACAACGTCA
AAAATACAGTGTATCTGCAGATGAACAGCCTGACACCTGAGGACACGG
CCGTCTATTACTGTAATGTTCGAAGTTTCGTTAGAACCTACTGGGGCCA
GGGGACCCAGGTCACCGTCTCCTCAACTAGTGGCCCGGGAGGCCAAC
ACCATCACCACCATCATGGCGCAGAACAAAAACTCATCTCAGAAGAGG
ATCTGTCTTAG | 258 | 124 |
| 55-S-sR2-1G3 | ATGAAATACCTATTGCCTACGGCGGCCGCTGGATTGTTATTACTCGCGG
CCCAGCCGGCCATGGCGCAGGTGCAGCTGCAGGAGTCTGGGGGAGGC
TTGGTCCAGGCTGGGGGGTCTCTGAGCGCTCTCCTGTGTAGCCTCTGGA
AGCCGCTTCAGTATCAATACCATGGGCTGGTACCGCCAGGCTCCAGGG
AAGCAGCGCGAGTTGGTCGCAGGTATTACTAGCCTTGGTTTCACAAAC
TATGCAGACTCCGTGAAGGGCCGATTCACCATCTCCAGAGACAACGCC
AAGAACACAGTGTATCTGCAAATGAACAACCTGAAAGTTGAGGACACG
GCCGTCTATTACTGTAACCGCAGAGGATTTCGGAGCTACTGGGGCCAG
GGGACCCTGGTCACCGTCTCCTCAACTAGTGGCCCGGGAGGCCAACAC
CATCACCACCATCATGGCGCAGAACAAAAACTCATCTCAGAAGAGGAT
CTGTCTTAG | 259 | 125 |
| 56-S-sR2-2H1 | ATGAAATACCTATTGCCTACGGCGGCCGCTGGATTGTTATTACTCGCGG
CCCAGCCGGCCATGGCGCAGGTGCAGCTGCAGGAGTCTGGGGGAGGC
TTCGTGCAGGCTGGGGGGTCTCTGAGACTCTCCTGTGCAGCCTCTGGA
AGCATCTTCAGTATCAATTATGGTAACTGGTACCGCCAGGCTCCAGGG
AAGCAGCGCGAATTGGTCGCAGGTATTAGTCGTGGAGGCCGCACAAA
GTATGCAGACTCCGTGAAGGGCCGATTCACCATCTCCAGAGATAGCGC
CAAGACACTGACGCTGCAGATGACTAGCTTGAAACCTGAGGACACGGC
CGTCTATTACTGTAATGTTCGAAGTTTCGTTCGAACCTACTGGGGCCAG
GGGACCCAGGTCACCGTTTCCTCAACTAGTGGCCCGGGAGGCCAACAC
CATCACCACCATCATGGCGCAGAACAAAAACTCATCTCAGAAGAGGAT
CTGTCTTAG | 260 | 126 |
| 58-S-sR1-2B4 | ATGAAATACCTATTGCCTACGGCGGCCGCTGGATTGTTATTACTCGCGG
CCCAGCCGGCCATGGCGCAGGTGCAGCTGCAGGAGTCTGGGGGAGGC
TTGGTGCAGTCGGGGGGGTCTCTGAGACTCTCCTGTTCGGCCTCCGGA
AGCATCTTCAGGATCAATCTCATGGGCTGGTACCGCCAGGCTCCAGGG
AAGCAGCGCGAGTTGGTCGCAACTATTACTAATGAAGGTAACATAC
TACGCAGACTCCGTGAAGGGCCGTTTCACCATCTCCAGAGACAACGCC
AACAACACGTGGTATCTGCAAATGAACAGCCTGAAACCTGAGGACACA
GCCGTCTATGAATGTGCAGGAAAGGTCATTAGATGGTACTGGGGCCA
GGGGACCCAGGTCACCGTTTCCTCAACTAGTGGCCCGGGAGGCCAACA
CCATCACCACCATCATGGCGCAGAACAAAAACTCATCTCAGAAGAGGA
TCTGTCTTAG | 261 | 127 |
| 62-S-sR2-1A9 | ATGAAATACCTATTGCCTACGGCGGCCGCTGGATTGTTATTACTCGCGG
CCCAGCCGGCCATGGCGCAGGTGCAGCTGCAGGAGTTTGGGGGAGGC
TTGGTGCAGCCTGGGGGGTCTCTGAGACTCTCCTGTCAAGCCTCTACA
AGTGTCTTCGGTAACACTGCCATGGCCTGGTACCGCCAGGCTCCTGGG
AAGCAGCGCGAGTTGGTCGCACGAATTACTACCCTTGGTTTCACATACT
ATGCAGACTCCGCGAAGGGCCGATTCACCATCTCTAGAGACAGCGCCA
TGAACACGGTGTATCTGCAAATGAACAGCCTGAAACCTGAGGACACGG
CCGTTTATTACTGTCGTGCACGTCGCGCTCTGCGAGAATCGCACTGGG
GCCAGGGGACCCAGGTCACCGTCTCCTCAACTAGTGGCCCGGGAGGC
CAACACCATCACCACCATCATGGCGCAGAACAAAAACTCATCTCAGAA
GAGGATCTGTCTTAG | 262 | 128 |
| 63-S-sR2-1G9 | ATGAAATACCTATTGCCTACGGCGGCCGCTGGATTGTTATTACTCGCGG
CCCAGCCGGCCATGGCGCAGGTGCAGCTGCAGGAGTCTGGGGGAGGC
TTCGTGCAGGCTGGGGGGTCTCTGAGACTCTCCTGTGCAGCCTCTGGA
AGCATCTTCAGTATCAATTATGGTAACTGGTACCGCCAGGCTCCAGGG
AAGCAGCGCGAATTGGTCGCAGGTATTAGTCGTGGAGGCCGCACAAA | 263 | 129 |

TABLE 3-continued

Polynucleotide Sequences of Synuclein Antibodies
Enriched by Solid Phase Panning

| Antibody ID | Nucleotide Sequence | NA SEQ ID NO: | AA SEQ ID NO: |
|---|---|---|---|
| | GTATGCAGACTCCGTGAAGGGCCGATTCACCATCTCCAGAGATAGCGC<br>CAAGACACTGACGCTGCAGATGACTAGCTTGAAACCTGAGGACACGGC<br>CATCTATTCTTGTAATGCTCGAAGTTTCGTTAGAACTTACTGGGGCCAG<br>GGGACCCTGGTCACCGTCTCCTCAACTAGTGGCCCGGGAGGCCAACAC<br>CATCACCACCATCATGGCGCAGAACAAAAACTCATCTCAGAAGAGGAT<br>CTGTCTTAG | | |
| 64-S-sR2-2H2 | ATGAAATACCTATTGCCTACGGCGGCCGCTGGATTGTTATTACTCGCGG<br>CCCAGCCGGCCATGGCGCAGGTGCAGCTGCAGGAGTCTGGGGGAGGC<br>TTGGTGACGGCTGGAGGGTCTCTGAGACTCTCCTGTGCAGCCTCTAGA<br>AACTTCTTCACTTTCAGAGCCATGGGCTGGTACCGCCAGGCTCCAGGG<br>AAGCAGCGCGAAATGGTCGCATCTATTACTACCGGTGGTCGCACCGTC<br>TATGCAGACTCCGTGAAGGGCCGATTCACCATCTCCAAATCCAACGCCA<br>ATAACACAGTGTATCTCCAAATGAACAGCCTGGAAGCTGAGGACACGG<br>CCGTCTATTACTGTAATGCACGACGCAGATTTCCGGTGCCGGGCCCGA<br>CCGACTACTGGGGCCGGGGGACCCTGGTCACCGTCTCCTCAACTAGTG<br>GCCCGGGAGGCCAACACCATCACCACCATCATGGCGCAGAACAAAAAC<br>TCATCTCAGAAGAGGATCTGTCTTAG | 264 | 130 |
| 66-S-sR1-2B10 | ATGAAATACCTATTGCCTACGGCGGCCGCTGGATTGTTATTACTCGCGG<br>CCCAGCCGGCCATGGCGCAGGTGCAGCTGCAGGAGTCTGGGGGAGGC<br>TTGGTGCAGGCTGGGGGGTCTCTGAGACTCTCCTGTGCAGCCTCTGGA<br>ATCACCTTCAGGTTCAATGCCATGGGCTGGTACCGCCAGGCTCCAGGG<br>AAAGAGCGCGAGTTGGTCGCAAGGGTTAGTAGTGGTGGTAGCACAAC<br>CTATGCAGACTCCGTGAAGGGCCCGATTCACCACCTTCAGAGACAACGT<br>CAAGAACATAGGGTATCTGCAAATGACCAGCCTGAAACCTGAGGACAC<br>GGCCGTCTATTACTGTAATGTGGGGAATTTCTGGGGCCAGGGGACCCA<br>GGTCACCGTCTCCTCAACTAGTGGCCCGGGAGGCCAACACCATCACCA<br>CCATCATGGCGCAGAACAAAAACTCATCTCAGAAGAGGATCTGTCTTA<br>G | 265 | 131 |
| 70-S-sR2-1B3 | ATGAAATACCTATTGCCTACGGCGGCCGCTGGATTGTTATTACTCGCGG<br>CCCAGCCGGCCATGGCGCAGGTGCAGCTGCAGGAGTCTGGGGGAGGC<br>TTGGTGCGGACTGGGGAGTCTCTGGGACTCTCCTGTGCAGCCTCTGGA<br>CGCAGCATCCTGATCAAAGGCATGGGCTGGTACCGCCAGGCTCCAGG<br>GAAGGAGCGCGAAATGGTCGCGACTATTAGTATGGCCGGTGTCACTA<br>ACTATTCAGACTCCGTGAAGGGCCGGTTCACCATCTCCAGAGATAACT<br>ACAAGAAGACAGTGTCCCTGCAGATGAACAATTTGAGACCGGAGGAC<br>ACGGCCGTCTATGTGTGTAATGCACAAACCCGACTCTGGAGCTACTGG<br>GGCCAGGGGACCCAGGTCACCGTCTCCTCAACTAGTGGCCCGGGAGG<br>CCAACACCATCACCACCATCATGGCGCAGAACAAAAACTCATCTCAGA<br>AGAGGATCTGTCTTAG | 266 | 132 |
| 71-S-sR2-2A8 | ATGAAATACCTATTGCCTACGGCGGCCGCTGGATTGTTATTACTCGCGG<br>CCCAGCCGGCCATGGCGCAGGTGCAGCTCGTGGAGTCTGGGGGAGGC<br>CTGGTGCAGGCTGGAGGGTCTCTGAGACTCTCCTGTGCAGCCTCTGGA<br>AGGATTTTCGGGCGCAATGCCATGGCCTGGTACCGCCAGGTTCCAGGG<br>AAGGAGCGCGAGCTGGTTGCACGTATTACTAGGGATGGACGGACAAT<br>GTATGTAGACTCCGCGAAGGGACGATTCACCATCTCCAGGGACAACGC<br>CAAGAACACAGCGTATCTGCACATGGACAGCCTGAAACCTGAGGACAC<br>GGCCGTCTATTACTGTAATGCACAAACCCGACTCTGGAGCTACTGGGG<br>CCAGGGGACCCAGGTCACCGTCTCCTCAACTAGTGGCCCGGGAGGCCA<br>ACACCATCACCACCATCATGGCGCAGAACAAAAACTCATCTCAGAAGA<br>GGATCTGTCTTAG | 267 | 133 |
| 72-S-sR2-2H3 | ATGAAATACCTATTGCCTACGGCGGCCGCTGGATTGTTATTACTCGCGG<br>CCCAGCCGGCCATGGCGCAGNNNNCAGCTGCAGGAGTCTGGGGGAG<br>GCTTGGTGCAGGCTGGGGGGTCTCTGAGACTCTCCTGTGCAGCCTCTA<br>GAAGCACCTTCAGATTCAATGTCATGGGCTGGTACCGCCAGGCTCCAG<br>GGAAGCAGCGCGAGTTGGTCGCAGCTATTAGTAGTCGTGGTGGTAGT<br>ACAAACTATGCAGACTCCGTGCAGGGCCGATTCACCATCTCCAGAGAC<br>AACGCCAAGAACACAGTGTCTCTGCAAATGAACAGCCTGAAACCTGAG<br>GACACGGCCGTCTATTACTGTAATGTTCGAAGTTTCGTTAGAACCTACT<br>GGGGCCAGGGGACCCAGGTCACCGTCTCCTCAACTAGTGGCCCGGGA<br>GGCCAACACCATCACCACCATCATGGCGCAGAACAAAAACTCATCTCA<br>GAAGAGGATCTGTCTTAG | 268 | 134 |
| 74-S-sR1-2B12 | ATGAAATACCTATTGCCTACGGCGGCCGCTGGATTGTTATTACTCGCGG<br>CCCAGCCGGCCATGGCGCAGGTGCAGCTGCAGGAGTTTGGGGGAGGC<br>TTGGTGCAGGCTGGGGGGTCTCTGAGACTCTCCTGTGCAACCTCTGGA<br>AGCATCTTCAGTATCAACGCCGTGGGCTGGTACCGCCAGGCTCCAGGG<br>AATCAGCGCGAGTTGGTCGCAGCTATTAGTGGACGTGGTAGTACACAC | 269 | 135 |

TABLE 3-continued

Polynucleotide Sequences of Synuclein Antibodies
Enriched by Solid Phase Panning

| Antibody ID | Nucleotide Sequence | NA SEQ ID NO: | AA SEQ ID NO: |
|---|---|---|---|
| | TATGCAGACTCCGTGAAGGGCCGATTCACCATCTCCAGAGACACCGCC<br>AAGAACACGGTGTATCTGCAAATGAACAGCCTGAAACCTGAGGACACA<br>GCCGTCTATTACTGTGCATTAGATCAACATATGGAGGTTATTGTATCGC<br>CGGGACGTATTGGTTCCTGGGGCCAGGGGACCCTGGTCACCGTCTCCT<br>CAACTAGTGGCCCGGGAGGCCAACACCATCACCACCATCATGGCGCAG<br>AACAAAAACTCATCTCAGAAGAGGATCTGTCTTAG | | |
| 78-S-sR2-1C9 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>TTGGTGCAGGCTGGGGAGTCTCTGACACTCTCCTGTGCACTCTCAACAA<br>CCATGTTCGGTTTCTGGCCCATGGCCTGGTTCCGCCAGACTCCAGGACA<br>GCGGCGCGAATTGATTGCGACTATTGATAGTCGTGGTCGCACAAACAT<br>CGCAGACTCCGTGAAGGGCCGATTTACCATCTCCAGAGACAACACCAA<br>GAACACACTGTATCTGCGGATGAACAGCCTGAAACCTGAGGACACGGC<br>CGTCTATTACTGTAATGCCCAGCGGAGGTGGCCTCTTCGTGACTATTGG<br>GGCCAGGGGACCCAGGTCACCGTCTCCTCAACTAGTGGCCCGGGAGG<br>CCAACACCATCACCACCATCATGGCGCAGAACAAAAACTCATCTCAGA<br>AGAGGATCTGTCTTAG | 270 | 136 |
| 79-S-sR2-2B3 | ATGAAATACCTATTGCCTACGGCGGCCGCTGGATTGTTATTACTCGCGG<br>CCCAGCCGGCCATGGCGCAGGTGCAGCTGCAGGAGTTTGGGGGAGGC<br>GTGGTGCAGTCTGGGGGGTCTCTGAGACTCTCCTGTGTAGCCTCTGGA<br>AACATCTTCAGGATCAATGCCATGGGCTGGTACCGCCAGGCTCCAGGG<br>AAGCAGCGCGAGTTGGTCGCCCGTATTAGTAGTGGTGGTAGCACAAA<br>CTATGCAGACTCCGTGAAGGGCCGATTCACCATCTCCAGAGACAACGT<br>CAAGAACACAGTGACTCTGCAAATGAACAGCCTGAAACCTGAGGACAC<br>GGCCGTCTATTACTGTAATGCGCGGAGGCCATTGCGTTGGTATGAGTA<br>CTGGGGCCAGGGGACCCTGGTCACCGTCTCCTCAACTAGTGGCCCGGG<br>AGGCCAACACCATCACCACCATCATGGCGCAGAACAAAAACTCATCTC<br>AGAAGAGGATCTGTCTTAG | 271 | 137 |
| 80-S-sR2-2H5 | ATGAAATACCTATTGCCTACGGCGGCCGCTGGATTGTTATTACTCGCGG<br>CCCAGCCGGCCATGGCGCAGGTGCAGCTGCAGGCGTCTGGGGGAGGC<br>TTGGTGCAGCCTGGGGGATCTCTGAGACTCTCCTGTGCAGCCTCGGGA<br>AGCATCTTCAGTACCAATGCCATGGGCTGGTACCGCCAGGCTCCAGGG<br>AAGCAGCGCGAGGTGATCGCATCTATTACAAAATTTGGGAACACAGAC<br>TATGCAGACTCTGTGAAGGGCCGATTCACCATCTCCAGAGACAACGCC<br>AAGAACATAGTGTATCTGCAAATGAACAGCCTGAAACCTGAGGACACG<br>GCCGTTTATTACTGTTATCAAAACAGTCGGGGGCGCTGGTATGATATTT<br>TCAGGGACTACTGGGGCCAGGGGACCCTGGTCACCGTCTCCTCAACTA<br>GTGGCCCGGGAGGCCAACACCATCACCACCATCATGGCGCAGAACAA<br>AAACTCATCTCAGAAGAGGATCTGTCTTAG | 272 | 138 |
| 80-S-sR2-2H9 | >80-S-sR2-2H9<br>ATGAAATACCTATTGCCTACGGCGGCCGCTGGATTGTTATTACTCGCGG<br>CCCAGCCGGCCATGGCGCAGGTGCAGCTGCGTGGAGTCTGGGGGTGGC<br>TTCGTGCAGGCAGGGGGATCTCTAAGACTCTCCTGTGTAGCCTCGCGA<br>AGCAGCTTCAGGATCACTACCATGAACTGGTACCGCCAGGCTCCAGGG<br>AAGCAGCGCGAAATGGTCGCATCTATTACTACCGGTGGTCGCACCGTC<br>TATGCAGACTCCGTGAAGGGCCGATTCACCATCTCCAAATCCAACGCA<br>ATAACACAGTGTATCTCCAAATGAACAGCCTGGAAGCTGAGGACACGG<br>CCGTCTATTACTGTAATGCCCAGCGGAGGTGGCCTCTTCGTGACTATTG<br>GGGCCAGGGGACCCTGGTCACCGTCTCCTCAACTAGTGGCCCGGGAG<br>GCCAACACCATCACCACCATCATGGCGCAGAACAAAAACTCATCTCAG<br>AAGAGGATCTGTCTTAG | 273 | 139 |
| 82-S-sR1-2C11 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>GTGGTGCAGTCTGGGGGGTCTCTGAGACTCTCCTGTGTAGCCTCTGGA<br>AACATCTTCAGGATCAATGTCATGGGCTGGTACCGCCAGGCTCCAGGG<br>AAGCAGCGCGAGTTGGTCGCGGTTGTAAAGAGTGGTGGTAGCACAAA<br>CTATGTAGACTCCGCGAAGGGACGATTCACCATCTCCAGGGACAACGC<br>CAAGAACACAGCGTATCTGCACATGGACAGCCTGAAACCTGAGGACAC<br>GGCCGTCTATTACTGTAATGCACAAACCCGACTCTGGAGCTACTGGGG<br>CCAGGGGACCCTGGTCACCGTCTCCTCAACTAGTGGCCCGGGAGGCCA<br>ACACCATCACCACCATCATGGCGCAGAACAAAAACTCATCTCAGAAGA<br>GGATCTGTCTTAG | 274 | 140 |
| 86-S-sR2-1D5 | ATGAAATACCTATTGCCTACGGCGGCCGCTGGATTGTTATTACTCGCGG<br>CCCAGCCGGCCATGGCGCAGGTGCAGCTGCAGGAGTTTGGGGGAGGC<br>GTGGTGCAGTCTGGGGGGTCTCTGAGACTCTCCTGTGTAGCCTCTGGA<br>AACATCTTCAGGATCAATGCCATGGGCTGGTACCGCCAGGCTCCAGGG | 275 | 141 |

TABLE 3-continued

Polynucleotide Sequences of Synuclein Antibodies Enriched by Solid Phase Panning

| Antibody ID | Nucleotide Sequence | NA SEQ ID NO: | AA SEQ ID NO: |
|---|---|---|---|
| | AAGCAGCGCGAGTTGGTCGCACATATTATTAGTGGTGGTAGCACAAAC<br>TATGCAGACTCCGTGAAGGGCCGATTCACCATCTCCAGAGAATACGCC<br>AAGAATATGGTGTATCTGCAAATGAACAGCCTGAAACCTGAGGACACG<br>GCCGTCTATTACTGTAATGCCGAAAGGAGATTCGGGATGAGACAGGTC<br>TGGGGCCAGGGGACCCAGGTCACCGTCTCCTCAACTAGTGGCCCGGG<br>AGGCCAACACCATCACCACCATCATGGCGCAGAACAAAAACTCATCTC<br>AGAAGAGGATCTGTCTTAG | | |
| 87-S-sR2-2D8 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>TTGGTGCAGGCTGGGGGGTCTCTGAGACTCTCCTGTGCAGCCTCTGTG<br>GTTCCCTTCAGATACTTTCCCATGGGCTGGTACCGCCAGGCTCCAGGGA<br>GACAGCGCGAGTTGGTCGCGTCTATTACCAGCGGTGGTGGCGTAAACT<br>ATGCAGATTTCGTAGAGGGCCGATTCACCATCTCCAGAGACAATGCCA<br>AGAACACATTTTATCTACAAATGAGCAGCCTGAAACCTGAGGACACGG<br>CCGTCTATTACTGTGCACGACTTCTCAGTCTGGGTAGTAGGTGGGGAT<br>ACGGCATGTTCACCTGGGGCAAAGGGACCCTGGTCACCGTCTCCTCAA<br>CTAGTGGCCCGGGAGGCCAACACCATCACCACCATCATGGCGCAGAAC<br>AAAAACTCATCTCAGAAGAGGATCTGTCTTAG | 276 | 142 |
| 88-S-sR2-2H8 | ATGAAATACCTATTGCCTACGGCGGCCGCTGGATTGTTATTACTCGCGG<br>CCCAGCCGGCCATGGCGCAGGTGCAGNTNCAGGAGTCTGGGGGAGG<br>CTTGGTGCAGCCTGGGGGGTCTCTGAGACTCTCCTGTGCAGCCTCTGG<br>AAGCATCTTCAGTATCAAGACCATGGGCTGGTACCGCCAGGCTCCAGG<br>GAAGCAGCGCGAGTTGGTCGCTGCTATAGCTAGTGGTGGTTTCACAAA<br>CTATGCAGACTCCGTGAAGGGCCGATTCACCATCTCCAGAGACAACGC<br>CAGGAACACGGTGTATCTGCAAATGAACAGCCTGAAACCTGAGGACAC<br>GGCCGTCTATTACTGTAATGCCCAGCGGAGGTGGCCTCTTCGTGACTAT<br>TGGGGCCAGGGGACCCTGGTCACCGTTTCCTCAACTAGTGGCCCGGGA<br>GGCCAACACCATCACCACCATCATGGCGCAGAACAAAAACTCATCTCA<br>GAAGAGGATCTGTCTTAG | 277 | 143 |
| 94-S-sR2-1D10 | ATGAAATACCTATTGCCTACGGCGGCCGCTGGATTGTTATTACTCGCGG<br>CCCAGCCGGCCATGGCGCAGGTGCAGNTGCAGNAGTCAGGGGGAGG<br>CTTGGTACGGGACGGGGGGTCTCTGACACTCTCCTGTGCAGCCTCTGG<br>AAGTGCCTTCAGGATGAATTCCATGGCCTGGTACCGCCAGGTTCCTGG<br>GAAACAGCGCGAGTTAGTCGCAGCTATTAGCTTCCGTGGGAGCGCAA<br>ATTATGCTAACTCCGTGAAGGGCCGATTCACCATCTCCAGAGACAACG<br>GCAAGAACACGGTATATCTACAAATGAACAGCCTGAAACCTGAGGACA<br>CAGCCGTCTATTACTGTGCAGCAGGCCGTCCATGGCAAAGGACTTTCT<br>ACTGGGGCCAGGGGACCCAGGTCACCGTCTCCTCAACTAGTGGCCCGG<br>GAGGCCAACACCATCACCACCATCATGGCGCAGAACAAAAACTCATCT<br>CAGAAGAGGATCTGTCTTAG | 278 | 144 |
| 95-S-sR2-2D10 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>TTCGTGCAGGCTGGGGGGTCTCTGAGACTCTCCTGTGCAGCCTCTGGA<br>AGCATCTTCAGTATCAATTATGGTAACTGGTACCGCCAGGCTCCAGGG<br>AAGCAGCGCGAATTGGTCGCAGGTATTAGTCGTGGAGGCCGCACAAA<br>GTATGCAGACTCCGTGAAGGGCCGATTCACCATCTCCAGAGATAGCGC<br>CAAGACACTGACGCTGCAGATGACTAGCTTGAAACCTGAGGATTCGGG<br>CGTCTACTACTGTGCTGCGACCCGCTGGAGTTGGGGTACTAAGAGTTA<br>CTGGGGCCAGGGAACCCAGGTCACCGTCTCCTCAACTAGTGGCCCGGG<br>AGGCCAACACCATCACCACCATCATGGCGCAGAACAAAAACTCATCTC<br>AGAAGAGGATCTGTCTTAG | 279 | 145 |
| S-sR2-2H7 | ATGAAATACCTATTGCCTACGGCGGCCGCTGGATTGTTATTACTCGCGG<br>CCCAGCCGGCCATGGCGCAGGTGCAGCTGCAGGAGTTTGGGGGAGGC<br>GTGGTGCAGTCTGGGGGGTCTCTGAGACTCTCCTGTGTAGCCTCTGGA<br>AACATCTTCAGGATCAATGCCATGGGCTGGTACCGCCAGGCTCCAGGC<br>AAGTCACGCGTACTGGTCGCAAGCATTGATAGTGCCGGTAGGACAAAC<br>TATGGTGACGCCGTAGAGGATCGATTCACCATCTCCAGAGACATCGCC<br>AACAACATAGTGAATCTACAGATGAATAGCCTAAAACCTGAGGACACG<br>GCCGTCTATTACTGTTCTACATGGCGACTAGGACGAACTACTGGGGC<br>CAGGGGACCCAGGTCACCGTCTCCTCAACTAGTGGCCCGGGAGGCCA<br>ACACCATCACCACCATCATGGCGCAGAACAAAAACTCATCTCAGAAGA<br>GGATCTGTCTTAG | 280 | 221 |
| 90-SsR1-2D1 | ATGAAATACCTATTGCCTACGGCGGCCGCTGGATTGTTATTACTCGCGG<br>CCCAGCCGGCCATGGCGCAGGTGCAGTTGCAGGAGTCTGGGGGAGGC<br>TTGGTGCAGGCTGGGGGCTCTCTGAGACTCTCCTGTGCAGCCTCTGGA<br>AGCATCTTCCGTATCAATGGCATGGGCTGGATCCGCCAGGCTCCAGGG | 281 | 343 |

TABLE 3-continued

Polynucleotide Sequences of Synuclein Antibodies
Enriched by Solid Phase Panning

| Antibody ID | Nucleotide Sequence | NA SEQ ID NO: | AA SEQ ID NO: |
|---|---|---|---|
| | AAGGAGCGTGAGGTTGTAGCAGCCGTTAACTGGAGTGGTGAACGCAC<br>ATACTATGTTGACTCCGTGAAGGGCCGATTCACCATCTCCAGAGAAAA<br>AGGCAACAGGATATATCTACAAATGAACGATTTGGAACCTGACGACAC<br>GGCCGTTTATTACTGTGCAGCAGATACGGATTACCGTTTAGACGGTAG<br>TACGTGGATTACCAACCTCTACTCTGGGTCCTTGGGCCAGGGGACCCA<br>GGTCACCGTCTCCTCAACTAGTGGCCCGGGAGGCCAACACCATCACCA<br>CCATCATGGCGCAGAACAAAAACTCATCTCAGAAGAGGATCTGTCTTA<br>G | | |
| S-sR2-1F6 | CAGGTGCAGCTGCAGGAGTCTGGGGGAGGCTTGGTGCAGGCTGGGG<br>GGTCTCTGAGACTCTCCTGTGCAGCCTCTGGAAGCACCTTCAGTAACAA<br>TGCCATGGCCTGGTACCGCCAGGCTCCAGGGAAGCAGCGCGAGTTGG<br>TCGCCTATATTAGTAGTGGTGGTTTCACAAATTATGGCGACTCCGTGAA<br>GGGCCGATTCACCATCTCCGAAGACAACGCCAAGAGTACAGTGTATCT<br>ACAAATGACCAGCCTGAAACCTGAGGACACGGCCGTCTATTATTGTAG<br>CGCCGGGGGTACATACCGTAGTGGTAATGTCTACTTCTTTCCGCGTTCC<br>TGGGGCCAGGGGACCCAGGTCACCGTCTCCTCAACTAGTGGCCCGGG<br>AGGCCAA | 282 | 225 |
| S-sR2-1G4 | CAGGTGCAGTTGCAGCAGTCTGGGGGAGGGTTGGTGCAGCCTGGGG<br>GGTCTCTGAGACTCTCCTGTGCAGCCTCTGGAAGCATCTTCAGTATCAA<br>TTCCATGGCCTGGTACCGCCAGGCTCCAGGGAACCAGCGCGAGTTGGT<br>CGCGACTATTAGTAGTCGTAGTACCACGTACTATGCGCCTTCCGTGAAG<br>GGCCGGTTCACCATCTCCAGAGACAACGCCAAGAACATAGTGTACCTG<br>CAAATGAACAGCCTCAAACCTGAGGACACGGCCGTGTATTACTGTAAG<br>GCGGGTTCAGTGGGTCGCGTGTACTGGGGCCAGGGGACCCTGGTCAC<br>CGTCTCCTCAACTAGTGGCCCGGGAGGCCAA | 283 | 229 |
| S-sR2-2C10 | CAGGTGCAGTTGCAGGAGTCTGGGGGAGGCTTGGTGCAGGCTGGGG<br>GGTCTCTGAGACTCTCCTGTTTAGCCTCTATGACTACCCTCGGGTTCAA<br>GACCATGGGCTGGTACCGCCAGGCTCCAGGGAAGCAGCGCGAGTTGG<br>TCGCCGCTATTACGAGTGGTGGTACCGCAAACTATGCAGACTCCGTGA<br>AGGGCCGATTCGCCATCTCCAGAGAGAACGCCAAGAACACGCTGTATC<br>TGCAAATGAACAGCCTGAAACCTGAGGACACGGCCCTGTATTACTGTG<br>CATCGACTACGGGTTGGACAGAGGTCGGCGGACGAAATGACTACTGG<br>GGCCAGGGGACCCTGGTCACCGTTTCCTCAACTAGTGGCCCGGGAGGC<br>CAA | 284 | 233 |
| S-sR2-2E9 | CAGGTGCAGCTGCAGGAGTCTGGGGGAGGATTGGTGCAGACTGGGG<br>GGTCTCTTAGACTCTCCTGTGCGGCCTCTGGGCGCACCTTCAGAGTCAA<br>TGCCATGGCCTGGTACCGCCAGGCTCCAGGGAAGCAGCGCGAGTTCG<br>TCGCAGCTGTTACAAATGGTGGTAGTACAACCTATGCAGATTCCGTGA<br>AGGGCCGATTCACCATCTCCAGGGACAACGCCAAGAATACAATATATC<br>TGCAAATGAACAGACTGGAACCTGAAGCACGGCCCTCTATTATTGTA<br>ATGCCGAAAGGAGATTCGGGATGAGACAGGTCTGGGGCCAGGGGAC<br>CCTGGTCACCGTTTCCTCAACTAGTGGCCCGGGAGGCCAA | 285 | 237 |
| S-sR2-2G11 | CAGGTGCAGCTGCAGGAGTCTGGGGGAGGCTTGGTGCAGCCTGGGG<br>GGTCTCTGAGACTCTCCTGTGCAGCCTCTGGAAGAGTCTTCAGTATCAA<br>TACCATGGGCTGGTACCGCCAGGCTCCAGGGAAGCAGCGCGAGTTGG<br>TCGCATCTATGACTAGAGGTGGTAGCGCAAATTATGCAGACTCCGTGA<br>AGGGCCGATTCACCACATCCAGAGACAACGCCAAGAACATGGTGTATC<br>TGCAAATGAATAGACTGAAAGCTGAGGACACGGCCGTCTATTACTGTA<br>ATGCAGCTCGGGGTTGGAGGATCTACTGGGGCAAAGGGACCCTGGTC<br>ACCGTTTCCTCAACTAGTGGCCCGGGAGGCCAA | 286 | 241 |

TABLE 4

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| 02-S-bR1-2C7 | ATGAAATACCTATTGCCTACGGCGGCCGCTGGATTGTTATTACTCGCGGC<br>CCAGCCGGCCATGGCGCAGGTGCAGCTGCAGGAGTCTGGGGGAGGCTT<br>GGTGCAGCCCGGGGACTCTCTGAAGCTCTCTTGTGCAGCCTCTGGCGGC<br>ACCTTCGGTGCCGGTGTCGTGGCCTGGTACCGCCAGTCTCCAGGGAAAC<br>AGCGTGAGATGGTCGGAAGTATGGGTAGTGATGGTTTCACGCAAATCGA<br>AAACGGCATGAAGGGCCGATTCACTATCTCCGGGGCCGGCGACAAGAAA<br>ACAGTGTTTTTACAGATGAACAATTTGAAGCCTGAGGACACGGCCGTCTA<br>TTTCTGTCATTACGCCGATGGCCGGTTTGGCTCTTGGGGTCAGGGGACCC<br>AGGTCACCGTCTCCTCAACTAGTGGCCCGGGAGGCCAACACCATCACCAC<br>CATCATGGCGCAGAACAAAAACTCATCTCAGAAGAGGATCTGTCTTAG | 287 | 191 |
| 04-S-bR2-1C4 | ATGAAATACCTATTGCCTACGGCGGCCGCTGGATTGTTATTACTCGCGGC<br>CCAGCCGGCCATGGCGCAGGTGCAGCTGCAGGAGTCTGGGGGAGGCTT<br>GGTGCAGGCTGGGGGGTCTCTGAGACTCTCCTGTGCAGCCTCTGGAAGT<br>AACATCAGTACTAATGTGATGGCCTGGTACCGCCGCGCTCCAGGGAACC<br>AGCGCGACATGGTTGCTTCTATCAGTACTAGTGGTACTACCAATTATCTA<br>GCCTCCGTGAAGGGCCGATTCACTATCTCCAGAGACAACGCCAAGAACA<br>CGGTGTCGCTGCAAATGAACAGCCTGAAACCTGAGGACACGGCCGTCTA<br>CACTTGTTATGCAGCCTGGCCGTTGAACACTTGGGGCCAGGGGACCCAG<br>GTCACCGTCTCCTCAACTAGTGGCCCGGGAGGCCAACACCATCACCACCA<br>TCATGGCGCAGAACAAAAACTCATCTCAGAAGAGGATCTGTCTTAG | 288 | 192 |
| 20-S-bR2-1C9 | ATGAAATACCTATTGCCTACGGCGGCCGCTGGATTGTTATTACTCGCGGC<br>CCAGCCGGCCATGAAACAGGTGCAGCTGCAGGAGTCTGGGGGAGGCTT<br>GGTGCAGGCTGGGGGGTCTCTGAGACTCTCCTGTGCAGCCTCTGGAAGT<br>AACATCAGTACTAATGTGATGGCCTGGTACCGCCGCGCTCCAGGGAACC<br>AGCGCGACATGGTTGCTTCTATCAGTACTAGTGGTACTACCAATTATCTA<br>GCCTCCGTGAAGGGCCGATTCACTATCTCCAGAGACAACGCCAAGAACA<br>CGGTGTCGCTGCAAATGAACAGCCTGAAACCTGAGGACACGGCCGTCTA<br>CACTTGTTATGCAGCCTGGCCGTTGAACACTTGGGGCCAGGGGACCCAG<br>GTCACCGTCTCCTCAACTAGTGGCCCGGGAGGCCAACACCATCACCACCA<br>TCATGGCGCAGAACAAAAACTCATCTCAGAAGAGGATCTGTCTTAG | 289 | 192 |
| 27-S-bR2-1B1 | ATGAAATACCTATTGCCTACGGCGGCCGCTGGATTGTTATTACTCGCGGC<br>CCAGCCGGCCATGAAACAGGTGCAGCTGCAGGAGTCTGGGGGAGGCTT<br>GGTGCAGGCTGGGGGGTCTCTGAGACTCTCCTGTGCAGCCTCTGGAAGT<br>AACATCAGTACTAATGTGATGGCCTGGTACCGCCGCGCTCCAGGGAACC<br>AGCGCGACATGGTTGCTTCTATCAGTACTAGTGGTACTACCAATTATCTA<br>GCCTCCGTGAAGGGCCGATTCACTATCTCCAGAGACAACGCCAAGAACA<br>CGGTGTCGCTGCAAATGAACAGCCTGAAACCTGAGGACACGGCCGTCTA<br>CACTTGTTATGCAGCCTGGCCGTTGAACACTTGGGGCCAGGGGACCCAG<br>GTCACCGTCTCCTCAACTAGTGGCCCGGGAGGCCAACACCATCACCACCA<br>TCATGGCGCAGAACAAAAACTCATCTCAGAAGAGGATCTGTCTTAG | 290 | 192 |
| 28-S-bR2 1C12 | ATGAAATACCTATTGCCTACGGCGGCCGCTGGATTGTTATTACTCGCGGC<br>CCAGCCGGCCATGGCGCAGGTGCAGCTGCAGGAGTCTGGGGGAGGCTT<br>GGTCCAGGCTGGGGGGTCTCTGAGACTCTCCTGTGCAGCCTCTGGAAGT<br>AACATCAGTACTAATGTGATGGCCTGGTACCGCCGCGCTCCAGGGAACC<br>AGCGCGACATGGTTGCTTCTATCAGTACTAGTGGTACCACCAATTATCTA<br>GCCTCCGTGAAGGGCCGATTCACTATCTCCAGAGACAACGCCAAGAACA<br>CGGTGTCGCTACAAATGAACAGCCTGAAACCTGAGGACACGGCCGTCTA<br>CACTTGTTATGCAGCCTGGCCGTTGAACACTTGGGGCCAGGGGACCCAG<br>GTCACCGTCTCCTCAACTAGTGGCCCGGGAGGCCAACACCATCACCACCA<br>TCATGGCGCAGAACAAAAACTCATCTCAGAAGAGGATCTGTCTTAG | 291 | 192 |
| 38-S-bR2-1H7 | ATGAAATACCTATTGCCTACGGCGGCCGCTGGATTGTTATTACTCGCGGC<br>CCAGCCGGCCATGNNNCAGGTGCAGCTGCAGGAGTCTGGGGGAGGCTT<br>GGTGCAGGCTGGGGGGTCTCTGAGACTCTCCTGTGCAGCCTCTGGAAGT<br>AACATCAGTACTAATGTGATGGCCTGGTACCGCCGCGCTCCAGGGAACC<br>AGCGCGACATGGTTGCTTCTATCAGTACTAGTGGTACTACCAATTATCTA<br>GCCTCCGTGAAGGGCCGATTCACTATCTCCAGAGACAACGCCAAGAACA<br>CGGTGTCGCTGCAAATGAACAGCCTGAAACCTGAGGACACGGCCGTCTA<br>CACTTGTTATGCAGCCTGGCCGTTGAACACTTGGGGCCAGGGGACCCAG<br>GTCACCGTCTCCTCAACTAGTGGCCCGGGAGGCCAACACCATCACCACCA<br>TCATGGCGCAGAACAAAAACTCATCTCAGAAGAGGATCTGTCTTAG | 292 | 192 |
| 44-S-bR2-1D2 | ATGAAATACCTATTGCCTACGGCGGCCGCTGGATTGTTATTACTCGCGGC<br>CCAGCCGGCCATGGCACAGGTGCAGCTGCAGGAGTCTGGGGGAGGCTT<br>GGTGCAGGCTGGGGGGTCTCTGAGACTCTCCTGTGCAGCCTCTGGAAGT<br>AACATCAGTACTAATGTGATGGCCTGGTACCGCCGCGCTCCAGGGAACC<br>AGCGCGACATGGTTGCTTCTATCAGTACTAGTGGTACTACCAATTATCTA<br>GCCTCCGTGAAGGGCCGATTCACTATCTCCAGAGACAACGCCAAGAACA | 293 | 192 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| | CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | | |
| 60-S-bR2-1D12 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | 294 | 192 |
| 69-S-bR2-1F10 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | 295 | 192 |
| 75-S-bR2-1B11 | ATGAAATACCTATTGCCTACGGCGGCCGCTGGATTGTTATTACTCGCGGC CCAGCCGGCCATGAAACAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | 296 | 192 |
| 91-S-bR2-1C3 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | 297 | 192 |
| 05-S-bR2-1E10 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 298 | 193 |
| 26-S-bR1-2H12 | ATGAAATACCTATTGCCTACGGCGGCCGCTGGATTGTTATTACTCGCGGC CCAGCCGGCCATGGCGCAGGTGCAGCTGCAGNAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTTTCCTCAACTAGTGGCCCGGGAGGCCA ACACCATCACCACCATCATGGCGCAGAACAAAAACTCATCTCAGAAGAG GATCTGTCTTAG | 299 | 193 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| 46-S-bR2-1H11 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 300 | 193 |
| 57-S-bR1-1H3 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 301 | 193 |
| 83-S-bR2-1C1 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 302 | 193 |
| 93-S-bR2-1G4 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTTTCCTCAACTAGTGGCCCGGGAGGCCA ACACCATCACCACCATCATGGCGCAGAACAAAAACTCATCTCAGAAGAG GATCTGTCTTAG | 303 | 193 |
| 06-S-bR2-1G5 | ATGAAATACCTATTGCCTACGGCGGCCGCTGGATTGTTATTACTCGCGGC CCAGCCGGCCATGGCGCAGGTGCAGTTGCAGCAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 304 | 194 |
| 09-S-bR1-1B5 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTC GGTGCAGGCTGGGGGGTCTCTGAGACTCTCCTGTGCAGACTCTAGAACC ATCTTCATTTTCAACGCCATGGCCTGGTACCGCCAGGCTCCAGGGAAGCA GCGCGAGTTGGTCGCAGCTATTTCTAGTGGTGGCAGTACAAAGTATGCA GACTCCGTGAAGGGCCGATTCACCATCTCCAGTAGCAACGCCAAGAACA CGAAGTATCTGCAGATGAACAGGCTGAAACCTGAGGACACAGCCGTCTA TTACTGTGCAGCCTCAAGGTCGGGTAGGTGGTTAGATGATGCACGAGAC TATGAGTACTGGGGCCCGGGGACCCAGGTCACCGTCTCCTCAACTAGTG GCCCGGGAGGCAACACCATCACCACCATCATGGCGCAGAACAAAAACT CATCTCAGAAGAGGATCTGTCTTAG | 305 | 195 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| 10-S-bR1-2D8 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 306 | 196 |
| 13-S-bR2-1E12 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGTTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 307 | 196 |
| 67-S-bR2-1B9 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 308 | 196 |
| 81-S-bR1-2B7 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 309 | 196 |
| 92-S-bR2-1E6 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 310 | 196 |
| 18-S-bR1-2F1 | ATGAAATACCTATTGCCTACGGCGGCCGCTGGATTGTTATTACTCGCGGC CCAGCCGGCCATGAAACAGGTGCAGCTGCAGGAGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 311 | 196 |
| 12-S-bR2-1C5 | ATGAAATACCTATTGCCTACGGCGGCCGCTGGATTGTTATTACTCGCGGC CCAGCCGGCCATGGCGCAGGTGCAGNNNNANCAGTCTGGGGGAGGCTT GGTGCAGGCTGGGGGGTCTCTGAGACTCTCCTGTGCAGCCTCTGGAATT CCCTTCAGTATCATCTACATGGCCTGGTTCCGCCAGGCTCCAGAAAAGCA GCGCGAGTTGGTCGCAGAAATGAGTAGTCGTGGTAGTAAATTCTATGCA | 312 | 197 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| | GACTCCGTGAAGGGCCGATTCACCATCTCTAGAGACAACGCCAAGAACA CACTCTATCTGCAAATGAACAGCCTAGAACCTGAAGATACGGCCGTCTAT TATTGCAGTGTAGGCGCACGTCGCGACGACAATGATTATGTGTATTGGG GCCAGGGGACCCAGGTCACCGTTTCCTCAACTAGTGGCCCGGGAGGCCA ACACCATCACCACCATCATGGCGCAGAACAAAAACTCATCTCAGAAGAG GATCTGTCTTAG | | |
| 14-S-bR2-1G7 | ATGAAATACCTATTGCCTACGGCGGCCGCTGGATTGTTATTACTCGCGGC CCAGCCGGCCATGGCGCAGGTGCAGTTGCAGGCGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | 313 | 198 |
| 17-S-bR1-1C11 | ATGAAATACCTATTGCCTACGGCGGCCGCTGGATTGTTATTACTCGCGGC CCAGCCGGCCATGGCGCAGGTGCAGTTGCAGGCGTCTGGGGGAGGCTT GGTGCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCAG GTCACCGTCTCCTCAACTAGTGGCCCGGGAGGCCAACACCATCACCACCA TCATGGCGCAGAACAAAAACTCATCTCAGAAGAGGATCTGTCTTAG | 314 | 198 |
| 21-S-bR2-1F1 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT GGTGCAGGCTGGGGGGTCTCTGAGACTCTCCTGTGCAGCCTCTGGAATT CCCTTCAGTATCATCTACATGGCCTGGTTCCGCCAGGCTCCAGAAAAGCA GCGCGAGTTGGTCGCAGAAATGAGTAGTCGTGGTAGTAAATTCTATGCA GACTCCGTGAAGGGCCGATTCACCATCTCTAGAGACAACGCCAAGAACA CACTCTATCTGCAAATGAACAGCCTAGAACCTGAAGATACGGCCGTCTAT TATTGCAGTGTAGGCGCACGTCGCGACGACAATGATTATGTGTATTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 315 | 199 |
| 25-S-bR1-1D9 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGCAGCCTCTGGAATT CCCTTCAGTATCATCTACATGGCCTGGTTCCGCCAGGCTCCAGAAAAGCA GCGCGAGTTGGTCGCAGAAATGAGTAGTCGTGGTAGTAAATTCTATGCA GACTCCGTGAAGGGCCGATTCACCATCTCTAGAGACAACGCCAAGAACA CACTCTATCTGCAAATGAACAGCCTAGAACCTGAAGATACGGCCGTCTAT TATTGCAGTGTAGGCGCACGTCGCGACGACAATGATTATGTGTATTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 316 | 199 |
| 35-S-bR2-1B2 | ATGAAATACCTATTGCCTACGGCGGCCGCTGGATTGTTATTACTCGCGGC CCAGCCGGCCATGGCGCAGGTGCAGTTGNNNGAGTCTGGGGGAGGCTT GGTGCAGGCTGGGGGGTCTCTGAGACTCTCCTGTGCAGCCTCTGGAATT CCCTTCAGTATCATCTACATGGCCTGGTTCCGCCAGGCTCCAGAAAAGCA GCGCGAGTTGGTCGCAGAAATGAGTAGTCGTGGTAGTAAATTCTATGCA GACTCCGTGAAGGGCCGATTCACCATCTCTAGAGACAACGCCAAGAACA CACTCTATCTGCAAATGAACAGCCTAGAACCTGAAGATACGGCCGTCTAT TATTGCAGTGTAGGCGCACGTCGCGACGACAATGATTATGTGTATTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 317 | 199 |
| 43-S-bR2-1B3 | ATGAAATACCTATTGCCTACGGCGGCCGCTGGATTGTTATTACTCGCGGC CCAGCCGGCCATGGCGCAGGTGCAGNNNCAGGAGTCTGGGGGAGGCTT GGTGCAGGCTGGGGGGTCTCTGAGACTCTCCTGTGCAGCCTCTGGAATT CCCTTCAGTATCATCTACATGGCCTGGTTCCGCCAGGCTCCAGAAAAGCA GCGCGAGTTGGTCGCAGAAATGAGTAGTCGTGGTAGTAAATTCTATGCA GACTCCGTGAAGGGCCGATTCACCATCTCTAGAGACAACGCCAAGAACA CACTCTATCTGCAAATGAACAGCCTAGAACCTGAAGATACGGCCGTCTAT | 318 | 199 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| | TATTGCAGTGTAGGCGCACGTCGCGACGACAATGATTATGTGTATTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | | |
| 22-S-bR2-1G10 | ATGAAATACCTATTGCCTACGGCGGCCGCTGGATTGTTATTACTCGCGGC CCAGCCGGCCATGGCGCAGGTGCAGTTGCAGNNGTNATGGGGGAGGCG TGGTGCAGTCTGGGGGGTCTCTGAGACTCTCCTGTGTAGCCTCTGGAAAC ATCTTCGGGATCAATTCCATGGCCTGGTACCGCCAGGCTCCAGGGAAGC AGCGCGAATTGGTCGCTGACATTACACGTGGTAATAGAAAGTATGCAGA TTCCGTGAAGGGCCGATTCACCATCTCCCAAGACAACGCCAAGAACACG GTGTATCTGCAAATGAACAGGCTGAAACCAGAGGACACGGCCGTCTATT TCTGCAATGCAGAAATCGTCACGCAAATCCCTTTCCCGCCGCGTGAGTTC TGGGGCCGGGGGACCCTGGTCACCGTCTCCTCAACTAGTGGCCCGGGAG GCCAACACCATCACCACCATCATGGCGCAGAACAAAAACTCATCTCAGAA GAGGATCTGTCTTAG | 319 | 200 |
| 29-S-bR2-1F2 | ATGAAATACCTATTGCCTACGGCGGCCGCTGGATTGTTATTACTCGCGGC CCAGCCGGCCATGGCGCAGGTGCAGTTGCAGGCGTCTGGGGGAGNNNN TGGTGCAGCCTGGGGGGTCTCTGAGACTCTCCTGTGCAGCCTCTGGATTC ACCTTTAGTAGCTACTGGATGTATTGGGTCCGTCAGGCTCCAGGGAAGG GGCTCGAGTGGGTCTCAACAATTAATACTGGTGGTTATACCACATACTAT TCAGACTCCGTGAAGGGCCGATTCACCATCTCCAGAGACAACGGCAAGA ACACGCTGTATCTGAAATGAACAGTCTGAAATCTGAGGACACGGCCGT GTATTACTGTGCAAAGGCGTACGGTAGTATGTGGTCAGGGATCTGGGGC GGCATGGACTACTGGGGCAAAGGGACCCAGGTCACCGTCTCCTCAACTA GTGGCCCGGGAGGCCAACACCATCACCACCATCATGGCGCAGAACAAAA ACTCATCTCAGAAGAGGATCTGTCTTAG | 320 | 201 |
| 30-S-bR2-1H1 | ATGAAATACCTATTGCCTACGGCGGCCGCTGGATTGTTATTACTCGCGGC CCAGCCGGCCATGGGGCAGGTCCAGTTGCAGCAGTCTGGGGGAGGCTT GGTCCAGGCTGGGGGGTCTCTGAGACTCTCCTGTGCAGCCTCTGGAAGT AACATCAGTACTAATGTGATGGCCTGGTACCGCCGCGCTCCAGGGAACC AGCGCGACATGGTTGCTTCTATCAGTACTAGTGGTACCACCAATTATCTA GCCTCCGTGAAGGGCCGATTCACTATCTCCAGAGACAACGCCAAGAACA CGGTGTCGCTACAAATGAACAGCCTGAAACCTGAGGACACGGCCGTCTA CACTTGTTATGCAGCCTGGCCGTTGAACACTTGGGGCAGGGGACCCAG GTCACCCTCTCCTCAACTAGTGGCCCGGGAGGCCAACACCATCACCACCA TCATGGCGCAGAACAAAAACTCATCTCAGAAGAGGATCTGTCTTAG | 321 | 202 |
| 33-S-bR1-1G3 | ATGAAATACCTATTGCCTACGGCGGCCGCTGGATTGTTATTACTCGCGGC CCAGCCGGCCATGGCGCAGGTGCAGNTGCAGGAGTCTGGGGGAGGCTT GGTCCAGGCTGGGGGGTCTCTGAGACTCTCCTGNGCAGTCTCTGGAAGT ATCATCAGTCATAATGTGATGGCCTGGTACCGCCGCGCTCCAGGGAAGC AGCGCGACAAGGTTGCTTGTATCAGTGGTAGTGGTTTCACCAATTATATA GCCTCCGTGAAGGGCCGATTCACTATCTCCAGAGACAACGCCAAGACA CGGTGTCTCTACAAATGAACAACCTGAAACCTGAGGACACGGCCGTCTAC TCTTGTTATACAGCCTGGCCGTAGAACACTTGGGGCAGGGGACCCAGG TCACCGTCTCCTCAACTAGTGGCCCGGGAGGCCAACACCATCACCACCAT CATGGCGCAGAACAAAAACTCATCTCAGAAGAGGATCTGTCTTAG | 322 | 203 |
| 36-S-bR2-1D1 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT TGTGCACCCTGGAGGGTCTCTGACGCTCTCCTGTGCAGCCTCTGGCAGGA TCTTCAATATCGAGGACATGGGCTGGTATCGCCAGGGTCCAGGGGAACA GCGCGACTTGGTCGCAACGATCACCCGTACTGGTGCGCCAACCTATGCAA ACTCCGTGAAGGGCCGGTTCACCATCTCCAGAGACAACGCCAAGAACAC GGTTTATCTGCAGATGACCAGGCTGAAACCTGAGGACACGGCCGTCTATT ACTGTAATGCAAAAGACGTAACAGTCATACCTTTCCCCCCGAAAGACTAT TGGGGCCGGGGGACCCAGGTCACCGTCTCCTCAACTAGTGGCCCGGGAG GCCAACACCATCACCACCATCATGGCGCAGAACAAAAACTCATCTCAGAA GAGGATCTGTCTTAG | 323 | 204 |
| 41-S-bR1-1H1 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGGCTGGGGGGTCTCTGAGACTCTCCTGTGAAGCCTCTGGAAGC GTTTCCGCGATCGAAACCATGGGCTGGTACCGCCAGGCTCCGGATGAAC AGCGCACATTTGTCGCGGTTATCAGTACGGGTGGAACCACAAAATACGC GCCCTCCGTGAAGGGCCGATTCACCATCTCCATAGACAACGCCAAGAGC ACGGTGACGCTTCAAATGAACAGCCTGAAACCTGAGGACACAGCCGTCT ACTACTGTGCAGCGGACTGGCGAACCATTTTGGGTTGGAAGACAAGGGA GCCCAACTACTTTGGCCAGGGGACCCTGGTCACCGTCTCCTCAACTAGTG | 324 | 205 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| | GCCCGGGAGGCCAACACCATCACCACCATCATGGCGCAGAACAAAAACT<br>CATCTCAGAAGAGGATCTGTCTTAG | | |
| 45-S-bR2-1F6 | ATGAAATACCTATTGCCTACGGCGGCCGCTGGATTGTTATTACTCGCGGC<br>CCAGCCGGCCATGGCGCAGGTGCAGTTGCAGGAGTCTGGGGGAGGCTT<br>GGTGCAGGCTGGGGGGTCTCTGAGACTCTCCTGTGCAGCCTTTGGAAGC<br>ACCTCCAGTATCACGTACATGGCCTGGTTCCGCCAGGCTCCAGAAAAGCA<br>GCGCGAGTTGGTCGCAGAAATGAGTAGGCGTGGTAGCACATTCTATGCA<br>GACTCCGTGAAGGGCCGATTCACCATTTATAGAGACAACACCAAGAACA<br>CAGTCTATCTGCAAATGAACAGCCTAGAACCTGAAGACACGGCCGTCTAT<br>TATTGTAGTGTAGGCGCACGTCGCGACGAGGATGATTATGTCTACTGGG<br>GCCAGGGGACCCAGGTCACCGTCTCCTCAACTAGTGGCCCGGGAGGCCA<br>ACACCATCACCACCATCATGGCGCAGAACAAAAACTCATCTCAGAAGAG<br>GATCTGTCTTAG | 325 | 206 |
| 61-S-bR2-1F8 | ATGAAATACCTATTGCCTACGGCGGCCGCTGGATTGTTATTACTCGCGGC<br>CCAGCCGGCCATGGCGCAGGTGCAGTTGCAGGAGTCTGGGGGAGGCTT<br>GGTGCAGGCTGGGGGGTCTCTGAGACTCTCCTGTGCAGCCTTTGGAAGC<br>ACCTCCAGTATCACGTACATGGCCTGGTTCCGCCAGGCTCCAGAAAAGCA<br>GCGCGAGTTGGTCGCAGAAATGAGTAGGCGTGGTAGCACATTCTATGCA<br>GACTCCGTGAAGGGCCGATTCACCATTTATAGAGACAACACCAAGAACA<br>CAGTCTATCTGCAAATGAACAGCCTAGAACCTGAAGACACGGCCGTCTAT<br>TATTGTAGTGTAGGCGCACGTCGCGACGAGGATGATTATGTCTACTGGG<br>GCCAGGGGACCCAGGTCACCGTTTCCTCAACTAGTGGCCCGGGAGGCCA<br>ACACCATCACCACCATCATGGCGCAGAACAAAAACTCATCTCAGAAGAG<br>GATCTGTCTTAG | 326 | 206 |
| 84-S-bR2-1E5 | ATGAAATACCTATTGCCTACGGCGGCCGCTGGATTGTTATTACTCGCGGC<br>CCAGCCGGCCATGGCGCAGGTGCAGNNNNNANNAGTNNGGGGGAGGC<br>TTGGTGCAGGCTGGGGGGTCTCTGAGACTCTCCTGTGCAGCCTTTGGAA<br>GCACCTCCAGTATCACGTACATGGCCTGGTTCCGCCAGGCTCCAGAAAAG<br>CAGCGCGAGTTGGTCGCAGAAATGAGTAGGCGTGGTAGCACATTCTATG<br>CAGACTCCGTGAAGGGCCGATTCACCATTTATAGAGACAACACCAAGAA<br>CACAGTCTATCTGCAAATGAACAGCCTAGAACCTGAAGACACGGCCGTCT<br>ATTATTGTAGTGTAGGCGCACGTCGCGACGAGGATGATTATGTCTACTGG<br>GGCCAGGGGACCCAGGTCACCGTCTCCTCAACTAGTGGCCCGGGAGGCC<br>AACACCATCACCACCATCATGGCGCAGAACAAAAACTCATCTCAGAAGAG<br>GATCTGTCTTAG | 327 | 206 |
| 49-S-bR1-1H2 | ATGAAATACCTATTGCCTACGGCGGCCGCTGGATTGTTATTACTCGCGGC<br>CCAGCCGGCCATGGCGCAGGTGCAGTTGCAGGAGTCTGGGGGAGGCTT<br>GGTGCAGGCTGGGGGGTCTCTGAGACTCTCCTGTGCAGCCTCTGGAGGA<br>CCTGTCAGTGACAATGTCATGGCCTGGTTCCGCCAGGCTCCAGGGAGCC<br>AGCGCGAATTGGTCGCACAGATTACAAGTGGTGGGGCCACAAGCTACGC<br>GGACTCCGTGAAGGGCCGATTCACCATCTCCAGAGACAACGCCAGGAGC<br>ACAGTGGACCTGCAAATGAACAGCCTGAAACCTGAGGACACGGCCGTCT<br>ATTACTGTAACGTCGCCTTACGTTACTGGGGCCGGGGGACCCAGGTCACC<br>GTCTCCTCAACTAGTGGCCCGGGAGGCCAACACCATCACCACCATCATGG<br>CGCAGAACAAAAACTCATCTCAGAAGAGGATCTGTCTTAG | 328 | 207 |
| 51-S-bR2-1B7 | ATGAAATACCTATTGCCTACGGCGGCCGCTGGATTGTTATTACTCGCGGC<br>CCAGCCGGCCATGGCGCAGGTGCAGNNNNNAANCAGTNTGGGGGAGGC<br>TTGGTGCAGGCTGGGGGGTCTCTGAGACTCTCCTGTGCAGCCTCTGGAA<br>GCACCTTCAGTATCACCTACATGGCCTGGTTCCGCCAGGCTCCAGGGAAA<br>CAGCGCGAATTGGTCGCAGAAATAAGTAGCCGTGGTAGTGTGTTCTATG<br>CAGACTCCGTGAAGGGCCGATTCACCATCTCCAGAGACAACGCCAAGAA<br>GACAGTGTATCTGCAAATGAACAGCCTGGAAACTGAAGACACGGCCGCC<br>TATTATTGTAGTGTAGGCGCACGTCGCGACGAAGATGACTATGTCTACTG<br>GGGCCAGGGGACCCAGGTCACCGTTTCCTCAACTAGTGGCCCGGGAGGC<br>CAACACCATCACCANCNNCATGGCGCAGAACAAAAACTCATCTCAGAAG<br>AGGATCTGTCTTAG | 329 | 208 |
| 52-S-bR2-1D6 | ATGAAATACCTATTGCCTACGGCGGCCGCTGGATTGTTATTACTCGCGGC<br>CCAGCCGGCCATGGCGCAGGTGCAGTTGCAGGAGTCTGGGGGAGGCTT<br>GGTGCAGGCTGGGGGGTCTCTGAGACTCTCCTGTGCAGCCTCTGGAAGC<br>ACCTTCAGTATCACGTACATGGCCTGGTTCCGCCAGGCTCCAGAAAAGCA<br>GCGCGAGTTGGTCGCAGAAATGAGTAGGCGTGGTAGTACATTCTATGCA<br>GACTCCGTGAAGGGCCGATTCACCATCTCCAGAGACAACACCAAGAACA<br>CAGTCTATCTGCAAATGAACAGCCTAGAACCTGAAGACACGGCCGTCTAT<br>TATTGTAGTGTAGGCGCACGTCGCGACGAGGATGATTATGTCTACTGGG<br>GCCAGGGGACCCTGGTCACCGTTTCCTCAACTAGTGGCCCGGGAGGCCA | 330 | 209 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| | ACACCATCACCACCATCATGGCGCAGAACAAAAACTCATCTCAGAAGAG GATCTGTCTTAG | | |
| 54-S-bR2-1H12 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCTGGTCACCGTCTCCTCAACTAGTGGCCCGGGAGGCCA ACACCATCACCACCATCATGGCGCAGAACAAAAACTCATCTCAGAAGAG GATCTGTCTTAG | 331 | 209 |
| 53-S-bR2-1F7 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT GGTGCAGGCTGGGGGGTCTCTGAGACTCTCCTGTGCAGCCTCTGGAATT CCCTTCAGTATCATCTACATGGCCTGGTTCCGCCAGGCTCCAGAAAAGCA GCGCGAGTTGGTCGCAGAAATGAGTAGTCGTGGTAGTAAATTCTATGCA GACTCCGTGAAGGGCCGATTCACCATCTCTAGAGACAACGCCAAGAACA CACTCTATCTGCAAATGAACAGCCTAGAACCTGAAGATACGGCCGTCTAT TATTGCAGTGTAGGCGCACGTCGCGACGACAATGATTATGTGTATTGGG GCCAGGGGACCCTGGTCACCGTCTCCTCAACTAGTGGCCCGGGAGGCCA ACACCATCACCACCATCATGGCGCAGAACAAAAACTCATCTCAGAAGAG GATCTGTCTTAG | 332 | 210 |
| 59-S-bR2-1B8 | ATGAAATACCTATTGCCTACGGCGGCCGCTGGATTGTTATTACTCGCGGC CCAGCCGGCCATGGCGCAGGTGCAGCTGCAGGAGTTTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCAGGTCACCGTCTCCTCAACTAGTGGCCCGGGAGGCCA ACACCATCACCACCATCATGGCGCAGAACAAAAACTCATCTCAGAAGAG GATCTGTCTTAG | 333 | 211 |
| 68-S-bR2-1E2 | ATGAAATACCTATTGCCTACGGCGGCCGCTGGATTGTTATTACTCGCGGC CCAGCCGGCCATGGCGCAGGTGCAGCTGCAGGAGTTTGGGGGAGGCTT GGTGCAGGCAGGGGAATCTCTAAGACTCTCCTGTGTAGCCTCTGGAAGT AACATCAGTACTAATGTGATGGCCTGGTACCGCCGCGCTCCAGGGAACC AGCGCGACATGGTTGCTTCTATCAGTACTAGTGGTACTACCAATTATCTA GCCTCCGTGAAGGGCCGATTCACTATCTCCAGAGACAACGCCAAGAACA CGGTGTCGCTGCAAATGAACAGCCTGAAACCTGAGGACACGGCCGTCTA CACTTGTTATGCAGCCTGGCCGTTGAACACTTGGGGCCAGGGGACCCTG GTCACCGTCTCCTCAACTAGTGGCCCGGGAGGCCAACACCATCACCACCA TCATGGCGCAGAACAAAAACTCATCTCAGAAGAGGATCTGTCTTAG | 334 | 212 |
| 73-S-bR1-2B2 | ATGAAATACCTATTGCCTACGGCGGCCGCTGGATTGTTATTACTCGCGGC CCAGCCGGCCATGGCGCAGGTGCAGTTGCAGGAGTCTGGGGGAGGCTT GGTGCAGGCCGGGGGGTCTCTGAGACTCTCCTGTGTAGGCGCTGGAAGC GCCTTCGGTTGGAATGCCGTGCACTGGTACCGCCAGGCTCCAGGTCAGC AGCGCGAATGGCTCGCCACTATTGAGAGTGGTGGCTGGGCAGACTATTC AGTGTCCGTGAAGGGCCGATTCATCGTCTCCAGAGACAACGCCAGGAAC ACAGCGTATTTGCAAATGAACAACCTAAAACTTGAAGACACGGCCGTCTA TTACTGTAATCAACTTACTTACTGGGGCCAGGGGACCCAGGTCACCGTCT CCTCAACTAGTGGCCCGGGAGGCCAACACCATCACCACCATCATGGCGC AGAACAAAAACTCATCTCAGAAGAGGATCTGTCTTAG | 335 | 213 |
| 76-S-bR2-1E3 | ATGAAATACCTATTGCCTACGGCGGCCGCTGGATTGTTATTACTCGCGGC CCAGCCGGCCATGGCGCAGGTGCANCTGCAGGAGTNTGGGGGAGGCTT GGTGCAGGCTGGGGGGTCTCTGAGACTCTCCTGTGCAGCCTCTGGAAGC ACCTTCAGTATCACGTACATGACCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA AGTCTATCTGCAAATGAACAGCCTAGAACCTGAAGACACGGCCGTCTATT ATTGTAGTGTAGGCGCACGTCGCGACGAGGATGATTATGTCTACTGGGG CCAGGGGACCCAGGTCACCGTCTCCTCAACTAGTGGCCCGGGAGGCCAA CACCATCACCACCATCATGGCGCAGAACAAAAACTCATCTCAGAAGAGG ATCTGTCTTAG | 336 | 214 |

TABLE 4-continued

Polynucleotide Sequences of Synuclein
Antibodies Enriched by Solution Phase Panning

| Antibody ID | Nucleotide Sequence | NA SEQ ID NO: | AA SEQ ID NO: |
|---|---|---|---|
| 77S-bR2-1G1 | ATGAAATACCTATTGCCTACGGCGGCCGCTGGATTGTTATTACTCGCGGC CCAGCCGGCCATGGCGCAGGTGCAGTTGCAGGAGTTTGGGGGAGGCTT GGTGCAGGCTGGGGGGTCTCTGAGACTCTCCTGTGCAGCCTCTGGAAGC ACCTTCAGTATCACGTACATGGCCTGGTTCCGCCAGGCTCCAGAAAAGCA GCGCGAGTTGGTCGCAGAAATGAGTAGGCGTGGTAGTACATTCTATGCA GACTCCGTGAAGGGCCGATTCACCATCTCCAGAGACAACACCAAGAACA CAGTCTATCTGCAAATGAACAGCCTAGAACCTGAAGACACGGCCGTCTAT TATTGTAGTGTAGGCGCACGTCGCGACGAGGATGATTATGTCTACTGGG GCCAGGGGACCCTGGTCACCGTTTCCTCAACTAGTGGCCCGGGAGGCCA ACACCATCACCACCATCATGGCGCAGAACAAAAACTCATCTCAGAAGAG GATCTGTCTTAG | 337 | 215 |
| 85-S-bR2-1G2 | ATGAAATACCTATTGCCTACGGCGGCCGCTGGATTGTTATTACTCGCGGC CCAGCCGGCCATGGCGCAGGTGCAGTTGCAGCAGTCTGGGGGAGGCTT GGTGCAGGCTGGGGGGTCTCTGAGACTCTCCTGTGCAGCCTCTGGAAGC ACCTTCAGTATCACCTACATGGCCTGGTTCCGCCAGGCTCCAGGGAAACA GCGCGAATTGGTCGCAGAAATAAGTAGCCGTGGTAGTGTGTTCTATGCA GACTCCGTGAAGGGCCGATTCACCATCTCCAGAGACAACGCCAAGAAGA CAGTGTATCTGCAAATGAACAGCCTGGAAACTGAAGACACGGCCGCCTA TTATTGTAGTGTAGGCGCACGTCGCGACGAAGATGACTATGTCTACTGG GGCCAGGGGACCCTGGTCACCGTCTCCTCAACTAGTGGCCCGGGAGGCC AACACCATCACCACCATCATGGCGCAGAACAAAAACTCATCTCAGAAGAG GATCTGTCTTAG | 338 | 216 |
| 89-S-bR1-2C6 | ATGAAATACCTATTGCCTACGGCGGCCGCTGGATTGTTATTACTCGCGGC CCAGCCGGCCATGGCGCAGGTGCAGCTGCAGGAGTCTGGGGGAGGCTT GGTGCAGCCTGGGGGGTCTCTGAGACTCTCCTGCACACCCTCTGGATCTA TCTTCAGTTTCGATGTCATGGCCTGGTATCGCCAGGCCCCAGGGAAGCGG CGCGAGTTGGTCGCACAGCATCGTACTCCGGGTGCTATAGATTATGCCGA TCCTGTCCGGGGCCGATTCACTATTAGCAGAGACGCTGGGGACGTACTG CTGCAAATGGACAGCCTGAAACCCGAAGCACGGCCGTCTACTTCTG TAATCTCCGAAGGTGGTCTTACGACTACTGGGGCCAGGGGACCCTGGTC ACCGTCTCCTCAACTAGTGGCCCGGGAGGCCAACACCATCACCACCATCA TGGCGCAGAACAAAAACTCATCTCAGAAGAGGATCTGTCTTAG | 339 | 217 |

EXAMPLES

Examples are provided herein to illustrate the present invention. These examples are not meant to constrain the present invention to any particular application or theory of operation.

Example 1—Production of Llama Single Domain Antibodies Against Human α-Synuclein Immunizations: A llama was immunized with alpha-synuclein according to the following schedule. In general, immunizations occurred once per month, with serum and/or PBMCs taken 1 week after boosts.

| α-synuclein Immunization Schedule | | |
|---|---|---|
| Pre-bleed | | Day 0 |
| Immunization 1 | 200 ug CFA, SQ | Day 0 |
| Immunization 2 | 100 ug IFA, SQ | Day 21 |
| Bleed 1 | | Day 28 |
| Immunization 3 | 100 ug IFA 100 ug Adjuplex, SQ | Day 49 |
| Bleed 2 | | Day 56 |
| Immunization 4 | 100 ug IFA 100 ug Adjuplex, SQ | Day 77 |
| Bleed 3 | | Day 84 |
| Immunization 5 | 100 ug IFA 100 ug Adjuplex, SQ | Day 105 |
| Bleed 4 | | Day 112 ~1 × 10$^8$ PBMCs |
| Immunization 6 | 200 ug Adjuplex split IM/SQ | Day 144 |
| Bleed 5 | | Day 151 ~1 × 10$^8$ PBMCs |
| Immunization 7 | 200 ug Adjuplex split IM/SQ | Day 188 |
| Bleed 6 | | Day 196 |

Complete Freund's Adjuvant (CFA), Incomplete Freund's Adjuvant(IFA), Adjuplex Adjuvant(Sigma), Subcutaneous (SQ), Intramuscular(IM).

Serum titer levels were determined by indirect ELISA using the following protocol.

1) Antigen was coated in ½ well Corning 9018 high-binding polystyrene assay plates at 2 ug/mL in PBS, 4 degrees ON.
2) Wash plate 4 times with PBS containing 0.05% Tween20 (PBST).
3) Block with PBST/5% non-fat dried milk (PBST/milk) for 2 hr at room temperature.
4) Wash 4 times with PBST.
5) Dilutions of sera were made in PBST/milk and incubated in plate for 1 hr at room temperature.
6) Wash 4 times with PBST.

7) Incubate with Rabbit anti-Llama IgG(H+L) (Life Technologies), 1:10,000 dilution in PBST/milk, 1 hr room temperature.
8) Wash 4 times with PBST.
9) Bound antibody was detected with Gt anti-Rb IgG(H+L)-HRP (Jackson), 1:10,000 in PBST/milk, 45 min room temperature.

Library Construction: Approximately 100 mL of llama blood was collected in EDTA-coated tubes (Becton Dickenson) and peripheral blood mononuclear cells (PBMCs) were isolated using Hisotpaque-1077 (Sigma). Approximately $1\times10^8$ PBMCs were isolated from the specific bleeds listed above and RNA prepared using RNeasy (Qiagen). cDNA was synthesized from a total of 50 ug of RNA (25 ug from each bleed) using random hexanucleotide primers and Superscript reverse transcriptase (Life Technologies). Single domain antibodies (VHH) were cloned in a two step PCR process using the cDNA as template. The first PCR amplified the variable domains of all immunoglobulin heavy chains, both single chain (VHH) and conventional antibodies (VH) using CaL1/CaL2 primers:

(SEQ ID NO: 344)
5'-GTCCTGGCTGCTCTTCTACAAGG-3'

(SEQ ID NO: 345)
5'-GGTACGTGCTGTTGAACTGTTCC-3'

The second nested PCR specifically amplified llama single domain antibodies (ProSci proprietary primers). PCR products were gel purified and the DNA fragments encoding the VHH domains were cloned into phage display vector pADL-23c (Antibody Design Labs) and electroporated into *E. coli* TG1 cells, yielding a library of approximately $1\times10^9$ in size.

Example 2—Selection of Single Domain Antibodies Against α-Synuclein

Phage displaying VHH antibodies were rescued from individual libraries with helper phage M13K07 and subjected to biopanning in two different ways: solid-phase and solution-phase panning. For solid-phase panning, α-synuclein was adsorbed on 2 um diameter polystyrene beads (Polysciences, Inc), blocked with PBST containing 5% non-fat dried milk, and incubated with $2\times10^{11}$ phage in 1 mL PBST/milk for 1 hr at room temperature. For solution-phase panning, proteins were biotinylated using Lightning-Link Rapid Biotin (Innova Biosciences) and 1 ug of biotinylated α-synuclein incubated with $2\times10^{11}$ phage in 1 mL PBST/milk for 1 hr at room temperature. Polystyrene beads were captured by centrifugation and washed extensively with PBST. Biotinylated proteins bound to phage were captured with streptavidin-coated magnetic Dynabeads (Life Technologies) and extensively washed with PBST. In both cases, bound phage were eluted with both high pH (100 mM triethylamine, pH~10) and low pH (100 mM glycine, pH~2.5) for 5 min and neutralized with 1M Tris pH 7.5. *E. coli* strains TG1 and SS320 were then infected with eluted phage and used for a subsequent round of panning (TG1) or to express antibodies (SS320).

Example 3—Expression of Single Domain Antibodies for Screening

Individual SS320 clones were grown in 96 well plate format in 100 uL of 2YT/1% glucose/100 ug/mL ampicillin overnight at 37° C. 10 uL of the overnight cultures were inoculated into 1 mL each of 2YT/0.1% glucose/100 ug/mL ampicillin in deep 96 well blocks and grown at 37° C., 200 rpm for 3 hrs until cells were in log phase. Single domain antibody expression was then induced with IPTG (1 mM final) and the temperature reduced to 30° C. overnight. The next day, bacterial cultures were centrifuged at 3200 g for 10 min and supernatant removed. The remaining bacterial pellets were frozen at −70° C. Bacterial pellets were then thawed, resuspended in 300 uL of PBS, and incubated for 30 min at room temperature. Cellular debris was removed by centrifugation at 3200 g for 10 min and the antibody-containing supernatants transferred to a fresh 96 well plate for storage at −70° C. until used.

ELISA screening of the supernatants was performed using the following protocol:
1) coat antigen at 2 ug/mL in PBS, 4 degrees ON (use 96 well Corning 9018 high-binding polystyrene assay plates).
2) wash 4 times with PBST
3) 2 hr block with PBST/5% milk, room temp
4) wash 4 times PBST
5) add dilutions of sdAb supes (1:1) in PBST/5% milk, 1 hr room temp
6) wash 4 times PBST
7) add ProSci's anti-c-myc-tag antibody (Cat. No. PM-7669), 1:1,000 in PBST/5% milk, 1 hr room temp
8) wash 4 times PBST
9) detect with goat anti-mouse IgG-HRP (Jackson Cat No. 115-035-164), 1:5,000 in PBST/5% milk, incubate 30 to 45 min room temperature
10) wash 4 times PBST
11) develop 10 min to 1 hr depending on signal

Example 4—Single Domain Antibody Purification

Single Domain Antibodies were purified from 50 mL cultures as follows. Inoculated 3 mL of 2YT/1% glucose/100 ug/mL Amp with specific clone in SS320 cells and grew overnight 37 degrees, 200 rpm. Next day, 500 uL of overnight culture was added to 50 mL of 2YT/0.1% glucose/100 ug/mL ampicillin and grown at 37 degrees, 200 rpm. After $OD_{600}$ reached 0.7, induced the culture with IPTG (1 mM final) and grown overnight at 30 degrees.

The next day, bacteria was collected by centrifugation for 15 min, 3500 g at room temperature. The cell pellet was resuspended in 2.5 mL of ice-cold TES(20 mM Tris, 0.5 mM EDTA, 17% sucrose), and incubated for 1 hr on ice. 5 mL of TES/4 (TES diluted 1 to 4 in water) was added, and incubation on ice continued for 45 min mixing occasionally. The suspension was centrifuged at 10,000 g for 30 min, 4 degrees and the supernatant was collected. The His-tagged single domain antibodies were purified by using IMAC (Immobilized Metal Affinity Chromatography) according to the manufacturer's instructions (Qiagen).

Example 5—Characterization of Alpha-Synuclein Single Domain Antibodies

Figure 1B:
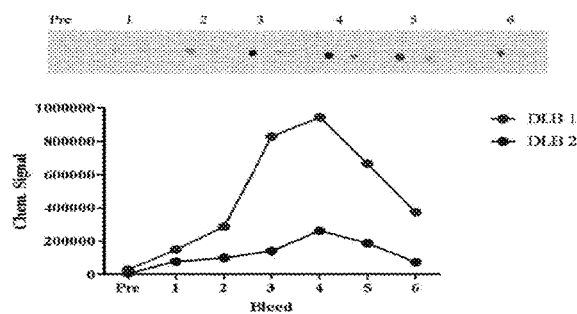
FIG. 1B shows immunoreactivity of the α-synuclein sdAb with brain homogenates from subjects with suspected dementia with Lewy Bodies (DLB).

Single domain antibody (sdAb) titer following administration of α-synuclein as described in Example 1 was measured by ELISA. ELISA plates were coated with 2 μg/ml of recombinant (rec) α-synuclein (140 aa) and reacted with various bleeds obtained after several immunizations with rec α-synuclein. The hydrogen peroxidase (HRP)-linked secondary antibody recognizes single-domain llama antibodies. Some auto-sdAbs against α-synuclein were detected in the pre-bleed but a strong sdAb response against α-synuclein was detected in bleed 2 and onwards. FIG. 1 (left graph) shows that llamas immunized with the α-synuclein produced a strong sdAb titer against the immunogen after the sixth immunization.

All of the collected bleeds (1:1000 dilution) were reacted on a dot blot with brain homogenate from two different human brains. These brain samples were selected based on their strong reactivity with commercial α-synuclein antibodies suggesting extensive Lewy bodies. The secondary antibody detects single domain llama antibodies. All blots were developed together for direct comparison of binding. For both cases, signal was strongest in bleeds 3-5. As shown in FIG. 1 (right graph), the single domain antibodies from an α-synuclein immunized llama are strongly immunoreactive with brain homogenates from cases with suspected Dementia with Lewy Bodies (DLB).

Figure 2A:
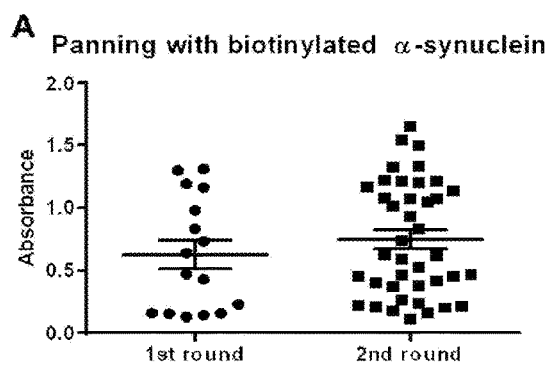
FIGS. 2A-2B shows enrichment of α-synuclein sdAbs by phage display library panning against biotinylated-α-synuclein solution phase (FIG. 2A) and solid phase (FIG. 2B).
Figure 2B:
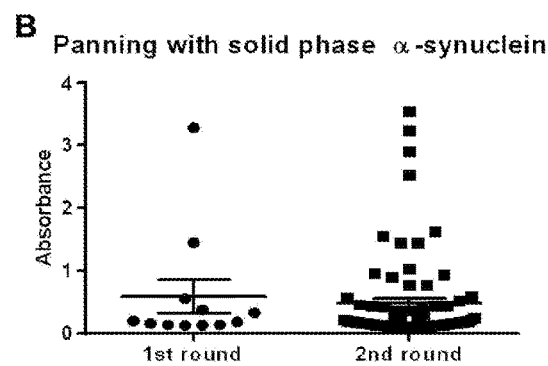

The α-synuclein sdAbs were next selected for by binding to α-synuclein. Phage display library panning against biotinylated-α-synuclein (solution phase) resulted in enrichment of positive clones (Abs>0.1) with 9% ($1^{st}$ round: two 96 well plates) and 48% ($2^{nd}$ round—one plate) positivity (FIG. 2A). Panning against solid phase α-synuclein resulted in 6% ($1^{st}$ round) and 43% ($2^{nd}$ round, 2 plates) positivity (FIG. 2B).

Figure 3:
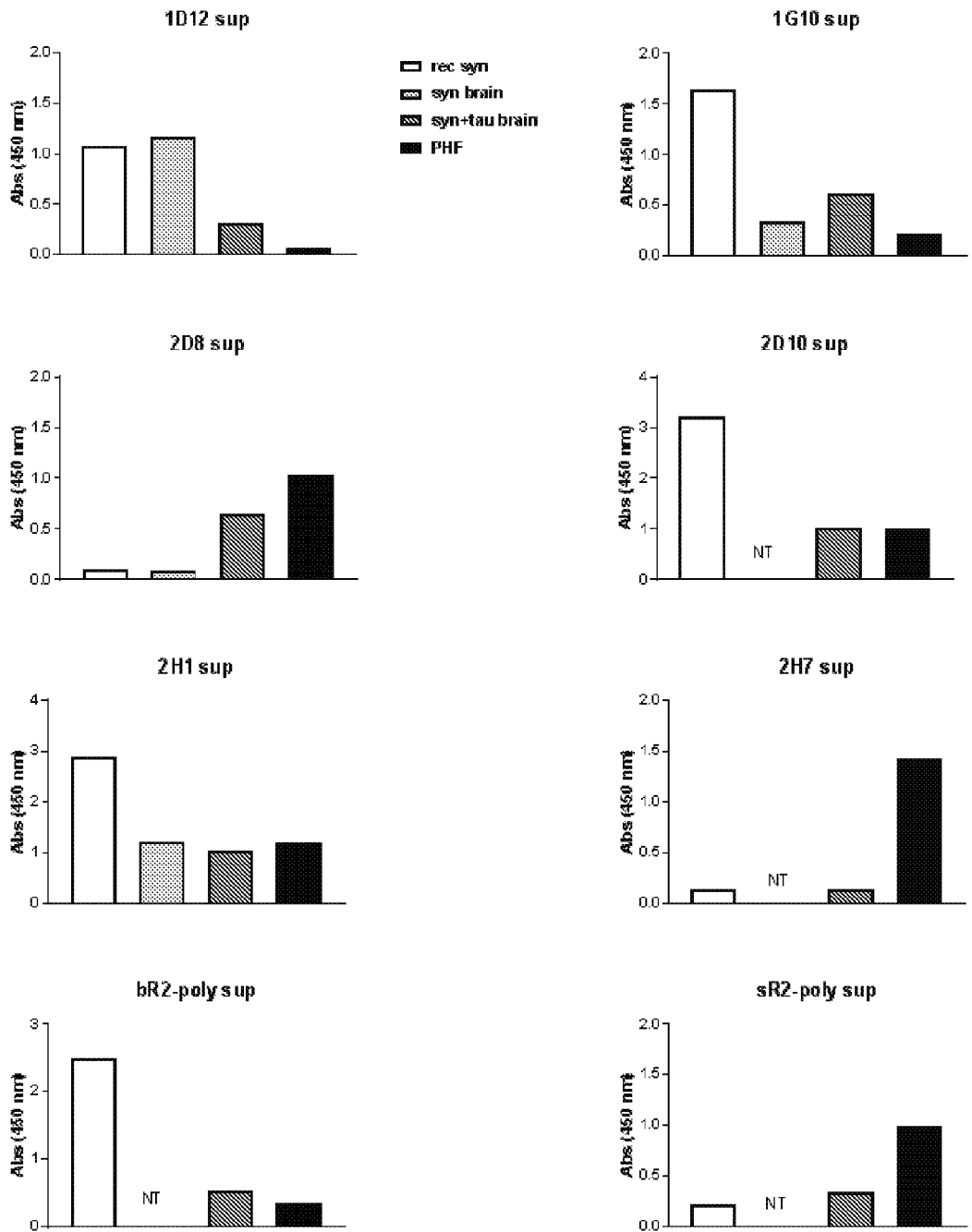
FIG. 3 shows the diverse binding profiles of the α-synuclein sdAb clones to different brain/protein fractions including (i) recombinant α-synuclein protein (rec syn), (ii) human brain having high levels of α-synuclein expression (syn brain), (iii) supernatant from DLB brain positive for tau and α-synuclein (syn+tau brain), and (iv) PHF-tau-enriched brain fraction from Alzheimer's brain (PHF).

To test the binding profiles of the selected sdAbs, cell culture supernatant from sdAb clones was incubated with ELISA plates that were coated with: 1) recombinant α-synuclein protein (rec syn); 2) supernatant from a human brain with a strong α-synuclein signal (syn brain) on western blots as detected by a commercial α-synuclein antibody; 3) supernatant from a DLB brain, positive for tau and α-synuclein on western (syn+tau brain), and; 4) PHF-tau-enriched brain fraction from Alzheimer's brain. As shown in FIG. 3, the α-synuclein sdAb clones have diverse binding profiles to the different brain/protein fractions. Note that the concentration of sdAb in each supernatant is unknown. Hence, it is not appropriate to compare binding strength of individual clones, only their profile of binding to the different proteins/brains.

Figures 4A, 4B, 4C, 4D, 4E, 4F, 4G, 4H, 4I:
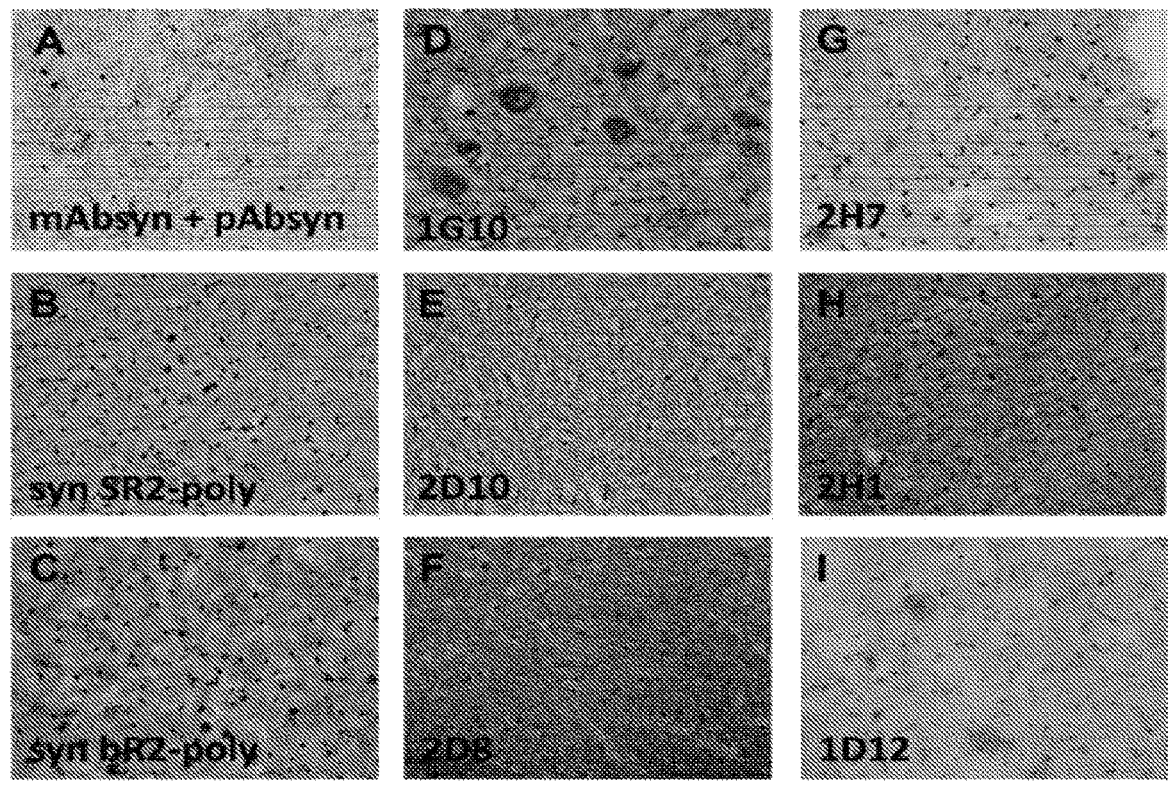
FIGS. 4A-4I show immunohistochemical binding profiles of various sdAbs to human brain tissue with Lewy Body Dementia.

To examine sdAb binding in human brain tissue, purified sdAbs were incubated with tissue sections of human brain with Lewy Body Dementia (LBD). A mixture of two commercial α-synuclein antibodies, i.e., mAb 211 and pAb C20 (Santa Cruz), known to stain Lewy bodies (LB) and Lewy neurites (LN) that sometimes circulate plaques were used as positive controls (FIG. 4A). As shown in FIGS. 4B and 4C, the polyclonal sdAbs panned against solid phase α-synuclein (sR2) (FIG. 4B) and biotinylated soluble phase α-synuclein (bR2) (FIG. 4C) recognize LB like structures and some plaques. sdAb 1G10 binds to various structures including LB, LN and plaques (FIG. 4D), as well as vasculature and axons. sdAb 2D10 and 2D8 binds to LB (FIGS. 4E, 4F). sdAb 2H7 binds to diverse structures including LB, plaques (FIG. 4G) and axons (not shown). sdAb 2H1 binds to LB (FIG. 4H). sdAb 1D12 is the least reactive and binds to plaques, LB and vasculature (FIG. 4I). The plaque-like structures that some of the sdAbs bind to are peculiar but α-synuclein antibodies have previously been shown to stain plaques, because α-synuclein can accumulate in dystrophic neurites (Yang F et al, *Brain Res* 853: 381-383 (2000), which is hereby incorporated by reference in its entirety.

Figures 5A, 5B:
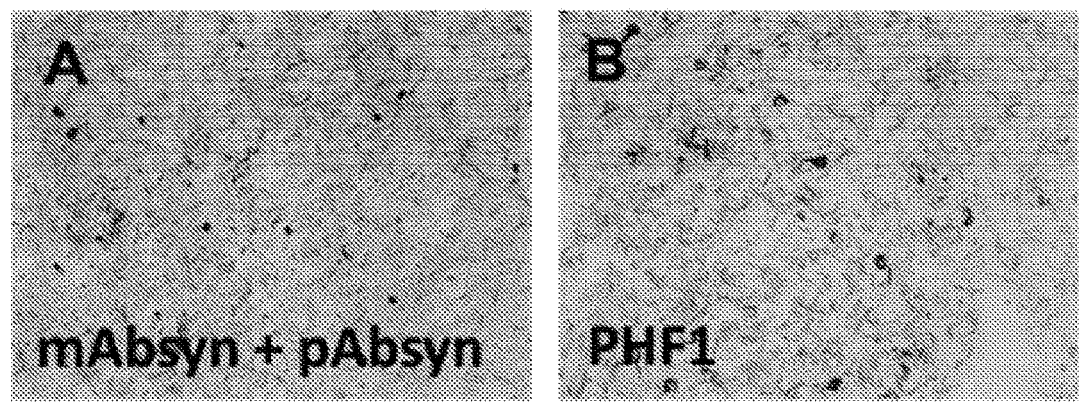
FIGS. 5A-5B show that DLB brain has α-synuclein pathology (FIG. 5A) and tau pathology (FIG. 5B).
Figure 6:
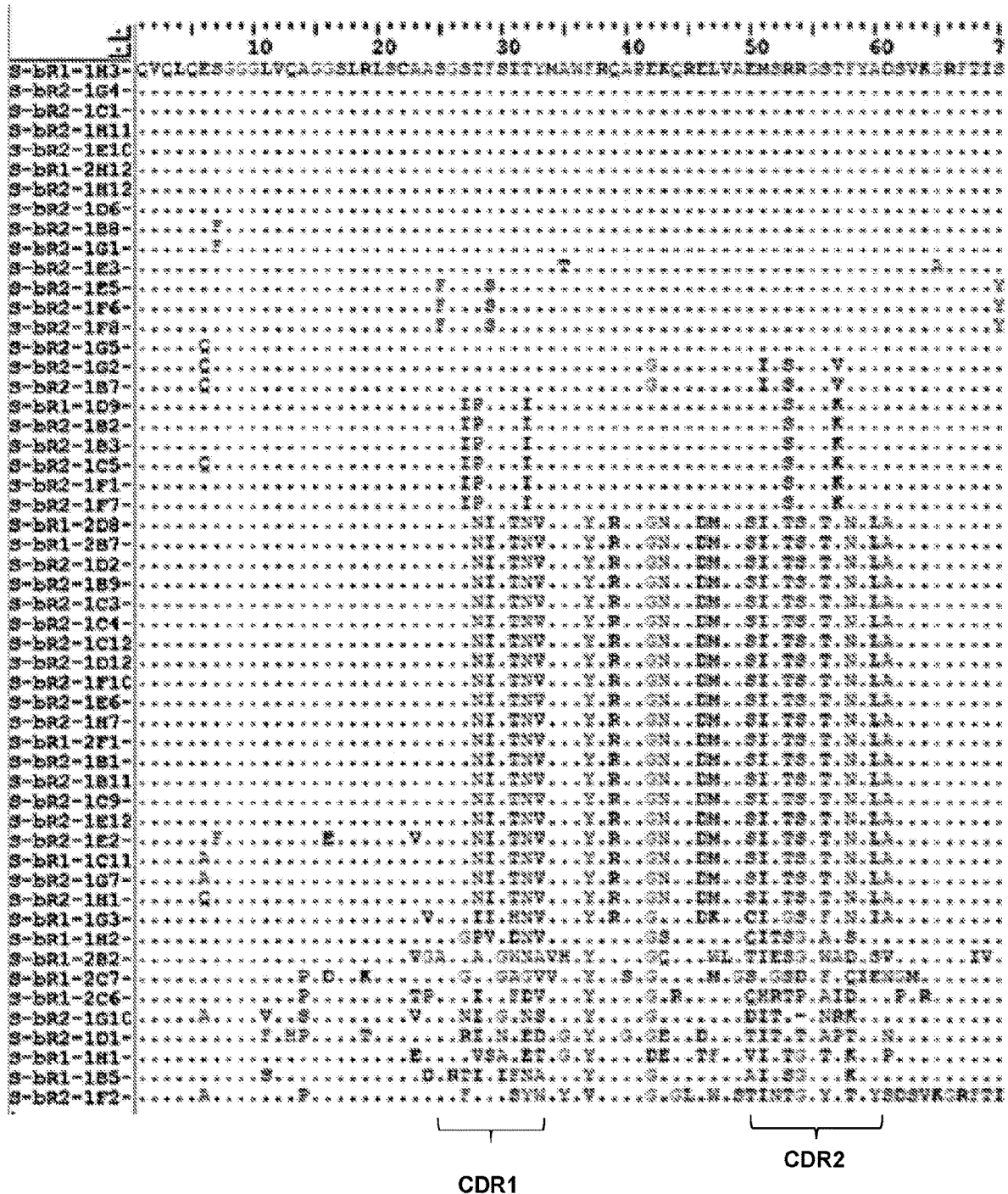
FIG. 6 is a sequence alignment of the anti-synuclein sdAb selected via solid-phase panning. The complementarity determining regions are shown.
Figure 6:
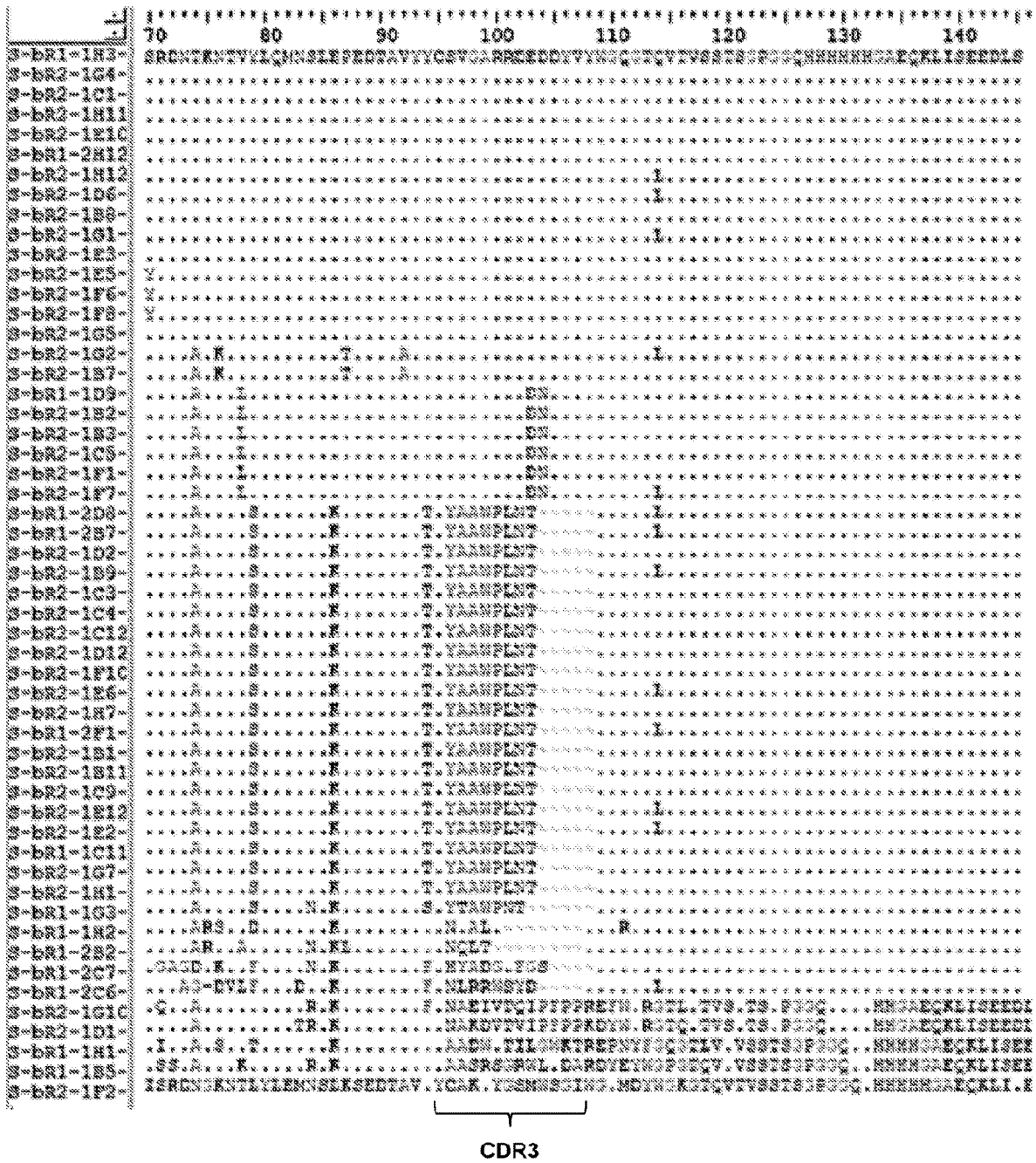

As shown in FIGS. 4A-4I, extensive Lewy bodies and Lewy neurites are seen in the DLB brain. The DLB brain also contains extensive tau pathology neurofibrillary tangles, pretangles and dystrophic neurites as shown by positive immunoreactivity with the PHF1 antibody (FIG. 5B). Although some of the sdAbs bind to tau fractions on ELISA, they do not appear to bind to pathological tau on brain sections as shown in FIGS. 4A-4I.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An anti-alpha-synuclein single-domain antibody or binding fragment thereof, said antibody or binding fragment thereof comprising a heavy chain variable region that comprises:
   a complementarity-determining region 1 (H-CDR1) comprising the amino acid sequence of ASGSIFSIN (SEQ ID NO: 18, 21, or 36);
   a complementarity-determining region 2 (H-CDR2) comprising the amino acid sequence of AGISRGGRTK (SEQ ID NO: 54, 57, or 72); and
   a complementarity-determining region 3 (H-CDR3) comprising the amino acid sequence of any one of NVRSFVRTY (SEQ ID NO: 90), NARSFVRTY (SEQ ID NO: 93), and AATRWSWGTKSY (SEQ ID NO: 108).

2. The antibody or binding fragment thereof of claim 1, wherein said antibody or binding fragment thereof is a camelid antibody or binding fragment thereof.

3. The antibody or binding fragment thereof of claim 1, wherein said heavy chain variable region comprises:
   the H-CDR1 comprising the amino acid sequence of ASGSIFSIN (SEQ ID NO: 18);
   the H-CDR2 comprising the amino acid sequence of AGISRGGRTK (SEQ ID NO: 54); and
   the H-CDR3 comprising the amino acid sequence of NVRSFVRTY (SEQ ID NO: 90).

4. The antibody or binding fragment thereof of claim 1, wherein said heavy chain variable region comprises:
   the H-CDR1 comprising the amino acid sequence of ASGSIFSIN (SEQ ID NO: 21);
   the H-CDR2 comprising the amino acid sequence of AGISRGGRTK (SEQ ID NO: 57); and the H-CDR3 comprising the amino acid sequence of NARSFVRTY (SEQ ID NO: 93).

5. The antibody or binding fragment thereof of claim 1, wherein said heavy chain variable region comprises:
the H-CDR1 comprising the amino acid sequence of ASGSIFSIN (SEQ ID NO: 36);
the H-CDR2 comprising the amino acid sequence of AGISRGGRTK (SEQ ID NO: 72); and
the H-CDR3 comprising the amino acid sequence of AATRWSWGTKSY (SEQ ID NO: 108).

6. The antibody or binding fragment thereof of claim 1, wherein said heavy chain variable region further comprises human or humanized immunoglobulin heavy chain framework regions.

7. A fusion polypeptide comprising two or more of the heavy chain variable regions of the anti-alpha-synuclein single-domain antibody according to claim 1.

8. The antibody or binding fragment thereof of claim 1, wherein the heavy chain variable region comprises the amino acid sequence selected from the group consisting of SEQ ID NOs: 126, 129, and 145.

9. A composition comprising two or more antibodies or binding fragments thereof of claim 1.

10. A diagnostic kit comprising:
the antibody or binding fragment thereof of claim 1 and a detectable label.

11. An isolated polynucleotide encoding the antibody or binding fragment thereof of claim 1.

12. A vector comprising the isolated polynucleotide of claim 11.

13. The vector of claim 12, wherein said vector is an adeno-associated viral vector.

14. A host cell comprising the vector of claim 12.

15. A pharmaceutical composition comprising:
the antibody or binding fragment thereof of claim 1 and a pharmaceutical carrier.

16. A method of inhibiting onset of one or more symptoms of an α-synucleinopathy in a subject, said method comprising:
administering to the subject the pharmaceutical composition of claim 15, wherein said composition is administered in an amount effective to inhibit onset of one or more symptoms of the α-synucleinopathy in the subject.

17. A method of treating an α-synucleinopathy in a subject, said method comprising:
administering to the subject the pharmaceutical composition of claim 15, wherein said composition is administered in an amount effective to treat the α-synucleinopathy in the subject.

18. A method of diagnosing an α-synucleinopathy in a subject, said method comprising:
detecting, in the subject, the presence of accumulated α-synuclein protein or peptide using the antibody or binding fragment thereof of claim 1, and
diagnosing the α-synucleinopathy in the subject based on said detecting.

19. A method of monitoring the progression of an α-synucleinopathy in a subject, said method comprising:
detecting, in the subject, the presence of α-synuclein protein or peptide using the antibody or binding fragment thereof of claim 1;
repeating said detecting periodically; and
monitoring the progression of the α-synucleinopathy in the subject based on said repeated detecting.

* * * * *

SEQUENCE LISTING

```
<160> NUMBER OF SEQ ID NOS: 343

<210> SEQ ID NO 1
<211> LENGTH: 9
<212> TYPE: PRT
<213> ORGANISM: Artificial Sequence
<220> FEATURE:
<223> OTHER INFORMATION: antibody sequence

<400> SEQUENCE: 1

Ala Thr Val Ser Gly Phe Ser Ile Gly
1               5

<210> SEQ ID NO 2
<211> LENGTH: 9
<212> TYPE: PRT
<213> ORGANISM: Artificial Sequence
<220> FEATURE:
<223> OTHER INFORMATION: antibody sequence

<400> SEQUENCE: 2

Ala Ser Gly Phe Thr Phe Ser Ser Ser
1               5

<210> SEQ ID NO 3
<211> LENGTH: 9
```

```
<212> TYPE: PRT
<213> ORGANISM: Artificial Sequence
<220> FEATURE:
<223> OTHER INFORMATION: antibody sequence

<400> SEQUENCE: 3

Ala Ser Gly Arg Thr Phe Ser Ser Phe
1               5

<210> SEQ ID NO 4
<211> LENGTH: 9
<212> TYPE: PRT
<213> ORGANISM: Artificial Sequence
<220> FEATURE:
<223> OTHER INFORMATION: antibody sequence

<400> SEQUENCE: 4

Ala Ser Gly Leu Ile Phe Ser Ile Asn
1               5

<210> SEQ ID NO 5
<211> LENGTH: 9
<212> TYPE: PRT
<213> ORGANISM: Artificial Sequence
<220> FEATURE:
<223> OTHER INFORMATION: antibody sequence

<400> SEQUENCE: 5

Ala Ser Gly Asn Ile Phe Arg Ile Asn
1               5

<210> SEQ ID NO 6
<211> LENGTH: 9
<212> TYPE: PRT
<213> ORGANISM: Artificial Sequence
<220> FEATURE:
<223> OTHER INFORMATION: antibody sequence

<400> SEQUENCE: 6

Ala Ser Thr Ser Val Phe Gly Asn Thr
1               5

<210> SEQ ID NO 7
<211> LENGTH: 9
<212> TYPE: PRT
<213> ORGANISM: Artificial Sequence
<220> FEATURE:
<223> OTHER INFORMATION: antibody sequence

<400> SEQUENCE: 7

Ala Ser Gly Ser Ile Tyr His Val Asn
1               5

<210> SEQ ID NO 8
<211> LENGTH: 9
<212> TYPE: PRT
<213> ORGANISM: Artificial Sequence
<220> FEATURE:
<223> OTHER INFORMATION: antibody sequence

<400> SEQUENCE: 8

Ala Ser Gly Asn Ile Phe Arg Ile Asn
1               5

<210> SEQ ID NO 9
<211> LENGTH: 9
<212> TYPE: PRT
```

```
<213> ORGANISM: Artificial Sequence
<220> FEATURE:
<223> OTHER INFORMATION: antibody sequence

<400> SEQUENCE: 9

Ala Ser Gly Asn Ile Phe Arg Ile Asn
1               5

<210> SEQ ID NO 10
<211> LENGTH: 9
<212> TYPE: PRT
<213> ORGANISM: Artificial Sequence
<220> FEATURE:
<223> OTHER INFORMATION: antibody sequence

<400> SEQUENCE: 10

Ala Ser Arg Ser Phe Phe Ser Ile Asn
1               5

<210> SEQ ID NO 11
<211> LENGTH: 9
<212> TYPE: PRT
<213> ORGANISM: Artificial Sequence
<220> FEATURE:
<223> OTHER INFORMATION: antibody sequence

<400> SEQUENCE: 11

His Ser Thr Ile Thr Phe Arg Ile Asn
1               5

<210> SEQ ID NO 12
<211> LENGTH: 9
<212> TYPE: PRT
<213> ORGANISM: Artificial Sequence
<220> FEATURE:
<223> OTHER INFORMATION: antibody sequence

<400> SEQUENCE: 12

Ala Ser Met Thr Thr Leu Gly Phe Lys
1               5

<210> SEQ ID NO 13
<211> LENGTH: 9
<212> TYPE: PRT
<213> ORGANISM: Artificial Sequence
<220> FEATURE:
<223> OTHER INFORMATION: antibody sequence

<400> SEQUENCE: 13

Ala Ser Thr Ser Val Phe Gly Asn Thr
1               5

<210> SEQ ID NO 14
<211> LENGTH: 9
<212> TYPE: PRT
<213> ORGANISM: Artificial Sequence
<220> FEATURE:
<223> OTHER INFORMATION: antibody sequence

<400> SEQUENCE: 14

Ala Ser Gly Met Arg Ser Ser Leu Ala
1               5

<210> SEQ ID NO 15
<211> LENGTH: 10
<212> TYPE: PRT
<213> ORGANISM: Artificial Sequence
```

```
<220> FEATURE:
<223> OTHER INFORMATION: antibody sequence

<400> SEQUENCE: 15

Ala Ser Gly Ser Thr Phe Ile Ser Ile Lys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: antibody sequence

<400> SEQUENCE: 16

Ala Ser Gly Ser Thr Phe Arg Phe Asn
1               5

<210> SEQ ID NO 17
<211> LENGTH: 9
<212> TYPE: PRT
<213> ORGANISM: Artificial Sequence
<220> FEATURE:
<223> OTHER INFORMATION: antibody sequence

<400> SEQUENCE: 17

Ala Ser Gly Ser Arg Phe Ser Ile Asn
1               5

<210> SEQ ID NO 18
<211> LENGTH: 9
<212> TYPE: PRT
<213> ORGANISM: Artificial Sequence
<220> FEATURE:
<223> OTHER INFORMATION: antibody sequence

<400> SEQUENCE: 18

Ala Ser Gly Ser Ile Phe Ser Ile Asn
1               5

<210> SEQ ID NO 19
<211> LENGTH: 9
<212> TYPE: PRT
<213> ORGANISM: Artificial Sequence
<220> FEATURE:
<223> OTHER INFORMATION: antibody sequence

<400> SEQUENCE: 19

Ala Ser Gly Ser Ile Phe Arg Ile Asn
1               5

<210> SEQ ID NO 20
<211> LENGTH: 9
<212> TYPE: PRT
<213> ORGANISM: Artificial Sequence
<220> FEATURE:
<223> OTHER INFORMATION: antibody sequence

<400> SEQUENCE: 20

Ala Ser Thr Ser Val Phe Gly Asn Thr
1               5

<210> SEQ ID NO 21
<211> LENGTH: 9
<212> TYPE: PRT
<213> ORGANISM: Artificial Sequence
<220> FEATURE:
```

```
<223> OTHER INFORMATION: antibody sequence

<400> SEQUENCE: 21

Ala Ser Gly Ser Ile Phe Ser Ile Asn
1               5

<210> SEQ ID NO 22
<211> LENGTH: 9
<212> TYPE: PRT
<213> ORGANISM: Artificial Sequence
<220> FEATURE:
<223> OTHER INFORMATION: antibody sequence

<400> SEQUENCE: 22

Ala Ser Arg Asn Phe Phe Thr Phe Arg
1               5

<210> SEQ ID NO 23
<211> LENGTH: 9
<212> TYPE: PRT
<213> ORGANISM: Artificial Sequence
<220> FEATURE:
<223> OTHER INFORMATION: antibody sequence

<400> SEQUENCE: 23

Ala Ser Gly Ile Thr Phe Arg Phe Asn
1               5

<210> SEQ ID NO 24
<211> LENGTH: 9
<212> TYPE: PRT
<213> ORGANISM: Artificial Sequence
<220> FEATURE:
<223> OTHER INFORMATION: antibody sequence

<400> SEQUENCE: 24

Ala Ser Gly Arg Ser Ile Leu Ile Lys
1               5

<210> SEQ ID NO 25
<211> LENGTH: 9
<212> TYPE: PRT
<213> ORGANISM: Artificial Sequence
<220> FEATURE:
<223> OTHER INFORMATION: antibody sequence

<400> SEQUENCE: 25

Ala Ser Gly Arg Ile Phe Gly Arg Asn
1               5

<210> SEQ ID NO 26
<211> LENGTH: 9
<212> TYPE: PRT
<213> ORGANISM: Artificial Sequence
<220> FEATURE:
<223> OTHER INFORMATION: antibody sequence

<400> SEQUENCE: 26

Ala Ser Arg Ser Thr Phe Arg Phe Asn
1               5

<210> SEQ ID NO 27
<211> LENGTH: 9
<212> TYPE: PRT
<213> ORGANISM: Artificial Sequence
<220> FEATURE:
<223> OTHER INFORMATION: antibody sequence
```

```
<400> SEQUENCE: 27

Thr Ser Gly Ser Ile Phe Ser Ile Asn
1               5

<210> SEQ ID NO 28
<211> LENGTH: 9
<212> TYPE: PRT
<213> ORGANISM: Artificial Sequence
<220> FEATURE:
<223> OTHER INFORMATION: antibody sequence

<400> SEQUENCE: 28

Leu Ser Thr Thr Met Phe Gly Phe Trp
1               5

<210> SEQ ID NO 29
<211> LENGTH: 9
<212> TYPE: PRT
<213> ORGANISM: Artificial Sequence
<220> FEATURE:
<223> OTHER INFORMATION: antibody sequence

<400> SEQUENCE: 29

Ala Ser Gly Asn Ile Phe Arg Ile Asn
1               5

<210> SEQ ID NO 30
<211> LENGTH: 9
<212> TYPE: PRT
<213> ORGANISM: Artificial Sequence
<220> FEATURE:
<223> OTHER INFORMATION: antibody sequence

<400> SEQUENCE: 30

Ala Ser Gly Ser Ile Phe Ser Thr Asn
1               5

<210> SEQ ID NO 31
<211> LENGTH: 9
<212> TYPE: PRT
<213> ORGANISM: Artificial Sequence
<220> FEATURE:
<223> OTHER INFORMATION: antibody sequence

<400> SEQUENCE: 31

Ala Ser Arg Ser Ser Phe Arg Ile Thr
1               5

<210> SEQ ID NO 32
<211> LENGTH: 9
<212> TYPE: PRT
<213> ORGANISM: Artificial Sequence
<220> FEATURE:
<223> OTHER INFORMATION: antibody sequence

<400> SEQUENCE: 32

Ala Ser Gly Asn Ile Phe Arg Ile Asn
1               5

<210> SEQ ID NO 33
<211> LENGTH: 9
<212> TYPE: PRT
<213> ORGANISM: Artificial Sequence
<220> FEATURE:
<223> OTHER INFORMATION: antibody sequence
```

```
<400> SEQUENCE: 33

Ala Ser Val Val Pro Phe Arg Tyr Phe
1               5

<210> SEQ ID NO 34
<211> LENGTH: 9
<212> TYPE: PRT
<213> ORGANISM: Artificial Sequence
<220> FEATURE:
<223> OTHER INFORMATION: antibody sequence

<400> SEQUENCE: 34

Ala Ser Gly Ser Ile Phe Ser Ile Lys
1               5

<210> SEQ ID NO 35
<211> LENGTH: 9
<212> TYPE: PRT
<213> ORGANISM: Artificial Sequence
<220> FEATURE:
<223> OTHER INFORMATION: antibody sequence

<400> SEQUENCE: 35

Ala Ser Gly Ser Ala Phe Arg Met Asn
1               5

<210> SEQ ID NO 36
<211> LENGTH: 9
<212> TYPE: PRT
<213> ORGANISM: Artificial Sequence
<220> FEATURE:
<223> OTHER INFORMATION: antibody sequence

<400> SEQUENCE: 36

Ala Ser Gly Ser Ile Phe Ser Ile Asn
1               5

<210> SEQ ID NO 37
<211> LENGTH: 10
<212> TYPE: PRT
<213> ORGANISM: Artificial Sequence
<220> FEATURE:
<223> OTHER INFORMATION: antibody sequence

<400> SEQUENCE: 37

Ala Asn Val Ser Pro Ser Gly Ala Lys Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: antibody sequence

<400> SEQUENCE: 38

Ala Ser Ile Met Arg Tyr Gly Thr Thr Thr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: antibody sequence

<400> SEQUENCE: 39
```

```
Thr Ala Ile Asn Trp Ser Gly Ser Ser Thr Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: antibody sequence

<400> SEQUENCE: 40

Ala Arg Ile Thr Thr Gly Gly Ser Thr Asn
1               5                   10

<210> SEQ ID NO 41
<211> LENGTH: 10
<212> TYPE: PRT
<213> ORGANISM: Artificial Sequence
<220> FEATURE:
<223> OTHER INFORMATION: antibody sequence

<400> SEQUENCE: 41

Ala His Ile Ile Ser Gly Gly Ser Thr Asn
1               5                   10

<210> SEQ ID NO 42
<211> LENGTH: 10
<212> TYPE: PRT
<213> ORGANISM: Artificial Sequence
<220> FEATURE:
<223> OTHER INFORMATION: antibody sequence

<400> SEQUENCE: 42

Ala Arg Ile Thr Thr Leu Gly Phe Thr Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: antibody sequence

<400> SEQUENCE: 43

Ala Thr Leu Thr His Asn Asn Arg Val Thr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: antibody sequence

<400> SEQUENCE: 44

Ala Val Val Lys Ser Gly Gly Ser Thr Asn
1               5                   10

<210> SEQ ID NO 45
<211> LENGTH: 10
<212> TYPE: PRT
<213> ORGANISM: Artificial Sequence
<220> FEATURE:
<223> OTHER INFORMATION: antibody sequence

<400> SEQUENCE: 45
```

```
Ala His Ile Ile Ser Gly Gly Ser Thr Asn
1               5                   10

<210> SEQ ID NO 46
<211> LENGTH: 10
<212> TYPE: PRT
<213> ORGANISM: Artificial Sequence
<220> FEATURE:
<223> OTHER INFORMATION: antibody sequence

<400> SEQUENCE: 46

Ala Thr Ile Thr Ser Arg Asp Ser Thr Asn
1               5                   10

<210> SEQ ID NO 47
<211> LENGTH: 10
<212> TYPE: PRT
<213> ORGANISM: Artificial Sequence
<220> FEATURE:
<223> OTHER INFORMATION: antibody sequence

<400> SEQUENCE: 47

Ala Arg Ile Asn Pro Ala Gly Arg Thr Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: antibody sequence

<400> SEQUENCE: 48

Ala Thr Ile Ser Ser Ile Gly Ile Ser Thr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: antibody sequence

<400> SEQUENCE: 49

Ala Arg Ile Thr Thr Leu Gly Phe Thr Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: antibody sequence

<400> SEQUENCE: 50

Ala Thr Ile Thr Ile Gly Gly Asn Thr Asn
1               5                   10

<210> SEQ ID NO 51
<211> LENGTH: 10
<212> TYPE: PRT
<213> ORGANISM: Artificial Sequence
<220> FEATURE:
<223> OTHER INFORMATION: antibody sequence

<400> SEQUENCE: 51

Ala Gly Ile Thr Lys Asn Asn Tyr Ile Asn
```

```
1               5                   10

<210> SEQ ID NO 52
<211> LENGTH: 10
<212> TYPE: PRT
<213> ORGANISM: Artificial Sequence
<220> FEATURE:
<223> OTHER INFORMATION: antibody sequence

<400> SEQUENCE: 52

Ala Asn Ile Asn Ser Ser Gly Arg Thr Met
1               5                   10

<210> SEQ ID NO 53
<211> LENGTH: 10
<212> TYPE: PRT
<213> ORGANISM: Artificial Sequence
<220> FEATURE:
<223> OTHER INFORMATION: antibody sequence

<400> SEQUENCE: 53

Ala Gly Ile Thr Ser Leu Gly Phe Thr Asn
1               5                   10

<210> SEQ ID NO 54
<211> LENGTH: 10
<212> TYPE: PRT
<213> ORGANISM: Artificial Sequence
<220> FEATURE:
<223> OTHER INFORMATION: antibody sequence

<400> SEQUENCE: 54

Ala Gly Ile Ser Arg Gly Gly Arg Thr Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: antibody sequence

<400> SEQUENCE: 55

Ala Thr Ile Thr Asn Glu Gly Asn Thr Tyr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: antibody sequence

<400> SEQUENCE: 56

Ala Arg Ile Thr Thr Leu Gly Phe Thr Tyr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: antibody sequence

<400> SEQUENCE: 57

Ala Gly Ile Ser Arg Gly Gly Arg Thr Lys
1               5                   10
```

<210> SEQ ID NO 58
<211> LENGTH: 10
<212> TYPE: PRT
<213> ORGANISM: Artificial Sequence
<220> FEATURE:
<223> OTHER INFORMATION: antibody sequence

<400> SEQUENCE: 58

Ala Ser Ile Thr Thr Gly Gly Arg Thr Val
1               5                   10

<210> SEQ ID NO 59
<211> LENGTH: 10
<212> TYPE: PRT
<213> ORGANISM: Artificial Sequence
<220> FEATURE:
<223> OTHER INFORMATION: antibody sequence

<400> SEQUENCE: 59

Ala Arg Val Ser Ser Gly Gly Ser Thr Thr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: antibody sequence

<400> SEQUENCE: 60

Ala Thr Ile Ser Met Ala Gly Val Thr Asn
1               5                   10

<210> SEQ ID NO 61
<211> LENGTH: 10
<212> TYPE: PRT
<213> ORGANISM: Artificial Sequence
<220> FEATURE:
<223> OTHER INFORMATION: antibody sequence

<400> SEQUENCE: 61

Ala Arg Ile Thr Arg Asp Gly Arg Thr Met
1               5                   10

<210> SEQ ID NO 62
<211> LENGTH: 11
<212> TYPE: PRT
<213> ORGANISM: Artificial Sequence
<220> FEATURE:
<223> OTHER INFORMATION: antibody sequence

<400> SEQUENCE: 62

Ala Ala Ile Ser Ser Arg Gly Gly Ser Thr Asn
1               5                   10

<210> SEQ ID NO 63
<211> LENGTH: 10
<212> TYPE: PRT
<213> ORGANISM: Artificial Sequence
<220> FEATURE:
<223> OTHER INFORMATION: antibody sequence

<400> SEQUENCE: 63

Ala Ala Ile Ser Gly Arg Gly Ser Thr His
1               5                   10

```
<210> SEQ ID NO 64
<211> LENGTH: 10
<212> TYPE: PRT
<213> ORGANISM: Artificial Sequence
<220> FEATURE:
<223> OTHER INFORMATION: antibody sequence

<400> SEQUENCE: 64

Ala Thr Ile Asp Ser Arg Gly Arg Thr Asn
1               5                   10

<210> SEQ ID NO 65
<211> LENGTH: 10
<212> TYPE: PRT
<213> ORGANISM: Artificial Sequence
<220> FEATURE:
<223> OTHER INFORMATION: antibody sequence

<400> SEQUENCE: 65

Ala Arg Ile Ser Ser Gly Gly Ser Thr Asn
1               5                   10

<210> SEQ ID NO 66
<211> LENGTH: 10
<212> TYPE: PRT
<213> ORGANISM: Artificial Sequence
<220> FEATURE:
<223> OTHER INFORMATION: antibody sequence

<400> SEQUENCE: 66

Ala Ser Ile Thr Lys Phe Gly Asn Thr Asp
1               5                   10

<210> SEQ ID NO 67
<211> LENGTH: 10
<212> TYPE: PRT
<213> ORGANISM: Artificial Sequence
<220> FEATURE:
<223> OTHER INFORMATION: antibody sequence

<400> SEQUENCE: 67

Ala Ser Ile Thr Thr Gly Gly Arg Thr Val
1               5                   10

<210> SEQ ID NO 68
<211> LENGTH: 10
<212> TYPE: PRT
<213> ORGANISM: Artificial Sequence
<220> FEATURE:
<223> OTHER INFORMATION: antibody sequence

<400> SEQUENCE: 68

Ala His Ile Ile Ser Gly Gly Ser Thr Asn
1               5                   10

<210> SEQ ID NO 69
<211> LENGTH: 10
<212> TYPE: PRT
<213> ORGANISM: Artificial Sequence
<220> FEATURE:
<223> OTHER INFORMATION: antibody sequence

<400> SEQUENCE: 69

Ala Ser Ile Thr Ser Gly Gly Gly Val Asn
1               5                   10
```

-continued

```
<210> SEQ ID NO 70
<211> LENGTH: 10
<212> TYPE: PRT
<213> ORGANISM: Artificial Sequence
<220> FEATURE:
<223> OTHER INFORMATION: antibody sequence

<400> SEQUENCE: 70

Ala Ala Ile Ala Ser Gly Gly Phe Thr Asn
1               5                   10

<210> SEQ ID NO 71
<211> LENGTH: 10
<212> TYPE: PRT
<213> ORGANISM: Artificial Sequence
<220> FEATURE:
<223> OTHER INFORMATION: antibody sequence

<400> SEQUENCE: 71

Ala Ala Ile Ser Phe Arg Gly Ser Ala Asn
1               5                   10

<210> SEQ ID NO 72
<211> LENGTH: 10
<212> TYPE: PRT
<213> ORGANISM: Artificial Sequence
<220> FEATURE:
<223> OTHER INFORMATION: antibody sequence

<400> SEQUENCE: 72

Ala Gly Ile Ser Arg Gly Gly Arg Thr Lys
1               5                   10

<210> SEQ ID NO 73
<211> LENGTH: 11
<212> TYPE: PRT
<213> ORGANISM: Artificial Sequence
<220> FEATURE:
<223> OTHER INFORMATION: antibody sequence

<400> SEQUENCE: 73

Asn Ile Arg Arg Phe Ser Tyr Leu Ser Gly Asp
1               5                   10

<210> SEQ ID NO 74
<211> LENGTH: 9
<212> TYPE: PRT
<213> ORGANISM: Artificial Sequence
<220> FEATURE:
<223> OTHER INFORMATION: antibody sequence

<400> SEQUENCE: 74

Asn Val Arg Ser Phe Val Arg Thr Tyr
1               5

<210> SEQ ID NO 75
<211> LENGTH: 11
<212> TYPE: PRT
<213> ORGANISM: Artificial Sequence
<220> FEATURE:
<223> OTHER INFORMATION: antibody sequence

<400> SEQUENCE: 75

Asn Ala Gln Arg Arg Trp Pro Leu Arg Asp Tyr
1               5                   10

<210> SEQ ID NO 76
```

```
<211> LENGTH: 12
<212> TYPE: PRT
<213> ORGANISM: Artificial Sequence
<220> FEATURE:
<223> OTHER INFORMATION: antibody sequence

<400> SEQUENCE: 76

Ala Ala Asp Val Arg Phe Gly Glu Arg Thr Pro Tyr
1               5                   10

<210> SEQ ID NO 77
<211> LENGTH: 9
<212> TYPE: PRT
<213> ORGANISM: Artificial Sequence
<220> FEATURE:
<223> OTHER INFORMATION: antibody sequence

<400> SEQUENCE: 77

Asn Ala Arg Thr Phe Val Arg Thr Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: antibody sequence

<400> SEQUENCE: 78

Asn Arg Arg Gly Phe Arg Ser Tyr
1               5

<210> SEQ ID NO 79
<211> LENGTH: 18
<212> TYPE: PRT
<213> ORGANISM: Artificial Sequence
<220> FEATURE:
<223> OTHER INFORMATION: antibody sequence

<400> SEQUENCE: 79

Tyr Tyr Phe Val Pro Arg Asn Pro Leu Phe Gly Arg Arg Ile Asp Phe
1               5                   10                  15

Asp Ala

<210> SEQ ID NO 80
<211> LENGTH: 9
<212> TYPE: PRT
<213> ORGANISM: Artificial Sequence
<220> FEATURE:
<223> OTHER INFORMATION: antibody sequence

<400> SEQUENCE: 80

Asn Ala Gln Thr Arg Leu Trp Ser Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: antibody sequence

<400> SEQUENCE: 81

Asn Ala Gln Thr Arg Leu Trp Ser Tyr
1               5
```

```
<210> SEQ ID NO 82
<211> LENGTH: 10
<212> TYPE: PRT
<213> ORGANISM: Artificial Sequence
<220> FEATURE:
<223> OTHER INFORMATION: antibody sequence

<400> SEQUENCE: 82

Tyr Ala Asp Gln Pro Trp Arg Gly Arg Ala
1               5                   10

<210> SEQ ID NO 83
<211> LENGTH: 9
<212> TYPE: PRT
<213> ORGANISM: Artificial Sequence
<220> FEATURE:
<223> OTHER INFORMATION: antibody sequence

<400> SEQUENCE: 83

Ser Thr Trp Arg Leu Gly Arg Asn Tyr
1               5

<210> SEQ ID NO 84
<211> LENGTH: 11
<212> TYPE: PRT
<213> ORGANISM: Artificial Sequence
<220> FEATURE:
<223> OTHER INFORMATION: antibody sequence

<400> SEQUENCE: 84

His Val Ile Arg Pro Ser Trp Met Pro Gln Tyr
1               5                   10

<210> SEQ ID NO 85
<211> LENGTH: 8
<212> TYPE: PRT
<213> ORGANISM: Artificial Sequence
<220> FEATURE:
<223> OTHER INFORMATION: antibody sequence

<400> SEQUENCE: 85

Asn Arg Leu Trp Arg Pro Leu Ala
1               5

<210> SEQ ID NO 86
<211> LENGTH: 9
<212> TYPE: PRT
<213> ORGANISM: Artificial Sequence
<220> FEATURE:
<223> OTHER INFORMATION: antibody sequence

<400> SEQUENCE: 86

Asn Val Arg Ser Phe Val Arg Thr Tyr
1               5

<210> SEQ ID NO 87
<211> LENGTH: 10
<212> TYPE: PRT
<213> ORGANISM: Artificial Sequence
<220> FEATURE:
<223> OTHER INFORMATION: antibody sequence

<400> SEQUENCE: 87

Thr Val Gln Arg Arg Leu Gly Arg Val Tyr
1               5                   10

<210> SEQ ID NO 88
```

```
<211> LENGTH: 9
<212> TYPE: PRT
<213> ORGANISM: Artificial Sequence
<220> FEATURE:
<223> OTHER INFORMATION: antibody sequence

<400> SEQUENCE: 88

Asn Val Arg Ser Phe Val Arg Thr Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: antibody sequence

<400> SEQUENCE: 89

Asn Arg Arg Gly Phe Arg Ser Tyr
1               5

<210> SEQ ID NO 90
<211> LENGTH: 9
<212> TYPE: PRT
<213> ORGANISM: Artificial Sequence
<220> FEATURE:
<223> OTHER INFORMATION: antibody sequence

<400> SEQUENCE: 90

Asn Val Arg Ser Phe Val Arg Thr Tyr
1               5

<210> SEQ ID NO 91
<211> LENGTH: 8
<212> TYPE: PRT
<213> ORGANISM: Artificial Sequence
<220> FEATURE:
<223> OTHER INFORMATION: antibody sequence

<400> SEQUENCE: 91

Ala Gly Lys Val Ile Arg Trp Tyr
1               5

<210> SEQ ID NO 92
<211> LENGTH: 10
<212> TYPE: PRT
<213> ORGANISM: Artificial Sequence
<220> FEATURE:
<223> OTHER INFORMATION: antibody sequence

<400> SEQUENCE: 92

Arg Ala Arg Arg Ala Leu Arg Glu Ser His
1               5                   10

<210> SEQ ID NO 93
<211> LENGTH: 9
<212> TYPE: PRT
<213> ORGANISM: Artificial Sequence
<220> FEATURE:
<223> OTHER INFORMATION: antibody sequence

<400> SEQUENCE: 93

Asn Ala Arg Ser Phe Val Arg Thr Tyr
1               5

<210> SEQ ID NO 94
<211> LENGTH: 14
```

```
<212> TYPE: PRT
<213> ORGANISM: Artificial Sequence
<220> FEATURE:
<223> OTHER INFORMATION: antibody sequence

<400> SEQUENCE: 94

Asn Ala Arg Arg Arg Phe Pro Val Pro Gly Pro Thr Asp Tyr
1               5                   10

<210> SEQ ID NO 95
<211> LENGTH: 5
<212> TYPE: PRT
<213> ORGANISM: Artificial Sequence
<220> FEATURE:
<223> OTHER INFORMATION: antibody sequence

<400> SEQUENCE: 95

Asn Val Gly Asn Phe
1               5

<210> SEQ ID NO 96
<211> LENGTH: 9
<212> TYPE: PRT
<213> ORGANISM: Artificial Sequence
<220> FEATURE:
<223> OTHER INFORMATION: antibody sequence

<400> SEQUENCE: 96

Asn Ala Gln Thr Arg Leu Trp Ser Tyr
1               5

<210> SEQ ID NO 97
<211> LENGTH: 9
<212> TYPE: PRT
<213> ORGANISM: Artificial Sequence
<220> FEATURE:
<223> OTHER INFORMATION: antibody sequence

<400> SEQUENCE: 97

Asn Ala Gln Thr Arg Leu Trp Ser Tyr
1               5

<210> SEQ ID NO 98
<211> LENGTH: 9
<212> TYPE: PRT
<213> ORGANISM: Artificial Sequence
<220> FEATURE:
<223> OTHER INFORMATION: antibody sequence

<400> SEQUENCE: 98

Asn Val Arg Ser Phe Val Arg Thr Tyr
1               5

<210> SEQ ID NO 99
<211> LENGTH: 17
<212> TYPE: PRT
<213> ORGANISM: Artificial Sequence
<220> FEATURE:
<223> OTHER INFORMATION: antibody sequence

<400> SEQUENCE: 99

Ala Leu Asp Gln His Met Glu Val Ile Val Ser Pro Gly Arg Ile Gly
1               5                   10                  15

Ser

<210> SEQ ID NO 100
```

<211> LENGTH: 11
<212> TYPE: PRT
<213> ORGANISM: Artificial Sequence
<220> FEATURE:
<223> OTHER INFORMATION: antibody sequence

<400> SEQUENCE: 100

Asn Ala Gln Arg Arg Trp Pro Leu Arg Asp Tyr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: antibody sequence

<400> SEQUENCE: 101

Asn Ala Arg Arg Pro Leu Arg Trp Tyr Glu Tyr
1               5                   10

<210> SEQ ID NO 102
<211> LENGTH: 15
<212> TYPE: PRT
<213> ORGANISM: Artificial Sequence
<220> FEATURE:
<223> OTHER INFORMATION: antibody sequence

<400> SEQUENCE: 102

Tyr Gln Asn Ser Arg Gly Arg Trp Tyr Asp Ile Phe Arg Asp Tyr
1               5                   10                  15

<210> SEQ ID NO 103
<211> LENGTH: 11
<212> TYPE: PRT
<213> ORGANISM: Artificial Sequence
<220> FEATURE:
<223> OTHER INFORMATION: antibody sequence

<400> SEQUENCE: 103

Asn Ala Gln Arg Arg Trp Pro Leu Arg Asp Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: antibody sequence

<400> SEQUENCE: 104

Asn Ala Glu Arg Arg Phe Gly Met Arg Gln Val
1               5                   10

<210> SEQ ID NO 105
<211> LENGTH: 16
<212> TYPE: PRT
<213> ORGANISM: Artificial Sequence
<220> FEATURE:
<223> OTHER INFORMATION: antibody sequence

<400> SEQUENCE: 105

Ala Arg Leu Leu Ser Leu Gly Ser Arg Trp Gly Tyr Gly Met Phe Thr
1               5                   10                  15

<210> SEQ ID NO 106
<211> LENGTH: 11

```
<212> TYPE: PRT
<213> ORGANISM: Artificial Sequence
<220> FEATURE:
<223> OTHER INFORMATION: antibody sequence

<400> SEQUENCE: 106

Asn Ala Gln Arg Arg Trp Pro Leu Arg Asp Tyr
1               5                   10

<210> SEQ ID NO 107
<211> LENGTH: 11
<212> TYPE: PRT
<213> ORGANISM: Artificial Sequence
<220> FEATURE:
<223> OTHER INFORMATION: antibody sequence

<400> SEQUENCE: 107

Ala Ala Gly Arg Pro Trp Gln Arg Thr Phe Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: antibody sequence

<400> SEQUENCE: 108

Ala Ala Thr Arg Trp Ser Trp Gly Thr Lys Ser Tyr
1               5                   10

<210> SEQ ID NO 109
<211> LENGTH: 117
<212> TYPE: PRT
<213> ORGANISM: Artificial Sequence
<220> FEATURE:
<223> OTHER INFORMATION: antibody sequence

<400> SEQUENCE: 109

Gln Val Gln Leu Gln Gln Ser Gly Gly Gly Leu Val Gln Ala Gly Gly
1               5                   10                  15

Ser Leu Ile Leu Arg Cys Arg Ala Thr Val Ser Gly Phe Ser Ile Gly
            20                  25                  30

Thr Met Gly Trp Tyr Arg Gln Ala Pro Gly Lys Glu Arg Glu Phe Val
        35                  40                  45

Ala Asn Val Ser Pro Ser Gly Ala Lys Tyr Phe Ala Asp Ser Val Lys
    50                  55                  60

Gly Arg Phe Thr Ile Ser Arg Asp Asn Ala Asn Thr Val Tyr Leu
65                  70                  75                  80

Gln Met Asn Ser Leu Lys Pro Glu Asp Thr Gly Val Tyr Tyr Cys Asn
                85                  90                  95

Ile Arg Arg Phe Ser Tyr Leu Ser Gly Asp Trp Gly Gln Gly Thr Gln
            100                 105                 110

Val Thr Val Ser Ser
        115

<210> SEQ ID NO 110
<211> LENGTH: 115
<212> TYPE: PRT
<213> ORGANISM: Artificial Sequence
<220> FEATURE:
<223> OTHER INFORMATION: antibody sequence

<400> SEQUENCE: 110
```

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Phe Thr Phe Ser Ser Ser
            20                  25                  30

Ser Met Gly Trp Tyr Arg Gln Ala Pro Gly Lys Gln Arg Glu Leu Val
        35                  40                  45

Ala Ser Ile Met Arg Tyr Gly Thr Thr Thr Thr Asp Ser Val Lys
    50                  55                  60

Gly Arg Phe Thr Ile Ser Arg Asp Asn Gly Gln Arg Thr Val Tyr Leu
65                  70                  75                  80

Gln Met Asn Ser Leu Lys Pro Glu Asp Thr Ala Val Tyr Tyr Cys Asn
                85                  90                  95

Val Arg Ser Phe Val Arg Thr Tyr Trp Gly Gln Gly Thr Leu Val Thr
            100                 105                 110

Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: antibody sequence

<400> SEQUENCE: 111

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Phe
            20                  25                  30

Ala Met Gly Trp Phe Arg Gln Ala Pro Gly Lys Glu Arg Glu Phe Val
        35                  40                  45

Thr Ala Ile Asn Trp Ser Gly Ser Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Gln Arg Arg Trp Pro Leu Arg Asp Tyr Trp Gly Gln Gly Thr
            100                 105                 110

Gln Val Thr Val Ser Ser
        115

<210> SEQ ID NO 112
<211> LENGTH: 118
<212> TYPE: PRT
<213> ORGANISM: Artificial Sequence
<220> FEATURE:
<223> OTHER INFORMATION: antibody sequence

<400> SEQUENCE: 112

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Leu Ile Phe Ser Ile Asn
            20                  25                  30

Ala Met Ala Trp Tyr Arg Gln Ala Pro Gly Asn Gln Arg Glu Leu Val
        35                  40                  45

Ala Arg Ile Thr Thr Gly Gly Ser Thr Asn Tyr Ala Asp Ser Val Lys
```

```
                    50                  55                  60
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Phe Cys Ala
                 85                  90                  95

Ala Asp Val Arg Phe Gly Glu Arg Thr Pro Tyr Trp Gly Gln Gly Thr
                100                 105                 110

Gln Val Thr Val Ser Ser
            115

<210> SEQ ID NO 113
<211> LENGTH: 115
<212> TYPE: PRT
<213> ORGANISM: Artificial Sequence
<220> FEATURE:
<223> OTHER INFORMATION: antibody sequence

<400> SEQUENCE: 113

Gln Val Gln Leu Gln Ala Ser Gly Gly Gly Val Val Gln Ser Gly Gly
  1               5                  10                  15

Ser Leu Arg Leu Ser Cys Val Ala Ser Gly Asn Ile Phe Arg Ile Asn
                 20                  25                  30

Ala Met Gly Trp Tyr Arg Gln Ala Pro Gly Lys Gln Arg Glu Leu Val
             35                  40                  45

Ala His Ile Ile Ser Gly Gly Ser Thr Asn Tyr Ala Asp Ser Val Lys
         50                  55                  60

Gly Arg Phe Thr Ile Ser Arg Glu Tyr Ala Lys Asn Met Val Tyr Leu
 65                  70                  75                  80

Gln Met Asn Ser Leu Lys Pro Glu Asp Thr Ala Val Tyr Tyr Cys Asn
                 85                  90                  95

Ala Arg Thr Phe Val Arg Thr Tyr Trp Gly Gln Gly Thr Gln Val Thr
                100                 105                 110

Val Ser Ser
        115

<210> SEQ ID NO 114
<211> LENGTH: 114
<212> TYPE: PRT
<213> ORGANISM: Artificial Sequence
<220> FEATURE:
<223> OTHER INFORMATION: antibody sequence

<400> SEQUENCE: 114

Gln Val Gln Leu Gln Gln Phe Gly Gly Gly Leu Val Gln Pro Gly Gly
  1               5                  10                  15

Ser Leu Arg Leu Ser Cys Gln Ala Ser Thr Ser Val Phe Gly Asn Thr
                 20                  25                  30

Ala Met Ala Trp Tyr Arg Gln Ala Pro Gly Lys Gln Arg Glu Leu Val
             35                  40                  45

Ala Arg Ile Thr Thr Leu Gly Phe Thr Tyr Tyr Ala Asp Ser Ala Lys
         50                  55                  60

Gly Arg Phe Thr Ile Ser Arg Asp Ser Ala Met Asn Thr Val Tyr Leu
 65                  70                  75                  80

Gln Met Asn Ser Leu Lys Pro Glu Asp Thr Ala Val Tyr Tyr Cys Asn
                 85                  90                  95

Arg Arg Gly Phe Arg Ser Tyr Trp Gly Gln Gly Thr Leu Val Thr Val
                100                 105                 110
```

Ser Ser

<210> SEQ ID NO 115
<211> LENGTH: 124
<212> TYPE: PRT
<213> ORGANISM: Artificial Sequence
<220> FEATURE:
<223> OTHER INFORMATION: antibody sequence

<400> SEQUENCE: 115

Gln Val Gln Leu Gln Glu Ser Gly Gly Gly Leu Val Gln Ser Gly Asp
1               5                   10                  15

Ser Leu Arg Leu Ser Cys Ala Ala Ser Gly Ser Ile Tyr His Val Asn
            20                  25                  30

Thr Met Gly Trp Tyr Arg Gln Ser Pro Gly Lys Gln Arg Glu Leu Val
        35                  40                  45

Ala Thr Leu Thr His Asn Asn Arg Val Thr Tyr Ala Asp Ser Val Lys
    50                  55                  60

Gly Arg Phe Thr Ile Ser Arg Asp Asn Ala Lys Met Thr Val Tyr Leu
65                  70                  75                  80

Gln Met Asp Ser Leu Lys Pro Asp Asp Thr Ala Val Tyr Tyr Cys Tyr
                85                  90                  95

Tyr Phe Val Pro Arg Asn Pro Leu Phe Gly Arg Arg Ile Asp Phe Asp
            100                 105                 110

Ala Trp Gly Gln Gly Thr Gln Val Thr Val Ser Ser
        115                 120

<210> SEQ ID NO 116
<211> LENGTH: 115
<212> TYPE: PRT
<213> ORGANISM: Artificial Sequence
<220> FEATURE:
<223> OTHER INFORMATION: antibody sequence

<400> SEQUENCE: 116

Gln Val Gln Leu Gln Glu Ser Gly Gly Gly Val Val Gln Ser Gly Gly
1               5                   10                  15

Ser Leu Arg Leu Ser Cys Val Ala Ser Gly Asn Ile Phe Arg Ile Asn
            20                  25                  30

Val Met Gly Trp Tyr Arg Gln Ala Pro Gly Lys Gln Arg Glu Leu Val
        35                  40                  45

Ala Val Val Lys Ser Gly Gly Ser Thr Asn Tyr Val Asp Ser Ala Lys
    50                  55                  60

Gly Arg Phe Thr Ile Ser Arg Asp Asn Ala Lys Asn Thr Ala Tyr Leu
65                  70                  75                  80

His Met Asp Ser Leu Lys Pro Glu Asp Thr Ala Val Tyr Tyr Cys Asn
                85                  90                  95

Ala Gln Thr Arg Leu Trp Ser Tyr Trp Gly Gln Gly Thr Gln Val Thr
            100                 105                 110

Val Ser Ser
        115

<210> SEQ ID NO 117
<211> LENGTH: 115
<212> TYPE: PRT
<213> ORGANISM: Artificial Sequence
<220> FEATURE:
<223> OTHER INFORMATION: antibody sequence

<400> SEQUENCE: 117

Gln Val Gln Leu Gln Glu Phe Gly Gly Val Val Gln Ser Gly Gly
1               5                   10                  15

Ser Leu Arg Leu Ser Cys Val Ala Ser Gly Asn Ile Phe Arg Ile Asn
            20                  25                  30

Ala Met Gly Trp Tyr Arg Gln Ala Pro Gly Lys Gln Arg Glu Leu Val
            35                  40                  45

Ala His Ile Ile Ser Gly Gly Ser Thr Asn Tyr Ala Asp Ser Val Lys
        50                  55                  60

Gly Arg Phe Thr Ile Ser Arg Glu Tyr Ala Lys Asn Met Val Tyr Leu
65                  70                  75                  80

Gln Met Asn Ser Leu Lys Pro Glu Asp Thr Ala Val Tyr Tyr Cys Asn
            85                  90                  95

Ala Gln Thr Arg Leu Trp Ser Tyr Trp Gly Gln Gly Thr Gln Val Thr
            100                 105                 110

Val Ser Ser
        115

<210> SEQ ID NO 118
<211> LENGTH: 116
<212> TYPE: PRT
<213> ORGANISM: Artificial Sequence
<220> FEATURE:
<223> OTHER INFORMATION: antibody sequence

<400> SEQUENCE: 118

Gln Val Gln Leu Gln Glu Ser Gly Gly Gly Leu Val Gln Pro Gly Gly
1               5                   10                  15

Ser Leu Arg Leu Ser Cys Ala Ala Ser Arg Ser Phe Phe Ser Ile Asn
            20                  25                  30

Ala Met Gly Trp Tyr Arg Gln Ala Pro Gly Lys Gln Arg Glu Leu Val
            35                  40                  45

Ala Thr Ile Thr Ser Arg Asp Ser Thr Asn Val Ala Asp Ser Val Lys
        50                  55                  60

Gly Arg Phe Thr Ile Ser Arg Asp Tyr Ala Lys Asn Ile Val Tyr Leu
65                  70                  75                  80

Gln Met Asp Ser Leu Arg Pro Glu Asp Thr Ala Thr Tyr Tyr Cys Tyr
            85                  90                  95

Ala Asp Gln Pro Trp Arg Gly Arg Ala Trp Gly Gln Gly Thr Gln Val
            100                 105                 110

Thr Val Ser Ser
        115

<210> SEQ ID NO 119
<211> LENGTH: 115
<212> TYPE: PRT
<213> ORGANISM: Artificial Sequence
<220> FEATURE:
<223> OTHER INFORMATION: antibody sequence

<400> SEQUENCE: 119

Gln Val Gln Leu Gln Glu Ser Gly Gly Val Val Gln Ala Gly Gly
1               5                   10                  15

Ser Leu Asn Leu Ser Cys Thr His Ser Thr Ile Thr Phe Arg Ile Asn
            20                  25                  30

Thr Met Ala Tyr Tyr Arg Gln Ala Pro Gly Ser Gln Arg Ala Leu Val
            35                  40                  45

Ala Arg Ile Asn Pro Ala Gly Arg Thr Tyr Tyr Pro Asp Ser Val Lys

```
                    50                  55                  60
Gly Arg Phe Thr Ile Ser Arg Asp Asn Ala Lys Asn Gln Val Tyr Leu
 65                  70                  75                  80

Gln Met Asn Asp Leu Lys Pro Glu Asp Thr Ala Val Tyr Tyr Cys Ser
                     85                  90                  95

Thr Trp Arg Leu Gly Arg Asn Tyr Trp Gly Gln Gly Thr Leu Val Thr
                100                 105                 110

Val Ser Ser
        115

<210> SEQ ID NO 120
<211> LENGTH: 117
<212> TYPE: PRT
<213> ORGANISM: Artificial Sequence
<220> FEATURE:
<223> OTHER INFORMATION: antibody sequence

<400> SEQUENCE: 120

Gln Val Gln Leu Gln Glu Phe Gly Gly Gly Leu Val Gln Ala Gly Gly
 1               5                  10                  15

Val Leu Arg Leu Ser Cys Val Ala Ser Met Thr Thr Leu Gly Phe Lys
                 20                  25                  30

Thr Met Gly Trp Tyr Arg Gln Ala Pro Gly Lys Gln Arg Glu Leu Val
             35                  40                  45

Ala Thr Ile Ser Ser Ile Gly Ile Ser Thr Tyr Ala Asn Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Phe Cys His
                 85                  90                  95

Val Ile Arg Pro Ser Trp Met Pro Gln Tyr Trp Gly Gln Gly Thr Leu
                100                 105                 110

Val Thr Val Ser Ser
        115

<210> SEQ ID NO 121
<211> LENGTH: 114
<212> TYPE: PRT
<213> ORGANISM: Artificial Sequence
<220> FEATURE:
<223> OTHER INFORMATION: antibody sequence

<400> SEQUENCE: 121

Gln Val Gln Leu Gln Glu Phe Gly Gly Gly Leu Val Gln Pro Gly Gly
 1               5                  10                  15

Ser Leu Arg Leu Ser Cys Gln Ala Ser Thr Ser Val Phe Gly Asn Thr
                 20                  25                  30

Ala Met Ala Trp Tyr Arg Gln Ala Pro Gly Lys Gln Arg Glu Leu Val
             35                  40                  45

Ala Arg Ile Thr Thr Leu Gly Phe Thr Tyr Tyr Ala Asp Ser Ala Lys
         50                  55                  60

Gly Arg Phe Thr Ile Ser Arg Asp Ser Ala Met Asn Thr Val Tyr Leu
 65                  70                  75                  80

Gln Met Asn Ser Leu Lys Pro Glu Asp Thr Ala Val Tyr Tyr Cys Asn
                 85                  90                  95

Arg Leu Trp Arg Pro Leu Ala Trp Gly Gln Gly Thr Gln Val Thr Val
                100                 105                 110
```

Ser Ser

<210> SEQ ID NO 122
<211> LENGTH: 115
<212> TYPE: PRT
<213> ORGANISM: Artificial Sequence
<220> FEATURE:
<223> OTHER INFORMATION: antibody sequence

<400> SEQUENCE: 122

Gln Val Gln Leu Gln Glu Ser Gly Gly Gly Leu Val Gln Pro Gly Gly
1               5                   10                  15

Ser Leu Arg Leu Ser Cys Ala Ala Ser Gly Met Arg Ser Ser Leu Ala
            20                  25                  30

Ile Met Gly Trp Tyr Arg Gln Ala Pro Gly Lys Gln Arg Glu Leu Val
        35                  40                  45

Ala Thr Ile Thr Ile Gly Gly Asn Thr Asn Tyr Ala Asp Ser Val Lys
    50                  55                  60

Gly Arg Phe Ala Ile Ser Arg Asp Asn Thr Lys Arg Thr Val Tyr Leu
65                  70                  75                  80

Gln Met Asn Ser Leu Thr Pro Glu Asp Thr Ala Val Tyr Tyr Cys Asn
                85                  90                  95

Val Arg Ser Phe Val Arg Thr Tyr Trp Gly Gln Gly Thr Gln Val Thr
            100                 105                 110

Val Ser Ser
        115

<210> SEQ ID NO 123
<211> LENGTH: 117
<212> TYPE: PRT
<213> ORGANISM: Artificial Sequence
<220> FEATURE:
<223> OTHER INFORMATION: antibody sequence

<400> SEQUENCE: 123

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Thr Phe Ile Ser Ile
            20                  25                  30

Lys Thr Met Gly Trp Tyr Arg Gln Ala Pro Gly Lys Gln Arg Glu Leu
        35                  40                  45

Val Ala Gly Ile Thr Lys Asn Asn Tyr Ile Asn Tyr Ala Asp Ser Val
    50                  55                  60

Lys Gly Arg Phe Thr Ile Ser Arg Asp Asn Gly Lys Asn Thr Val Tyr
65                  70                  75                  80

Leu Gln Met Asn Gly Leu Lys Pro Glu Asp Thr Ala Val Tyr Tyr Cys
                85                  90                  95

Thr Val Gln Arg Arg Leu Gly Arg Val Tyr Trp Gly Gln Gly Thr Leu
            100                 105                 110

Val Thr Val Ser Ser
        115

<210> SEQ ID NO 124
<211> LENGTH: 115
<212> TYPE: PRT
<213> ORGANISM: Artificial Sequence
<220> FEATURE:
<223> OTHER INFORMATION: antibody sequence

<400> SEQUENCE: 124

```
Gln Val Gln Leu Gln Glu Ser Gly Gly Gly Leu Val Gln Ala Gly Gly
1               5                   10                  15

Ser Leu Arg Leu Ser Cys Thr Ala Ser Gly Ser Thr Phe Arg Phe Asn
            20                  25                  30

Asp Met Gly Trp Tyr Arg Gln Ala Pro Gly Lys Gln Arg Glu Leu Val
            35                  40                  45

Ala Asn Ile Asn Ser Ser Gly Arg Thr Met Tyr Pro Asp Ser Val Lys
50                  55                  60

Gly Arg Phe Thr Ile Ser Lys Asp Asn Val Lys Asn Thr Val Tyr Leu
65                  70                  75                  80

Gln Met Asn Ser Leu Thr Pro Glu Asp Thr Ala Val Tyr Tyr Cys Asn
            85                  90                  95

Val Arg Ser Phe Val Arg Thr Tyr Trp Gly Gln Gly Thr Gln Val Thr
            100                 105                 110

Val Ser Ser
        115

<210> SEQ ID NO 125
<211> LENGTH: 114
<212> TYPE: PRT
<213> ORGANISM: Artificial Sequence
<220> FEATURE:
<223> OTHER INFORMATION: antibody sequence

<400> SEQUENCE: 125

Gln Val Gln Leu Gln Glu Ser Gly Gly Gly Leu Val Gln Ala Gly Gly
1               5                   10                  15

Ser Leu Thr Leu Ser Cys Val Ala Ser Gly Ser Arg Phe Ser Ile Asn
            20                  25                  30

Thr Met Gly Trp Tyr Arg Gln Ala Pro Gly Lys Gln Arg Glu Leu Val
            35                  40                  45

Ala Gly Ile Thr Ser Leu Gly Phe Thr Asn Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Asn Leu Lys Val Glu Asp Thr Ala Val Tyr Tyr Cys Asn
            85                  90                  95

Arg Arg Gly Phe Arg Ser Tyr Trp Gly Gln Gly Thr Leu Val Thr Val
            100                 105                 110

Ser Ser

<210> SEQ ID NO 126
<211> LENGTH: 114
<212> TYPE: PRT
<213> ORGANISM: Artificial Sequence
<220> FEATURE:
<223> OTHER INFORMATION: antibody sequence

<400> SEQUENCE: 126

Gln Val Gln Leu Val Glu Ser Gly Gly Gly Phe Val Gln Ala Gly Gly
1               5                   10                  15

Ser Leu Arg Leu Ser Cys Ala Ala Ser Gly Ser Ile Phe Ser Ile Asn
            20                  25                  30

Tyr Gly Asn Trp Tyr Arg Gln Ala Pro Gly Lys Gln Arg Glu Leu Val
            35                  40                  45

Ala Gly Ile Ser Arg Gly Gly Arg Thr Lys Tyr Ala Asp Ser Val Lys
50                  55                  60
```

Gly Arg Phe Thr Ile Ser Arg Asp Ser Ala Lys Thr Leu Thr Leu Gln
65                  70                  75                  80

Met Thr Ser Leu Lys Pro Glu Asp Thr Ala Val Tyr Tyr Cys Asn Val
            85                  90                  95

Arg Ser Phe Val Arg Tyr Trp Gly Gln Gly Thr Val Thr Val
            100                 105                 110

Ser Ser

<210> SEQ ID NO 127
<211> LENGTH: 114
<212> TYPE: PRT
<213> ORGANISM: Artificial Sequence
<220> FEATURE:
<223> OTHER INFORMATION: antibody sequence

<400> SEQUENCE: 127

Gln Val Gln Leu Gln Glu Ser Gly Gly Gly Leu Val Gln Ser Gly Gly
1               5                   10                  15

Ser Leu Arg Leu Ser Cys Ser Ala Ser Gly Ser Ile Phe Arg Ile Asn
            20                  25                  30

Leu Met Gly Trp Tyr Arg Gln Ala Pro Gly Lys Gln Arg Glu Leu Val
        35                  40                  45

Ala Thr Ile Thr Asn Glu Gly Asn Thr Tyr Tyr Ala Asp Ser Val Lys
    50                  55                  60

Gly Arg Phe Thr Ile Ser Arg Asp Asn Ala Asn Asn Thr Trp Tyr Leu
65                  70                  75                  80

Gln Met Asn Ser Leu Lys Pro Glu Asp Thr Ala Val Tyr Glu Cys Ala
            85                  90                  95

Gly Lys Val Ile Arg Trp Tyr Trp Gly Gln Gly Thr Gln Val Thr Val
            100                 105                 110

Ser Ser

<210> SEQ ID NO 128
<211> LENGTH: 116
<212> TYPE: PRT
<213> ORGANISM: Artificial Sequence
<220> FEATURE:
<223> OTHER INFORMATION: antibody sequence

<400> SEQUENCE: 128

Gln Val Gln Leu Gln Glu Phe Gly Gly Gly Leu Val Gln Pro Gly Gly
1               5                   10                  15

Ser Leu Arg Leu Ser Cys Gln Ala Ser Thr Ser Val Phe Gly Asn Thr
            20                  25                  30

Ala Met Ala Trp Tyr Arg Gln Ala Pro Gly Lys Gln Arg Glu Leu Val
        35                  40                  45

Ala Arg Ile Thr Thr Leu Gly Phe Thr Tyr Tyr Ala Asp Ser Ala Lys
    50                  55                  60

Gly Arg Phe Thr Ile Ser Arg Asp Ser Ala Met Asn Thr Val Tyr Leu
65                  70                  75                  80

Gln Met Asn Ser Leu Lys Pro Glu Asp Thr Ala Val Tyr Tyr Cys Arg
            85                  90                  95

Ala Arg Arg Ala Leu Arg Glu Ser His Trp Gly Gln Gly Thr Gln Val
            100                 105                 110

Thr Val Ser Ser
        115

```
<210> SEQ ID NO 129
<211> LENGTH: 114
<212> TYPE: PRT
<213> ORGANISM: Artificial Sequence
<220> FEATURE:
<223> OTHER INFORMATION: antibody sequence

<400> SEQUENCE: 129

Gln Val Gln Leu Gln Glu Ser Gly Gly Phe Val Gln Ala Gly Gly
1               5                   10                  15

Ser Leu Arg Leu Ser Cys Ala Ala Ser Gly Ser Ile Phe Ser Ile Asn
            20                  25                  30

Tyr Gly Asn Trp Tyr Arg Gln Ala Pro Gly Lys Gln Arg Glu Leu Val
            35                  40                  45

Ala Gly Ile Ser Arg Gly Gly Arg Thr Lys Tyr Ala Asp Ser Val Lys
        50                  55                  60

Gly Arg Phe Thr Ile Ser Arg Asp Ser Ala Lys Thr Leu Thr Leu Gln
65              70                  75                  80

Met Thr Ser Leu Lys Pro Glu Asp Thr Ala Ile Tyr Ser Cys Asn Ala
                85                  90                  95

Arg Ser Phe Val Arg Thr Tyr Trp Gly Gln Gly Thr Leu Val Thr Val
            100                 105                 110

Ser Ser

<210> SEQ ID NO 130
<211> LENGTH: 120
<212> TYPE: PRT
<213> ORGANISM: Artificial Sequence
<220> FEATURE:
<223> OTHER INFORMATION: antibody sequence

<400> SEQUENCE: 130

Gln Val Gln Leu Gln Glu Ser Gly Gly Gly Leu Val Thr Ala Gly Gly
1               5                   10                  15

Ser Leu Arg Leu Ser Cys Ala Ala Ser Arg Asn Phe Phe Thr Phe Arg
            20                  25                  30

Ala Met Gly Trp Tyr Arg Gln Ala Pro Gly Lys Gln Arg Glu Met Val
            35                  40                  45

Ala Ser Ile Thr Thr Gly Gly Arg Thr Val Tyr Ala Asp Ser Val Lys
        50                  55                  60

Gly Arg Phe Thr Ile Ser Lys Ser Asn Ala Asn Asn Thr Val Tyr Leu
65              70                  75                  80

Gln Met Asn Ser Leu Glu Ala Glu Asp Thr Ala Val Tyr Tyr Cys Asn
                85                  90                  95

Ala Arg Arg Arg Phe Pro Val Pro Gly Pro Thr Asp Tyr Trp Gly Arg
            100                 105                 110

Gly Thr Leu Val Thr Val Ser Ser
        115                 120

<210> SEQ ID NO 131
<211> LENGTH: 111
<212> TYPE: PRT
<213> ORGANISM: Artificial Sequence
<220> FEATURE:
<223> OTHER INFORMATION: antibody sequence

<400> SEQUENCE: 131

Gln Val Gln Leu Gln Glu Ser Gly Gly Gly Leu Val Gln Ala Gly Gly
1               5                   10                  15
```

```
Ser Leu Arg Leu Ser Cys Ala Ala Ser Gly Ile Thr Phe Arg Phe Asn
            20                  25                  30

Ala Met Gly Trp Tyr Arg Gln Ala Pro Gly Lys Glu Arg Glu Leu Val
        35                  40                  45

Ala Arg Val Ser Ser Gly Gly Ser Thr Thr Tyr Ala Asp Ser Val Lys
 50                  55                  60

Ala Arg Phe Thr Thr Phe Arg Asp Asn Val Lys Asn Ile Gly Tyr Leu
 65                  70                  75                  80

Gln Met Thr Ser Leu Lys Pro Glu Asp Thr Ala Val Tyr Tyr Cys Asn
                85                  90                  95

Val Gly Asn Phe Trp Gly Gln Thr Gln Val Thr Val Ser Ser
            100                 105                 110
```

```
<210> SEQ ID NO 132
<211> LENGTH: 115
<212> TYPE: PRT
<213> ORGANISM: Artificial Sequence
<220> FEATURE:
<223> OTHER INFORMATION: antibody sequence

<400> SEQUENCE: 132

Gln Val Gln Leu Gln Glu Ser Gly Gly Gly Leu Val Arg Thr Gly Glu
 1               5                  10                  15

Ser Leu Gly Leu Ser Cys Ala Ala Ser Gly Arg Ser Ile Leu Ile Lys
            20                  25                  30

Gly Met Gly Trp Tyr Arg Gln Ala Pro Gly Lys Glu Arg Glu Met Val
        35                  40                  45

Ala Thr Ile Ser Met Ala Gly Val Thr Asn Tyr Ser Asp Ser Val Lys
 50                  55                  60

Gly Arg Phe Thr Ile Ser Arg Asp Asn Tyr Lys Lys Thr Val Ser Leu
 65                  70                  75                  80

Gln Met Asn Asn Leu Arg Pro Glu Asp Thr Ala Val Tyr Val Cys Asn
                85                  90                  95

Ala Gln Thr Arg Leu Trp Ser Tyr Trp Gly Gln Gly Thr Gln Val Thr
            100                 105                 110

Val Ser Ser
        115
```

```
<210> SEQ ID NO 133
<211> LENGTH: 115
<212> TYPE: PRT
<213> ORGANISM: Artificial Sequence
<220> FEATURE:
<223> OTHER INFORMATION: antibody sequence

<400> SEQUENCE: 133

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Ile Phe Gly Arg Asn
            20                  25                  30

Ala Met Ala Trp Tyr Arg Gln Val Pro Gly Lys Glu Arg Glu Leu Val
        35                  40                  45

Ala Arg Ile Thr Arg Asp Gly Arg Thr Met Tyr Val Asp Ser Ala Lys
 50                  55                  60

Gly Arg Phe Thr Ile Ser Arg Asp Asn Ala Lys Asn Thr Ala Tyr Leu
 65                  70                  75                  80

His Met Asp Ser Leu Lys Pro Glu Asp Thr Ala Val Tyr Tyr Cys Asn
```

```
                        85                  90                  95

Ala Gln Thr Arg Leu Trp Ser Tyr Trp Gly Gln Gly Thr Gln Val Thr
                100                 105                 110

Val Ser Ser
        115

<210> SEQ ID NO 134
<211> LENGTH: 116
<212> TYPE: PRT
<213> ORGANISM: Artificial Sequence
<220> FEATURE:
<223> OTHER INFORMATION: antibody sequence

<400> SEQUENCE: 134

Gln Val Gln Leu Gln Glu Ser Gly Gly Gly Leu Val Gln Ala Gly Gly
1               5                   10                  15

Ser Leu Arg Leu Ser Cys Ala Ala Ser Arg Ser Thr Phe Arg Phe Asn
            20                  25                  30

Val Met Gly Trp Tyr Arg Gln Ala Pro Gly Lys Gln Arg Glu Leu Val
        35                  40                  45

Ala Ala Ile Ser Ser Arg Gly Gly Ser Thr Asn Tyr Ala Asp Ser Val
    50                  55                  60

Gln Gly Arg Phe Thr Ile Ser Arg Asp Asn Ala Lys Asn Thr Val Ser
65                  70                  75                  80

Leu Gln Met Asn Ser Leu Lys Pro Glu Asp Thr Ala Val Tyr Tyr Cys
                85                  90                  95

Asn Val Arg Ser Phe Val Arg Thr Tyr Trp Gly Gln Gly Thr Gln Val
                100                 105                 110

Thr Val Ser Ser
        115

<210> SEQ ID NO 135
<211> LENGTH: 123
<212> TYPE: PRT
<213> ORGANISM: Artificial Sequence
<220> FEATURE:
<223> OTHER INFORMATION: antibody sequence

<400> SEQUENCE: 135

Gln Val Gln Leu Gln Glu Phe Gly Gly Gly Leu Val Gln Ala Gly Gly
1               5                   10                  15

Ser Leu Arg Leu Ser Cys Ala Thr Ser Gly Ser Ile Phe Ser Ile Asn
            20                  25                  30

Ala Val Gly Trp Tyr Arg Gln Ala Pro Gly Asn Gln Arg Glu Leu Val
        35                  40                  45

Ala Ala Ile Ser Gly Arg Gly Ser Thr His Tyr Ala Asp Ser Val Lys
    50                  55                  60

Gly Arg Phe Thr Ile Ser Arg Asp Thr Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Leu Asp Gln His Met Glu Val Ile Val Ser Pro Gly Arg Ile Gly Ser
                100                 105                 110

Trp Gly Gln Gly Thr Leu Val Thr Val Ser Ser
        115                 120

<210> SEQ ID NO 136
<211> LENGTH: 117
```

```
<212> TYPE: PRT
<213> ORGANISM: Artificial Sequence
<220> FEATURE:
<223> OTHER INFORMATION: antibody sequence

<400> SEQUENCE: 136

Gln Val Gln Leu Gln Glu Ser Gly Gly Gly Leu Val Gln Ala Gly Glu
1               5                   10                  15

Ser Leu Thr Leu Ser Cys Ala Leu Ser Thr Thr Met Phe Gly Phe Trp
            20                  25                  30

Pro Met Ala Trp Phe Arg Gln Thr Pro Gly Gln Arg Glu Leu Ile
        35                  40                  45

Ala Thr Ile Asp Ser Arg Gly Arg Thr Asn Ile Ala Asp Ser Val Lys
    50                  55                  60

Gly Arg Phe Thr Ile Ser Arg Asp Asn Thr Lys Asn Thr Leu Tyr Leu
65                  70                  75                  80

Arg Met Asn Ser Leu Lys Pro Glu Asp Thr Ala Val Tyr Tyr Cys Asn
                85                  90                  95

Ala Gln Arg Arg Trp Pro Leu Arg Asp Tyr Trp Gly Gln Gly Thr Gln
            100                 105                 110

Val Thr Val Ser Ser
        115

<210> SEQ ID NO 137
<211> LENGTH: 117
<212> TYPE: PRT
<213> ORGANISM: Artificial Sequence
<220> FEATURE:
<223> OTHER INFORMATION: antibody sequence

<400> SEQUENCE: 137

Gln Val Gln Leu Gln Glu Phe Gly Gly Gly Val Val Gln Ser Gly Gly
1               5                   10                  15

Ser Leu Arg Leu Ser Cys Val Ala Ser Gly Asn Ile Phe Arg Ile Asn
            20                  25                  30

Ala Met Gly Trp Tyr Arg Gln Ala Pro Gly Lys Gln Arg Glu Leu Val
        35                  40                  45

Ala Arg Ile Ser Ser Gly Gly Ser Thr Asn Tyr Ala Asp Ser Val Lys
    50                  55                  60

Gly Arg Phe Thr Ile Ser Arg Asp Asn Val Lys Asn Thr Val Thr Leu
65                  70                  75                  80

Gln Met Asn Ser Leu Lys Pro Glu Asp Thr Ala Val Tyr Tyr Cys Asn
                85                  90                  95

Ala Arg Arg Pro Leu Arg Trp Tyr Glu Tyr Trp Gly Gln Gly Thr Leu
            100                 105                 110

Val Thr Val Ser Ser
        115

<210> SEQ ID NO 138
<211> LENGTH: 121
<212> TYPE: PRT
<213> ORGANISM: Artificial Sequence
<220> FEATURE:
<223> OTHER INFORMATION: antibody sequence

<400> SEQUENCE: 138

Gln Val Gln Leu Gln Ala Ser Gly Gly Gly Leu Val Gln Pro Gly Gly
1               5                   10                  15

Ser Leu Arg Leu Ser Cys Ala Ala Ser Gly Ser Ile Phe Ser Thr Asn
```

```
            20                  25                  30

Ala Met Gly Trp Tyr Arg Gln Ala Pro Gly Lys Gln Arg Glu Val Ile
         35                  40                  45

Ala Ser Ile Thr Lys Phe Gly Asn Thr Asp Tyr Ala Asp Ser Val Lys
 50                  55                  60

Gly Arg Phe Thr Ile Ser Arg Asp Asn Ala Lys Asn Ile Val Tyr Leu
 65                  70                  75                  80

Gln Met Asn Ser Leu Lys Pro Glu Asp Thr Ala Val Tyr Tyr Cys Tyr
                 85                  90                  95

Gln Asn Ser Arg Gly Arg Trp Tyr Asp Ile Phe Arg Asp Tyr Trp Gly
                100                 105                 110

Gln Gly Thr Leu Val Thr Val Ser Ser
                115                 120
```

<210> SEQ ID NO 139
<211> LENGTH: 117
<212> TYPE: PRT
<213> ORGANISM: Artificial Sequence
<220> FEATURE:
<223> OTHER INFORMATION: antibody sequence

<400> SEQUENCE: 139

```
Gln Val Gln Leu Val Glu Ser Gly Gly Phe Val Gln Ala Gly Gly
 1               5                  10                  15

Ser Leu Arg Leu Ser Cys Val Ala Arg Ser Ser Phe Arg Ile Thr
                 20                  25                  30

Thr Met Asn Trp Tyr Arg Gln Ala Pro Gly Lys Gln Arg Glu Met Val
         35                  40                  45

Ala Ser Ile Thr Thr Gly Gly Arg Thr Val Tyr Ala Asp Ser Val Lys
 50                  55                  60

Gly Arg Phe Thr Ile Ser Lys Ser Asn Ala Asn Asn Thr Val Tyr Leu
 65                  70                  75                  80

Gln Met Asn Ser Leu Glu Ala Glu Asp Thr Ala Val Tyr Tyr Cys Asn
                 85                  90                  95

Ala Gln Arg Arg Trp Pro Leu Arg Asp Tyr Trp Gly Gln Gly Thr Leu
                100                 105                 110

Val Thr Val Ser Ser
        115
```

<210> SEQ ID NO 140
<211> LENGTH: 115
<212> TYPE: PRT
<213> ORGANISM: Artificial Sequence
<220> FEATURE:
<223> OTHER INFORMATION: antibody sequence

<400> SEQUENCE: 140

```
Gln Val Gln Leu Gln Glu Ser Gly Gly Gly Val Val Gln Ser Gly Gly
 1               5                  10                  15

Ser Leu Arg Leu Ser Cys Val Ala Ser Gly Asn Ile Phe Arg Ile Asn
                 20                  25                  30

Val Met Gly Trp Tyr Arg Gln Ala Pro Gly Lys Gln Arg Glu Leu Val
         35                  40                  45

Ala Val Val Lys Ser Gly Gly Ser Thr Asn Tyr Val Asp Ser Ala Lys
 50                  55                  60

Gly Arg Phe Thr Ile Ser Arg Asp Asn Ala Lys Asn Thr Ala Tyr Leu
 65                  70                  75                  80
```

```
His Met Asp Ser Leu Lys Pro Glu Asp Thr Ala Val Tyr Tyr Cys Asn
                85                  90                  95

Ala Gln Thr Arg Leu Trp Ser Tyr Trp Gly Gln Gly Thr Leu Val Thr
            100                 105                 110

Val Ser Ser
        115

<210> SEQ ID NO 141
<211> LENGTH: 117
<212> TYPE: PRT
<213> ORGANISM: Artificial Sequence
<220> FEATURE:
<223> OTHER INFORMATION: antibody sequence

<400> SEQUENCE: 141

Gln Val Gln Leu Gln Glu Phe Gly Gly Gly Val Val Gln Ser Gly Gly
1               5                   10                  15

Ser Leu Arg Leu Ser Cys Val Ala Ser Gly Asn Ile Phe Arg Ile Asn
            20                  25                  30

Ala Met Gly Trp Tyr Arg Gln Ala Pro Gly Lys Gln Arg Glu Leu Val
            35                  40                  45

Ala His Ile Ile Ser Gly Gly Ser Thr Asn Tyr Ala Asp Ser Val Lys
    50                  55                  60

Gly Arg Phe Thr Ile Ser Arg Glu Tyr Ala Lys Asn Met Val Tyr Leu
65              70                  75                  80

Gln Met Asn Ser Leu Lys Pro Glu Asp Thr Ala Val Tyr Tyr Cys Asn
                85                  90                  95

Ala Glu Arg Arg Phe Gly Met Arg Gln Val Trp Gly Gln Gly Thr Gln
            100                 105                 110

Val Thr Val Ser Ser
        115

<210> SEQ ID NO 142
<211> LENGTH: 122
<212> TYPE: PRT
<213> ORGANISM: Artificial Sequence
<220> FEATURE:
<223> OTHER INFORMATION: antibody sequence

<400> SEQUENCE: 142

Gln Val Gln Leu Gln Glu Ser Gly Gly Gly Leu Val Gln Ala Gly Gly
1               5                   10                  15

Ser Leu Arg Leu Ser Cys Ala Ala Ser Val Val Pro Phe Arg Tyr Phe
            20                  25                  30

Pro Met Gly Trp Tyr Arg Gln Ala Pro Gly Arg Gln Arg Glu Leu Val
            35                  40                  45

Ala Ser Ile Thr Ser Gly Gly Val Asn Tyr Ala Asp Phe Val Glu
    50                  55                  60

Gly Arg Phe Thr Ile Ser Arg Asp Asn Ala Lys Asn Thr Phe Tyr Leu
65              70                  75                  80

Gln Met Ser Ser Leu Lys Pro Glu Asp Thr Ala Val Tyr Tyr Cys Ala
                85                  90                  95

Arg Leu Leu Ser Leu Gly Ser Arg Trp Gly Tyr Gly Met Phe Thr Trp
            100                 105                 110

Gly Lys Gly Thr Leu Val Thr Val Ser Ser
        115                 120

<210> SEQ ID NO 143
```

<211> LENGTH: 117
<212> TYPE: PRT
<213> ORGANISM: Artificial Sequence
<220> FEATURE:
<223> OTHER INFORMATION: antibody sequence

<400> SEQUENCE: 143

```
Gln Val Gln Leu Gln Glu Ser Gly Gly Gly Leu Val Gln Pro Gly Gly
1               5                   10                  15
Ser Leu Arg Leu Ser Cys Ala Ala Ser Gly Ser Ile Phe Ser Ile Lys
            20                  25                  30
Thr Met Gly Trp Tyr Arg Gln Ala Pro Gly Lys Gln Arg Glu Leu Val
        35                  40                  45
Ala Ala Ile Ala Ser Gly Gly Phe Thr Asn Tyr Ala Asp Ser Val Lys
    50                  55                  60
Gly Arg Phe Thr Ile Ser Arg Asp Asn Ala Arg Asn Thr Val Tyr Leu
65                  70                  75                  80
Gln Met Asn Ser Leu Lys Pro Glu Asp Thr Ala Val Tyr Tyr Cys Asn
                85                  90                  95
Ala Gln Arg Arg Trp Pro Leu Arg Asp Tyr Trp Gly Gln Gly Thr Leu
            100                 105                 110
Val Thr Val Ser Ser
        115
```

<210> SEQ ID NO 144
<211> LENGTH: 117
<212> TYPE: PRT
<213> ORGANISM: Artificial Sequence
<220> FEATURE:
<223> OTHER INFORMATION: antibody sequence

<400> SEQUENCE: 144

```
Gln Val Gln Leu Gln Glu Ser Gly Gly Gly Leu Val Arg Asp Gly Gly
1               5                   10                  15
Ser Leu Thr Leu Ser Cys Ala Ala Ser Gly Ser Ala Phe Arg Met Asn
            20                  25                  30
Ser Met Ala Trp Tyr Arg Gln Val Pro Gly Lys Gln Arg Glu Leu Val
        35                  40                  45
Ala Ala Ile Ser Phe Arg Gly Ser Ala Asn Tyr Ala Asn Ser Val Lys
    50                  55                  60
Gly Arg Phe Thr Ile Ser Arg Asp Asn Gly Lys Asn Thr Val Tyr Leu
65                  70                  75                  80
Gln Met Asn Ser Leu Lys Pro Glu Asp Thr Ala Val Tyr Tyr Cys Ala
                85                  90                  95
Ala Gly Arg Pro Trp Gln Arg Thr Phe Tyr Trp Gly Gln Gly Thr Gln
            100                 105                 110
Val Thr Val Ser Ser
        115
```

<210> SEQ ID NO 145
<211> LENGTH: 117
<212> TYPE: PRT
<213> ORGANISM: Artificial Sequence
<220> FEATURE:
<223> OTHER INFORMATION: antibody sequence

<400> SEQUENCE: 145

```
Gln Val Gln Leu Gln Glu Ser Gly Gly Gly Phe Val Gln Ala Gly Gly
1               5                   10                  15
```

Ser Leu Arg Leu Ser Cys Ala Ala Ser Gly Ser Ile Phe Ser Ile Asn
            20                  25                  30

Tyr Gly Asn Trp Tyr Arg Gln Ala Pro Gly Lys Gln Arg Glu Leu Val
        35                  40                  45

Ala Gly Ile Ser Arg Gly Gly Arg Thr Lys Tyr Ala Asp Ser Val Lys
    50                  55                  60

Gly Arg Phe Thr Ile Ser Arg Asp Ser Ala Lys Thr Leu Thr Leu Gln
65                  70                  75                  80

Met Thr Ser Leu Lys Pro Glu Asp Ser Gly Val Tyr Tyr Cys Ala Ala
                85                  90                  95

Thr Arg Trp Ser Trp Gly Thr Lys Ser Tyr Trp Gly Gln Gly Thr Gln
            100                 105                 110

Val Thr Val Ser Ser
        115

<210> SEQ ID NO 146
<211> LENGTH: 10
<212> TYPE: PRT
<213> ORGANISM: Artificial Sequence
<220> FEATURE:
<223> OTHER INFORMATION: antibody sequence

<400> SEQUENCE: 146

Ala Ser Gly Gly Thr Phe Gly Ala Gly Val
1               5                   10

<210> SEQ ID NO 147
<211> LENGTH: 10
<212> TYPE: PRT
<213> ORGANISM: Artificial Sequence
<220> FEATURE:
<223> OTHER INFORMATION: antibody sequence

<400> SEQUENCE: 147

Ala Ser Gly Ser Asn Ile Ser Thr Asn Val
1               5                   10

<210> SEQ ID NO 148
<211> LENGTH: 10
<212> TYPE: PRT
<213> ORGANISM: Artificial Sequence
<220> FEATURE:
<223> OTHER INFORMATION: antibody sequence

<400> SEQUENCE: 148

Ala Ser Gly Ser Thr Phe Ser Ile Thr Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: antibody sequence

<400> SEQUENCE: 149

Asp Ser Arg Thr Ile Phe Ile Phe Asn Ala
1               5                   10

<210> SEQ ID NO 150
<211> LENGTH: 10
<212> TYPE: PRT
<213> ORGANISM: Artificial Sequence
<220> FEATURE:

<223> OTHER INFORMATION: antibody sequence

<400> SEQUENCE: 150

Ala Ser Gly Ile Pro Phe Ser Ile Ile Tyr
1               5                   10

<210> SEQ ID NO 151
<211> LENGTH: 10
<212> TYPE: PRT
<213> ORGANISM: Artificial Sequence
<220> FEATURE:
<223> OTHER INFORMATION: antibody sequence

<400> SEQUENCE: 151

Ala Ser Gly Asn Ile Phe Gly Ile Asn Ser
1               5                   10

<210> SEQ ID NO 152
<211> LENGTH: 10
<212> TYPE: PRT
<213> ORGANISM: Artificial Sequence
<220> FEATURE:
<223> OTHER INFORMATION: antibody sequence

<400> SEQUENCE: 152

Ala Ser Gly Phe Thr Phe Ser Ser Tyr Trp
1               5                   10

<210> SEQ ID NO 153
<211> LENGTH: 10
<212> TYPE: PRT
<213> ORGANISM: Artificial Sequence
<220> FEATURE:
<223> OTHER INFORMATION: antibody sequence

<400> SEQUENCE: 153

Val Ser Gly Ser Ile Ile Ser His Asn Val
1               5                   10

<210> SEQ ID NO 154
<211> LENGTH: 10
<212> TYPE: PRT
<213> ORGANISM: Artificial Sequence
<220> FEATURE:
<223> OTHER INFORMATION: antibody sequence

<400> SEQUENCE: 154

Ala Ser Gly Arg Ile Phe Asn Ile Glu Asp
1               5                   10

<210> SEQ ID NO 155
<211> LENGTH: 10
<212> TYPE: PRT
<213> ORGANISM: Artificial Sequence
<220> FEATURE:
<223> OTHER INFORMATION: antibody sequence

<400> SEQUENCE: 155

Ala Ser Gly Ser Val Ser Ala Ile Glu Thr
1               5                   10

<210> SEQ ID NO 156
<211> LENGTH: 10
<212> TYPE: PRT
<213> ORGANISM: Artificial Sequence
<220> FEATURE:
<223> OTHER INFORMATION: antibody sequence

```
<400> SEQUENCE: 156

Ala Phe Gly Ser Thr Ser Ser Ile Thr Tyr
1               5                   10

<210> SEQ ID NO 157
<211> LENGTH: 10
<212> TYPE: PRT
<213> ORGANISM: Artificial Sequence
<220> FEATURE:
<223> OTHER INFORMATION: antibody sequence

<400> SEQUENCE: 157

Ala Ser Gly Gly Pro Val Ser Asp Asn Val
1               5                   10

<210> SEQ ID NO 158
<211> LENGTH: 10
<212> TYPE: PRT
<213> ORGANISM: Artificial Sequence
<220> FEATURE:
<223> OTHER INFORMATION: antibody sequence

<400> SEQUENCE: 158

Ala Ser Gly Ser Thr Phe Ser Ile Thr Tyr
1               5                   10

<210> SEQ ID NO 159
<211> LENGTH: 10
<212> TYPE: PRT
<213> ORGANISM: Artificial Sequence
<220> FEATURE:
<223> OTHER INFORMATION: antibody sequence

<400> SEQUENCE: 159

Gly Ala Gly Ser Ala Phe Gly Trp Asn Ala
1               5                   10

<210> SEQ ID NO 160
<211> LENGTH: 10
<212> TYPE: PRT
<213> ORGANISM: Artificial Sequence
<220> FEATURE:
<223> OTHER INFORMATION: antibody sequence

<400> SEQUENCE: 160

Pro Ser Gly Ser Ile Phe Ser Phe Asp Val
1               5                   10

<210> SEQ ID NO 161
<211> LENGTH: 12
<212> TYPE: PRT
<213> ORGANISM: Artificial Sequence
<220> FEATURE:
<223> OTHER INFORMATION: antibody sequence

<400> SEQUENCE: 161

Ser Met Gly Ser Asp Gly Phe Thr Gln Ile Glu Asn
1               5                   10

<210> SEQ ID NO 162
<211> LENGTH: 12
<212> TYPE: PRT
<213> ORGANISM: Artificial Sequence
<220> FEATURE:
<223> OTHER INFORMATION: antibody sequence
```

```
<400> SEQUENCE: 162

Ser Ile Ser Thr Ser Gly Thr Thr Asn Tyr Leu Ala
1               5                   10

<210> SEQ ID NO 163
<211> LENGTH: 12
<212> TYPE: PRT
<213> ORGANISM: Artificial Sequence
<220> FEATURE:
<223> OTHER INFORMATION: antibody sequence

<400> SEQUENCE: 163

Glu Met Ser Arg Arg Gly Ser Thr Phe Tyr Ala Asp
1               5                   10

<210> SEQ ID NO 164
<211> LENGTH: 12
<212> TYPE: PRT
<213> ORGANISM: Artificial Sequence
<220> FEATURE:
<223> OTHER INFORMATION: antibody sequence

<400> SEQUENCE: 164

Ala Ile Ser Ser Gly Gly Ser Thr Lys Tyr Ala Asp
1               5                   10

<210> SEQ ID NO 165
<211> LENGTH: 12
<212> TYPE: PRT
<213> ORGANISM: Artificial Sequence
<220> FEATURE:
<223> OTHER INFORMATION: antibody sequence

<400> SEQUENCE: 165

Glu Met Ser Ser Arg Gly Ser Lys Phe Tyr Ala Asp
1               5                   10

<210> SEQ ID NO 166
<211> LENGTH: 11
<212> TYPE: PRT
<213> ORGANISM: Artificial Sequence
<220> FEATURE:
<223> OTHER INFORMATION: antibody sequence

<400> SEQUENCE: 166

Asp Ile Thr Arg Gly Asn Arg Lys Tyr Ala Asp
1               5                   10

<210> SEQ ID NO 167
<211> LENGTH: 12
<212> TYPE: PRT
<213> ORGANISM: Artificial Sequence
<220> FEATURE:
<223> OTHER INFORMATION: antibody sequence

<400> SEQUENCE: 167

Thr Ile Asn Thr Gly Gly Tyr Thr Thr Tyr Tyr Ser
1               5                   10

<210> SEQ ID NO 168
<211> LENGTH: 12
<212> TYPE: PRT
<213> ORGANISM: Artificial Sequence
<220> FEATURE:
<223> OTHER INFORMATION: antibody sequence

<400> SEQUENCE: 168
```

```
Cys Ile Ser Gly Ser Gly Phe Thr Asn Tyr Ile Ala
1               5                   10
```

<210> SEQ ID NO 169
<211> LENGTH: 12
<212> TYPE: PRT
<213> ORGANISM: Artificial Sequence
<220> FEATURE:
<223> OTHER INFORMATION: antibody sequence

<400> SEQUENCE: 169

```
Thr Ile Thr Arg Thr Gly Ala Pro Thr Tyr Ala Asn
1               5                   10
```

<210> SEQ ID NO 170
<211> LENGTH: 12
<212> TYPE: PRT
<213> ORGANISM: Artificial Sequence
<220> FEATURE:
<223> OTHER INFORMATION: antibody sequence

<400> SEQUENCE: 170

```
Val Ile Ser Thr Gly Gly Thr Thr Lys Tyr Ala Pro
1               5                   10
```

<210> SEQ ID NO 171
<211> LENGTH: 12
<212> TYPE: PRT
<213> ORGANISM: Artificial Sequence
<220> FEATURE:
<223> OTHER INFORMATION: antibody sequence

<400> SEQUENCE: 171

```
Glu Met Ser Arg Arg Gly Ser Thr Phe Tyr Ala Asp
1               5                   10
```

<210> SEQ ID NO 172
<211> LENGTH: 12
<212> TYPE: PRT
<213> ORGANISM: Artificial Sequence
<220> FEATURE:
<223> OTHER INFORMATION: antibody sequence

<400> SEQUENCE: 172

```
Gln Ile Thr Ser Gly Gly Ala Thr Ser Tyr Ala Asp
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: antibody sequence

<400> SEQUENCE: 173

```
Glu Ile Ser Ser Arg Gly Ser Val Phe Tyr Ala Asp
1               5                   10
```

<210> SEQ ID NO 174
<211> LENGTH: 12
<212> TYPE: PRT
<213> ORGANISM: Artificial Sequence
<220> FEATURE:
<223> OTHER INFORMATION: antibody sequence

<400> SEQUENCE: 174

Thr Ile Glu Ser Gly Gly Trp Ala Asp Tyr Ser Val
1               5                   10

<210> SEQ ID NO 175
<211> LENGTH: 12
<212> TYPE: PRT
<213> ORGANISM: Artificial Sequence
<220> FEATURE:
<223> OTHER INFORMATION: antibody sequence

<400> SEQUENCE: 175

Gln His Arg Thr Pro Gly Ala Ile Asp Tyr Ala Asp
1               5                   10

<210> SEQ ID NO 176
<211> LENGTH: 9
<212> TYPE: PRT
<213> ORGANISM: Artificial Sequence
<220> FEATURE:
<223> OTHER INFORMATION: antibody sequence

<400> SEQUENCE: 176

His Tyr Ala Asp Gly Arg Phe Gly Ser
1               5

<210> SEQ ID NO 177
<211> LENGTH: 8
<212> TYPE: PRT
<213> ORGANISM: Artificial Sequence
<220> FEATURE:
<223> OTHER INFORMATION: antibody sequence

<400> SEQUENCE: 177

Tyr Ala Ala Trp Pro Leu Asn Thr
1               5

<210> SEQ ID NO 178
<211> LENGTH: 13
<212> TYPE: PRT
<213> ORGANISM: Artificial Sequence
<220> FEATURE:
<223> OTHER INFORMATION: antibody sequence

<400> SEQUENCE: 178

Ser Val Gly Ala Arg Arg Asp Glu Asp Tyr Val Tyr
1               5                   10

<210> SEQ ID NO 179
<211> LENGTH: 13
<212> TYPE: PRT
<213> ORGANISM: Artificial Sequence
<220> FEATURE:
<223> OTHER INFORMATION: antibody sequence

<400> SEQUENCE: 179

Ala Ala Ser Arg Ser Gly Arg Trp Leu Asp Asp Ala Arg
1               5                   10

<210> SEQ ID NO 180
<211> LENGTH: 13
<212> TYPE: PRT
<213> ORGANISM: Artificial Sequence
<220> FEATURE:
<223> OTHER INFORMATION: antibody sequence

<400> SEQUENCE: 180

Ser Val Gly Ala Arg Arg Asp Asp Asn Asp Tyr Val Tyr
1               5                   10

```
1               5                   10
```

<210> SEQ ID NO 181
<211> LENGTH: 13
<212> TYPE: PRT
<213> ORGANISM: Artificial Sequence
<220> FEATURE:
<223> OTHER INFORMATION: antibody sequence

<400> SEQUENCE: 181

```
Asn Ala Glu Ile Val Thr Gln Ile Pro Phe Pro Pro Arg
1               5                   10
```

<210> SEQ ID NO 182
<211> LENGTH: 13
<212> TYPE: PRT
<213> ORGANISM: Artificial Sequence
<220> FEATURE:
<223> OTHER INFORMATION: antibody sequence

<400> SEQUENCE: 182

```
Cys Ala Lys Ala Tyr Gly Ser Met Trp Ser Gly Ile Trp
1               5                   10
```

<210> SEQ ID NO 183
<211> LENGTH: 7
<212> TYPE: PRT
<213> ORGANISM: Artificial Sequence
<220> FEATURE:
<223> OTHER INFORMATION: antibody sequence

<400> SEQUENCE: 183

```
Tyr Thr Ala Trp Pro Asn Thr
1               5
```

<210> SEQ ID NO 184
<211> LENGTH: 13
<212> TYPE: PRT
<213> ORGANISM: Artificial Sequence
<220> FEATURE:
<223> OTHER INFORMATION: antibody sequence

<400> SEQUENCE: 184

```
Asn Ala Lys Asp Val Thr Val Ile Pro Phe Pro Pro Lys
1               5                   10
```

<210> SEQ ID NO 185
<211> LENGTH: 13
<212> TYPE: PRT
<213> ORGANISM: Artificial Sequence
<220> FEATURE:
<223> OTHER INFORMATION: antibody sequence

<400> SEQUENCE: 185

```
Ala Ala Asp Trp Arg Thr Ile Leu Gly Trp Lys Thr Arg
1               5                   10
```

<210> SEQ ID NO 186
<211> LENGTH: 13
<212> TYPE: PRT
<213> ORGANISM: Artificial Sequence
<220> FEATURE:
<223> OTHER INFORMATION: antibody sequence

<400> SEQUENCE: 186

```
Ser Val Gly Ala Arg Arg Asp Glu Asp Asp Tyr Val Tyr
1               5                   10
```

<210> SEQ ID NO 187
<211> LENGTH: 6
<212> TYPE: PRT
<213> ORGANISM: Artificial Sequence
<220> FEATURE:
<223> OTHER INFORMATION: antibody sequence

<400> SEQUENCE: 187

Asn Val Ala Leu Arg Tyr
1               5

<210> SEQ ID NO 188
<211> LENGTH: 13
<212> TYPE: PRT
<213> ORGANISM: Artificial Sequence
<220> FEATURE:
<223> OTHER INFORMATION: antibody sequence

<400> SEQUENCE: 188

Ser Val Gly Ala Arg Arg Asp Glu Asp Asp Tyr Val Tyr
1               5                   10

<210> SEQ ID NO 189
<211> LENGTH: 5
<212> TYPE: PRT
<213> ORGANISM: Artificial Sequence
<220> FEATURE:
<223> OTHER INFORMATION: antibody sequence

<400> SEQUENCE: 189

Asn Gln Leu Thr Tyr
1               5

<210> SEQ ID NO 190
<211> LENGTH: 9
<212> TYPE: PRT
<213> ORGANISM: Artificial Sequence
<220> FEATURE:
<223> OTHER INFORMATION: antibody sequence

<400> SEQUENCE: 190

Asn Leu Arg Arg Trp Ser Tyr Asp Tyr
1               5

<210> SEQ ID NO 191
<211> LENGTH: 115
<212> TYPE: PRT
<213> ORGANISM: Artificial Sequence
<220> FEATURE:
<223> OTHER INFORMATION: antibody sequence

<400> SEQUENCE: 191

Gln Val Gln Leu Gln Glu Ser Gly Gly Gly Leu Val Gln Pro Gly Asp
1               5                   10                  15

Ser Leu Lys Leu Ser Cys Ala Ala Ser Gly Gly Thr Phe Gly Ala Gly
                20                  25                  30

Val Val Ala Trp Tyr Arg Gln Ser Pro Gly Lys Gln Arg Glu Met Val
            35                  40                  45

Gly Ser Met Gly Ser Asp Gly Phe Thr Gln Ile Glu Asn Gly Met Lys
        50                  55                  60

Gly Arg Phe Thr Ile Ser Gly Ala Gly Asp Lys Lys Thr Val Phe Leu
65                  70                  75                  80

Gln Met Asn Asn Leu Lys Pro Glu Asp Thr Ala Val Tyr Phe Cys His

```
                85                  90                  95
Tyr Ala Asp Gly Arg Phe Gly Ser Trp Gly Gln Gly Thr Gln Val Thr
            100                 105                 110
Val Ser Ser
        115

<210> SEQ ID NO 192
<211> LENGTH: 114
<212> TYPE: PRT
<213> ORGANISM: Artificial Sequence
<220> FEATURE:
<223> OTHER INFORMATION: antibody sequence

<400> SEQUENCE: 192

Gln Val Gln Leu Gln Glu Ser Gly Gly Gly Leu Val Gln Ala Gly Gly
1               5                   10                  15
Ser Leu Arg Leu Ser Cys Ala Ala Ser Gly Ser Asn Ile Ser Thr Asn
            20                  25                  30
Val Met Ala Trp Tyr Arg Arg Ala Pro Gly Asn Gln Arg Asp Met Val
        35                  40                  45
Ala Ser Ile Ser Thr Ser Gly Thr Thr Asn Tyr Leu Ala Ser Val Lys
    50                  55                  60
Gly Arg Phe Thr Ile Ser Arg Asp Asn Ala Lys Asn Thr Val Ser Leu
65                  70                  75                  80
Gln Met Asn Ser Leu Lys Pro Glu Asp Thr Ala Val Tyr Thr Cys Tyr
                85                  90                  95
Ala Ala Trp Pro Leu Asn Thr Trp Gly Gln Gly Thr Gln Val Thr Val
            100                 105                 110
Ser Ser

<210> SEQ ID NO 193
<211> LENGTH: 119
<212> TYPE: PRT
<213> ORGANISM: Artificial Sequence
<220> FEATURE:
<223> OTHER INFORMATION: antibody sequence

<400> SEQUENCE: 193

Gln Val Gln Leu Gln Glu Ser Gly Gly Gly Leu Val Gln Ala Gly Gly
1               5                   10                  15
Ser Leu Arg Leu Ser Cys Ala Ala Ser Gly Ser Thr Phe Ser Ile Thr
            20                  25                  30
Tyr Met Ala Trp Phe Arg Gln Ala Pro Glu Lys Gln Arg Glu Leu Val
        35                  40                  45
Ala Glu Met Ser Arg Arg Gly Ser Thr Phe Tyr Ala Asp Ser Val Lys
    50                  55                  60
Gly Arg Phe Thr Ile Ser Arg Asp Asn Thr Lys Asn Thr Val Tyr Leu
65                  70                  75                  80
Gln Met Asn Ser Leu Glu Pro Glu Asp Thr Ala Val Tyr Tyr Cys Ser
                85                  90                  95
Val Gly Ala Arg Arg Asp Glu Asp Asp Tyr Val Tyr Trp Gly Gln Gly
            100                 105                 110
Thr Gln Val Thr Val Ser Ser
        115

<210> SEQ ID NO 194
<211> LENGTH: 119
<212> TYPE: PRT
```

<213> ORGANISM: Artificial Sequence
<220> FEATURE:
<223> OTHER INFORMATION: antibody sequence

<400> SEQUENCE: 194

Gln Val Gln Leu Gln Gln Ser Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Tyr Met Ala Trp Phe Arg Gln Ala Pro Glu Lys Gln Arg Glu Leu Val
        35                  40                  45

Ala Glu Met Ser Arg Arg Gly Ser Thr Phe Tyr Ala Asp Ser Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Glu Pro Glu Asp Thr Ala Val Tyr Tyr Cys Ser
                85                  90                  95

Val Gly Ala Arg Arg Asp Glu Asp Tyr Val Tyr Trp Gly Gln Gly
            100                 105                 110

Thr Gln Val Thr Val Ser Ser
        115

<210> SEQ ID NO 195
<211> LENGTH: 123
<212> TYPE: PRT
<213> ORGANISM: Artificial Sequence
<220> FEATURE:
<223> OTHER INFORMATION: antibody sequence

<400> SEQUENCE: 195

Gln Val Gln Leu Gln Glu Ser Gly Gly Gly Ser Val Gln Ala Gly Gly
1               5                   10                  15

Ser Leu Arg Leu Ser Cys Ala Asp Ser Arg Thr Ile Phe Ile Phe Asn
            20                  25                  30

Ala Met Ala Trp Tyr Arg Gln Ala Pro Gly Lys Gln Arg Glu Leu Val
        35                  40                  45

Ala Ala Ile Ser Ser Gly Gly Ser Thr Lys Tyr Ala Asp Ser Val Lys
    50                  55                  60

Gly Arg Phe Thr Ile Ser Ser Ser Asn Ala Lys Asn Thr Lys Tyr Leu
65                  70                  75                  80

Gln Met Asn Arg Leu Lys Pro Glu Asp Thr Ala Val Tyr Tyr Cys Ala
                85                  90                  95

Ala Ser Arg Ser Gly Arg Trp Leu Asp Asp Ala Arg Asp Tyr Glu Tyr
            100                 105                 110

Trp Gly Pro Gly Thr Gln Val Thr Val Ser Ser
        115                 120

<210> SEQ ID NO 196
<211> LENGTH: 114
<212> TYPE: PRT
<213> ORGANISM: Artificial Sequence
<220> FEATURE:
<223> OTHER INFORMATION: antibody sequence

<400> SEQUENCE: 196

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Asn Ile Ser Thr Asn
            20                  25                  30

```
Val Met Ala Trp Tyr Arg Arg Ala Pro Gly Asn Gln Arg Asp Met Val
            35                  40                  45

Ala Ser Ile Ser Thr Ser Gly Thr Thr Asn Tyr Leu Ala Ser Val Lys
 50                  55                  60

Gly Arg Phe Thr Ile Ser Arg Asp Asn Ala Lys Asn Thr Val Ser Leu
 65                  70                  75                  80

Gln Met Asn Ser Leu Lys Pro Glu Asp Thr Ala Val Tyr Thr Cys Tyr
                 85                  90                  95

Ala Ala Trp Pro Leu Asn Thr Trp Gly Gln Gly Thr Leu Val Thr Val
            100                 105                 110

Ser Ser
```

<210> SEQ ID NO 197
<211> LENGTH: 119
<212> TYPE: PRT
<213> ORGANISM: Artificial Sequence
<220> FEATURE:
<223> OTHER INFORMATION: antibody sequence

<400> SEQUENCE: 197

```
Gln Val Gln Leu Gln Gln Ser Gly Gly Gly Leu Val Gln Ala Gly Gly
 1               5                  10                  15

Ser Leu Arg Leu Ser Cys Ala Ala Ser Gly Ile Pro Phe Ser Ile Ile
                 20                  25                  30

Tyr Met Ala Trp Phe Arg Gln Ala Pro Glu Lys Gln Arg Glu Leu Val
            35                  40                  45

Ala Glu Met Ser Ser Arg Gly Ser Lys Phe Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Glu Pro Glu Asp Thr Ala Val Tyr Tyr Cys Ser
                 85                  90                  95

Val Gly Ala Arg Arg Asp Asp Asn Asp Tyr Val Tyr Trp Gly Gln Gly
            100                 105                 110

Thr Gln Val Thr Val Ser Ser
        115
```

<210> SEQ ID NO 198
<211> LENGTH: 114
<212> TYPE: PRT
<213> ORGANISM: Artificial Sequence
<220> FEATURE:
<223> OTHER INFORMATION: antibody sequence

<400> SEQUENCE: 198

```
Gln Val Gln Leu Gln Ala Ser Gly Gly Gly Leu Val Gln Ala Gly Gly
 1               5                  10                  15

Ser Leu Arg Leu Ser Cys Ala Ala Ser Gly Ser Asn Ile Ser Thr Asn
                 20                  25                  30

Val Met Ala Trp Tyr Arg Arg Ala Pro Gly Asn Gln Arg Asp Met Val
            35                  40                  45

Ala Ser Ile Ser Thr Ser Gly Thr Thr Asn Tyr Leu Ala Ser Val Lys
 50                  55                  60

Gly Arg Phe Thr Ile Ser Arg Asp Asn Ala Lys Asn Thr Val Ser Leu
 65                  70                  75                  80

Gln Met Asn Ser Leu Lys Pro Glu Asp Thr Ala Val Tyr Thr Cys Tyr
                 85                  90                  95
```

Ala Ala Trp Pro Leu Asn Thr Trp Gly Gln Gly Thr Gln Val Thr Val
            100                 105                 110

Ser Ser

<210> SEQ ID NO 199
<211> LENGTH: 119
<212> TYPE: PRT
<213> ORGANISM: Artificial Sequence
<220> FEATURE:
<223> OTHER INFORMATION: antibody sequence

<400> SEQUENCE: 199

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Pro Phe Ser Ile Ile
            20                  25                  30

Tyr Met Ala Trp Phe Arg Gln Ala Pro Glu Lys Gln Arg Glu Leu Val
            35                  40                  45

Ala Glu Met Ser Ser Arg Gly Ser Lys Phe Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Glu Pro Glu Asp Thr Ala Val Tyr Tyr Cys Ser
                85                  90                  95

Val Gly Ala Arg Arg Asp Asp Asn Asp Tyr Val Tyr Trp Gly Gln Gly
            100                 105                 110

Thr Gln Val Thr Val Ser Ser
        115

<210> SEQ ID NO 200
<211> LENGTH: 120
<212> TYPE: PRT
<213> ORGANISM: Artificial Sequence
<220> FEATURE:
<223> OTHER INFORMATION: antibody sequence

<400> SEQUENCE: 200

Gln Val Gln Leu Gln Ala Ser Gly Gly Gly Val Val Gln Ser Gly Gly
1               5                   10                  15

Ser Leu Arg Leu Ser Cys Val Ala Ser Gly Asn Ile Phe Gly Ile Asn
            20                  25                  30

Ser Met Ala Trp Tyr Arg Gln Ala Pro Gly Lys Gln Arg Glu Leu Val
            35                  40                  45

Ala Asp Ile Thr Arg Gly Asn Arg Lys Tyr Ala Asp Ser Val Lys Gly
        50                  55                  60

Arg Phe Thr Ile Ser Gln Asp Asn Ala Lys Asn Thr Val Tyr Leu Gln
65                  70                  75                  80

Met Asn Arg Leu Lys Pro Glu Asp Thr Ala Val Tyr Phe Cys Asn Ala
                85                  90                  95

Glu Ile Val Thr Gln Ile Pro Phe Pro Pro Arg Glu Phe Trp Gly Arg
            100                 105                 110

Gly Thr Leu Val Thr Val Ser Ser
        115                 120

<210> SEQ ID NO 201
<211> LENGTH: 124
<212> TYPE: PRT
<213> ORGANISM: Artificial Sequence -continued
<220> FEATURE:
<223> OTHER INFORMATION: antibody sequence

<400> SEQUENCE: 201

Gln Val Gln Leu Gln Ala Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Thr Ile Asn Thr Gly Gly Tyr Thr Thr Tyr Tyr Ser Asp Ser Val
    50                  55                  60

Lys Gly Arg Phe Thr Ile Ser Arg Asp Asn Gly Lys Asn Thr Leu Tyr
65                  70                  75                  80

Leu Glu Met Asn Ser Leu Lys Ser Glu Asp Thr Ala Val Tyr Tyr Cys
                85                  90                  95

Ala Lys Ala Tyr Gly Ser Met Trp Ser Gly Ile Trp Gly Met Asp
            100                 105                 110

Tyr Trp Gly Lys Gly Thr Gln Val Thr Val Ser Ser
        115                 120

<210> SEQ ID NO 202
<211> LENGTH: 114
<212> TYPE: PRT
<213> ORGANISM: Artificial Sequence
<220> FEATURE:
<223> OTHER INFORMATION: antibody sequence

<400> SEQUENCE: 202

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Asn Ile Ser Thr Asn
            20                  25                  30

Val Met Ala Trp Tyr Arg Arg Ala Pro Gly Asn Gln Arg Asp Met Val
        35                  40                  45

Ala Ser Ile Ser Thr Ser Gly Thr Thr Asn Tyr Leu Ala Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Thr Cys Tyr
                85                  90                  95

Ala Ala Trp Pro Leu Asn Thr Trp Gly Gln Gly Thr Gln Val Thr Val
            100                 105                 110

Ser Ser

<210> SEQ ID NO 203
<211> LENGTH: 113
<212> TYPE: PRT
<213> ORGANISM: Artificial Sequence
<220> FEATURE:
<223> OTHER INFORMATION: antibody sequence

<400> SEQUENCE: 203

Gln Val Gln Leu Gln Glu Ser Gly Gly Gly Leu Val Gln Ala Gly Gly
1               5                   10                  15

Ser Leu Arg Leu Ser Cys Ala Val Ser Gly Ser Ile Ile Ser His Asn
            20                  25                  30

Val Met Ala Trp Tyr Arg Arg Ala Pro Gly Lys Gln Arg Asp Lys Val

```
            35                  40                  45
Ala Cys Ile Ser Gly Ser Gly Phe Thr Asn Tyr Ile Ala Ser Val Lys
 50                  55                  60

Gly Arg Phe Thr Ile Ser Arg Asp Asn Ala Lys Asn Thr Val Ser Leu
 65                  70                  75                  80

Gln Met Asn Asn Leu Lys Pro Glu Asp Thr Ala Val Tyr Ser Cys Tyr
                 85                  90                  95

Thr Ala Trp Pro Asn Thr Trp Gly Gln Gly Thr Gln Val Thr Val Ser
                100                 105                 110

Ser

<210> SEQ ID NO 204
<211> LENGTH: 121
<212> TYPE: PRT
<213> ORGANISM: Artificial Sequence
<220> FEATURE:
<223> OTHER INFORMATION: antibody sequence

<400> SEQUENCE: 204

Gln Val Gln Leu Gln Glu Ser Gly Gly Gly Phe Val His Pro Gly Gly
  1               5                  10                  15

Ser Leu Thr Leu Ser Cys Ala Ala Ser Gly Arg Ile Phe Asn Ile Glu
                 20                  25                  30

Asp Met Gly Trp Tyr Arg Gln Gly Pro Gly Glu Gln Arg Asp Leu Val
             35                  40                  45

Ala Thr Ile Thr Arg Thr Gly Ala Pro Thr Tyr Ala Asn Ser Val Lys
 50                  55                  60

Gly Arg Phe Thr Ile Ser Arg Asp Asn Ala Lys Asn Thr Val Tyr Leu
 65                  70                  75                  80

Gln Met Thr Arg Leu Lys Pro Glu Asp Thr Ala Val Tyr Tyr Cys Asn
                 85                  90                  95

Ala Lys Asp Val Thr Val Ile Pro Phe Pro Lys Asp Tyr Trp Gly
                100                 105                 110

Arg Gly Thr Gln Val Thr Val Ser Ser
        115                 120

<210> SEQ ID NO 205
<211> LENGTH: 123
<212> TYPE: PRT
<213> ORGANISM: Artificial Sequence
<220> FEATURE:
<223> OTHER INFORMATION: antibody sequence

<400> SEQUENCE: 205

Gln Val Gln Leu Gln Glu Ser Gly Gly Gly Leu Val Gln Ala Gly Gly
  1               5                  10                  15

Ser Leu Arg Leu Ser Cys Glu Ala Ser Gly Ser Val Ser Ala Ile Glu
                 20                  25                  30

Thr Met Gly Trp Tyr Arg Gln Ala Pro Asp Glu Gln Arg Thr Phe Val
             35                  40                  45

Ala Val Ile Ser Thr Gly Gly Thr Thr Lys Tyr Ala Pro Ser Val Lys
 50                  55                  60

Gly Arg Phe Thr Ile Ser Ile Asp Asn Ala Lys Ser Thr Val Thr Leu
 65                  70                  75                  80

Gln Met Asn Ser Leu Lys Pro Glu Asp Thr Ala Val Tyr Tyr Cys Ala
                 85                  90                  95

Ala Asp Trp Arg Thr Ile Leu Gly Trp Lys Thr Arg Glu Pro Asn Tyr
```

```
                100                 105                 110
Phe Gly Gln Gly Thr Leu Val Thr Val Ser Ser
        115                 120

<210> SEQ ID NO 206
<211> LENGTH: 119
<212> TYPE: PRT
<213> ORGANISM: Artificial Sequence
<220> FEATURE:
<223> OTHER INFORMATION: antibody sequence

<400> SEQUENCE: 206

Gln Val Gln Leu Gln Glu Ser Gly Gly Gly Leu Val Gln Ala Gly Gly
1               5                   10                  15

Ser Leu Arg Leu Ser Cys Ala Ala Phe Gly Ser Thr Ser Ser Ile Thr
            20                  25                  30

Tyr Met Ala Trp Phe Arg Gln Ala Pro Glu Lys Gln Arg Glu Leu Val
        35                  40                  45

Ala Glu Met Ser Arg Arg Gly Ser Thr Phe Tyr Ala Asp Ser Val Lys
    50                  55                  60

Gly Arg Phe Thr Ile Tyr Arg Asp Asn Thr Lys Asn Thr Val Tyr Leu
65                  70                  75                  80

Gln Met Asn Ser Leu Glu Pro Glu Asp Thr Ala Val Tyr Tyr Cys Ser
                85                  90                  95

Val Gly Ala Arg Arg Asp Glu Asp Tyr Val Tyr Trp Gly Gln Gly
            100                 105                 110

Thr Gln Val Thr Val Ser Ser
        115

<210> SEQ ID NO 207
<211> LENGTH: 112
<212> TYPE: PRT
<213> ORGANISM: Artificial Sequence
<220> FEATURE:
<223> OTHER INFORMATION: antibody sequence

<400> SEQUENCE: 207

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Pro Val Ser Asp Asn
            20                  25                  30

Val Met Ala Trp Phe Arg Gln Ala Pro Gly Ser Gln Arg Glu Leu Val
        35                  40                  45

Ala Gln Ile Thr Ser Gly Gly Ala Thr Ser Tyr Ala Asp Ser Val Lys
    50                  55                  60

Gly Arg Phe Thr Ile Ser Arg Asp Asn Ala Arg Ser Thr Val Asp Leu
65                  70                  75                  80

Gln Met Asn Ser Leu Lys Pro Glu Asp Thr Ala Val Tyr Tyr Cys Asn
                85                  90                  95

Val Ala Leu Arg Tyr Trp Gly Arg Gly Thr Gln Val Thr Val Ser Ser
            100                 105                 110

<210> SEQ ID NO 208
<211> LENGTH: 119
<212> TYPE: PRT
<213> ORGANISM: Artificial Sequence
<220> FEATURE:
<223> OTHER INFORMATION: antibody sequence

<400> SEQUENCE: 208
```

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Tyr Met Ala Trp Phe Arg Gln Ala Pro Gly Lys Gln Arg Glu Leu Val
        35                  40                  45

Ala Glu Ile Ser Ser Arg Gly Ser Val Phe Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Ser Leu Glu Thr Glu Asp Thr Ala Ala Tyr Tyr Cys Ser
                85                  90                  95

Val Gly Ala Arg Arg Asp Glu Asp Asp Tyr Val Tyr Trp Gly Gln Gly
            100                 105                 110

Thr Gln Val Thr Val Ser Ser
        115

<210> SEQ ID NO 209
<211> LENGTH: 119
<212> TYPE: PRT
<213> ORGANISM: Artificial Sequence
<220> FEATURE:
<223> OTHER INFORMATION: antibody sequence

<400> SEQUENCE: 209

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Tyr Met Ala Trp Phe Arg Gln Ala Pro Glu Lys Gln Arg Glu Leu Val
        35                  40                  45

Ala Glu Met Ser Arg Arg Gly Ser Thr Phe Tyr Ala Asp Ser Val Lys
    50                  55                  60

Gly Arg Phe Thr Ile Ser Arg Asp Asn Thr Lys Asn Thr Val Tyr Leu
65                  70                  75                  80

Gln Met Asn Ser Leu Glu Pro Glu Asp Thr Ala Val Tyr Tyr Cys Ser
                85                  90                  95

Val Gly Ala Arg Arg Asp Glu Asp Asp Tyr Val Tyr Trp Gly Gln Gly
            100                 105                 110

Thr Leu Val Thr Val Ser Ser
        115

<210> SEQ ID NO 210
<211> LENGTH: 119
<212> TYPE: PRT
<213> ORGANISM: Artificial Sequence
<220> FEATURE:
<223> OTHER INFORMATION: antibody sequence

<400> SEQUENCE: 210

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Pro Phe Ser Ile Ile
            20                  25                  30

Tyr Met Ala Trp Phe Arg Gln Ala Pro Glu Lys Gln Arg Glu Leu Val
        35                  40                  45

Ala Glu Met Ser Ser Arg Gly Ser Lys Phe Tyr Ala Asp Ser Val Lys

```
                    50                  55                  60
Gly Arg Phe Thr Ile Ser Arg Asp Asn Ala Lys Asn Thr Leu Tyr Leu
 65                  70                  75                  80

Gln Met Asn Ser Leu Glu Pro Glu Asp Thr Ala Val Tyr Tyr Cys Ser
                 85                  90                  95

Val Gly Ala Arg Arg Asp Asp Asn Asp Tyr Val Tyr Trp Gly Gln Gly
            100                 105                 110

Thr Leu Val Thr Val Ser Ser
            115

<210> SEQ ID NO 211
<211> LENGTH: 119
<212> TYPE: PRT
<213> ORGANISM: Artificial Sequence
<220> FEATURE:
<223> OTHER INFORMATION: antibody sequence

<400> SEQUENCE: 211

Gln Val Gln Leu Gln Glu Phe Gly Gly Gly Leu Val Gln Ala Gly Gly
 1               5                  10                  15

Ser Leu Arg Leu Ser Cys Ala Ala Ser Gly Ser Thr Phe Ser Ile Thr
                20                  25                  30

Tyr Met Ala Trp Phe Arg Gln Ala Pro Glu Lys Gln Arg Glu Leu Val
             35                  40                  45

Ala Glu Met Ser Arg Arg Gly Ser Thr Phe Tyr Ala Asp Ser Val Lys
         50                  55                  60

Gly Arg Phe Thr Ile Ser Arg Asp Asn Thr Lys Asn Thr Val Tyr Leu
 65                  70                  75                  80

Gln Met Asn Ser Leu Glu Pro Glu Asp Thr Ala Val Tyr Tyr Cys Ser
                 85                  90                  95

Val Gly Ala Arg Arg Asp Glu Asp Asp Tyr Val Tyr Trp Gly Gln Gly
            100                 105                 110

Thr Gln Val Thr Val Ser Ser
            115

<210> SEQ ID NO 212
<211> LENGTH: 114
<212> TYPE: PRT
<213> ORGANISM: Artificial Sequence
<220> FEATURE:
<223> OTHER INFORMATION: antibody sequence

<400> SEQUENCE: 212

Gln Val Gln Leu Gln Glu Phe Gly Gly Gly Leu Val Gln Ala Gly Glu
 1               5                  10                  15

Ser Leu Arg Leu Ser Cys Val Ala Ser Gly Ser Asn Ile Ser Thr Asn
                20                  25                  30

Val Met Ala Trp Tyr Arg Arg Ala Pro Gly Asn Gln Arg Asp Met Val
             35                  40                  45

Ala Ser Ile Ser Thr Ser Gly Thr Thr Asn Tyr Leu Ala Ser Val Lys
         50                  55                  60

Gly Arg Phe Thr Ile Ser Arg Asp Asn Ala Lys Asn Thr Val Ser Leu
 65                  70                  75                  80

Gln Met Asn Ser Leu Lys Pro Glu Asp Thr Ala Val Tyr Thr Cys Tyr
                 85                  90                  95

Ala Ala Trp Pro Leu Asn Thr Trp Gly Gln Gly Thr Leu Val Thr Val
            100                 105                 110
```

Ser Ser

<210> SEQ ID NO 213
<211> LENGTH: 111
<212> TYPE: PRT
<213> ORGANISM: Artificial Sequence
<220> FEATURE:
<223> OTHER INFORMATION: antibody sequence

<400> SEQUENCE: 213

Gln Val Gln Leu Gln Glu Ser Gly Gly Gly Leu Val Gln Ala Gly Gly
1               5                   10                  15

Ser Leu Arg Leu Ser Cys Val Gly Ala Gly Ser Ala Phe Gly Trp Asn
            20                  25                  30

Ala Val His Trp Tyr Arg Gln Ala Pro Gly Gln Gln Arg Glu Trp Leu
        35                  40                  45

Ala Thr Ile Glu Ser Gly Gly Trp Ala Asp Tyr Ser Val Ser Val Lys
    50                  55                  60

Gly Arg Phe Ile Val Ser Arg Asp Asn Ala Arg Asn Thr Ala Tyr Leu
65                  70                  75                  80

Gln Met Asn Asn Leu Lys Leu Glu Asp Thr Ala Val Tyr Tyr Cys Asn
                85                  90                  95

Gln Leu Thr Tyr Trp Gly Gln Gly Thr Gln Val Thr Val Ser Ser
            100                 105                 110

<210> SEQ ID NO 214
<211> LENGTH: 119
<212> TYPE: PRT
<213> ORGANISM: Artificial Sequence
<220> FEATURE:
<223> OTHER INFORMATION: antibody sequence

<400> SEQUENCE: 214

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Tyr Met Thr Trp Phe Arg Gln Ala Pro Glu Lys Gln Arg Glu Leu Val
        35                  40                  45

Ala Glu Met Ser Arg Arg Gly Ser Thr Phe Tyr Ala Asp Ser Val Lys
    50                  55                  60

Ala Arg Phe Thr Ile Ser Arg Asp Asn Thr Lys Asn Thr Val Tyr Leu
65                  70                  75                  80

Gln Met Asn Ser Leu Glu Pro Glu Asp Thr Ala Val Tyr Tyr Cys Ser
                85                  90                  95

Val Gly Ala Arg Arg Asp Glu Asp Asp Tyr Val Tyr Trp Gly Gln Gly
            100                 105                 110

Thr Gln Val Thr Val Ser Ser
        115

<210> SEQ ID NO 215
<211> LENGTH: 119
<212> TYPE: PRT
<213> ORGANISM: Artificial Sequence
<220> FEATURE:
<223> OTHER INFORMATION: antibody sequence

<400> SEQUENCE: 215

Gln Val Gln Leu Gln Glu Phe Gly Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Tyr Met Ala Trp Phe Arg Gln Ala Pro Glu Lys Gln Arg Glu Leu Val
            35                  40                  45

Ala Glu Met Ser Arg Arg Gly Ser Thr Phe Tyr Ala Asp Ser Val Lys
50                  55                  60

Gly Arg Phe Thr Ile Ser Arg Asp Asn Thr Lys Asn Thr Val Tyr Leu
65                  70                  75                  80

Gln Met Asn Ser Leu Glu Pro Glu Asp Thr Ala Val Tyr Tyr Cys Ser
                85                  90                  95

Val Gly Ala Arg Arg Asp Glu Asp Tyr Val Tyr Trp Gly Gln Gly
            100                 105                 110

Thr Leu Val Thr Val Ser Ser
            115

<210> SEQ ID NO 216
<211> LENGTH: 119
<212> TYPE: PRT
<213> ORGANISM: Artificial Sequence
<220> FEATURE:
<223> OTHER INFORMATION: antibody sequence

<400> SEQUENCE: 216

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Thr Phe Ser Ile Thr
            20                  25                  30

Tyr Met Ala Trp Phe Arg Gln Ala Pro Gly Lys Gln Arg Glu Leu Val
            35                  40                  45

Ala Glu Ile Ser Ser Arg Gly Ser Val Phe Tyr Ala Asp Ser Val Lys
50                  55                  60

Gly Arg Phe Thr Ile Ser Arg Asp Asn Ala Lys Lys Thr Val Tyr Leu
65                  70                  75                  80

Gln Met Asn Ser Leu Glu Thr Glu Asp Thr Ala Ala Tyr Tyr Cys Ser
                85                  90                  95

Val Gly Ala Arg Arg Asp Glu Asp Tyr Val Tyr Trp Gly Gln Gly
            100                 105                 110

Thr Leu Val Thr Val Ser Ser
            115

<210> SEQ ID NO 217
<211> LENGTH: 114
<212> TYPE: PRT
<213> ORGANISM: Artificial Sequence
<220> FEATURE:
<223> OTHER INFORMATION: antibody sequence

<400> SEQUENCE: 217

Gln Val Gln Leu Gln Glu Ser Gly Gly Gly Leu Val Gln Pro Gly Gly
1               5                   10                  15

Ser Leu Arg Leu Ser Cys Thr Pro Ser Gly Ser Ile Phe Ser Phe Asp
            20                  25                  30

Val Met Ala Trp Tyr Arg Gln Ala Pro Gly Lys Arg Arg Glu Leu Val
            35                  40                  45

Ala Gln His Arg Thr Pro Gly Ala Ile Asp Tyr Ala Asp Pro Val Arg
50                  55                  60

Gly Arg Phe Thr Ile Ser Arg Asp Ala Gly Asp Val Leu Phe Leu Gln

```
                65                  70                  75                  80
Met Asp Ser Leu Lys Pro Glu Asp Thr Ala Val Tyr Phe Cys Asn Leu
                    85                  90                  95

Arg Arg Trp Ser Tyr Asp Tyr Trp Gly Gln Gly Thr Leu Val Thr Val
                100                 105                 110

Ser Ser

<210> SEQ ID NO 218
<211> LENGTH: 10
<212> TYPE: PRT
<213> ORGANISM: Artificial Sequence
<220> FEATURE:
<223> OTHER INFORMATION: antibody sequence

<400> SEQUENCE: 218

Ala Ser Gly Asn Ile Phe Arg Ile Asn Ala
1               5                   10

<210> SEQ ID NO 219
<211> LENGTH: 12
<212> TYPE: PRT
<213> ORGANISM: Artificial Sequence
<220> FEATURE:
<223> OTHER INFORMATION: antibody sequence

<400> SEQUENCE: 219

Ala Ser Ile Asp Ser Ala Gly Arg Thr Asn Tyr Gly
1               5                   10

<210> SEQ ID NO 220
<211> LENGTH: 10
<212> TYPE: PRT
<213> ORGANISM: Artificial Sequence
<220> FEATURE:
<223> OTHER INFORMATION: antibody sequence

<400> SEQUENCE: 220

Cys Ser Thr Trp Arg Leu Gly Arg Asn Tyr
1               5                   10

<210> SEQ ID NO 221
<211> LENGTH: 115
<212> TYPE: PRT
<213> ORGANISM: Artificial Sequence
<220> FEATURE:
<223> OTHER INFORMATION: antibody sequence

<400> SEQUENCE: 221

Gln Val Gln Leu Gln Glu Phe Gly Gly Gly Val Val Gln Ser Gly Gly
1               5                   10                  15

Ser Leu Arg Leu Ser Cys Val Ala Ser Gly Asn Ile Phe Arg Ile Asn
                20                  25                  30

Ala Met Gly Trp Tyr Arg Gln Ala Pro Gly Lys Ser Arg Val Leu Val
            35                  40                  45

Ala Ser Ile Asp Ser Ala Gly Arg Thr Asn Tyr Gly Asp Ala Val Glu
        50                  55                  60

Asp Arg Phe Thr Ile Ser Arg Asp Ile Ala Asn Asn Ile Val Asn Leu
65                  70                  75                  80

Gln Met Asn Ser Leu Lys Pro Glu Asp Thr Ala Val Tyr Tyr Cys Ser
                85                  90                  95

Thr Trp Arg Leu Gly Arg Asn Tyr Trp Gly Gln Gly Thr Gln Val Thr
                100                 105                 110
```

Val Ser Ser
        115

<210> SEQ ID NO 222
<211> LENGTH: 10
<212> TYPE: PRT
<213> ORGANISM: Artificial Sequence
<220> FEATURE:
<223> OTHER INFORMATION: antibody sequence

<400> SEQUENCE: 222

Ala Ser Gly Ser Thr Phe Ser Asn Asn Ala
1               5                   10

<210> SEQ ID NO 223
<211> LENGTH: 10
<212> TYPE: PRT
<213> ORGANISM: Artificial Sequence
<220> FEATURE:
<223> OTHER INFORMATION: antibody sequence

<400> SEQUENCE: 223

Ala Tyr Ile Ser Ser Gly Gly Phe Thr Asn
1               5                   10

<210> SEQ ID NO 224
<211> LENGTH: 17
<212> TYPE: PRT
<213> ORGANISM: Artificial Sequence
<220> FEATURE:
<223> OTHER INFORMATION: antibody sequence

<400> SEQUENCE: 224

Ser Ala Gly Gly Thr Tyr Arg Ser Gly Asn Val Tyr Phe Phe Pro Arg
1               5                   10                  15

Ser

<210> SEQ ID NO 225
<211> LENGTH: 123
<212> TYPE: PRT
<213> ORGANISM: Artificial Sequence
<220> FEATURE:
<223> OTHER INFORMATION: antibody sequence

<400> SEQUENCE: 225

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Asn Asn
            20                  25                  30

Ala Met Ala Trp Tyr Arg Gln Ala Pro Gly Lys Gln Arg Glu Leu Val
        35                  40                  45

Ala Tyr Ile Ser Ser Gly Gly Phe Thr Asn Tyr Gly Asp Ser Val Lys
    50                  55                  60

Gly Arg Phe Thr Ile Ser Glu Asp Asn Ala Lys Ser Thr Val Tyr Leu
65                  70                  75                  80

Gln Met Thr Ser Leu Lys Pro Glu Asp Thr Ala Val Tyr Tyr Cys Ser
                85                  90                  95

Ala Gly Gly Thr Tyr Arg Ser Gly Asn Val Tyr Phe Phe Pro Arg Ser
            100                 105                 110

Trp Gly Gln Gly Thr Gln Val Thr Val Ser Ser
        115                 120

<210> SEQ ID NO 226
<211> LENGTH: 10
<212> TYPE: PRT
<213> ORGANISM: Artificial Sequence
<220> FEATURE:
<223> OTHER INFORMATION: antibody sequence

<400> SEQUENCE: 226

Ala Ser Gly Ser Ile Phe Ser Ile Asn Ser
1               5                   10

<210> SEQ ID NO 227
<211> LENGTH: 10
<212> TYPE: PRT
<213> ORGANISM: Artificial Sequence
<220> FEATURE:
<223> OTHER INFORMATION: antibody sequence

<400> SEQUENCE: 227

Ala Thr Ile Ser Ser Arg Ser Thr Thr Tyr
1               5                   10

<210> SEQ ID NO 228
<211> LENGTH: 8
<212> TYPE: PRT
<213> ORGANISM: Artificial Sequence
<220> FEATURE:
<223> OTHER INFORMATION: antibody sequence

<400> SEQUENCE: 228

Lys Ala Gly Ser Val Gly Arg Val
1               5

<210> SEQ ID NO 229
<211> LENGTH: 115
<212> TYPE: PRT
<213> ORGANISM: Artificial Sequence
<220> FEATURE:
<223> OTHER INFORMATION: antibody sequence

<400> SEQUENCE: 229

Gln Val Gln Leu Gln Gln Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ser Met Ala Trp Tyr Arg Gln Ala Pro Gly Asn Gln Arg Glu Leu Val
        35                  40                  45

Ala Thr Ile Ser Ser Arg Ser Thr Thr Tyr Tyr Ala Pro Ser Val Lys
    50                  55                  60

Gly Arg Phe Thr Ile Ser Arg Asp Asn Ala Lys Asn Ile Val Tyr Leu
65                  70                  75                  80

Gln Met Asn Ser Leu Lys Pro Glu Asp Thr Ala Val Tyr Tyr Cys Lys
                85                  90                  95

Ala Gly Ser Val Gly Arg Val Tyr Trp Gly Gln Gly Thr Leu Val Thr
            100                 105                 110

Val Ser Ser
        115

<210> SEQ ID NO 230
<211> LENGTH: 10
<212> TYPE: PRT
<213> ORGANISM: Artificial Sequence
<220> FEATURE:

```
<223> OTHER INFORMATION: antibody sequence

<400> SEQUENCE: 230

Ala Ser Met Thr Thr Leu Gly Phe Lys Thr
1               5                   10

<210> SEQ ID NO 231
<211> LENGTH: 10
<212> TYPE: PRT
<213> ORGANISM: Artificial Sequence
<220> FEATURE:
<223> OTHER INFORMATION: antibody sequence

<400> SEQUENCE: 231

Ala Ala Ile Thr Ser Gly Gly Thr Ala Asn
1               5                   10

<210> SEQ ID NO 232
<211> LENGTH: 14
<212> TYPE: PRT
<213> ORGANISM: Artificial Sequence
<220> FEATURE:
<223> OTHER INFORMATION: antibody sequence

<400> SEQUENCE: 232

Ala Ser Thr Thr Gly Trp Thr Glu Val Gly Gly Arg Asn Asp
1               5                   10

<210> SEQ ID NO 233
<211> LENGTH: 121
<212> TYPE: PRT
<213> ORGANISM: Artificial Sequence
<220> FEATURE:
<223> OTHER INFORMATION: antibody sequence

<400> SEQUENCE: 233

Gln Val Gln Leu Gln Glu Ser Gly Gly Gly Leu Val Gln Ala Gly Gly
1               5                   10                  15

Ser Leu Arg Leu Ser Cys Leu Ala Ser Met Thr Thr Leu Gly Phe Lys
            20                  25                  30

Thr Met Gly Trp Tyr Arg Gln Ala Pro Gly Lys Gln Arg Glu Leu Val
        35                  40                  45

Ala Ala Ile Thr Ser Gly Gly Thr Ala Asn Tyr Ala Asp Ser Val Lys
    50                  55                  60

Gly Arg Phe Ala Ile Ser Arg Glu Asn Ala Lys Asn Thr Leu Tyr Leu
65                  70                  75                  80

Gln Met Asn Ser Leu Lys Pro Glu Asp Thr Ala Leu Tyr Tyr Cys Ala
                85                  90                  95

Ser Thr Thr Gly Trp Thr Glu Val Gly Gly Arg Asn Asp Tyr Trp Gly
            100                 105                 110

Gln Gly Thr Leu Val Thr Val Ser Ser
        115                 120

<210> SEQ ID NO 234
<211> LENGTH: 10
<212> TYPE: PRT
<213> ORGANISM: Artificial Sequence
<220> FEATURE:
<223> OTHER INFORMATION: antibody sequence

<400> SEQUENCE: 234

Ala Ser Gly Arg Thr Phe Arg Val Asn Ala
1               5                   10
```

<210> SEQ ID NO 235
<211> LENGTH: 10
<212> TYPE: PRT
<213> ORGANISM: Artificial Sequence
<220> FEATURE:
<223> OTHER INFORMATION: antibody sequence

<400> SEQUENCE: 235

Ala Ala Val Thr Asn Gly Gly Ser Thr Thr
1               5                   10

<210> SEQ ID NO 236
<211> LENGTH: 11
<212> TYPE: PRT
<213> ORGANISM: Artificial Sequence
<220> FEATURE:
<223> OTHER INFORMATION: antibody sequence

<400> SEQUENCE: 236

Asn Ala Glu Arg Arg Phe Gly Met Arg Gln Val
1               5                   10

<210> SEQ ID NO 237
<211> LENGTH: 117
<212> TYPE: PRT
<213> ORGANISM: Artificial Sequence
<220> FEATURE:
<223> OTHER INFORMATION: antibody sequence

<400> SEQUENCE: 237

Gln Val Gln Leu Gln Glu Ser Gly Gly Gly Leu Val Gln Thr Gly Gly
1               5                   10                  15

Ser Leu Arg Leu Ser Cys Ala Ala Ser Gly Arg Thr Phe Arg Val Asn
            20                  25                  30

Ala Met Gly Trp Tyr Arg Gln Ala Pro Gly Lys Gln Arg Glu Phe Val
        35                  40                  45

Ala Ala Val Thr Asn Gly Gly Ser Thr Thr Tyr Ala Asp Ser Val Lys
    50                  55                  60

Gly Arg Phe Thr Ile Ser Arg Asp Asn Ala Lys Asn Thr Ile Tyr Leu
65                  70                  75                  80

Gln Met Asn Arg Leu Glu Pro Glu Asp Thr Ala Leu Tyr Tyr Cys Asn
                85                  90                  95

Ala Glu Arg Arg Phe Gly Met Arg Gln Val Trp Gly Gln Gly Thr Leu
            100                 105                 110

Val Thr Val Ser Ser
        115

<210> SEQ ID NO 238
<211> LENGTH: 10
<212> TYPE: PRT
<213> ORGANISM: Artificial Sequence
<220> FEATURE:
<223> OTHER INFORMATION: antibody sequence

<400> SEQUENCE: 238

Ala Ser Gly Arg Val Phe Ser Ile Asn Thr
1               5                   10

<210> SEQ ID NO 239
<211> LENGTH: 10
<212> TYPE: PRT
<213> ORGANISM: Artificial Sequence

```
<220> FEATURE:
<223> OTHER INFORMATION: antibody sequence

<400> SEQUENCE: 239

Ala Ser Met Thr Arg Gly Gly Ser Ala Asn
1               5                   10

<210> SEQ ID NO 240
<211> LENGTH: 8
<212> TYPE: PRT
<213> ORGANISM: Artificial Sequence
<220> FEATURE:
<223> OTHER INFORMATION: antibody sequence

<400> SEQUENCE: 240

Asn Ala Ala Arg Gly Trp Arg Ile
1               5

<210> SEQ ID NO 241
<211> LENGTH: 115
<212> TYPE: PRT
<213> ORGANISM: Artificial Sequence
<220> FEATURE:
<223> OTHER INFORMATION: antibody sequence

<400> SEQUENCE: 241

Gln Val Gln Leu Gln Glu Ser Gly Gly Leu Val Gln Pro Gly Gly
1               5                   10                  15

Ser Leu Arg Leu Ser Cys Ala Ala Ser Gly Arg Val Phe Ser Ile Asn
            20                  25                  30

Thr Met Gly Trp Tyr Arg Gln Ala Pro Gly Lys Gln Arg Glu Leu Val
        35                  40                  45

Ala Ser Met Thr Arg Gly Gly Ser Ala Asn Tyr Ala Asp Ser Val Lys
    50                  55                  60

Gly Arg Phe Thr Thr Ser Arg Asp Asn Ala Lys Asn Met Val Tyr Leu
65                  70                  75                  80

Gln Met Asn Arg Leu Lys Ala Glu Asp Thr Ala Val Tyr Tyr Cys Asn
                85                  90                  95

Ala Ala Arg Gly Trp Arg Ile Tyr Trp Gly Lys Gly Thr Leu Val Thr
            100                 105                 110

Val Ser Ser
        115

<210> SEQ ID NO 242
<211> LENGTH: 498
<212> TYPE: DNA
<213> ORGANISM: Artificial Sequence
<220> FEATURE:
<223> OTHER INFORMATION: antibody sequence

<400> SEQUENCE: 242
atgaaatacc tattgcctac ggcggccgct ggattgttat tactcgcggc ccagccggcc    60
atggcgcagg tgcagttgca gcagtctggg ggaggcttgg tgcaggctgg gggatctctg   120
attctccgtt gtagagcaac tgtaagtggc ttcagtatcg ggaccatggg ctggtaccgc   180
caggctcccg ggaaggagcg cgagttcgtc gcgaacgtta gtcctagcgg tgcaaaatac   240
ttcgctgact ccgtgaaggg ccgattcacc atctccagag acaacgccaa taatacagtg   300
tatctgcaaa tgaacagtct gaaacctgaa gacacgggcg tctattattg taatatacga   360
aggttttcgt acctcagtgg cgactggggc caggggaccc aggtcaccgt ctcctcaact   420
```
agtggcccgg gaggccaaca ccatcaccac catcatggcg cagaacaaaa actcatctca    480
gaagaggatc tgtcttag    498

<210> SEQ ID NO 243
<211> LENGTH: 492
<212> TYPE: DNA
<213> ORGANISM: Artificial Sequence
<220> FEATURE:
<223> OTHER INFORMATION: antibody sequence

<400> SEQUENCE: 243
atgaaatacc tattgcctac ggcggccgct ggattgttat tactcgcggc ccagccggcc    60
atggcgcagg tgcagttgca ggagtctggg ggaggcttgg tgcaggctgg ggggtctctg    120
agactctcct gtgcagcctc tggattcacc ttcagtagca gttccatggg ctggtaccgc    180
caggctccag ggaagcagcg cgagttggtc gcttctatta tgcgttatgg tactacaacc    240
tatacagact ccgtgaaggg ccgattcacc atctccagag acaacggcca gagaacagtc    300
tatctgcaaa tgaacagcct gaagcctgag gacacggccg tctattattg taatgttcga    360
agtttcgttc gaacctactg gggccagggg accctggtca ccgtctcctc aactagtggc    420 ccggaggcc aacaccatca ccaccatcat ggcgcagaac aaaaactcat ctcagaagag    480
gatctgtctt ag    492

<210> SEQ ID NO 244
<211> LENGTH: 501
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(76)
<223> OTHER INFORMATION: n is a, c, g, or t

<400> SEQUENCE: 244
atgaaatacc tattgcctac ggcggccgct ggattgttat tactcgcggc ccagccggcc    60
atggcgcagg tgcagntgca ggagtctggg ggaggattgg tgcaggctgg gggctctctg    120
agactctcct gtgcagcctc tggacgcacc ttcagtagtt ttgccatggg ctggttccgc    180
caggctccag ggaaggagcg tgagtttgtt acagctatta actggagtgg tagtagcaca    240
tactatgcag actccgtgaa gggccgattc accatctcca gagacaacgc caagaacacg    300
gtgtatctgc aaatgaacag cctgaaacct gaggacacgg ccgtctatta ctgtaatgcc    360
cagcggaggt ggcctcttcg tgactattgg ggccagggga cccaggtcac cgtctcctca    420
actagtggcc cggaggcca acaccatcac caccatcatg gcgcagaaca aaaactcatc    480
tcagaagagg atctgtctta g    501

<210> SEQ ID NO 245
<211> LENGTH: 501
<212> TYPE: DNA
<213> ORGANISM: Artificial Sequence
<220> FEATURE:
<223> OTHER INFORMATION: antibody sequence

<400> SEQUENCE: 245
atgaaatacc tattgcctac ggcggccgct ggattgttat tactcgcggc ccagccggcc    60
atggcgcagg tgcaaaaaaa agagtctggg ggaggcttgg tgcaggctgg ggggtctctg    120
agactctcct gtgcagcctc tggactcatc ttcagtatca atgccatggc ctggtaccgc    180

-continued

```
caggctccag ggaaccagcg cgagttggtc gcacgtatta ctactggtgg tagcacaaac    240
tatgcagact ccgtgaaggg ccgattcacc atctccagag acaacgccaa gaacacggtg    300
tatctgcaaa tgaacagcct gaaacctgag acacagccg tctatttctg tgcagcagat    360
gtaaggtttg gggaacggac tccctactgg ggccagggga cccaggtcac cgtctcctca    420
actagtggcc cggggaggcca acaccatcac caccatcatg gcgcagaaca aaaactcatc    480
tcagaagagg atctgtctta g    501
```

<210> SEQ ID NO 246
<211> LENGTH: 492
<212> TYPE: DNA
<213> ORGANISM: Artificial Sequence
<220> FEATURE:
<223> OTHER INFORMATION: antibody sequence

<400> SEQUENCE: 246

```
atgaaatacc tattgcctac ggcggccgct ggattgttat tactcgcggc ccagccggcc    60
atggcgcagg tgcagttgca ggcgtctggg ggaggcgtgg tgcagtctgg ggggtctctg    120
agactctcct gtgtagcctc tggaaacatc ttcaggatca atgccatggg ctggtaccgc    180
caggctccag ggaagcagcg cgagttggtc gcacatatta ttagtggtgg tagcacaaac    240
tatgcagact ccgtgaaggg ccgattcacc atctccagag aatacgccaa gaatatggtg    300
tatctgcaaa tgaacagcct gaaacctgag acacggccg tctattactg taatgcccga    360
actttcgtga gaacctactg ggggccagggg acccaggtca ccgtctcctc aactagtggc    420 ccggggaggcc aacaccatca ccaccatcat ggcgcagaac aaaaactcat ctcagaagag    480
gatctgtctt ag    492
```

<210> SEQ ID NO 247
<211> LENGTH: 489
<212> TYPE: DNA
<213> ORGANISM: Artificial Sequence
<220> FEATURE:
<223> OTHER INFORMATION: antibody sequence

<400> SEQUENCE: 247

```
atgaaatacc tattgcctac ggcggccgct ggattgttat tactcgcggc ccagccggcc    60
atggcgcagg tgcagttgca gcagtttggg ggaggcttgg tgcagcctgg ggggtctctg    120
agactctcct gtcaagcctc tacaagtgtc ttcggtaaca ctgccatggc ctggtaccgc    180
caggctcctg ggaagcagcg cgagttggtc gcacgaatta ctacccttgg tttcacatac    240
tatgcagact ccgcgaaggg ccgattcacc atctctagag acagcgccat gaacacggtg    300
tatctgcaaa tgaacagcct gaaacctgag acacggccg tctattactg taaccgcaga    360
ggatttcgga gctactgggg ccaggggacc ctggtcaccg tctcctcaac tagtggcccg    420
ggaggccaac accatcacca ccatcatggc gcagaacaaa aactcatctc agaagaggat    480
ctgtcttag    489
```

<210> SEQ ID NO 248
<211> LENGTH: 520
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (97)..(97)

```
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t

<400> SEQUENCE: 248
atgaaatacc tattgcctac ggcggccgct ggattgttat tactcgcggc ccagccggcc      60
atggcgcagg tgcagttgca ggagtccggg ggaggcntng gtgcagtctg gcgattctct     120
gagactctcc tgtgcagcct ctggaagcat ctatcatgtc aataccatgg gttggtaccg     180
ccagtctcca ggaaagcagc gcgagttggt cgcaactctt acacataaca accgcgtaac     240
ctatgcagac tccgtgaagg gtcgattcac catctccaga caacgccaa agatgacggt      300 gtatctgcaa atggacagcc tgaaacccga tgacacggcc gtatattact gttactactt     360
cgtcccgcgt aatccattat cgggagaag gattgacttt gatgcctggg gccaggggac      420
ccaggtcacc gtctcctcaa ctagtggccc gggaggccaa caccatcacc accatcatgg     480
cgcagaacaa aaactcatct cagaagagga tctgtcttag                           520

<210> SEQ ID NO 249
<211> LENGTH: 492
<212> TYPE: DNA
<213> ORGANISM: Artificial Sequence
<220> FEATURE:
<223> OTHER INFORMATION: antibody sequence

<400> SEQUENCE: 249
atgaaatacc tattgcctac ggcggccgct ggattgttat tactcgcggc ccagccggcc      60
atggcgcagg tgcagttgca ggagtctggg ggaggcgtgg tgcagtctgg ggggtctctg     120
agactctcct gtgtagcctc tggaaacatc ttcaggatca atgtcatggg ctggtaccgc     180
caggctccag gaagcagcg cgagttggtc gcggttgtaa agagtggtgg tagcacaaac     240
tatgtagact ccgcgaaggg acgattcacc atctccaggg acaacgccaa gaacacagcg     300
tatctgcaca tggacagcct gaaacctgag gacacggccg tctattactg taatgcacaa     360
acccgactct ggagctactg gggccagggg acccaggtca ccgtttcctc aactagtggc     420 ccggggaggcc aacaccatca ccaccatcat ggcgcagaac aaaaactcat ctcagaagag     480
gatctgtctt ag                                                          492

<210> SEQ ID NO 250
<211> LENGTH: 492
<212> TYPE: DNA
<213> ORGANISM: Artificial Sequence
<220> FEATURE:
<223> OTHER INFORMATION: antibody sequence

<400> SEQUENCE: 250
atgaaatacc tattgcctac ggcggccgct ggattgttat tactcgcggc ccagccggcc      60
atggcgcagg tgcagctgca ggagtttggg ggaggcgtgg tgcagtctgg ggggtctctg     120
agactctcct gtgtagcctc tggaaacatc ttcaggatca atgccatggg ctggtaccgc     180
caggctccag gaagcagcg cgagttggtc gcacatatta ttagtggtgg tagcacaaac     240
tatgcagact ccgtgaaggg ccgattcacc atctccagag aatacgccaa gaatatggtg     300
tatctgcaaa tgaacagcct gaaacctgag gacacggccg tctattactg taatgcacaa     360
acccgactct ggagctactg gggccagggg acccaggtca ccgtctcctc aactagtggc     420 ccggggaggcc aacaccatca ccaccatcat ggcgcagaac aaaaactcat ctcagaagag     480
```
gatctgtctt ag                                                              492

<210> SEQ ID NO 251
<211> LENGTH: 495
<212> TYPE: DNA
<213> ORGANISM: Artificial Sequence
<220> FEATURE:
<223> OTHER INFORMATION: antibody sequence

<400> SEQUENCE: 251
atgaaatacc tattgcctac ggcggccgct ggattgttat tactcgcggc ccagccggcc    60
atggcgcagg tgcagctgca ggagtctggg ggaggcttgg tgcagcctgg ggggtctctg   120
agactctcct gtgcagcctc tcgaagcttc ttcagtatca atgccatggg ctggtaccgc   180
caggctccag ggaagcagcg cgagttggtc gcaactatta ctagtcgtga tagcacaaac   240
gttgcagact ccgtgaaggg ccgattcacc atctccagag actacgccaa gaacatagtg   300
tatctgcaaa tggacagcct gagacctgag gacacggcca catattactg ctacgctgat   360
caaccgtgga ggggtcgtgc ctggggccag ggacccagg tcaccgtctc ctcaactagt   420
ggcccgggag ccaacacca tcaccaccat catggcgcag aacaaaaact catctcagaa    480
gaggatctgt cttag                                                         495

<210> SEQ ID NO 252
<211> LENGTH: 492
<212> TYPE: DNA
<213> ORGANISM: Artificial Sequence
<220> FEATURE:
<223> OTHER INFORMATION: antibody sequence

<400> SEQUENCE: 252
atgaaatacc tattgcctac ggcggccgct ggattgttat tactcgcggc ccagccggcc    60
atggcgcagg tgcagttgca ggagtctggg ggaggcgtgg tgcaggccgg ggggtctctg   120
aacctctcct gtacacactc aacaatcacc ttcaggatca acaccatggc gtactatcgc   180
caggctccag gtctcagcg cgccctggtc gcgcggatta atccagcagg gaggacgtat   240
tatccagatt ccgtgaaggg ccgattcacc atctccagag acaacgccaa gaaccaagtg   300
tatctacaaa tgaacgacct caaacctgag gacacggccg tctattactg ttctacatgg   360
cgactaggac gcaactactg gggccagggg accctggtca ccgtctcctc aactagtggc   420 ccggggaggcc aacaccatca ccaccatcat ggcgcagaac aaaaactcat ctcagaagag   480
gatctgtctt ag                                                              492

<210> SEQ ID NO 253
<211> LENGTH: 498
<212> TYPE: DNA
<213> ORGANISM: Artificial Sequence
<220> FEATURE:
<223> OTHER INFORMATION: antibody sequence

<400> SEQUENCE: 253
atgaaatacc tattgcctac ggcggccgct ggattgttat tactcgcggc ccagccggcc    60
atggcgcagg tgcagttgca ggagtttggg ggaggcttgg tgcaggctgg gggggttctg   120
agactctcct gtgtagcctc tatgactacc ctcggtttca agaccatggg ctggtaccgc   180
caggctccag ggaagcagcg cgagttggtc gcaactatta gtagtattgg tatctcaacc   240
tatgcaaact ccgtgaaggg ccgattcacc atctccagag acaatgccaa gaacacagtg   300

```
tatctacaaa tgaacagcct gaaacctgag gacacggccg tctatttctg tcatgtaatt    360
cggcctagtt ggatgccgca gtactggggc caggggaccc tggtcaccgt ctcctcaact    420
agtggcccgg gaggccaaca ccatcaccac catcatggcg cagaacaaaa actcatctca    480
gaagaggatc tgtcttag                                                  498
```

```
<210> SEQ ID NO 254
<211> LENGTH: 490
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 254
```

```
atgaaatacc tattgcctac ggcggccgct ggattgttat tactcgcggc ccagccggcc     60
annaaancag gtgcagctgc aggagtttgg gggaggcttg gtgcagcctg ggggtgtctct   120 gagactctcc tgtcaagcct ctacaagtgt cttcggtaac actgccatgg cctggtaccg   180
ccaggctcct gggaagcagc gcgagttggt cgcacgaatt actacccttg gtttcacata   240
ctatgcagac tccgcgaagg gccgattcac catctctaga cagcgcca tgaacacggt    300 gtatctgcaa atgaacagcc tgaaacctga ggacacggcc gtgtattact gtaatagatt   360
atggcggcct ctagcgtggg gtcagggac ccaggtcacc gtctcctcaa ctagtggccc    420
gggaggccaa caccatcacc accatcatgg cgcagaacaa aaactcatct cagaagagga   480
tctgtcttag                                                          490
```

```
<210> SEQ ID NO 255
<211> LENGTH: 494
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 255
```

```
atgaaatacc tattgcctac ggcggccgct ggattgttat tactcgcggc ccagccggcc     60
atgnaaacan aaaacagctg caggagtctg ggggaggctt ggtgcagcct gggggtctc    120 tgagactctc ctgtgcagcc tctggaatgc gcagcagtct cgctatcatg gctggtacc    180 gccaggctcc agggaagcag cgcgagttgg tcgcaactat tactattggt ggtaacacaa   240
actatgcaga ctccgtgaag ggccggttcg ccatctccag agacaacacc aagcgcacgg   300
tgtatctgca gatgaacagc ctgacacctg aggacacggc cgtctattac tgtaatgttc   360
gaagtttcgt tagaacctac tggggccagg gacccaggt caccgtctcc tcaactagtg    420
gcccgggagg ccaacaccat caccaccatc atggcgcaga caaaaactc atctcagaag   480 aggatctgtc ttag                                                     494
```

<210> SEQ ID NO 256
<211> LENGTH: 492
<212> TYPE: DNA
<213> ORGANISM: Artificial Sequence
<220> FEATURE:
<223> OTHER INFORMATION: antibody sequence

<400> SEQUENCE: 256

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggagtctggg | ggaggcttgg | tgcaggctgg | ggggtctctg | 120 |
| agactctcct | gtgcagcctc | tggattcacc | ttcagtagca | gttccatggg | ctggtaccgc | 180 |
| caggctccag | ggaagcagcg | cgagttggtc | gcttctatta | tgcgttatgg | tactacaacc | 240 |
| tatacagact | ccgtgaaggg | ccgattcacc | atctccagag | acaacggcca | gagaacagtc | 300 |
| tatctgcaaa | tgaacagcct | gaagcctgag | gacacggccg | tctattattg | taatgttcga | 360 |
| agtttcgttc | gaacctactg | gggccagggg | accctggtca | ccgtctcctc | aactagtggc | 420 |
| ccggaggcc | aacaccatca | ccaccatcat | ggcgcagaac | aaaaactcat | ctcagaagag | 480 |
| gatctgtctt | ag | | | | | 492 |

<210> SEQ ID NO 257
<211> LENGTH: 498
<212> TYPE: DNA
<213> ORGANISM: Artificial Sequence
<220> FEATURE:
<223> OTHER INFORMATION: antibody sequence

<400> SEQUENCE: 257

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | gcagtctggg | ggaggcttgg | tgcaggctgg | ggggtctctg | 120 |
| agactctcct | gtgcagcctc | tggaagcacc | ttcatcagta | tcaaaaccat | gggctggtac | 180 |
| cgccaggctc | cagggaagca | gcgcgagttg | gtcgctggta | ttactaagaa | taattacata | 240 |
| aactatgcag | actccgtgaa | gggccgattc | accatctcca | gagacaacgg | caagaataca | 300 |
| gtgtatctgc | aaatgaacgg | cctgaaacct | gaggacacgg | ccgtctatta | ctgtactgta | 360 |
| caacgtcgct | tagggcgtgt | ctactggggc | caggggaccc | tggtcaccgt | ctcctcaact | 420 |
| agtggcccgg | gaggccaaca | ccatcaccac | catcatggcg | cagaacaaaa | actcatctca | 480 |
| gaagaggatc | tgtcttag | | | | | 498 |

<210> SEQ ID NO 258
<211> LENGTH: 492
<212> TYPE: DNA
<213> ORGANISM: Artificial Sequence
<220> FEATURE:
<223> OTHER INFORMATION: antibody sequence

<400> SEQUENCE: 258

| | | | | | |
|---|---|---|---|---|---|
| atgaaatacc | tattgcctac | ggcggccgct | ggattgttat | tactcgcggc | ccagccggcc | 60 |
| atggcgcagg | tgcagctgca | ggagtctggg | ggaggcttgg | tgcaggctgg | ggggtctctg | 120 |
| agactctcct | gtacggcctc | tggaagcacc | ttcaggttca | tgacatgggc | tggtaccgc | 180 |
| caggctccag | ggaagcagcg | cgaattggtc | gcaaatatta | atagtagtgg | tagaaccatg | 240 |
| tatccagact | ccgtcaaggg | ccgattcaca | atctccaaag | acaacgtcaa | aaatacagtg | 300 |
| tatctgcaga | tgaacagcct | gacacctgag | gacacggccg | tctattactg | taatgttcga | 360 |

| | | |
|---|---|---|
| agtttcgtta gaacctactg gggccagggg acccaggtca ccgtctcctc aactagtggc | 420 | |
| ccgggaggcc aacaccatca ccaccatcat ggcgcagaac aaaaactcat ctcagaagag | 480 | |
| gatctgtctt ag | 492 | |

<210> SEQ ID NO 259
<211> LENGTH: 489
<212> TYPE: DNA
<213> ORGANISM: Artificial Sequence
<220> FEATURE:
<223> OTHER INFORMATION: antibody sequence

<400> SEQUENCE: 259

| | | |
|---|---|---|
| atgaaatacc tattgcctac ggcggccgct ggattgttat tactcgcggc ccagccggcc | 60 | |
| atggcgcagg tgcagctgca ggagtctggg ggaggcttgg tccaggctgg ggggtctctg | 120 | |
| acgctctcct gtgtagcctc tggaagccgc ttcagtatca ataccatggg ctggtaccgc | 180 | |
| caggctccag ggaagcagcg cgagttggtc gcaggtatta ctagccttgg tttcacaaac | 240 | |
| tatgcagact ccgtgaaggg ccgattcacc atctccagag acaacgccaa gaacacagtg | 300 | |
| tatctgcaaa tgaacaacct gaaagttgag gacacggccg tctattactg taaccgcaga | 360 | |
| ggatttcgga gctactgggg ccaggggacc ctggtcaccg tctcctcaac tagtggcccg | 420 | |
| ggaggccaac accatcacca ccatcatggc gcagaacaaa aactcatctc agaagaggat | 480 | |
| ctgtcttag | 489 | |

<210> SEQ ID NO 260
<211> LENGTH: 489
<212> TYPE: DNA
<213> ORGANISM: Artificial Sequence
<220> FEATURE:
<223> OTHER INFORMATION: antibody sequence

<400> SEQUENCE: 260

| | | |
|---|---|---|
| atgaaatacc tattgcctac ggcggccgct ggattgttat tactcgcggc ccagccggcc | 60 | |
| atggcgcagg tgcagctcgt ggagtctggg ggaggcttcg tgcaggctgg ggggtctctg | 120 | |
| agactctcct gtgcagcctc tggaagcatc ttcagtatca attatggtaa ctggtaccgc | 180 | |
| caggctccag ggaagcagcg cgaattggtc gcaggtatta gtcgtggagg ccgcacaaag | 240 | |
| tatgcagact ccgtgaaggg ccgattcacc atctccagag atagcgccaa gacactgacg | 300 | |
| ctgcagatga ctagcttgaa acctgaggac acggccgtct attactgtaa tgttcgaagt | 360 | |
| ttcgttcgaa cctactgggg ccaggggacc caggtcaccg tttcctcaac tagtggcccg | 420 | |
| ggaggccaac accatcacca ccatcatggc gcagaacaaa aactcatctc agaagaggat | 480 | |
| ctgtcttag | 489 | |

<210> SEQ ID NO 261
<211> LENGTH: 489
<212> TYPE: DNA
<213> ORGANISM: Artificial Sequence
<220> FEATURE:
<223> OTHER INFORMATION: antibody sequence

<400> SEQUENCE: 261

| | | |
|---|---|---|
| atgaaatacc tattgcctac ggcggccgct ggattgttat tactcgcggc ccagccggcc | 60 | |
| atggcgcagg tgcagctgca ggagtctggg ggaggcttgg tgcagtcggg ggggtctctg | 120 | |
| agactctcct gttcggcctc cggaagcatc ttcaggatca atctcatggg ctggtaccgc | 180 | |
| caggctccag ggaagcagcg cgagttggtc gcaactatta ctaatgaagg taacacatac | 240 | |

```
tacgcagact ccgtgaaggg ccgtttcacc atctccagag acaacgccaa caacacgtgg    300
tatctgcaaa tgaacagcct gaaacctgag gacacagccg tctatgaatg tgcaggaaag    360
gtcattagat ggtactgggg ccaggggacc caggtcaccg tttcctcaac tagtggcccg    420
ggaggccaac accatcacca ccatcatggc gcagaacaaa aactcatctc agaagaggat    480
ctgtcttag                                                           489
```

<210> SEQ ID NO 262
<211> LENGTH: 495
<212> TYPE: DNA
<213> ORGANISM: Artificial Sequence
<220> FEATURE:
<223> OTHER INFORMATION: antibody sequence

<400> SEQUENCE: 262

```
atgaaatacc tattgcctac ggcggccgct ggattgttat tactcgcggc ccagccggcc    60
atggcgcagg tgcagctgca ggagtttggg ggaggcttgg tgcagcctgg ggggtctctg    120
agactctcct gtcaagcctc tacaagtgtc ttcggtaaca ctgccatggc ctggtaccgc    180
caggctcctg ggaagcagcg cgagttggtc gcacgaatta ctacccttgg tttcacatac    240
tatgcagact ccgcgaaggg ccgattcacc atctctagag acagcgccat gaacacggtg    300
tatctgcaaa tgaacagcct gaaacctgag gacacggccg tttattactg tgtgcacgt    360 cgcgctctgc gagaatcgca ctggggccag gggacccagg tcaccgtctc ctcaactagt    420
ggcccgggag ccaacaccat caccaccat catggcgcag aacaaaaact catctcagaa    480
gaggatctgt cttag                                                   495
```

<210> SEQ ID NO 263
<211> LENGTH: 489
<212> TYPE: DNA
<213> ORGANISM: Artificial Sequence
<220> FEATURE:
<223> OTHER INFORMATION: antibody sequence

<400> SEQUENCE: 263

```
atgaaatacc tattgcctac ggcggccgct ggattgttat tactcgcggc ccagccggcc    60
atggcgcagg tgcagctgca ggagtctggg ggaggcttcg tgcaggctgg ggggtctctg    120
agactctcct gtcagcctc tggaagcatc ttcagtatca attatggtaa ctggtaccgc    180
caggctccag ggaagcagcg cgaattggtc gcaggtatta gtcgtggagg ccgcacaaag    240
tatgcagact ccgtgaaggg ccgattcacc atctccagag atagcgccaa gacactgacg    300
ctgcagatga ctagcttgaa acctgaggac acggccatct attcttgtaa tgctcgaagt    360
ttcgttagaa cttactgggg ccaggggacc ctggtcaccg tctcctcaac tagtggcccg    420
ggaggccaac accatcacca ccatcatggc gcagaacaaa aactcatctc agaagaggat    480
ctgtcttag                                                           489
```

<210> SEQ ID NO 264
<211> LENGTH: 507
<212> TYPE: DNA
<213> ORGANISM: Artificial Sequence
<220> FEATURE:
<223> OTHER INFORMATION: antibody sequence

<400> SEQUENCE: 264

```
atgaaatacc tattgcctac ggcggccgct ggattgttat tactcgcggc ccagccggcc    60
```

```
atggcgcagg tgcagctgca ggagtctggg ggaggcttgg tgacggctgg agggtctctg    120
agactctcct gtgcagcctc tagaaacttc ttcactttca gagccatggg ctggtaccgc    180
caggctccag ggaagcagcg cgaaatggtc gcatctatta ctaccggtgg tcgcaccgtc    240
tatgcagact ccgtgaaggg ccgattcacc atctccaaat ccaacgccaa taacacagtg    300
tatctccaaa tgaacagcct ggaagctgag gacacggccg tctattactg taatgcacga    360
cgcagatttc cggtgccggg cccgaccgac tactggggcc gggggaccct ggtcaccgtc    420
tcctcaacta gtggcccggg aggccaacac catcaccacc atcatggcgc agaacaaaaa    480
ctcatctcag aagaggatct gtcttag                                         507
```

<210> SEQ ID NO 265
<211> LENGTH: 480
<212> TYPE: DNA
<213> ORGANISM: Artificial Sequence
<220> FEATURE:
<223> OTHER INFORMATION: antibody sequence

<400> SEQUENCE: 265

```
atgaaatacc tattgcctac ggcggccgct ggattgttat tactcgcggc ccagccggcc     60
atggcgcagg tgcagctgca ggagtctggg ggaggcttgg tgcaggctgg ggggtctctg    120
agactctcct gtgcagcctc tggaatcacc ttcaggttca atgccatggg ctggtaccgc    180
caggctccag ggaagagcg cgagttggtc gcaagggtta gtagtggtgg tagcacaacc    240
tatgcagact ccgtgaaggc ccgattcacc accttcagag acaacgtcaa gaacataggg    300
tatctgcaaa tgaccagcct gaaacctgag gacacggccg tctattactg taatgtgggg    360
aatttctggg gccaggggac ccaggtcacc gtctcctcaa ctagtggccc gggaggccaa    420
caccatcacc accatcatgg cgcagaacaa aaactcatct cagaagagga tctgtcttag    480
```

<210> SEQ ID NO 266
<211> LENGTH: 492
<212> TYPE: DNA
<213> ORGANISM: Artificial Sequence
<220> FEATURE:
<223> OTHER INFORMATION: antibody sequence

<400> SEQUENCE: 266

```
atgaaatacc tattgcctac ggcggccgct ggattgttat tactcgcggc ccagccggcc     60
atggcgcagg tgcagctgca ggagtctggg ggaggcttgg tgcggactgg ggagtctctg    120
ggactctcct gtgcagcctc tggacgcagc atcctgatca aaggcatggg ctggtaccgc    180
caggctccag ggaaggagcg cgaaatggtc gcgactatta gtatggccgg tgtcactaac    240
tattcagact ccgtgaaggg ccggttcacc atctccagag ataactacaa gaagacagtg    300
tccctgcaga tgaacaattt gagaccggag gacacggccg tctatgtgtg taatgcacaa    360
acccgactct ggagctactg gggccagggg acccaggtca ccgtctcctc aactagtggc    420
ccgggaggcc aacaccatca ccaccatcat ggcgcagaac aaaaactcat ctcagaagag    480
gatctgtctt ag                                                          492
```

<210> SEQ ID NO 267
<211> LENGTH: 492
<212> TYPE: DNA
<213> ORGANISM: Artificial Sequence
<220> FEATURE:
<223> OTHER INFORMATION: antibody sequence

<400> SEQUENCE: 267

```
atgaaatacc tattgcctac ggcggccgct ggattgttat tactcgcggc ccagccggcc    60
atggcgcagg tgcagctcgt ggagtctggg ggaggcctgg tgcaggctgg agggtctctg   120
agactctcct gtgcagcctc tggaaggatt tcgggcgca atgccatggc ctggtaccgc   180
caggttccag ggaaggagcg cgagctggtt gcacgtatta ctagggatgg acggacaatg   240
tatgtagact ccgcgaaggg acgattcacc atctccaggg acaacgccaa gaacacagcg   300
tatctgcaca tggacagcct gaaacctgag gacacggccg tctattactg taatgcacaa   360
acccgactct ggagctactg gggccagggg acccaggtca ccgtctcctc aactagtggc   420
ccgggaggcc aacaccatca ccaccatcat ggcgcagaac aaaaactcat ctcagaagag   480
gatctgtctt ag                                                       492
```

```
<210> SEQ ID NO 268
<211> LENGTH: 496
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (70)..(73)
<223> OTHER INFORMATION: n is a, c, g, or t

<400> SEQUENCE: 268
```

```
atgaaatacc tattgcctac ggcggccgct ggattgttat tactcgcggc ccagccggcc    60
atggcgcagn nnncagctgc aggagtctgg gggaggcttg gtgcaggctg ggggtctct    120 gagactctcc tgtgcagcct ctagaagcac cttcagattc aatgtcatgg ctggtaccg    180 ccaggctcca gggaagcagc gcgagttggt cgcagctatt agtagtcgtg gtggtagtac   240
aaactatgca gactccgtgc agggccgatt caccatctcc agagacaacg ccaagaacac   300
agtgtctctg caaatgaaca gcctgaaacc tgaggacacg gccgtctatt actgtaatgt   360
tcgaagtttc gttagaacct actggggcca ggggacccag gtcaccgtct cctcaactag   420
tggcccggga ggccaacacc atcaccacca tcatggcgca gaacaaaaac tcatctcaga   480
agaggatctg tcttag                                                  496
```

```
<210> SEQ ID NO 269
<211> LENGTH: 516
<212> TYPE: DNA
<213> ORGANISM: Artificial Sequence
<220> FEATURE:
<223> OTHER INFORMATION: antibody sequence

<400> SEQUENCE: 269
```

```
atgaaatacc tattgcctac ggcggccgct ggattgttat tactcgcggc ccagccggcc    60
atggcgcagg tgcagctgca ggagtttggg ggaggcttgg tgcaggctgg gggtctctg    120 agactctcct gtgcaacctc tggaagcatc ttcagtatca acgccgtggg ctggtaccgc   180
caggctccag ggaatcagcg cgagttggtc gcagctatta gtggacgtgg tagtacacac   240
tatgcagact ccgtgaaggg ccgattcacc atctccagag acaccgccaa gaacacggtg   300
tatctgcaaa tgaacagcct gaaacctgag gacacagccg tctattactg tgcattagat   360
caacatatgg aggttattgt atcgccggga cgtattggtt cctggggcca ggggaccctg   420
gtcaccgtct cctcaactag tggcccggga ggccaacacc atcaccacca tcatggcgca   480
gaacaaaaac tcatctcaga agaggatctg tcttag                            516
```

<210> SEQ ID NO 270
<211> LENGTH: 498
<212> TYPE: DNA
<213> ORGANISM: Artificial Sequence
<220> FEATURE:
<223> OTHER INFORMATION: antibody sequence

<400> SEQUENCE: 270

```
atgaaatacc tattgcctac ggcggccgct ggattgttat tactcgcggc ccagccggcc      60
atggcgcagg tgcagttgca ggagtctggg ggaggcttgg tgcaggctgg ggagtctctg     120
acactctcct gtgcactctc aacaaccatg ttcggtttct ggcccatggc ctggttccgc     180
cagactccag gacagcggcg cgaattgatt gcgactattg atagtcgtgg tcgcacaaac     240
atcgcagact ccgtgaaggg ccgatttacc atctccagag acaacaccaa gaacacactg     300
tatctgcgga tgaacagcct gaaacctgag gacacggccg tctattactg taatgcccag     360
cggaggtggc ctcttcgtga ctattggggc caggggaccc aggtcaccgt ctcctcaact     420
agtgccccgg gaggccaaca ccatcaccac catcatggcg cagaacaaaa actcatctca     480
gaagaggatc tgtcttag                                                   498
```

<210> SEQ ID NO 271
<211> LENGTH: 498
<212> TYPE: DNA
<213> ORGANISM: Artificial Sequence
<220> FEATURE:
<223> OTHER INFORMATION: antibody sequence

<400> SEQUENCE: 271

```
atgaaatacc tattgcctac ggcggccgct ggattgttat tactcgcggc ccagccggcc      60
atggcgcagg tgcagctgca ggagtttggg ggaggcgtgg tgcagtctgg ggggtctctg     120
agactctcct gtgtagcctc tggaaacatc ttcaggatca atgccatggg ctggtaccgc     180
caggctccag ggaagcagcg cgagttggtc gcccgtatta gtagtggtgg tagcacaaac     240
tatgcagact ccgtgaaggg ccgattcacc atctccagag acaacgtcaa gaacacagtg     300
actctgcaaa tgaacagcct gaaacctgag gacacggccg tctattactg taatgcgcgg     360
aggccattgc gttggtatga gtactggggc caggggaccc tggtcaccgt ctcctcaact     420
agtgccccgg gaggccaaca ccatcaccac catcatggcg cagaacaaaa actcatctca     480
gaagaggatc tgtcttag                                                   498
```

<210> SEQ ID NO 272
<211> LENGTH: 510
<212> TYPE: DNA
<213> ORGANISM: Artificial Sequence
<220> FEATURE:
<223> OTHER INFORMATION: antibody sequence

<400> SEQUENCE: 272

```
atgaaatacc tattgcctac ggcggccgct ggattgttat tactcgcggc ccagccggcc      60
atggcgcagg tgcagctgca ggcgtctggg ggaggcttgg tgcagcctgg gggatctctg     120
agactctcct gtgcagcctc gggaagcatc ttcagtacca atgccatggg ctggtaccgc     180
caggctccag ggaagcagcg cgaggtgatc gcatctatta caaaatttgg gaacacagac     240
tatgcagact ctgtgaaggg ccgattcacc atctccagag acaacgccaa gaacatagtg     300
tatctgcaaa tgaacagcct gaaacctgag gacacggccg tttattactg ttatcaaaac     360
agtcgggggc gctggtatga tattttcagg gactactggg gccaggggac cctggtcacc     420
```

```
gtctcctcaa ctagtggccc gggaggccaa caccatcacc accatcatgg cgcagaacaa    480
aaactcatct cagaagagga tctgtcttag                                     510

<210> SEQ ID NO 273
<211> LENGTH: 498
<212> TYPE: DNA
<213> ORGANISM: Artificial Sequence
<220> FEATURE:
<223> OTHER INFORMATION: antibody sequence

<400> SEQUENCE: 273
atgaaatacc tattgcctac ggcggccgct ggattgttat tactcgcggc ccagccggcc     60
atggcgcagg tgcagctcgt ggagtctggg ggtggcttcg tgcaggcagg gggatctcta    120
agactctcct gtgtagcctc gcgaagcagc ttcaggatca ctaccatgaa ctggtaccgc    180
caggctccag ggaagcagcg cgaaatggtc gcatctatta ctaccggtgg tcgcaccgtc    240
tatgcagact ccgtgaaggg ccgattcacc atctccaaat ccaacgccaa taacacagtg    300
tatctccaaa tgaacagcct ggaagctgag gacacggccg tctattactg taatgcccag    360
cggaggtggc ctcttcgtga ctattggggc caggggaccc tggtcaccgt ctcctcaact    420
agtggcccgg aggccaaca ccatcaccac catcatggcg cagaacaaaa actcatctca     480
gaagaggatc tgtcttag                                                  498

<210> SEQ ID NO 274
<211> LENGTH: 492
<212> TYPE: DNA
<213> ORGANISM: Artificial Sequence
<220> FEATURE:
<223> OTHER INFORMATION: antibody sequence

<400> SEQUENCE: 274
atgaaatacc tattgcctac ggcggccgct ggattgttat tactcgcggc ccagccggcc     60
atggcgcagg tgcagttgca ggagtctggg ggaggcgtgg tgcagtctgg ggggtctctg    120
agactctcct gtgtagcctc tggaaacatc ttcaggatca atgtcatggg ctggtaccgc    180
caggctccag ggaagcagcg cgagttggtc gcggttgtaa agagtggtgg tagcacaaac    240
tatgtagact ccgcgaaggg acgattcacc atctccaggg acaacgccaa gaacacagcg    300
tatctgcaca tggacagcct gaaacctgag gacacggccg tctattactg taatgcacaa    360
acccgactct ggagctactg gggccagggg accctggtca ccgtctcctc aactagtggc    420
ccgggaggcc aacaccatca ccaccatcat ggcgcagaac aaaaactcat ctcagaagag    480
gatctgtctt ag                                                        492

<210> SEQ ID NO 275
<211> LENGTH: 498
<212> TYPE: DNA
<213> ORGANISM: Artificial Sequence
<220> FEATURE:
<223> OTHER INFORMATION: antibody sequence

<400> SEQUENCE: 275
atgaaatacc tattgcctac ggcggccgct ggattgttat tactcgcggc ccagccggcc     60
atggcgcagg tgcagctgca ggagtttggg ggaggcgtgg tgcagtctgg ggggtctctg    120
agactctcct gtgtagcctc tggaaacatc ttcaggatca atgccatggg ctggtaccgc    180
caggctccag ggaagcagcg cgagttggtc gcacatatta ttagtggtgg tagcacaaac    240
```

| | |
|---|---|
| tatgcagact ccgtgaaggg ccgattcacc atctccagag aatacgccaa gaatatggtg | 300 |
| tatctgcaaa tgaacagcct gaaacctgag gacacggccg tctattactg taatgccgaa | 360 |
| aggagattcg ggatgagaca ggtctggggc caggggaccc aggtcaccgt ctcctcaact | 420 |
| agtggcccgg gaggccaaca ccatcaccac catcatggcg cagaacaaaa actcatctca | 480 |
| gaagaggatc tgtcttag | 498 |

```
<210> SEQ ID NO 276
<211> LENGTH: 513
<212> TYPE: DNA
<213> ORGANISM: Artificial Sequence
<220> FEATURE:
<223> OTHER INFORMATION: antibody sequence

<400> SEQUENCE: 276
```

| | |
|---|---|
| atgaaatacc tattgcctac ggcggccgct ggattgttat tactcgcggc ccagccggcc | 60 |
| atggcgcagg tgcagttgca ggagtctggg ggaggcttgg tgcaggctgg ggggtctctg | 120 |
| agactctcct gtgcagcctc tgtggttccc ttcagatact ttcccatggg ctggtaccgc | 180 |
| caggctccag ggagacagcg cgagttggtc gcgtctatta ccagcggtgg tggcgtaaac | 240 |
| tatgcagatt tcgtagaggg ccgattcacc atctccagag acaatgccaa gaacacattt | 300 |
| tatctacaaa tgagcagcct gaaacctgag gacacggccg tctattactg tgcacgactt | 360 |
| ctcagtctgg gtagtaggtg gggataccgg atgttcacct ggggcaaagg gaccctggtc | 420 |
| accgtctcct caactagtgg cccgggaggc aacaccatc accaccatca tggcgcagaa | 480 |
| caaaaactca tctcagaaga ggatctgtct tag | 513 |

```
<210> SEQ ID NO 277
<211> LENGTH: 498
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t

<400> SEQUENCE: 277
```

| | |
|---|---|
| atgaaatacc tattgcctac ggcggccgct ggattgttat tactcgcggc ccagccggcc | 60 |
| atggcgcagg tgcagntnca ggagtctggg ggaggcttgg tgcagcctgg ggggtctctg | 120 |
| agactctcct gtgcagcctc tggaagcatc ttcagtatca agaccatggg ctggtaccgc | 180 |
| caggctccag ggaagcagcg cgagttggtc gctgctatag ctagtggtgg tttcacaaac | 240 |
| tatgcagact ccgtgaaggg ccgattcacc atctccagag acaacgccag gaacacggtg | 300 |
| tatctgcaaa tgaacagcct gaaacctgag gacacggccg tctattactg taatgcccag | 360 |
| cggaggtggc ctcttcgtga ctattgggc caggggaccc tggtcaccgt ttcctcaact | 420 |
| agtggcccgg gaggccaaca ccatcaccac catcatggcg cagaacaaaa actcatctca | 480 |
| gaagaggatc tgtcttag | 498 |

```
<210> SEQ ID NO 278
<211> LENGTH: 498
<212> TYPE: DNA
<213> ORGANISM: Artificial Sequence
```

```
<220> FEATURE:
<223> OTHER INFORMATION: antibody sequence
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 278
atgaaatacc tattgcctac ggcggccgct ggattgttat tactcgcggc ccagccggcc      60
atggcgcagg tgcagntgca gnagtcaggg ggaggcttgg tacgggacgg ggggtctctg     120
acactctcct gtgcagcctc tggaagtgcc ttcaggatga attccatggc ctggtaccgc     180
caggttcctg ggaaacagcg cgagttagtc gcagctatta gcttccgtgg gagcgcaaat     240
tatgctaact ccgtgaaggg ccgattcacc atctccagag acaacggcaa gaacacggta     300
tatctacaaa tgaacagcct gaaacctgag gacacagccg tctattactg tgcagcaggc     360
cgtccatggc aaaggacttt ctactggggc caggggaccc aggtcaccgt ctcctcaact     420
agtggcccgg gaggccaaca ccatcaccac catcatggcg cagaacaaaa actcatctca     480
gaagaggatc tgtcttag                                                   498

<210> SEQ ID NO 279
<211> LENGTH: 498
<212> TYPE: DNA
<213> ORGANISM: Artificial Sequence
<220> FEATURE:
<223> OTHER INFORMATION: antibody sequence

<400> SEQUENCE: 279
atgaaatacc tattgcctac ggcggccgct ggattgttat tactcgcggc ccagccggcc      60
atggcgcagg tgcagttgca ggagtctggg ggaggcttcg tgcaggctgg ggggtctctg     120
agactctcct gtgcagcctc tggaagcatc ttcagtatca attatggtaa ctggtaccgc     180
caggctccag ggaagcagcg cgaattggtc gcaggtatta gtcgtggagg ccgcacaaag     240
tatgcagact ccgtgaaggg ccgattcacc atctccagag atagcgccaa gacactgacg     300
ctgcagatga ctagcttgaa acctgaggat tcgggcgtct actactgtgc tgcgacccgc     360
tggagttggg gtactaagag ttactggggc cagggaaccc aggtcaccgt ctcctcaact     420
agtggcccgg gaggccaaca ccatcaccac catcatggcg cagaacaaaa actcatctca     480
gaagaggatc tgtcttag                                                   498

<210> SEQ ID NO 280
<211> LENGTH: 492
<212> TYPE: DNA
<213> ORGANISM: Artificial Sequence
<220> FEATURE:
<223> OTHER INFORMATION: antibody sequence

<400> SEQUENCE: 280
atgaaatacc tattgcctac ggcggccgct ggattgttat tactcgcggc ccagccggcc      60
atggcgcagg tgcagctgca ggagtttggg ggaggcgtgg tgcagtctgg ggggtctctg     120
agactctcct gtgtagcctc tggaaacatc ttcaggatca atgccatggg ctggtaccgc     180
caggctccag gcaagtcacg cgtactggtc gcaagcattg atagtgccgg taggacaaac     240
tatggtgacg ccgtagagga tcgattcacc atctccagag acatcgccaa caacatagtg     300
```

```
aatctacaga tgaatagcct aaaacctgag gacacggccg tctattactg ttctacatgg    360
cgactaggac gcaactactg gggccagggg acccaggtca ccgtctcctc aactagtggc    420
ccgggaggcc aacaccatca ccaccatcat ggcgcagaac aaaaactcat ctcagaagag    480
gatctgtctt ag                                                        492
```

<210> SEQ ID NO 281
<211> LENGTH: 528
<212> TYPE: DNA
<213> ORGANISM: Artificial Sequence
<220> FEATURE:
<223> OTHER INFORMATION: antibody sequence

<400> SEQUENCE: 281

```
atgaaatacc tattgcctac ggcggccgct ggattgttat tactcgcggc ccagccggcc     60
atggcgcagg tgcagttgca ggagtctggg ggaggcttgg tgcaggctgg gggctctctg    120
agactctcct gtgcagcctc tggaagcatc ttccgtatca atggcatggg ctggatccgc    180
caggctccag ggaaggagcg tgaggttgta gcagccgtta actggagtgg tgaacgcaca    240
tactatgttg actccgtgaa gggccgattc accatctcca gagaaaaagg caacaggata    300
tatctacaaa tgaacgattt ggaacctgac gacacggccg tttattactg tgcagcagat    360
acggattacc gtttagacgg tagtacgtgg attaccaacc tctactctgg gtccttgggc    420
caggggaccc aggtcaccgt ctcctcaact agtggcccgg gaggccaaca ccatcaccac    480
catcatggcg cagaacaaaa actcatctca gaagaggatc tgtcttag                 528
```

<210> SEQ ID NO 282
<211> LENGTH: 390
<212> TYPE: DNA
<213> ORGANISM: Artificial Sequence
<220> FEATURE:
<223> OTHER INFORMATION: antibody sequence

<400> SEQUENCE: 282

```
caggtgcagc tgcaggagtc tgggggaggc ttggtgcagg ctggggggtc tctgagactc     60
tcctgtgcag cctctggaag caccttcagt aacaatgcca tggcctggta ccgccaggct    120
ccagggaagc agcgcgagtt ggtcgcctat attagtagtg gtggtttcac aaattatggc    180
gactccgtga agggccgatt caccatctcc aagacaacgc caagagtac agtgtatcta    240 caaatgacca gcctgaaacc tgaggacacg gccgtctatt attgtagcgc cggggtaca    300 taccgtagtg gtaatgtcta ctttctttccg cgttcctggg gccaggggac ccaggtcacc    360
gtctcctcaa ctagtggccc gggaggccaa                                     390
```

<210> SEQ ID NO 283
<211> LENGTH: 366
<212> TYPE: DNA
<213> ORGANISM: Artificial Sequence
<220> FEATURE:
<223> OTHER INFORMATION: antibody sequence

<400> SEQUENCE: 283

```
caggtgcagt tgcagcagtc tgggggaggg ttggtgcagc tggggggtc tctgagactc      60 tcctgtgcag cctctggaag catcttcagt atcaattcca tggcctggta ccgccaggct    120
ccagggaacc agcgcgagtt ggtcgcgact attagtagtc gtagtaccac gtactatgcg    180
ccttccgtga agggccggtt caccatctcc agagacaacg ccaagaacat agtgtacctg    240
caaatgaaca gcctcaaacc tgaggacacg gccgtgtatt actgtaaggc gggttcagtg    300
```

```
ggtcgcgtgt actggggcca ggggaccctg gtcaccgtct cctcaactag tggcccggga      360
ggccaa                                                                 366

<210> SEQ ID NO 284
<211> LENGTH: 384
<212> TYPE: DNA
<213> ORGANISM: Artificial Sequence
<220> FEATURE:
<223> OTHER INFORMATION: antibody sequence

<400> SEQUENCE: 284
caggtgcagt tgcaggagtc tgggggaggc ttggtgcagg ctgggggttc tctgagactc      60
tcctgtttag cctctatgac taccctcggg ttcaagacca tgggctggta ccgccaggct     120
ccagggaagc agcgcgagtt ggtcgccgct attacgagtg gtggtaccgc aaactatgca     180
gactccgtga agggccgatt cgccatctcc agagagaacg ccaagaacac gctgtatctg     240
caaatgaaca gcctgaaacc tgaggacacg gccctgtatt actgtgcatc gactacgggt     300
tggacagagg tcggcggacg aaatgactac tggggccagg gaccctggt caccgtttcc      360 tcaactagtg gcccggagg ccaa                                             384

<210> SEQ ID NO 285
<211> LENGTH: 372
<212> TYPE: DNA
<213> ORGANISM: Artificial Sequence
<220> FEATURE:
<223> OTHER INFORMATION: antibody sequence

<400> SEQUENCE: 285
caggtgcagc tgcaggagtc tgggggagga ttggtgcaga ctgggggttc tcttagactc      60
tcctgtgcgg cctctgggcg caccttcaga gtcaatgcca tgggctggta ccgccaggct     120
ccagggaagc agcgcgagtt cgtcgcagct gttacaaatg gtggtagtac aacctatgca     180
gattccgtga agggccgatt caccatctcc agggacaacg ccaagaatac aatatatctg     240
caaatgaaca gactggaacc tgaagacacg gccctctatt attgtaatgc cgaaaggaga     300
ttcgggatga gacaggtctg ggggccaggg accctggtca ccgtttcctc aactagtggc     360
ccgggaggcc aa                                                         372

<210> SEQ ID NO 286
<211> LENGTH: 366
<212> TYPE: DNA
<213> ORGANISM: Artificial Sequence
<220> FEATURE:
<223> OTHER INFORMATION: antibody sequence

<400> SEQUENCE: 286
caggtgcagc tgcaggagtc tgggggaggc ttggtgcagc ctgggggttc tctgagactc      60
tcctgtgcag cctctggaag agtcttcagt atcaatacca tgggctggta ccgccaggct     120
ccagggaagc agcgcgagtt ggtcgcatct atgactagag gtggtagcgc aaattatgca     180
gactccgtga agggccgatt caccacatcc agagacaacg ccaagaacat ggtgtatctg     240
caaatgaata gactgaaagc tgaggacacg gccgtctatt actgtaatgc agctcggggt     300
tggaggatct actggggcaa agggaccctg gtcaccgttt cctcaactag tgcccggga     360 ggccaa                                                                366

<210> SEQ ID NO 287
```

<211> LENGTH: 492
<212> TYPE: DNA
<213> ORGANISM: Artificial Sequence
<220> FEATURE:
<223> OTHER INFORMATION: antibody sequence

<400> SEQUENCE: 287

| | |
|---|---|
| atgaaatacc tattgcctac ggcggccgct ggattgttat tactcgcggc ccagccggcc | 60 |
| atggcgcagg tgcagctgca ggagtctggg ggaggcttgg tgcagccgg ggactctctg | 120 |
| aagctctctt gtgcagcctc tggcggcacc ttcggtgccg gtgtcgtggc ctggtaccgc | 180 |
| cagtctccag gaaacagcg tgagatggtc ggaagtatgg gtagtgatgg tttcacgcaa | 240 |
| atcgaaaacg gcatgaaggg ccgattcact atctccgggg ccggcgacaa gaaaacagtg | 300 |
| tttttacaga tgaacaattt gaagcctgag gacacggccg tctatttctg tcattacgcc | 360 |
| gatggccggt ttggctcttg gggtcagggg acccaggtca ccgtctcctc aactagtggc | 420 |
| ccgggaggcc aacaccatca ccaccatcat ggcgcagaac aaaaactcat ctcagaagag | 480 |
| gatctgtctt ag | 492 |

<210> SEQ ID NO 288
<211> LENGTH: 489
<212> TYPE: DNA
<213> ORGANISM: Artificial Sequence
<220> FEATURE:
<223> OTHER INFORMATION: antibody sequence

<400> SEQUENCE: 288

| | |
|---|---|
| atgaaatacc tattgcctac ggcggccgct ggattgttat tactcgcggc ccagccggcc | 60 |
| atggcgcagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag gaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc caggtcaccg tctcctcaac tagtggcccg | 420 |
| ggaggccaac accatcacca catcatggc gcagaacaaa aactcatctc agaagaggat | 480 |
| ctgtcttag | 489 |

<210> SEQ ID NO 289
<211> LENGTH: 489
<212> TYPE: DNA
<213> ORGANISM: Artificial Sequence
<220> FEATURE:
<223> OTHER INFORMATION: antibody sequence

<400> SEQUENCE: 289

| | |
|---|---|
| atgaaatacc tattgcctac ggcggccgct ggattgttat tactcgcggc ccagccggcc | 60 |
| atgaaacagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag gaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc caggtcaccg tctcctcaac tagtggcccg | 420 |
| ggaggccaac accatcacca catcatggc gcagaacaaa aactcatctc agaagaggat | 480 |

-continued

```
ctgtcttag                                                            489

<210> SEQ ID NO 290
<211> LENGTH: 489
<212> TYPE: DNA
<213> ORGANISM: Artificial Sequence
<220> FEATURE:
<223> OTHER INFORMATION: antibody sequence

<400> SEQUENCE: 290
atgaaatacc tattgcctac ggcggccgct ggattgttat tactcgcggc ccagccggcc     60
atgaaacagg tgcagctgca ggagtctggg ggaggcttgg tgcaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc caggtcaccg tctcctcaac tagtggcccg    420
ggaggccaac accatcacca ccatcatggc gcagaacaaa aactcatctc agaagaggat    480
ctgtcttag                                                            489

<210> SEQ ID NO 291
<211> LENGTH: 489
<212> TYPE: DNA
<213> ORGANISM: Artificial Sequence
<220> FEATURE:
<223> OTHER INFORMATION: antibody sequence

<400> SEQUENCE: 291
atgaaatacc tattgcctac ggcggccgct ggattgttat tactcgcggc ccagccggcc     60
atggcgcagg tgcagctgca ggagtctggg ggaggcttgg tccaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg taccaccaat    240
tatctagcct ccgtgaaggg ccgattcact atctccagag acaacgccaa gaacacggtg    300
tcgctacaaa tgaacagcct gaaacctgag gacacggccg tctacacttg ttatgcagcc    360
tggccgttga acacttgggg ccaggggacc caggtcaccg tctcctcaac tagtggcccg    420
ggaggccaac accatcacca ccatcatggc gcagaacaaa aactcatctc agaagaggat    480
ctgtcttag                                                            489

<210> SEQ ID NO 292
<211> LENGTH: 489
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (64)..(66)
<223> OTHER INFORMATION: n is a, c, g, or t

<400> SEQUENCE: 292
atgaaatacc tattgcctac ggcggccgct ggattgttat tactcgcggc ccagccggcc     60
atgnnncagg tgcagctgca ggagtctggg ggaggcttgg tgcaggctgg ggggtctctg    120
agactctcct gtgcagcctc tggaagtaac atcagtacta atgtgatggc ctggtaccgc    180
```

| | |
|---|---|
| cgcgctccag ggaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc caggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 293
<211> LENGTH: 489
<212> TYPE: DNA
<213> ORGANISM: Artificial Sequence
<220> FEATURE:
<223> OTHER INFORMATION: antibody sequence

<400> SEQUENCE: 293

| | |
|---|---|
| atgaaatacc tattgcctac ggcggccgct ggattgttat tactcgcggc ccagccggcc | 60 |
| atggcacagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag ggaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc caggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 294
<211> LENGTH: 489
<212> TYPE: DNA
<213> ORGANISM: Artificial Sequence
<220> FEATURE:
<223> OTHER INFORMATION: antibody sequence

<400> SEQUENCE: 294

| | |
|---|---|
| atgaaatacc tattgcctac ggcggccgct ggattgttat tactcgcggc ccagccggcc | 60 |
| atggcgcagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag ggaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc caggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 295
<211> LENGTH: 489
<212> TYPE: DNA
<213> ORGANISM: Artificial Sequence
<220> FEATURE:
<223> OTHER INFORMATION: antibody sequence

<400> SEQUENCE: 295

| | |
|---|---|
| atgaaatacc tattgcctac ggcggccgct ggattgttat tactcgcggc ccagccggcc | 60 |

```
atggcgcagg tgcagctgca ggagtctggg ggaggcttgg tgcaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc caggtcaccg tctcctcaac tagtggcccg    420
ggaggccaac accatcacca ccatcatggc gcagaacaaa aactcatctc agaagaggat    480
ctgtcttag                                                            489
```

<210> SEQ ID NO 296
<211> LENGTH: 489
<212> TYPE: DNA
<213> ORGANISM: Artificial Sequence
<220> FEATURE:
<223> OTHER INFORMATION: antibody sequence

<400> SEQUENCE: 296

```
atgaaatacc tattgcctac ggcggccgct ggattgttat tactcgcggc ccagccggcc     60
atgaaacagg tgcagctgca ggagtctggg ggaggcttgg tgcaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc caggtcaccg tctcctcaac tagtggcccg    420
ggaggccaac accatcacca ccatcatggc gcagaacaaa aactcatctc agaagaggat    480
ctgtcttag                                                            489
```

<210> SEQ ID NO 297
<211> LENGTH: 489
<212> TYPE: DNA
<213> ORGANISM: Artificial Sequence
<220> FEATURE:
<223> OTHER INFORMATION: antibody sequence

<400> SEQUENCE: 297

```
atgaaatacc tattgcctac ggcggccgct ggattgttat tactcgcggc ccagccggcc     60
atggcgcagg tgcagctgca ggagtctggg ggaggcttgg tgcaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc caggtcaccg tctcctcaac tagtggcccg    420
ggaggccaac accatcacca ccatcatggc gcagaacaaa aactcatctc agaagaggat    480
ctgtcttag                                                            489
```

<210> SEQ ID NO 298
<211> LENGTH: 504
<212> TYPE: DNA
<213> ORGANISM: Artificial Sequence
<220> FEATURE:

<223> OTHER INFORMATION: antibody sequence

<400> SEQUENCE: 298

```
atgaaatacc tattgcctac ggcggccgct ggattgttat tactcgcggc ccagccggcc    60
atggcgcagg tgcagctgca ggagtctggg ggaggcttgg tgcaggctgg ggggtctctg   120
agactctcct gtgcagcctc tggaagcacc ttcagtatca cgtacatggc ctggttccgc   180
caggctccag aaaagcagcg cgagttggtc gcagaaatga gtaggcgtgg tagtacattc   240
tatgcagact ccgtgaaggg ccgattcacc atctccagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg ggacccaggt caccgtctcc   420
tcaactagtg gcccgggagg ccaacaccat caccaccatc atggcgcaga acaaaaactc   480
atctcagaag aggatctgtc ttag                                          504
```

<210> SEQ ID NO 299
<211> LENGTH: 504
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (82)..(82)
<223> OTHER INFORMATION: n is a, c, g, or t

<400> SEQUENCE: 299

```
atgaaatacc tattgcctac ggcggccgct ggattgttat tactcgcggc ccagccggcc    60
atggcgcagg tgcagctgca gnagtctggg ggaggcttgg tgcaggctgg ggggtctctg   120
agactctcct gtgcagcctc tggaagcacc ttcagtatca cgtacatggc ctggttccgc   180
caggctccag aaaagcagcg cgagttggtc gcagaaatga gtaggcgtgg tagtacattc   240
tatgcagact ccgtgaaggg ccgattcacc atctccagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg ggacccaggt caccgttttcc   420
tcaactagtg gcccgggagg ccaacaccat caccaccatc atggcgcaga acaaaaactc   480
atctcagaag aggatctgtc ttag                                          504
```

<210> SEQ ID NO 300
<211> LENGTH: 504
<212> TYPE: DNA
<213> ORGANISM: Artificial Sequence
<220> FEATURE:
<223> OTHER INFORMATION: antibody sequence

<400> SEQUENCE: 300

```
atgaaatacc tattgcctac ggcggccgct ggattgttat tactcgcggc ccagccggcc    60
atggcgcagg tgcagctgca ggagtctggg ggaggcttgg tgcaggctgg ggggtctctg   120
agactctcct gtgcagcctc tggaagcacc ttcagtatca cgtacatggc ctggttccgc   180
caggctccag aaaagcagcg cgagttggtc gcagaaatga gtaggcgtgg tagtacattc   240
tatgcagact ccgtgaaggg ccgattcacc atctccagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg ggacccaggt caccgtctcc   420
tcaactagtg gcccgggagg ccaacaccat caccaccatc atggcgcaga acaaaaactc   480
```

```
atctcagaag aggatctgtc ttag                                          504
```

<210> SEQ ID NO 301
<211> LENGTH: 504
<212> TYPE: DNA
<213> ORGANISM: Artificial Sequence
<220> FEATURE:
<223> OTHER INFORMATION: antibody sequence

<400> SEQUENCE: 301

```
atgaaatacc tattgcctac ggcggccgct ggattgttat tactcgcggc ccagccggcc    60
atggcgcagg tgcagctgca ggagtctggg ggaggcttgg tgcaggctgg ggggtctctg   120
agactctcct gtgcagcctc tggaagcacc ttcagtatca cgtacatggc ctggttccgc   180
caggctccag aaaagcagcg cgagttggtc gcagaaatga gtaggcgtgg tagtacattc   240
tatgcagact ccgtgaaggg ccgattcacc atctccagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg ggacccaggt caccgtctcc   420
tcaactagtg gcccgggagg ccaacaccat caccaccatc atggcgcaga acaaaaactc   480
atctcagaag aggatctgtc ttag                                          504
```

<210> SEQ ID NO 302
<211> LENGTH: 504
<212> TYPE: DNA
<213> ORGANISM: Artificial Sequence
<220> FEATURE:
<223> OTHER INFORMATION: antibody sequence

<400> SEQUENCE: 302

```
atgaaatacc tattgcctac ggcggccgct ggattgttat tactcgcggc ccagccggcc    60
atggcgcagg tgcagttgca ggagtctggg ggaggcttgg tgcaggctgg ggggtctctg   120
agactctcct gtgcagcctc tggaagcacc ttcagtatca cgtacatggc ctggttccgc   180
caggctccag aaaagcagcg cgagttggtc gcagaaatga gtaggcgtgg tagtacattc   240
tatgcagact ccgtgaaggg ccgattcacc atctccagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg ggacccaggt caccgtctcc   420
tcaactagtg gcccgggagg ccaacaccat caccaccatc atggcgcaga acaaaaactc   480
atctcagaag aggatctgtc ttag                                          504
```

<210> SEQ ID NO 303
<211> LENGTH: 504
<212> TYPE: DNA
<213> ORGANISM: Artificial Sequence
<220> FEATURE:
<223> OTHER INFORMATION: antibody sequence

<400> SEQUENCE: 303

```
atgaaatacc tattgcctac ggcggccgct ggattgttat tactcgcggc ccagccggcc    60
atggcgcagg tgcagctgca ggagtctggg ggaggcttgg tgcaggctgg ggggtctctg   120
agactctcct gtgcagcctc tggaagcacc ttcagtatca cgtacatggc ctggttccgc   180
caggctccag aaaagcagcg cgagttggtc gcagaaatga gtaggcgtgg tagtacattc   240
tatgcagact ccgtgaaggg ccgattcacc atctccagag acaacaccaa gaacacagtc   300
```

```
tatctgcaaa tgaacagcct agaacctgaa gacacggccg tctattattg tagtgtaggc    360
gcacgtcgcg acgaggatga ttatgtctac tggggccagg ggacccaggt caccgtttcc    420
tcaactagtg gcccgggagg ccaacaccat caccaccatc atggcgcaga acaaaaactc    480
atctcagaag aggatctgtc ttag                                           504
```

<210> SEQ ID NO 304
<211> LENGTH: 504
<212> TYPE: DNA
<213> ORGANISM: Artificial Sequence
<220> FEATURE:
<223> OTHER INFORMATION: antibody sequence

<400> SEQUENCE: 304

```
atgaaatacc tattgcctac ggcggccgct ggattgttat tactcgcggc ccagccggcc     60
atggcgcagg tgcagttgca gcagtctggg ggaggcttgg tgcaggctgg ggggtctctg    120
agactctcct gtgcagcctc tggaagcacc ttcagtatca cgtacatggc ctggttccgc    180
caggctccag aaaagcagcg cgagttggtc gcagaaatga gtaggcgtgg tagtacattc    240
tatgcagact ccgtgaaggg ccgattcacc atctccagag acaacaccaa gaacacagtc    300
tatctgcaaa tgaacagcct agaacctgaa gacacggccg tctattattg tagtgtaggc    360
gcacgtcgcg acgaggatga ttatgtctac tggggccagg ggacccaggt caccgtctcc    420
tcaactagtg gcccgggagg ccaacaccat caccaccatc atggcgcaga acaaaaactc    480
atctcagaag aggatctgtc ttag                                           504
```

<210> SEQ ID NO 305
<211> LENGTH: 516
<212> TYPE: DNA
<213> ORGANISM: Artificial Sequence
<220> FEATURE:
<223> OTHER INFORMATION: antibody sequence

<400> SEQUENCE: 305

```
atgaaatacc tattgcctac ggcggccgct ggattgttat tactcgcggc ccagccggcc     60
atggcgcagg tgcagttgca ggagtctggg ggaggctcgg tgcaggctgg ggggtctctg    120
agactctcct gtgcagactc tagaaccatc ttcattttca cgccatggc ctggtaccgc     180 caggctccag ggaagcagcg cgagttggtc gcagctattt ctagtggtgg cagtacaaag    240
tatgcagact ccgtgaaggg ccgattcacc atctccagta gcaacgccaa gaacacgaag    300
tatctgcaga tgaacaggct gaaacctgag gacacagccg tctattactg tgcagcctca    360
aggtcgggta ggtggttaga tgatgcacga gactatgagt actggggccc ggggacccag    420
gtcaccgtct cctcaactag tggcccggga ggccaacacc atcaccacca tcatggcgca    480
gaacaaaaac tcatctcaga gaggatctg tcttag                               516
```

<210> SEQ ID NO 306
<211> LENGTH: 489
<212> TYPE: DNA
<213> ORGANISM: Artificial Sequence
<220> FEATURE:
<223> OTHER INFORMATION: antibody sequence

<400> SEQUENCE: 306

```
atgaaatacc tattgcctac ggcggccgct ggattgttat tactcgcggc ccagccggcc     60
atggcgcagg tgcagctgca ggagtctggg ggaggcttgg tgcaggctgg ggggtctctg    120
agactctcct gtgcagcctc tggaagtaac atcagtacta atgtgatggc ctggtaccgc    180
```

```
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc ctggtcaccg tctcctcaac tagtggcccg    420
ggaggccaac accatcacca ccatcatggc gcagaacaaa aactcatctc agaagaggat    480
ctgtcttag                                                            489
```

<210> SEQ ID NO 307
<211> LENGTH: 489
<212> TYPE: DNA
<213> ORGANISM: Artificial Sequence
<220> FEATURE:
<223> OTHER INFORMATION: antibody sequence

<400> SEQUENCE: 307

```
atgaaatacc tattgcctac ggcggccgct ggattgttat tactcgcggc ccagccggcc     60
atggcgcagg tgcagttgca ggagtctggg ggaggcttgg tgcaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc ctggtcaccg tctcctcaac tagtggcccg    420
ggaggccaac accatcacca ccatcatggc gcagaacaaa aactcatctc agaagaggat    480
ctgtcttag                                                            489
```

<210> SEQ ID NO 308
<211> LENGTH: 489
<212> TYPE: DNA
<213> ORGANISM: Artificial Sequence
<220> FEATURE:
<223> OTHER INFORMATION: antibody sequence

<400> SEQUENCE: 308

```
atgaaatacc tattgcctac ggcggccgct ggattgttat tactcgcggc ccagccggcc     60
atggcgcagg tgcagctgca ggagtctggg ggaggcttgg tgcaggctgg ggggtctctg    120
agactctcct gtgcagcctc tggaagtaac atcagtacta atgtgatggc ctggtaccgc    180
cgcgctccag ggaaccagcg cgacatggtt gcttctatca gtactagtgg tactaccaat    240
tatctagcct ccgtgaaggg ccgattcact atctccagag acaacgccaa gaacacggtg    300
tcgctgcaaa tgaacagcct gaaacctgag gacacggccg tctacacttg ttatgcagcc    360
tggccgttga acacttgggg ccaggggacc ctggtcaccg tctcctcaac tagtggcccg    420
ggaggccaac accatcacca ccatcatggc gcagaacaaa aactcatctc agaagaggat    480
ctgtcttag                                                            489
```

<210> SEQ ID NO 309
<211> LENGTH: 489
<212> TYPE: DNA
<213> ORGANISM: Artificial Sequence
<220> FEATURE:
<223> OTHER INFORMATION: antibody sequence

<400> SEQUENCE: 309

| | |
|---|---:|
| atgaaatacc tattgcctac ggcggccgct ggattgttat tactcgcggc ccagccggcc | 60 |
| atggcgcagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag ggaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc ctggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 310
<211> LENGTH: 489
<212> TYPE: DNA
<213> ORGANISM: Artificial Sequence
<220> FEATURE:
<223> OTHER INFORMATION: antibody sequence

<400> SEQUENCE: 310

| | |
|---|---:|
| atgaaatacc tattgcctac ggcggccgct ggattgttat tactcgcggc ccagccggcc | 60 |
| atggcgcagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag ggaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc ctggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 311
<211> LENGTH: 489
<212> TYPE: DNA
<213> ORGANISM: Artificial Sequence
<220> FEATURE:
<223> OTHER INFORMATION: antibody sequence

<400> SEQUENCE: 311

| | |
|---|---:|
| atgaaatacc tattgcctac ggcggccgct ggattgttat tactcgcggc ccagccggcc | 60 |
| atgaaacagg tgcagctgca ggagtctggg ggaggcttgg tgcaggctgg ggggtctctg | 120 |
| agactctcct gtgcagcctc tggaagtaac atcagtacta atgtgatggc ctggtaccgc | 180 |
| cgcgctccag ggaaccagcg cgacatggtt gcttctatca gtactagtgg tactaccaat | 240 |
| tatctagcct ccgtgaaggg ccgattcact atctccagag acaacgccaa gaacacggtg | 300 |
| tcgctgcaaa tgaacagcct gaaacctgag gacacggccg tctacacttg ttatgcagcc | 360 |
| tggccgttga acacttgggg ccaggggacc ctggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 312
<211> LENGTH: 504
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(79)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 312

| | | | | | |
|---|---|---|---|---|---|
| atgaaatacc | tattgcctac | ggcggccgct | ggattgttat | tactcgcggc | ccagccggcc | 60 |
| atggcgcagg | tgcagnnnna | ncagtctggg | ggaggcttgg | tgcaggctgg | ggggtctctg | 120 |
| agactctcct | gtgcagcctc | tggaattccc | ttcagtatca | tctacatggc | ctggttccgc | 180 |
| caggctccag | aaaagcagcg | cgagttggtc | gcagaaatga | gtagtcgtgg | tagtaaattc | 240 |
| tatgcagact | ccgtgaaggg | ccgattcacc | atctctagag | acaacgccaa | gaacacactc | 300 |
| tatctgcaaa | tgaacagcct | agaacctgaa | gatacggccg | tctattattg | cagtgtaggc | 360 |
| gcacgtcgcg | acgacaatga | ttatgtgtat | tggggccagg | gacccaggt | caccgtttcc | 420 |
| tcaactagtg | gcccggggagg | ccaacaccat | caccaccatc | atggcgcaga | acaaaaactc | 480 |
| atctcagaag | aggatctgtc | ttag | | | | 504 |

<210> SEQ ID NO 313
<211> LENGTH: 489
<212> TYPE: DNA
<213> ORGANISM: Artificial Sequence
<220> FEATURE:
<223> OTHER INFORMATION: antibody sequence

<400> SEQUENCE: 313

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggcgtctggg | ggaggcttgg | tgcaggctgg | ggggtctctg | 120 |
| agactctcct | gtgcagcctc | tggaagtaac | atcagtacta | atgtgatggc | ctggtaccgc | 180 |
| cgcgctccag | ggaaccagcg | cgacatggtt | gcttctatca | gtactagtgg | tactaccaat | 240 |
| tatctagcct | ccgtgaaggg | ccgattcact | atctccagag | acaacgccaa | gaacacggtg | 300 |
| tcgctgcaaa | tgaacagcct | gaaacctgag | gacacggccg | tctacacttg | ttatgcagcc | 360 |
| tggccgttga | cacttgggg | ccaggggacc | caggtcaccg | tctcctcaac | tagtggcccg | 420 |
| ggaggccaac | accatcacca | ccatcatggc | gcagaacaaa | aactcatctc | agaagaggat | 480 |
| ctgtcttag | | | | | | 489 |

<210> SEQ ID NO 314
<211> LENGTH: 489
<212> TYPE: DNA
<213> ORGANISM: Artificial Sequence
<220> FEATURE:
<223> OTHER INFORMATION: antibody sequence

<400> SEQUENCE: 314

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggcgtctggg | ggaggcttgg | tgcaggctgg | ggggtctctg | 120 |
| agactctcct | gtgcagcctc | tggaagtaac | atcagtacta | atgtgatggc | ctggtaccgc | 180 |
| cgcgctccag | ggaaccagcg | cgacatggtt | gcttctatca | gtactagtgg | tactaccaat | 240 |
| tatctagcct | ccgtgaaggg | ccgattcact | atctccagag | acaacgccaa | gaacacggtg | 300 |

| | |
|---|---|
| tcgctgcaaa tgaacagcct gaaacctgag gacacggccg tctacacttg ttatgcagcc | 360 |
| tggccgttga acacttgggg ccaggggacc caggtcaccg tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 315
<211> LENGTH: 504
<212> TYPE: DNA
<213> ORGANISM: Artificial Sequence
<220> FEATURE:
<223> OTHER INFORMATION: antibody sequence

<400> SEQUENCE: 315

| | |
|---|---|
| atgaaatacc tattgcctac ggcggccgct ggattgttat tactcgcggc ccagccggcc | 60 |
| atggcgcagg tgcagttgca ggagtctggg ggaggcttgg tgcaggctgg ggggtctctg | 120 |
| agactctcct gtgcagcctc tggaattccc ttcagtatca tctacatggc ctggttccgc | 180 |
| caggctccag aaaagcagcg cgagttggtc gcagaaatga gtagtcgtgg tagtaaattc | 240 |
| tatgcagact ccgtgaaggg ccgattcacc atctctagag acaacgccaa gaacacactc | 300 |
| tatctgcaaa tgaacagcct agaacctgaa gatacggccg tctattattg cagtgtaggc | 360 |
| gcacgtcgcg acgacaatga ttatgtgtat tggggccagg ggacccaggt caccgtctcc | 420 |
| tcaactagtg gcccgggagg ccaacaccat caccaccatc atggcgcaga acaaaaactc | 480 |
| atctcagaag aggatctgtc ttag | 504 |

<210> SEQ ID NO 316
<211> LENGTH: 504
<212> TYPE: DNA
<213> ORGANISM: Artificial Sequence
<220> FEATURE:
<223> OTHER INFORMATION: antibody sequence

<400> SEQUENCE: 316

| | |
|---|---|
| atgaaatacc tattgcctac ggcggccgct ggattgttat tactcgcggc ccagccggcc | 60 |
| atggcgcagg tgcagctgca ggagtctggg ggaggcttgg tgcaggctgg ggggtctctg | 120 |
| agactctcct gtgcagcctc tggaattccc ttcagtatca tctacatggc ctggttccgc | 180 |
| caggctccag aaaagcagcg cgagttggtc gcagaaatga gtagtcgtgg tagtaaattc | 240 |
| tatgcagact ccgtgaaggg ccgattcacc atctctagag acaacgccaa gaacacactc | 300 |
| tatctgcaaa tgaacagcct agaacctgaa gatacggccg tctattattg cagtgtaggc | 360 |
| gcacgtcgcg acgacaatga ttatgtgtat tggggccagg ggacccaggt caccgtctcc | 420 |
| tcaactagtg gcccgggagg ccaacaccat caccaccatc atggcgcaga acaaaaactc | 480 |
| atctcagaag aggatctgtc ttag | 504 |

<210> SEQ ID NO 317
<211> LENGTH: 504
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (79)..(81)
<223> OTHER INFORMATION: n is a, c, g, or t

<400> SEQUENCE: 317

| | |
|---|---|
| atgaaatacc tattgcctac ggcggccgct ggattgttat tactcgcggc ccagccggcc | 60 |

```
atggcgcagg tgcagttgnn ngagtctggg ggaggcttgg tgcaggctgg ggggtctctg    120
agactctcct gtgcagcctc tggaattccc ttcagtatca tctacatggc ctggttccgc    180
caggctccag aaaagcagcg cgagttggtc gcagaaatga gtagtcgtgg tagtaaattc    240
tatgcagact ccgtgaaggg ccgattcacc atctctagag acaacgccaa gaacacactc    300
tatctgcaaa tgaacagcct agaacctgaa gatacggccg tctattattg cagtgtaggc    360
gcacgtcgcg acgacaatga ttatgtgtat tggggccagg ggacccaggt caccgtctcc    420
tcaactagtg gcccgggagg ccaacaccat caccaccatc atggcgcaga acaaaaactc    480
atctcagaag aggatctgtc ttag                                            504
```

<210> SEQ ID NO 318
<211> LENGTH: 504
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(78)
<223> OTHER INFORMATION: n is a, c, g, or t

<400> SEQUENCE: 318

```
atgaaatacc tattgcctac ggcggccgct ggattgttat tactcgcggc ccagccggcc     60
atggcgcagg tgcagnnnca ggagtctggg ggaggcttgg tgcaggctgg ggggtctctg    120
agactctcct gtgcagcctc tggaattccc ttcagtatca tctacatggc ctggttccgc    180
caggctccag aaaagcagcg cgagttggtc gcagaaatga gtagtcgtgg tagtaaattc    240
tatgcagact ccgtgaaggg ccgattcacc atctctagag acaacgccaa gaacacactc    300
tatctgcaaa tgaacagcct agaacctgaa gatacggccg tctattattg cagtgtaggc    360
gcacgtcgcg acgacaatga ttatgtgtat tggggccagg ggacccaggt caccgtctcc    420
tcaactagtg gcccgggagg ccaacaccat caccaccatc atggcgcaga acaaaaactc    480
atctcagaag aggatctgtc ttag                                            504
```

<210> SEQ ID NO 319
<211> LENGTH: 508
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 319

```
atgaaatacc tattgcctac ggcggccgct ggattgttat tactcgcggc ccagccggcc     60
atggcgcagg tgcagtttgca gnngtnatgg gggaggcgtg gtgcagtctg gggggtctct    120
gagactctcc tgtgtagcct ctggaaacat cttcgggatc aattccatgg cctggtaccg    180
ccaggctcca gggaagcagc gcgaattggt cgctgacatt acacgtggta atagaaagta    240
tgcagattcc gtgaagggcc gattcaccat ctcccaagac aacgccaaga acacggtgta    300
tctgcaaatg aacaggctga aaccagagga cacggccgtc tatttctgca atgcagaaat    360
```

| | |
|---|---|
| cgtcacgcaa atcccttccc cgccgcgtga gttctggggc cggggggaccc tggtcaccgt | 420 |
| ctcctcaact agtggcccgg gaggccaaca ccatcaccac catcatggcg cagaacaaaa | 480 |
| actcatctca gaagaggatc tgtcttag | 508 |

<210> SEQ ID NO 320
<211> LENGTH: 520
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (95)..(98)
<223> OTHER INFORMATION: n is a, c, g, or t

<400> SEQUENCE: 320

| | |
|---|---|
| atgaaatacc tattgcctac ggcggccgct ggattgttat tactcgcggc ccagccggcc | 60 |
| atggcgcagg tgcagttgca ggcgtctggg ggagnnnntg gtgcagcctg ggggtctct | 120 |
| gagactctcc tgtgcagcct ctggattcac ctttagtagc tactggatgt attgggtccg | 180 |
| tcaggctcca gggaaggggc tcgagtgggt ctcaacaatt aatactggtg gttataccac | 240 |
| atactattca gactccgtga agggccgatt caccatctcc agagacaacg caagaacac | 300 |
| gctgtatctc gaaatgaaca gtctgaaatc tgaggacacg ccgtgtatt actgtgcaaa | 360 |
| ggcgtacggt agtatgtggt cagggatctg ggcggcatg gactactggg gcaaagggac | 420 |
| ccaggtcacc gtctcctcaa ctagtggccc gggaggccaa caccatcacc accatcatgg | 480 |
| cgcagaacaa aaactcatct cagaagagga tctgtcttag | 520 |

<210> SEQ ID NO 321
<211> LENGTH: 489
<212> TYPE: DNA
<213> ORGANISM: Artificial Sequence
<220> FEATURE:
<223> OTHER INFORMATION: antibody sequence

<400> SEQUENCE: 321

| | |
|---|---|
| atgaaatacc tattgcctac ggcggccgct ggattgttat tactcgcggc ccagccggcc | 60 |
| atggggcagg tccagttgca gcagtctggg ggaggcttgg tccaggctgg ggggtctctg | 120 |
| agactctcct gtgcagcctc tggaagtaac atcagtacta atgtgatggc ctggtaccgc | 180 |
| cgcgctccag ggaaccagcg cgacatggtt gcttctatca gtactagtgg taccaccaat | 240 |
| tatctagcct ccgtgaaggg ccgattcact atctccagag acaacgccaa gaacacggtg | 300 |
| tcgctacaaa tgaacagcct gaaacctgag gacacggccg tctacacttg ttatgcagcc | 360 |
| tggccgttga acacttgggg ccaggggacc caggtcaccc tctcctcaac tagtggcccg | 420 |
| ggaggccaac accatcacca ccatcatggc gcagaacaaa aactcatctc agaagaggat | 480 |
| ctgtcttag | 489 |

<210> SEQ ID NO 322
<211> LENGTH: 489
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature

```
<222> LOCATION: (132)..(132)
<223> OTHER INFORMATION: n is a, c, g, or t

<400> SEQUENCE: 322
atgaaatacc tattgcctac ggcggccgct ggattgttat tactcgcggc ccagccggcc      60
atggcgcagg tgcagntgca ggagtctggg ggaggcttgg tccaggctgg ggggtctctg     120
agactctcct gngcagtctc tggaagtatc atcagtcata atgtgatggc ctggtaccgc     180
cgcgctccag ggaagcagcg cgacaaggtt gcttgtatca gtggtagtgg tttcaccaat     240
tatatagcct ccgtgaaggg ccgattcact atctccagag acaacgccaa gaacacggtg     300
tctctacaaa tgaacaacct gaaacctgag gacacggccg tctactcttg ttatacagcc     360
tggccgtaga acacttgggg ccaggggacc caggtcaccg tctcctcaac tagtggcccg     420
ggaggccaac accatcacca ccatcatggc gcagaacaaa aactcatctc agaagaggat     480
ctgtcttag                                                             489

<210> SEQ ID NO 323
<211> LENGTH: 510
<212> TYPE: DNA
<213> ORGANISM: Artificial Sequence
<220> FEATURE:
<223> OTHER INFORMATION: antibody sequence

<400> SEQUENCE: 323
atgaaatacc tattgcctac ggcggccgct ggattgttat tactcgcggc ccagccggcc      60
atggcgcagg tgcagttgca ggagtctggg ggaggctttg tgcacctgg agggtctctg     120
acgctctcct gtgcagcctc tggcaggatc ttcaatatcg aggacatggg ctggtatcgc     180
cagggtccag gggaacagcg cgacttggtc gcaacgatca cccgtactgg tgcgccaacc     240
tatgcaaact ccgtgaaggg ccggttcacc atctccagag acaacgccaa gaacacggtt     300
tatctgcaga tgaccaggct gaaacctgag gacacggccg tctattactg taatgcaaaa     360
gacgtaacag tcatacccttt ccccccgaaa gactattggg gccgggggac ccaggtcacc     420
gtctcctcaa ctagtggccc gggaggccaa caccatcacc accatcatgg cgcagaacaa     480
aaactcatct cagaagagga tctgtcttag                                      510

<210> SEQ ID NO 324
<211> LENGTH: 516
<212> TYPE: DNA
<213> ORGANISM: Artificial Sequence
<220> FEATURE:
<223> OTHER INFORMATION: antibody sequence

<400> SEQUENCE: 324
atgaaatacc tattgcctac ggcggccgct ggattgttat tactcgcggc ccagccggcc      60
atggcgcagg tgcagctgca ggagtctggg ggaggcttgg tgcaggctgg ggggtctctg     120
agactctcct gtgaagcctc tggaagcgtt tccgcgatcg aaaccatggg ctggtaccgc     180
caggctccgg atgaacagcg cacatttgtc gcggttatca gtacgggtgg aaccacaaaa     240
tacgcgccct ccgtgaaggg ccgattcacc atctccatag acaacgccaa gagcacggtg     300
acgcttcaaa tgaacagcct gaaacctgag gacacagccg tctactactg tgcagcggac     360
tggcgaacca ttttggggttg gaagacaagg gagcccaact actttggcca ggggaccctg     420
gtcaccgtct cctcaactag tggcccggga ggccaacacc atcaccacca tcatggcgca     480
gaacaaaaac tcatctcaga agaggatctg tcttag                              516
```

<210> SEQ ID NO 325
<211> LENGTH: 504
<212> TYPE: DNA
<213> ORGANISM: Artificial Sequence
<220> FEATURE:
<223> OTHER INFORMATION: antibody sequence

<400> SEQUENCE: 325

```
atgaaatacc tattgcctac ggcggccgct ggattgttat tactcgcggc ccagccggcc    60
atggcgcagg tgcagttgca ggagtctggg ggaggcttgg tgcaggctgg ggggtctctg   120
agactctcct gtgcagcctt tggaagcacc tccagtatca cgtacatggc ctggttccgc   180
caggctccag aaaagcagcg cgagttggtc gcagaaatga gtaggcgtgg tagcacattc   240
tatgcagact ccgtgaaggg ccgattcacc atttatagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg gacccaggt caccgtctcc   420
tcaactagtg gcccgggagg ccaacaccat caccaccatc atggcgcaga acaaaaactc   480
atctcagaag aggatctgtc ttag                                          504
```

<210> SEQ ID NO 326
<211> LENGTH: 504
<212> TYPE: DNA
<213> ORGANISM: Artificial Sequence
<220> FEATURE:
<223> OTHER INFORMATION: antibody sequence

<400> SEQUENCE: 326

```
atgaaatacc tattgcctac ggcgccgct ggattgcttat tactcgcggc ccagccggcc    60
atggcgcagg tgcagttgca ggagtctggg ggaggcttgg tgcaggctgg ggggtctctg   120
agactctcct gtgcagcctt tggaagcacc tccagtatca cgtacatggc ctggttccgc   180
caggctccag aaaagcagcg cgagttggtc gcagaaatga gtaggcgtgg tagcacattc   240
tatgcagact ccgtgaaggg ccgattcacc atttatagag acaacaccaa gaacacagtc   300
tatctgcaaa tgaacagcct agaacctgaa gacacggccg tctattattg tagtgtaggc   360
gcacgtcgcg acgaggatga ttatgtctac tggggccagg ggacccaggt caccgttcc   420
tcaactagtg gcccgggagg ccaacaccat caccaccatc atggcgcaga acaaaaactc   480
atctcagaag aggatctgtc ttag                                          504
```

<210> SEQ ID NO 327
<211> LENGTH: 505
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(80)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t

<400> SEQUENCE: 327

```
atgaaatacc tattgcctac ggcggccgct ggattgttat tactcgcggc ccagccggcc    60
```

```
atggcgcagg tgcagnnnnn annagtnngg gggaggcttg gtgcaggctg ggggtctct     120 gagactctcc tgtgcagcct ttggaagcac ctccagtatc acgtacatgg cctggttccg    180
ccaggctcca gaaaagcagc gcgagttggt cgcagaaatg agtaggcgtg gtagcacatt    240
ctatgcagac tccgtgaagg gccgattcac catttataga caacaccca agaacacagt    300 ctatctgcaa atgaacagcc tagaacctga agacacggcc gtctattatt gtagtgtagg    360
cgcacgtcgc gacgaggatg attatgtcta ctggggccag gggacccagg tcaccgtctc    420
ctcaactagt ggcccgggag gccaacacca tcaccaccat catggcgcag aacaaaaact    480
catctcagaa gaggatctgt cttag                                          505
```

<210> SEQ ID NO 328
<211> LENGTH: 483
<212> TYPE: DNA
<213> ORGANISM: Artificial Sequence
<220> FEATURE:
<223> OTHER INFORMATION: antibody sequence

<400> SEQUENCE: 328

```
atgaaatacc tattgcctac ggcggccgct ggattgttat tactcgcggc ccagccggcc    60
atggcgcagg tgcagttgca ggagtctggg ggaggcttgg tgcaggctgg ggggtctctg    120
agactctcct gtgcagcctc tggaggaccc gtcagtgaca atgtcatggc ctggttccgc    180
caggctccag ggagccagcg cgaattggtc gcacagatta caagtggtgg ggccacaagc    240
tacgcggact ccgtgaaggg ccgattcacc atctccagag acaacgccag gagcacagtg    300
gacctgcaaa tgaacagcct gaaacctgag gacacggccg tctattactg taacgtcgcc    360
ttacgttact ggggccgggg gacccaggtc accgtctcct caactagtgg cccgggaggc    420
caacaccatc accaccatca tggcgcagaa caaaaactca tctcagaaga ggatctgtct    480
tag                                                                  483
```

<210> SEQ ID NO 329
<211> LENGTH: 505
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (76)..(79)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (459)..(460)
<223> OTHER INFORMATION: n is a, c, g, or t

<400> SEQUENCE: 329

```
atgaaatacc tattgcctac ggcggccgct ggattgttat tactcgcggc ccagccggcc    60
atggcgcagg tgcagnnnna ancagtntgg gggaggcttg gtgcaggctg ggggtctct    120
```

```
gagactctcc tgtgcagcct ctggaagcac cttcagtatc acctacatgg cctggttccg    180
ccaggctcca gggaaacagc gcgaattggt cgcagaaata agtagccgtg gtagtgtgtt    240
ctatgcagac tccgtgaagg gccgattcac catctccaga gacaacgcca agaagacagt    300
gtatctgcaa atgaacagcc tggaaactga agacacggcc gcctattatt gtagtgtagg    360
cgcacgtcgc gacgaagatg actatgtcta ctggggccag gggacccagg tcaccgtttc    420
ctcaactagt ggcccgggag gccaacacca tcaccancnn catggcgcag aacaaaaact    480
catctcagaa gaggatctgt cttag                                          505
```

```
<210> SEQ ID NO 330
<211> LENGTH: 504
<212> TYPE: DNA
<213> ORGANISM: Artificial Sequence
<220> FEATURE:
<223> OTHER INFORMATION: antibody sequence

<400> SEQUENCE: 330
atgaaatacc tattgcctac ggcggccgct ggattgttat tactcgcggc ccagccggcc     60
atggcgcagg tgcagttgca ggagtctggg ggaggcttgg tgcaggctgg ggggtctctg    120
agactctcct gtgcagcctc tggaagcacc ttcagtatca cgtacatggc ctggttccgc    180
caggctccag aaaagcagcg cgagttggtc gcagaaatga gtaggcgtgg tagtacattc    240
tatgcagact ccgtgaaggg ccgattcacc atctccagag acaacaccaa gaacacagtc    300
tatctgcaaa tgaacagcct agaacctgaa gacacggccg tctattattg tagtgtaggc    360
gcacgtcgcg acgaggatga ttatgtctac tggggccagg gaccctggt caccgtttcc    420 tcaactagtg gcccgggagg ccaacaccat caccaccatc atggcgcaga acaaaaactc    480
atctcagaag aggatctgtc ttag                                           504
```

```
<210> SEQ ID NO 331
<211> LENGTH: 504
<212> TYPE: DNA
<213> ORGANISM: Artificial Sequence
<220> FEATURE:
<223> OTHER INFORMATION: antibody sequence

<400> SEQUENCE: 331
atgaaatacc tattgcctac ggcggccgct ggattgttat tactcgcggc ccagccggcc     60
atggcgcagg tgcagttgca ggagtctggg ggaggcttgg tgcaggctgg ggggtctctg    120
agactctcct gtgcagcctc tggaagcacc ttcagtatca cgtacatggc ctggttccgc    180
caggctccag aaaagcagcg cgagttggtc gcagaaatga gtaggcgtgg tagtacattc    240
tatgcagact ccgtgaaggg ccgattcacc atctccagag acaacaccaa gaacacagtc    300
tatctgcaaa tgaacagcct agaacctgaa gacacggccg tctattattg tagtgtaggc    360
gcacgtcgcg acgaggatga ttatgtctac tggggccagg gaccctggt caccgtctcc    420 tcaactagtg gcccgggagg ccaacaccat caccaccatc atggcgcaga acaaaaactc    480
atctcagaag aggatctgtc ttag                                           504
```

```
<210> SEQ ID NO 332
<211> LENGTH: 504
<212> TYPE: DNA
<213> ORGANISM: Artificial Sequence
<220> FEATURE:
<223> OTHER INFORMATION: antibody sequence

<400> SEQUENCE: 332
```

```
atgaaatacc tattgcctac ggcggccgct ggattgttat tactcgcggc ccagccggcc      60
atggcgcagg tgcagttgca ggagtctggg ggaggcttgg tgcaggctgg ggggtctctg     120
agactctcct gtgcagcctc tggaattccc ttcagtatca tctacatggc ctggttccgc     180
caggctccag aaaagcagcg cgagttggtc gcagaaatga gtagtcgtgg tagtaaattc     240
tatgcagact ccgtgaaggg ccgattcacc atctctagag acaacgccaa gaacacactc     300
tatctgcaaa tgaacagcct agaacctgaa gatacggccg tctattattg cagtgtaggc     360
gcacgtcgcg acgacaatga ttatgtgtat tggggccagg ggaccctggt caccgtctcc     420
tcaactagtg gcccgggagg ccaacaccat caccaccatc atggcgcaga acaaaaactc     480
atctcagaag aggatctgtc ttag                                             504

<210> SEQ ID NO 333
<211> LENGTH: 504
<212> TYPE: DNA
<213> ORGANISM: Artificial Sequence
<220> FEATURE:
<223> OTHER INFORMATION: antibody sequence

<400> SEQUENCE: 333
atgaaatacc tattgcctac ggcggccgct ggattgttat tactcgcggc ccagccggcc      60
atggcgcagg tgcagctgca ggagtttggg ggaggcttgg tgcaggctgg ggggtctctg     120
agactctcct gtgcagcctc tggaagcacc ttcagtatca cgtacatggc ctggttccgc     180
caggctccag aaaagcagcg cgagttggtc gcagaaatga gtaggcgtgg tagtacattc     240
tatgcagact ccgtgaaggg ccgattcacc atctccagag acaacaccaa gaacacagtc     300
tatctgcaaa tgaacagcct agaacctgaa gacacggccg tctattattg tagtgtaggc     360
gcacgtcgcg acgaggatga ttatgtctac tggggccagg ggacccaggt caccgtctcc     420
tcaactagtg gcccgggagg ccaacaccat caccaccatc atggcgcaga acaaaaactc     480
atctcagaag aggatctgtc ttag                                             504

<210> SEQ ID NO 334
<211> LENGTH: 489
<212> TYPE: DNA
<213> ORGANISM: Artificial Sequence
<220> FEATURE:
<223> OTHER INFORMATION: antibody sequence

<400> SEQUENCE: 334
atgaaatacc tattgcctac ggcggccgct ggattgttat tactcgcggc ccagccggcc      60
atggcgcagg tgcagctgca ggagtttggg ggaggcttgg tgcaggcagg ggaatctcta     120
agactctcct gtgtagcctc tggaagtaac atcagtacta atgtgatggc ctggtaccgc     180
cgcgctccag ggaaccagcg cgacatggtt gcttctatca gtactagtgg tactaccaat     240
tatgcagcct ccgtgaaggg ccgattcact atctccagag acaacgccaa gaacacggtg     300
tcgctgcaaa tgaacagcct gaaacctgag gacacggccg tctacacttg ttatgcagcc     360
tggccgttga acacttgggg ccaggggacc ctggtcaccg tctcctcaac tagtggcccg     420
ggaggccaac accatcacca ccatcatggc gcagaacaaa aactcatctc agaagaggat     480
ctgtcttag                                                              489

<210> SEQ ID NO 335
<211> LENGTH: 480
<212> TYPE: DNA
```

<213> ORGANISM: Artificial Sequence
<220> FEATURE:
<223> OTHER INFORMATION: antibody sequence

<400> SEQUENCE: 335

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggagtctggg | ggaggcttgg | tgcaggccgg | ggggtctctg | 120 |
| agactctcct | gtgtaggcgc | tggaagcgcc | ttcggttgga | atgccgtgca | ctggtaccgc | 180 |
| caggctccag | gtcagcagcg | cgaatggctc | gccactattg | agagtggtgg | ctgggcagac | 240 |
| tattcagtgt | ccgtgaaggg | ccgattcatc | gtctccagag | acaacgccag | gaacacagcg | 300 |
| tatttgcaaa | tgaacaacct | aaaacttgaa | gacacggccg | tctattactg | taatcaactt | 360 |
| acttactggg | gccaggggac | ccaggtcacc | gtctcctcaa | ctagtggccc | gggaggccaa | 420 |
| caccatcacc | accatcatgg | cgcagaacaa | aaactcatct | cagaagagga | tctgtcttag | 480 |

<210> SEQ ID NO 336
<211> LENGTH: 504
<212> TYPE: DNA
<213> ORGANISM: Artificial Sequence
<220> FEATURE:
<223> OTHER INFORMATION: antibody sequence
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 336

| | | | | | |
|---|---|---|---|---|---|
| atgaaatacc | tattgcctac | ggcggccgct | ggattgttat | tactcgcggc | ccagccggcc | 60 |
| atggcgcagg | tgcanctgca | ggagtntggg | ggaggcttgg | tgcaggctgg | ggggtctctg | 120 |
| agactctcct | gtgcagcctc | tggaagcacc | ttcagtatca | cgtacatgac | ctggttccgc | 180 |
| caggctccag | aaaagcagcg | cgagttggtc | gcagaaatga | gtaggcgtgg | tagtacattc | 240 |
| tatgcagact | ccgtgaaggc | ccgattcacc | atctccagag | acaacaccaa | gaacacagtc | 300 |
| tatctgcaaa | tgaacagcct | agaacctgaa | gacacggccg | tctattattg | tagtgtaggc | 360 |
| gcacgtcgcg | acgaggatga | ttatgtctac | tggggccagg | ggacccaggt | caccgtctcc | 420 |
| tcaactagtg | gcccgggagg | ccaacaccat | caccaccatc | atggcgcaga | acaaaaactc | 480 |
| atctcagaag | aggatctgtc | ttag | | | | 504 |

<210> SEQ ID NO 337
<211> LENGTH: 504
<212> TYPE: DNA
<213> ORGANISM: Artificial Sequence
<220> FEATURE:
<223> OTHER INFORMATION: antibody sequence

<400> SEQUENCE: 337

| | | | | | |
|---|---|---|---|---|---|
| atgaaatacc | tattgcctac | ggcggccgct | ggattgttat | tactcgcggc | ccagccggcc | 60 |
| atggcgcagg | tgcagttgca | ggagtttggg | ggaggcttgg | tgcaggctgg | ggggtctctg | 120 |
| agactctcct | gtgcagcctc | tggaagcacc | ttcagtatca | cgtacatggc | ctggttccgc | 180 |
| caggctccag | aaaagcagcg | cgagttggtc | gcagaaatga | gtaggcgtgg | tagtacattc | 240 |
| tatgcagact | ccgtgaaggg | ccgattcacc | atctccagag | acaacaccaa | gaacacagtc | 300 |
| tatctgcaaa | tgaacagcct | agaacctgaa | gacacggccg | tctattattg | tagtgtaggc | 360 |

-continued

```
gcacgtcgcg acgaggatga ttatgtctac tggggccagg ggaccctggt caccgtttcc    420
tcaactagtg gcccgggagg ccaacaccat caccaccatc atggcgcaga acaaaaactc    480
atctcagaag aggatctgtc ttag                                          504
```

<210> SEQ ID NO 338
<211> LENGTH: 504
<212> TYPE: DNA
<213> ORGANISM: Artificial Sequence
<220> FEATURE:
<223> OTHER INFORMATION: antibody sequence

<400> SEQUENCE: 338

```
atgaaatacc tattgcctac ggcggccgct ggattgttat tactcgcggc ccagccggcc     60
atggcgcagg tgcagttgca gcagtctggg ggaggcttgg tgcaggctgg ggggtctctg    120
agactctcct gtgcagcctc tggaagcacc ttcagtatca cctacatggc ctggttccgc    180
caggctccag ggaaacagcg cgaattggtc gcagaaataa gtagccgtgg tagtgtgttc    240
tatgcagact ccgtgaaggg ccgattcacc atctccagag acaacgccaa gaagacagtg    300
tatctgcaaa tgaacagcct ggaaactgaa gacacggccg cctattattg tagtgtaggc    360
gcacgtcgcg acgaagatga ctatgtctac tggggccagg ggaccctggt caccgtctcc    420
tcaactagtg gcccgggagg ccaacaccat caccaccatc atggcgcaga acaaaaactc    480
atctcagaag aggatctgtc ttag                                          504
```

<210> SEQ ID NO 339
<211> LENGTH: 489
<212> TYPE: DNA
<213> ORGANISM: Artificial Sequence
<220> FEATURE:
<223> OTHER INFORMATION: antibody sequence

<400> SEQUENCE: 339

```
atgaaatacc tattgcctac ggcggccgct ggattgttat tactcgcggc ccagccggcc     60
atggcgcagg tgcagctgca ggagtctggg ggaggcttgg tgcagcctgg ggggtctctg    120
agactctcct gcacaccctc tggatctatc ttcagtttcg atgtcatggc ctggtatcgc    180
caggccccag ggaagcggcg cgagttggtc gcacagcatc gtactccggg tgctatagat    240
tatgccgatc tgtccggggg ccgattcact attagcagag acgctgggga cgtactgttt    300
ctgcaaatgg acagcctgaa acccgaagac acggccgtct acttctgtaa tctccgaagg    360
tggtcttacg actactgggg ccaggggacc ctggtcaccg tctcctcaac tagtggcccg    420
ggaggccaac accatcacca ccatcatggc gcagaacaaa aactcatctc agaagaggat    480
ctgtcttag                                                          489
```

<210> SEQ ID NO 340
<211> LENGTH: 9
<212> TYPE: PRT
<213> ORGANISM: Artificial Sequence
<220> FEATURE:
<223> OTHER INFORMATION: antibody sequence

<400> SEQUENCE: 340

Ser Gly Ser Ile Phe Arg Ile Asn Gly
1               5

<210> SEQ ID NO 341
<211> LENGTH: 11

```
<212> TYPE: PRT
<213> ORGANISM: Artificial Sequence
<220> FEATURE:
<223> OTHER INFORMATION: antibody sequence

<400> SEQUENCE: 341

Val Ala Ala Val Asn Trp Ser Gly Glu Arg Thr
1               5                   10

<210> SEQ ID NO 342
<211> LENGTH: 17
<212> TYPE: PRT
<213> ORGANISM: Artificial Sequence
<220> FEATURE:
<223> OTHER INFORMATION: antibody sequence

<400> SEQUENCE: 342

Ala Ala Asp Thr Asp Tyr Arg Leu Asp Gly Ser Thr Trp Ile Thr Asn
1               5                   10                  15

Leu

<210> SEQ ID NO 343
<211> LENGTH: 127
<212> TYPE: PRT
<213> ORGANISM: Artificial Sequence
<220> FEATURE:
<223> OTHER INFORMATION: antibody sequence

<400> SEQUENCE: 343

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Arg Ile Asn
                20                  25                  30

Gly Met Gly Trp Ile Arg Gln Ala Pro Gly Lys Glu Arg Glu Val Val
            35                  40                  45

Ala Ala Val Asn Trp Ser Gly Glu Arg Thr Tyr Tyr Val Asp Ser Val
        50                  55                  60

Lys Gly Arg Phe Thr Ile Ser Arg Glu Lys Gly Asn Arg Ile Tyr Leu
65                  70                  75                  80

Gln Met Asn Asp Leu Glu Pro Asp Asp Thr Ala Val Tyr Tyr Cys Ala
                85                  90                  95

Ala Asp Thr Asp Tyr Arg Leu Asp Gly Ser Thr Trp Ile Thr Asn Leu
            100                 105                 110

Tyr Ser Gly Ser Leu Gly Gln Gly Thr Gln Val Thr Val Ser Ser
            115                 120                 125
```